US010772928B2

(12) United States Patent
Blencowe et al.

(10) Patent No.: US 10,772,928 B2
(45) Date of Patent: Sep. 15, 2020

(54) MODULATION AND DETECTION OF A NEURONAL ALTERNATIVE SPLICING REGULATORY NETWORK FOR TREATMENT AND DIAGNOSIS OF NEUROLOGICAL DISORDERS

(71) Applicants: The Governing Council of the University of Toronto, Toronto (CA); Sinai Health System, Toronto (CA)

(72) Inventors: Benjamin J. Blencowe, Toronto (CA); Mathieu Quesnel-Vallieres, Scarborough (CA); Manuel Irimia, Barcelona (ES); Bushra Raj, Calgary (CA); Sabine P. Cordes, Toronto (CA)

(73) Assignees: The Governing Council of the University of Toronto, Toronto, Ontario (CA); Sinai Health System, Toronto, Ontario (CA)

( * ) Notice: Subject to any disclaimer, the term of this patent is extended or adjusted under 35 U.S.C. 154(b) by 0 days.

(21) Appl. No.: 15/536,416

(22) PCT Filed: Dec. 15, 2015

(86) PCT No.: PCT/CA2015/051328
§ 371 (c)(1),
(2) Date: Jun. 15, 2017

(87) PCT Pub. No.: WO2016/095037
PCT Pub. Date: Jun. 23, 2016

(65) Prior Publication Data
US 2017/0360873 A1   Dec. 21, 2017

Related U.S. Application Data

(60) Provisional application No. 62/093,192, filed on Dec. 17, 2014.

(51) Int. Cl.
| *A61K 38/55* | (2006.01) |
| *A61K 38/05* | (2006.01) |
| *A61K 31/7088* | (2006.01) |
| *G01N 33/68* | (2006.01) |
| *C12Q 1/6883* | (2018.01) |
| *A61K 38/46* | (2006.01) |
| *G01N 33/50* | (2006.01) |
| *A01K 67/027* | (2006.01) |
| *C07K 14/47* | (2006.01) |
| *A61K 45/06* | (2006.01) |
| *A61K 31/713* | (2006.01) |
| *A61K 49/00* | (2006.01) |

(52) U.S. Cl.
CPC .......... *A61K 38/05* (2013.01); *A01K 67/0276* (2013.01); *A01K 67/0278* (2013.01); *A61K 31/7088* (2013.01); *A61K 31/713* (2013.01); *A61K 38/46* (2013.01); *A61K 38/55* (2013.01); *A61K 45/06* (2013.01); *A61K 49/0008* (2013.01); *C07K 14/4702* (2013.01); *C12Q 1/6883* (2013.01); *G01N 33/5058* (2013.01); *G01N 33/5088* (2013.01); *G01N 33/6896* (2013.01); *A01K 2217/052* (2013.01); *A01K 2217/072* (2013.01); *A01K 2217/077* (2013.01); *A01K 2227/105* (2013.01); *A01K 2267/0306* (2013.01); *A01K 2267/0356* (2013.01); *C12Q 2600/156* (2013.01); *G01N 2800/28* (2013.01)

(58) Field of Classification Search
CPC ......... A61K 38/05; A61K 38/55; A61K 38/46
See application file for complete search history.

(56) References Cited

PUBLICATIONS

Jackowski, British J. Neurosurgery 9 (1995): 303-317.*
Quesnel-Vallieres, M. et al., "Dissecting the in vivo functions of the neural splicing regulator nSR100/SRRM4", Poster, RNA 2014 The Nineteenth Annual of the RNA Society Meeting, Quebec City, Canada, Jun. 3, 2014.
Calarco, J.A. et al., "Regulation of Vertebrate Nervous System Alternative Splicing and Development by an SR-Related Protein", Cell, Sep. 4, 2009, vol. 138, pp. 898-910.
Raj, B. et al., "Cross-Regulation between an Alternative Splicing Activator and a Transcription Repressor Controls Neurogenesis", Molecular Cell, Sep. 2, 2011, vol. 43, pp. 843-850.
Raj, B. et al., "A Global Regulatory Mechanism for Activating an Exon Network Required for Neurogenesis", Molecular Cell, Oct. 2, 2014, vol. 56, pp. 1-14.
Irimia, M. et al., "A Highly Conserved Program of Neuronal Microexons Is Misregulated in Autistic Brains", Cell, Dec. 18, 2014, vol. 159, pp. 1-13 and S1-S19.
Quesnel-Vallieres, M. et al., "Essential roles for the splicing regulator nSR100/SRRM4 during nervous system development", Genes and Development, Apr. 2015, vol. 29, pp. 746-759.
Parras et al., Autism-like phenotype and risk gene-RNA deadenylation by CPEB4 mis-splicing, Nature. Aug. 2018; 560(7719): 441-446 [online], [retrieved on Jan. 22, 2020]. Retrieved from the Internet: <URL: https://www.nature.com/articles/s41586-018-0423-5><DOI: 10.1038/s41586-018-0423-5>.

(Continued)

*Primary Examiner* — Robert C Hayes
(74) *Attorney, Agent, or Firm* — Ainslie Parsons; Melanie Szweras; Bereskin & Parr LLP/S.E.N.C.R.L., s.r.l.

(57) ABSTRACT

Methods for treatment and diagnosis of neurological disorders such as autism and autism spectrum disorder are disclosed. Also disclosed are modulators of alternative splicing regulators SRRM4 and/or SRRM3 for treating neurological disorders. Further disclosed are agents that modulate the expression of at least one splice variant for treating neurological disorders. Mouse models of neurological disorders having increased or decreased expression of SRRM4 and/or SRRM3 are also disclosed.

5 Claims, 57 Drawing Sheets

(56) References Cited

PUBLICATIONS

Ohnishi et al., SRRM4-dependent neuron-specific alternative splicing of protrudin transcripts regulates neurite outgrowth, Scientific Reports, 7:41130 [online], Jan. 20, 2017 [retrieved on Jan. 22, 2020]. Retrieved from the Internet: <https://www.researchgate.net/publication/312665784_SRRM4-dependent_neuron-specific_alternative_splicing_of_ protrudin_transcripts_regulates_neurite_outgrowth> <DOI: 10.1038/srep41130>.

Silbert et al., Fundamental Elements in Autism: From Neurogenesis and Neurite Growth to Synaptic Plasticity, Nov. 2017, Front. Cell. Neurosci. 11:359 [online], [retrieved on Jan. 22, 2020]. Retrieved from the Internet: <URL: https://www.ncbi.nlm.nih.gov/pmc/articles/PMC5701944/> <DOI: 10:3389/fncel.2017.00359>.

\* cited by examiner

A

MODULATION AND DETECTION OF A NEURONAL ALTERNATIVE SPLICING REGULATORY NETWORK FOR TREATMENT AND DIAGNOSIS OF NEUROLOGICAL DISORDERS

RELATED APPLICATIONS

This application is a national phase entry of PCT/CA2015/051328 filed Dec. 15, 2015 (which designates the U.S.), which claims priority from U.S. provisional application No. 62/093,192 filed on Dec. 17, 2014, the contents of which are incorporated herein by reference in their entirety.

FIELD OF THE DISCLOSURE

The disclosure relates to a neuronal alternative splicing regulatory network. In particular, the disclosure relates to methods of treating neurological diseases or disorders through the use of modulators of alternative splicing regulators SRRM4 (nSR100) and/or SRRM3. The disclosure also relates to methods of detecting and/or screening for neurological diseases or disorders and mouse models of neurological diseases or disorders.

BACKGROUND OF THE DISCLOSURE

Alternative splicing (AS)—the process by which different pairs of splice sites are selected in precursor mRNA to generate multiple mRNA and protein products—is responsible for greatly expanding the functional and regulatory capacity of metazoan genomes (Braunschweig et al., 2013; Chen and Manley, 2009; Kalsotra and Cooper, 2011). For example, transcripts from over 95% of human multi-exon genes undergo AS, and most of the resulting mRNA splice variants are variably expressed between different cell and tissue types (Pan et al., 2008; Wang et al., 2008). However, the function of the vast majority of AS events detected to date are not known, and new landscapes of AS regulation remain to be discovered and characterized (Braunschweig et al., 2014; Eom et al., 2013). Moreover, since the misregulation of AS frequently causes or contributes to human disease, there is a pressing need to systematically define the functions of splice variants in disease contexts.

AS generates transcriptomic complexity through differential selection of cassette alternative exons, alternative 5' and 3' splice sites, mutually exclusive exons, and alternative intron retention. These events are regulated by the interplay of cis-acting motifs and trans-acting factors that control the assembly of spliceosomes (Chen and Manley, 2009; Wahl et al., 2009). The assembly of spliceosomes at 5' and 3' splice sites is typically regulated by RNA binding proteins (RBPs) that recognize proximal cis-elements, referred to as exonic/intronic splicing enhancers and silencers (Chen and Manley, 2009). An important advance that is facilitating a more general understanding of the role of individual AS events is the observation that many cell/tissue type- and developmentally-regulated AS events are coordinately controlled by individual RBPs, and that these events are significantly enriched in genes that operate in common biological processes and pathways (Calarco et al., 2011; Irimia and Blencowe, 2012; Licatalosi and Darnell, 2010).

AS can have dramatic consequences on protein function, and/or affect the expression, localization and stability of spliced mRNAs (Irimia and Blencowe, 2012). While cell and tissue differentially-regulated AS events are significantly under-represented in functionally defined, folded domains in proteins, they are enriched in regions of protein disorder that typically are surface accessible and embed short linear interaction motifs (Buljan et al., 2012; Ellis et al., 2012; Romero et al., 2006). AS events located in these regions are predicted to participate in interactions with proteins and other ligands (Buljan et al., 2012; Weatheritt et al., 2012). Indeed, among a set of analyzed neural-specific exons enriched in disordered regions, approximately one third promoted or disrupted interactions with partner proteins (Ellis et al., 2012). These observations suggested that a widespread role for regulated exons is to specify cell and tissue type-specific protein interaction networks.

Human disease and disorder mutations often disrupt cis-elements that control splicing and result in aberrant AS patterns (Cartegni et al., 2002). Other disease changes affect the activity or expression of RBPs, causing entire programs of AS to be misregulated. For example, amyotrophic lateral sclerosis-causing mutations in the RBPs TLS/FUS and TDP43 affect AS and other aspects of post-transcriptional regulation (Polymenidou et al., 2012). It is also widely established that misregulation of AS plays important roles in altering the growth and invasiveness of various cancers (David and Manley, 2010). As is the case with assessing the normal functions of AS, it is generally not known which misregulated AS events cause or contribute to disease or disorder phenotypes.

Central to addressing the above questions is the importance of comprehensively defining AS programs associated with normal and disease biology. Gene prediction algorithms, high-throughput RNA sequencing (RNA-Seq) analysis methods, and RNA-Seq datasets generally lack the sensitivity and/or depth required to detect specific types of AS. In particular, microexons (Beachy et al., 1985; Coleman et al., 1987), defined here as 3-27 nucleotide (nt)-long exons, have been largely missed by genome annotations and transcriptome profiling studies (Volfovsky et al., 2003; Wu et al., 2013; Wu and Watanabe, 2005). This is especially true for microexons shorter than 15 nts. Furthermore, where alignment tools have been developed to capture microexons (Wu et al., 2013), they have not been applied to the analysis of different cell and tissue types, or disease states.

SUMMARY OF THE DISCLOSURE

The present inventors have demonstrated a program or set of highly conserved, neuronal-specific, 3-27 microexons that is concentrated in genes with neuronal functions. They have shown that this set of neuronal microexons is misregulated in individuals with autism spectrum disorder (ASD). They have also shown that at least half of all detected microexons are controlled by the AS regulator SRRM4 (also referred to as nSR100) and that microexon levels correlate significantly with SRRM4 expression levels in the brains of human subjects. They have further shown that microexons regulated by SRRM4 are also regulated by SRRM3. Consistent with these findings, the present inventors have shown that microexons are misregulated in mice deficient of SRRM4, and that these mice display autistic-like behaviors. Additional demonstrations made by the present inventors are that SRRM4 interacts with partner proteins that control its levels of expression.

Accordingly, one aspect of the present disclosure is directed to a method of treating a neurological disorder or disease or improving neurological function comprising administering a modulator of SRRM4 and/or a modulator of SRRM3 to a subject in need thereof.

In one embodiment, the neurological disorder or disease is autism or autism spectrum disorder, schizophrenia, epilepsy or mental retardation. In another embodiment, the neurological disorder is autism or autism spectrum disorder.

In another embodiment, the modulator increases or decreases the expression of SRRM4 and/or SRRM3 and/or expression of the gene encoding SRRM4 and/or SRRM3. In another embodiment, the modulator increases the expression of SRRM4 and/or SRRM3 and/or expression of the gene encoding SRRM4 and/or SRRM3.

In an embodiment, the modulator is a nucleic acid encoding SRRM4 and/or SRRM3 or is exogenous SRRM4 and/or SRRM3 protein.

In another embodiment, the modulator is a modified or unmodified endonuclease targeting the SRRM4 and/or SRRM3 gene loci, optionally wherein the endonuclease is CRISPR-Cas9. In a particular embodiment, the modulator is a mutant inactive endonuclease such as Cas9 fused to an effector domain such as a transcriptional activation domain.

In another embodiment, the modulator of SRRM4 and/or SRRM3 increases or decreases the expression of a protein associated with SRRM4 and/or SRRM3 stability or activity.

In another embodiment, the modulator of SRRM4 and/or SRRM3 is an antibody or peptide or nucleic acid-derived aptamer to the protein associated with SRRM4 and/or SRRM3 stability or activity, antisense RNA or small interfering RNA that increases or decreases the expression of the protein associated with SRRM4 and/or SRRM3 stability or activity, or a compound that inhibits the expression or function of the protein associated with SRRM4 and/or SRRM3 stability or activity.

In another embodiment, the protein associated with SRRM4 and/or SRRM3 stability or activity is an SRRM4 interaction partner selected from Table 4.

In another embodiment, the protein associated with SRRM4 stability or activity is FBXW11.

In another embodiment, the modulator of SRRM4 is a proteasome inhibitor, optionally MG132.

In an embodiment, the subject is a human.

Another aspect of the present disclosure is directed to a method of treating a neurological disorder or disease or improving neurological function comprising administering an agent that modulates the expression of at least one microexon splice variant listed in Table 1 or Table 2, to a subject in need thereof. In an embodiment, the subject is human and the at least one microexon splice variant is listed in Table 1. In another embodiment, the subject is mouse and the at least one microexon splice variant is listed in Table 2.

In an embodiment the at least one microexon splice variant is of a gene that is associated with neuronal differentiation, neurite outgrowth, axon guidance, and/or one or more neuronal functions including synaptic activity.

In one embodiment, the at least one microexon splice variant is of a gene wherein the level of the microexon splice variant in neural cells and tissues is regulated by SRRM4 and/or SRRM3.

In another embodiment, the agent is a nucleic acid molecule, optionally cDNA encoding a splice variant, wherein the splice variant either includes or skips the microexon.

In another embodiment, the nucleic acid molecule is contained in an expression construct.

In another embodiment, the microexon splice variant is an Unc13b microexon splice variant. In yet another embodiment, the microexon splice variant is a Slit2 microexon splice variant. In another embodiment, the microexon splice variant is an Apbb1 microexon splice variant. In a further embodiment, the microexon splice variant is an AP1S2 microexon splice variant.

Another aspect of the present disclosure is directed to a method of detecting and/or screening for a neurological disorder or disease, in a subject, comprising:

(a) determining a sample neuronal alternative splicing profile from a sample from said subject, said sample profile comprising the level of at least one, optionally at least 5, at least 10, at least 25, at least 50, at least 100, at least 150, at least 200, at least 250, at least 300, or all microexon splice variants from Table 1 or Table 2; and (b) determining the level of similarity of said sample profile to one or more control profiles, wherein (i) a high level of similarity of the sample profile to a neurological disorder or disease-specific control profile; (ii) a low level of similarity to a non-neurological disorder or disease control profile; and/or (iii) a higher level of similarity to a neurological disorder or disease control profile than to a non-neurological disorder or disease control profile indicates the presence of, or an increased likelihood of a neurological disorder or disease.

In an embodiment, the subject is human and the microexon splice variants are from Table 1. In another embodiment, the subject is mouse and the microexon splice variants are from Table 2.

In an embodiment, the sample comprises neurons derived from induced pluripotent cells from the subject.

In one embodiment, a higher level of similarity to the neurological disorder or disease control profile than to the non-neurological disorder or disease control profile is indicated by a higher correlation value computed between the sample profile and the neurological disorder or disease specific profile than an equivalent correlation value computed between the sample profile and the non-neurological disorder or disease control profile.

In another embodiment, the correlation value is a correlation coefficient.

Another aspect of the present disclosure is directed to a mouse, wherein the mouse has decreased or increased expression of at least one copy of the gene encoding SRRM4 and/or at least one copy of the gene encoding SRRM3, compared to a wild type control mouse.

In one embodiment, the mouse comprises a homozygous disruption of the gene encoding SRRM4 and/or SRRM3.

In another embodiment, the mouse comprises a heterozygous disruption of the gene encoding SRRM4 and/or SRRM3.

In another embodiment, the gene encoding SRRM4 lacks exons 7 and 8.

In another embodiment, the mouse exhibits autistic-like behavioural phenotypes.

Another aspect of the present disclosure is directed to a use of the mouse as described above as a model for a neurological disorder or disease.

Another aspect of the present disclosure is directed to a method of modeling a neurological disorder or disease, optionally autism or autism spectrum disorder, wherein the method comprises generating the mouse described above.

Another aspect of the present disclosure is directed to a method of identifying agents for treating a neurological disorder or disease, wherein the method comprises:

(a) contacting the mouse described above with at least one test agent, and (b) determining the effect of the test agent on the behaviour of the mouse.

Another aspect of the present disclosure is directed to a mouse cell, wherein the mouse cell has decreased or increased expression of at least one copy of the gene encoding SRRM4 and/or the gene encoding SRRM3 compared to a wild type control mouse cell.

In one embodiment, the mouse cell comprises a homozygous disruption of the gene encoding SRRM4 and/or SRRM3.

In another embodiment, the mouse cell comprises a heterozygous disruption of the gene encoding SRRM4 and/or SRRM3.

In another embodiment, the gene encoding SRRM4 lacks exons 7 and 8.

Another aspect of the present disclosure is directed to a use of the mouse cell described above as a model for a neurological disorder or disease. In one embodiment, the mouse cell is a neuronal cell and neurite growth is studied.

Another aspect of the present disclosure is directed to a method of modeling a neurological disorder or disease in vitro, optionally autism or autism spectrum disorder, wherein the method comprises generating the mouse cell described above.

Another aspect of the present disclosure is directed to a method of identifying agents for treating a neurological disorder or disease, wherein the method comprises:
(a) contacting the mouse cell described above with at least one test agent, and
(b) determining the effect of the test agent on the mouse cell.

In an embodiment, the mouse cell is a neuron and determining the effect of the test agent comprises measuring neurite length.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

N=23 WT and 18 nSR100$^{+/\Delta7\text{-}8}$ males; N=22 WT and 25 nSR100$^{+/\Delta7\text{-}8}$ females in the light-dark box. N=7 WT and 10 nSR100$^{+/\Delta7\text{-}8}$ males; N=10 WT and 7 nSR100$^{+/\Delta7\text{-}8}$ females in the elevated zero-maze. A-H, Two-way ANOVA. I-N, two-tailed t-test or Mann-Whitney test. Error bars: S.E.M. Whiskers: $10^{th}$-$90^{th}$ percentiles.

Figure 33:
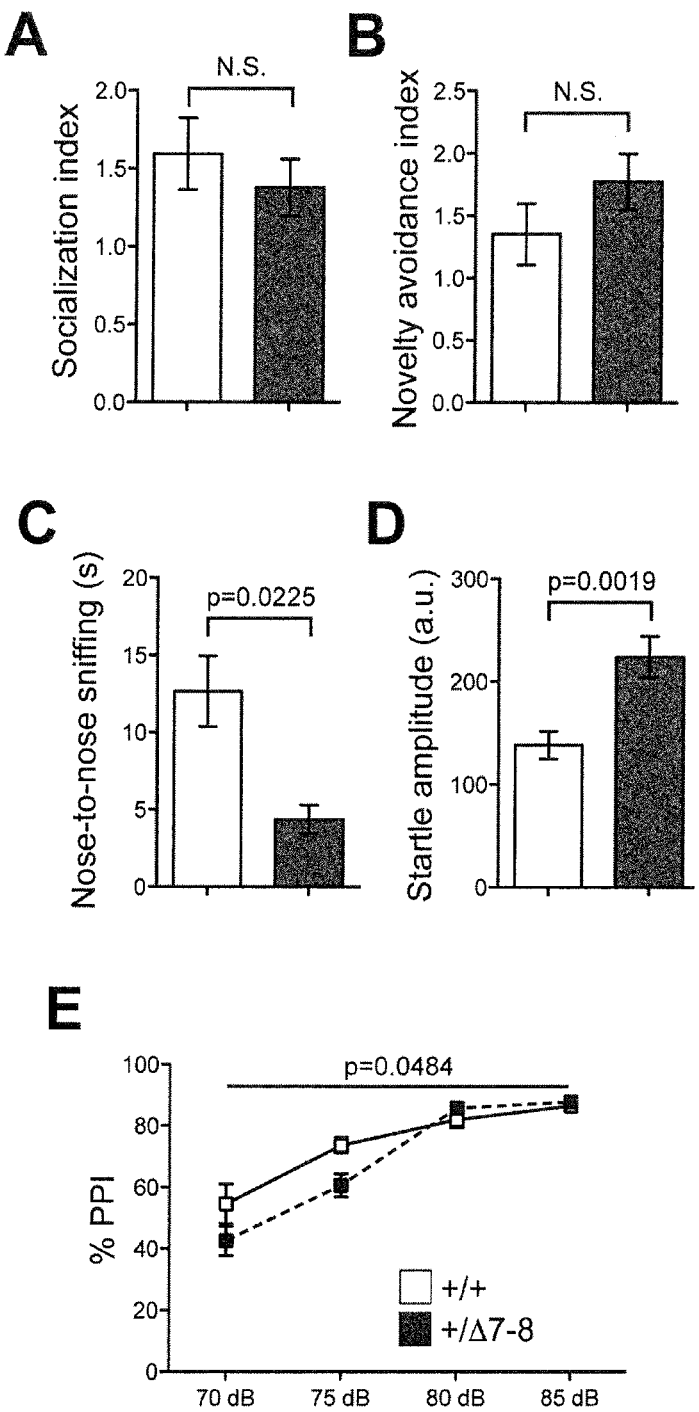

FIG. 33 shows that nSR100$^{+/\Delta7\text{-}8}$ female mice display moderate autistic-like behaviour. A and B) Social behavior was measured using the 3-chamber apparatus with a sociability index in the social choice test (A; time interacting with stranger/time interacting with object) and as a social novelty avoidance index in the social novelty test (B; time spent in chamber with familiar mouse or neutral chamber/time spent in chamber with stranger mouse). C) The reciprocal social interaction test was used to measure direct nose-to-nose interaction. D) The startle response and E) the PPI were measured in adult mice. A-D, two-tailed Mann-Whitney test; E, two-way ANOVA, $F(1,143)=3.962$, $p_{genotype}=0.0484$. N=17 WT and 21 nSR100$^{+/\Delta7\text{-}8}$ for 3-chamber apparatus; N=6 WT and 10 nSR100$^{+/\Delta7\text{-}8}$ for reciprocal social interaction test; N=17 WT and 22 nSR100$^{+/\Delta7\text{-}8}$ for PPI) Error bars: S.E.M.

Figure 34:
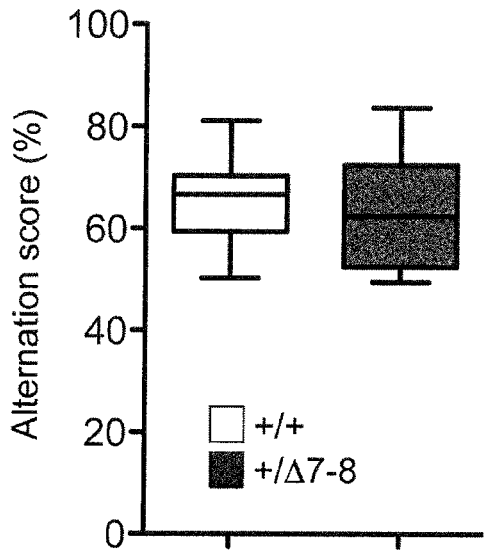
Figure 34:
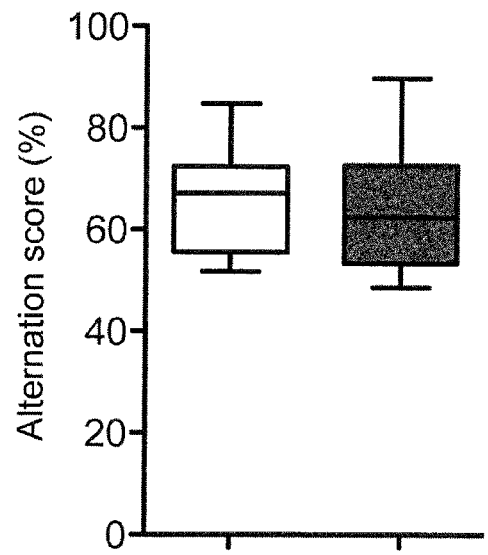

FIG. 34 shows that a decrease in nSR100 expression does not affect short-term memory in mouse. A-B) Short-term memory was assessed by scoring spontaneous alternation in a Y-maze in males (A) and females (B). N=22 WT and 20 nSR100$^{+/\Delta7\text{-}8}$ males; N=21 WT and 25 nSR100$^{+/\Delta7\text{-}8}$ females. Two-tailed t-test. Error bars: S.E.M.

Figure 35:
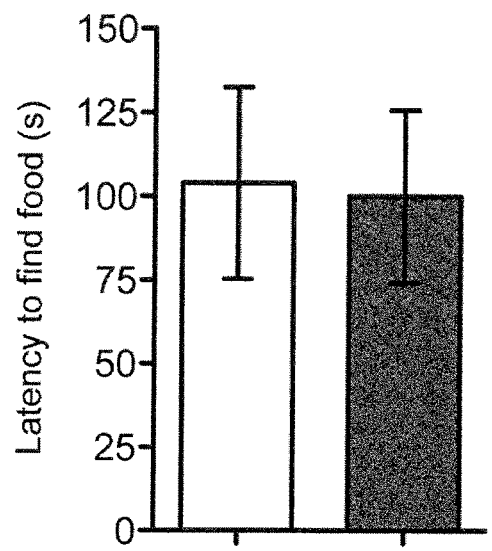
Figure 35:
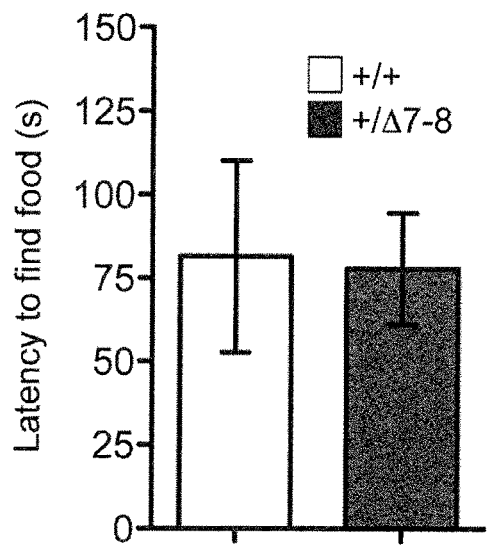

FIG. 35 shows that nSR100$^{+/\Delta7\text{-}8}$ mice have no apparent olfaction defects. A-B) Olfaction was assessed by measuring the amount of time necessary to retrieve food buried under cage bedding for males (A) and females (B). N=10 nSR100$^{+/+}$ males, 9 nSR100$^{+/\Delta7\text{-}8}$ males, 10 nSR100$^{+/+}$ females and 15 nSR100$^{+/\Delta7\text{-}8}$ females. Two-tailed Mann-Whitney test. Error bars: S.E.M.

Figure 36:
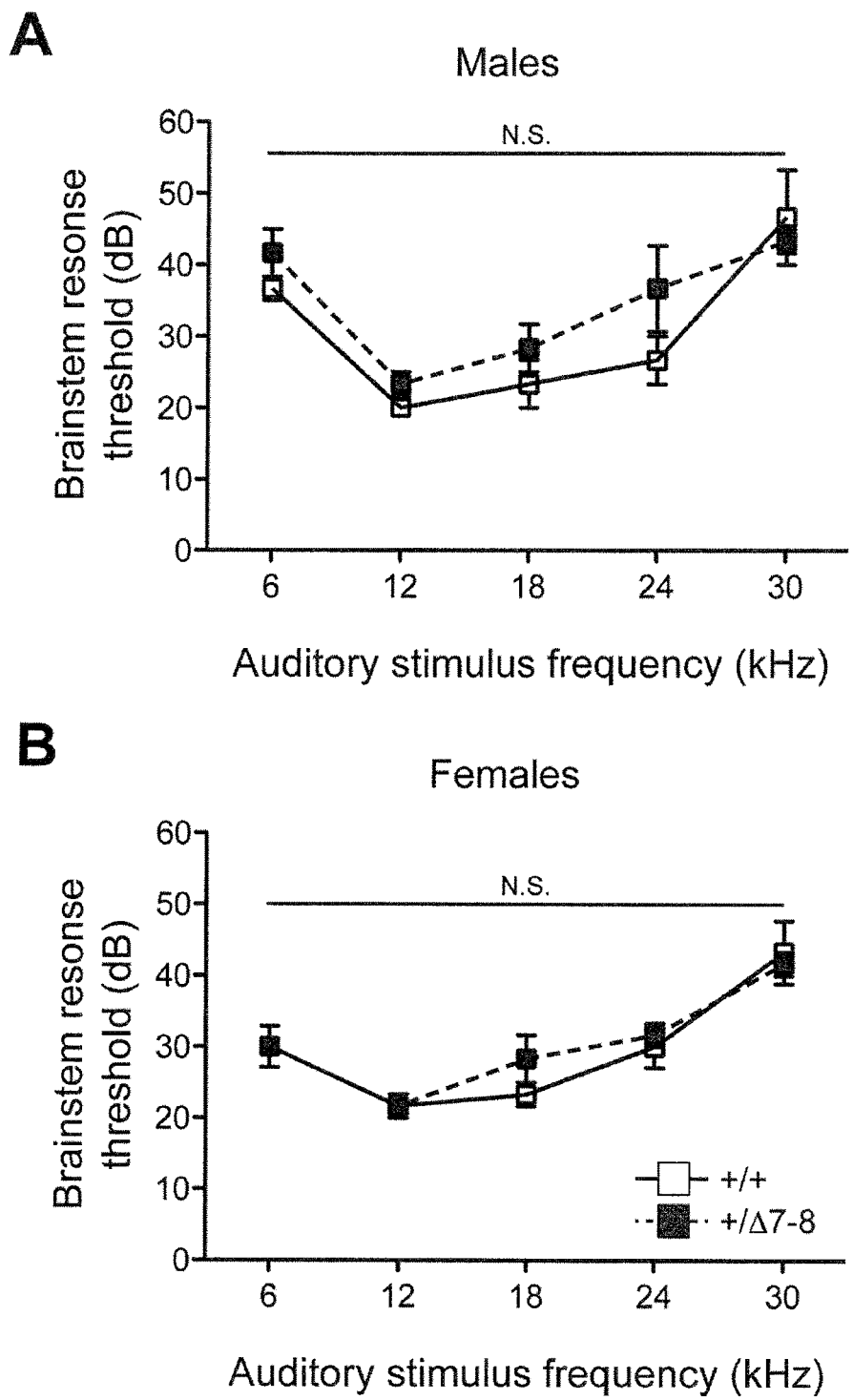

FIG. 36 shows that nSR100$^{+/\Delta7\text{-}8}$ mice have no apparent hearing defects. A-B) Hearing was assessed by measuring the auditory brainstem response in males (A) and females (B). N=3 mice per sex for each genotype. Two-way ANOVA, $F(1,20)=3.000$, $p_{genotype}=0.0987$ in males; $F(1, 20)=0.4091$, $p_{genotype}=0.5297$ in females. Error bars: S.E.M.

Figure 37:
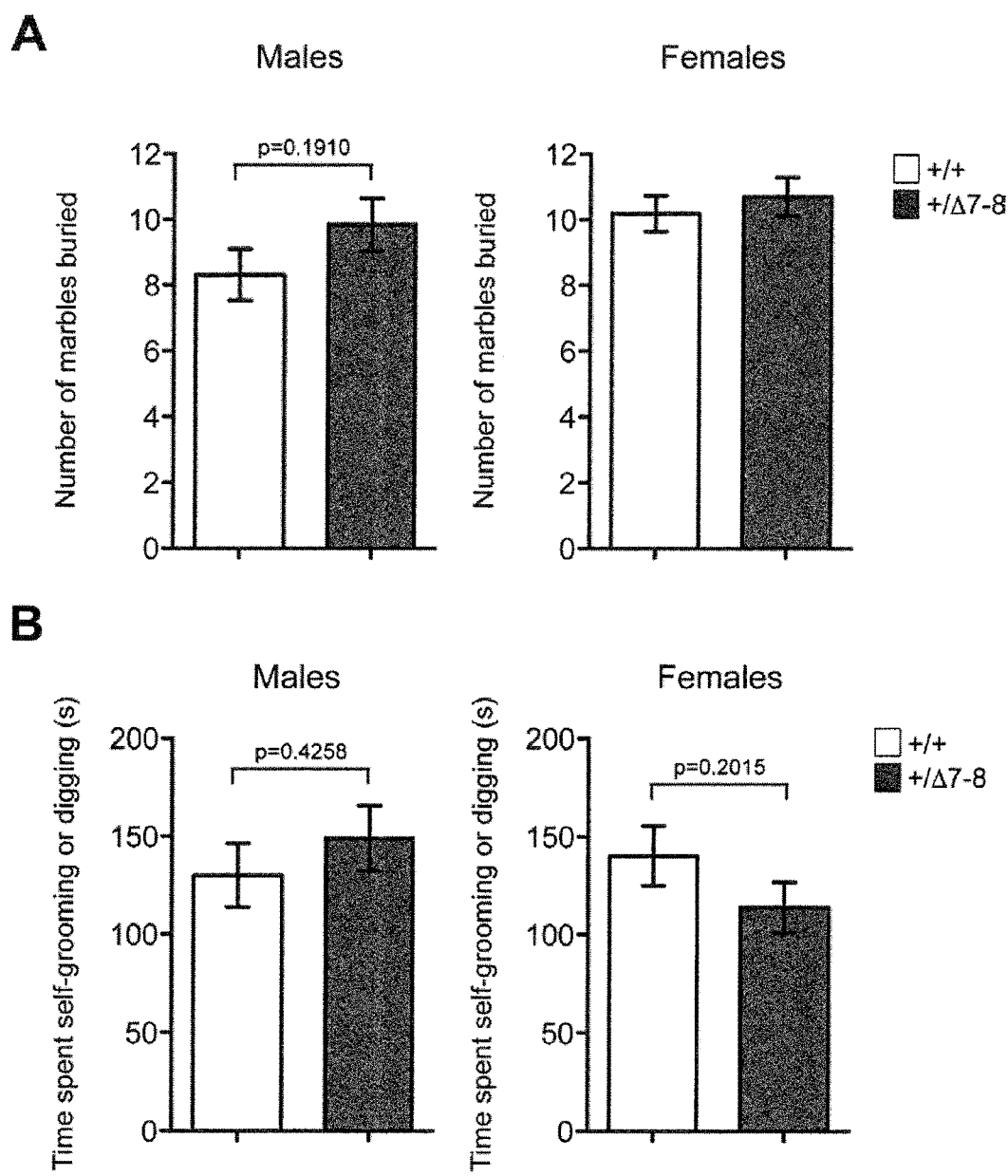

FIG. 37 shows that nSR100$^{+/\Delta7\text{-}8}$ mice have no apparent compulsive or repetitive behaviour. A) Number of marbles buried over 10 minutes by males (left plot) and females (right plot). 3 trials, N=23 nSR100$^{+/+}$ males, 18 nSR100$^{+/\Delta7\text{-}8}$ males, 22 nSR100$^{+/+}$ females and 24 nSR100$^{+/\Delta7\text{-}8}$ females. Unpaired two-tailed t-test. Error bars: S.E.M. B) Repetitive behaviour was assessed by measuring the amount of time spent self-grooming or digging over 10 minutes in an empty cage with bedding for males (left plot) and females (right plot). N=8 males of each genotype, 11 nSR100$^{+/+}$ females and 15 nSR100$^{+/\Delta7\text{-}8}$ females. Unpaired two-tailed t-test. Error bars: S.E.M.

Figure 38:
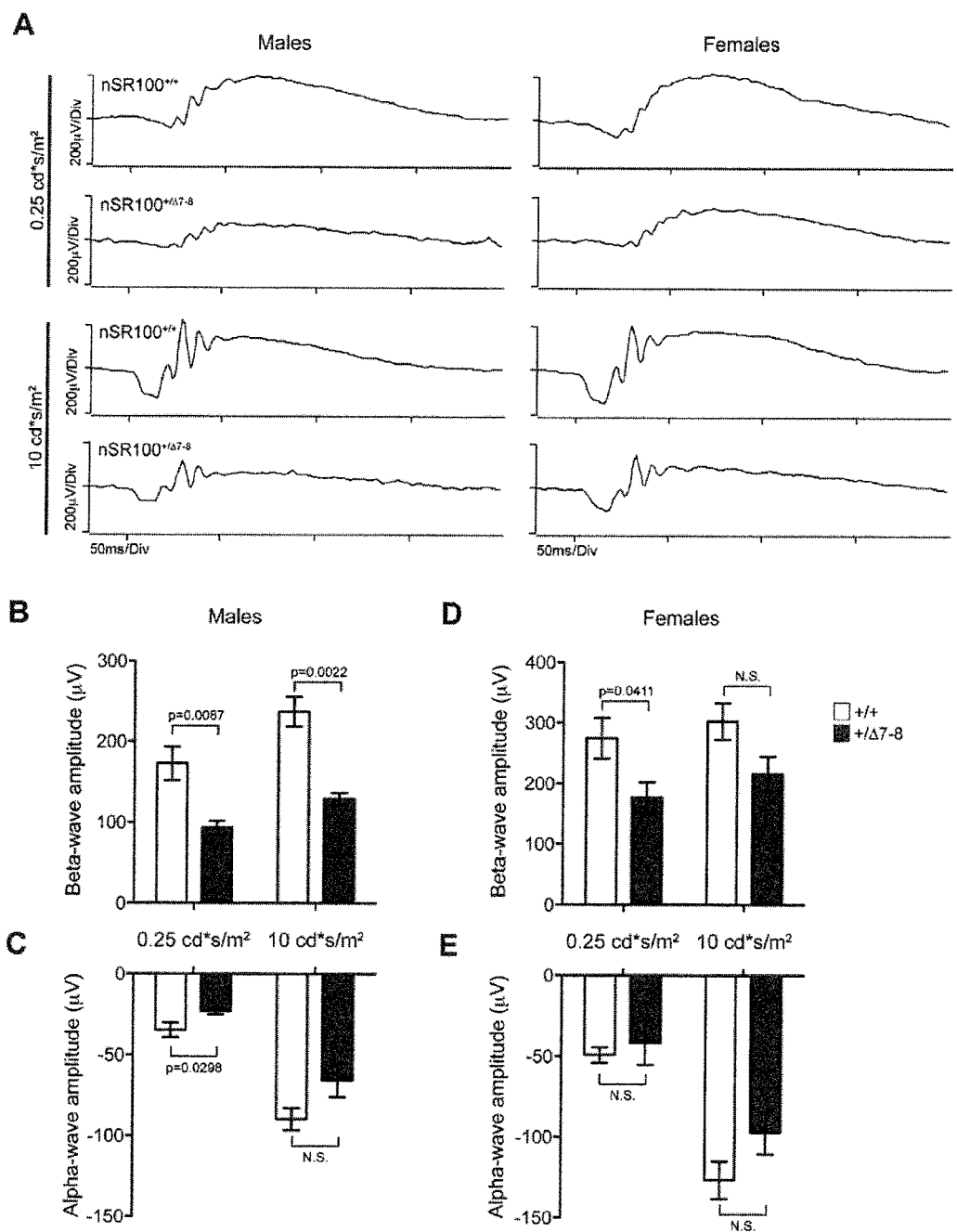

FIG. 38 shows lower responses to light stimulation in nSR100$^{+/\Delta7\text{-}8}$ mice. A) Representative electroretinograms from wild-type and nSR100$^{+/\Delta7\text{-}8}$ males and females. B-E) Reponses were recorded in males (B-C) and females (D-E) for stimulations at 0.25 cd*s/m$^2$ and 10 cd*s/m$^2$ from 3 males and 3 females of each genotype. Mann-Whitney test. Error bars: S.E.M.

Figure 39:
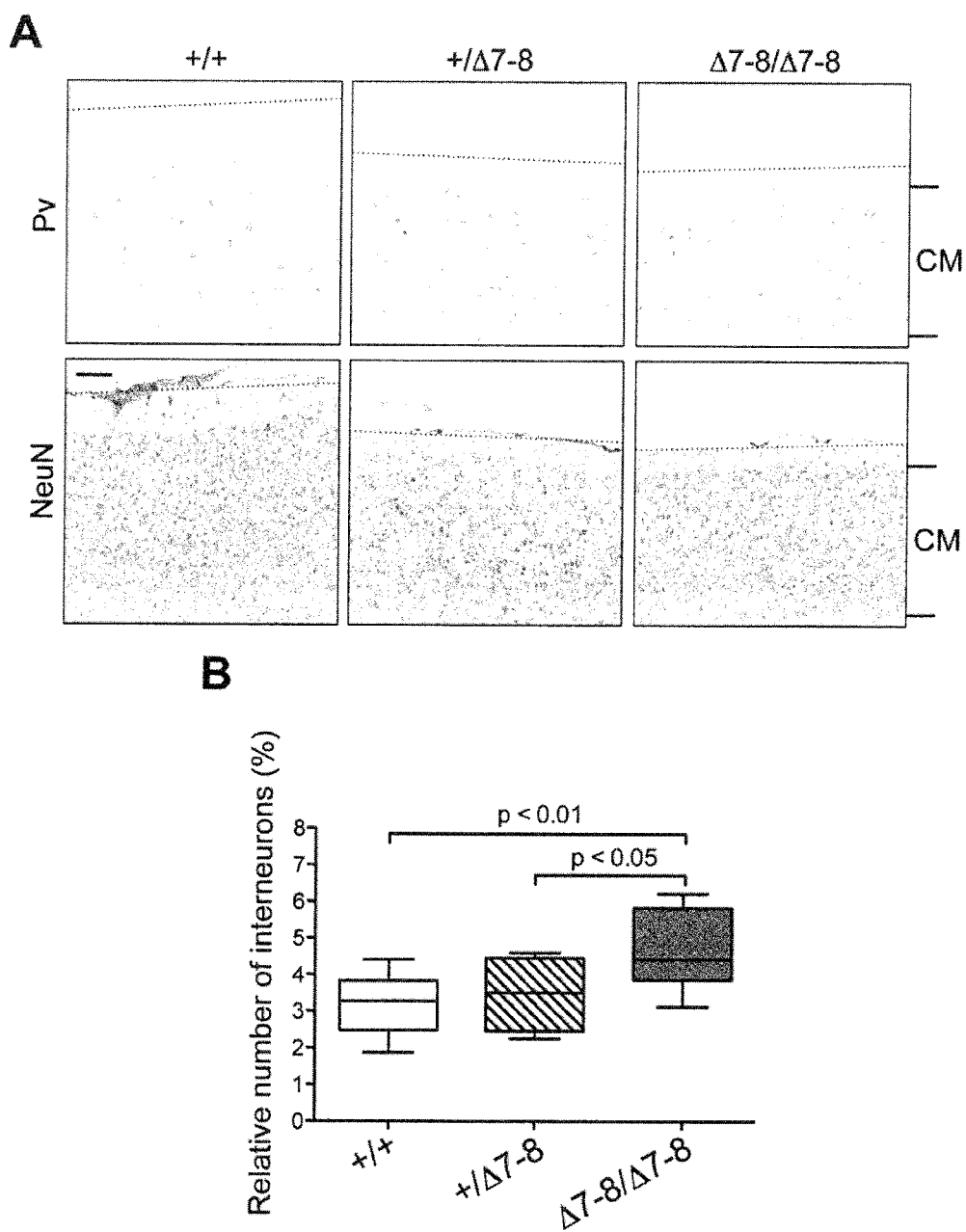

FIG. 39 shows increased number of parvalbumin-positive interneurons in the somatosensory cortex of nSR100 mutant mice. A) Adult cortical brain sections were stained with antibodies to parvalbumin (Pv, upper panels) and Rbfox3/NeuN (NeuN, lower panels). B) Cells were counted on a 777 µm radial section of the cortical mantle and Pv$^+$ cells were normalized to the number of NeuN$^+$ cells. N=3 brains per genotype, 3 sections per brain. One-way ANOVA with Tukey-Kramer post-hoc test. Scale bar: 100 m.

Figure 40:
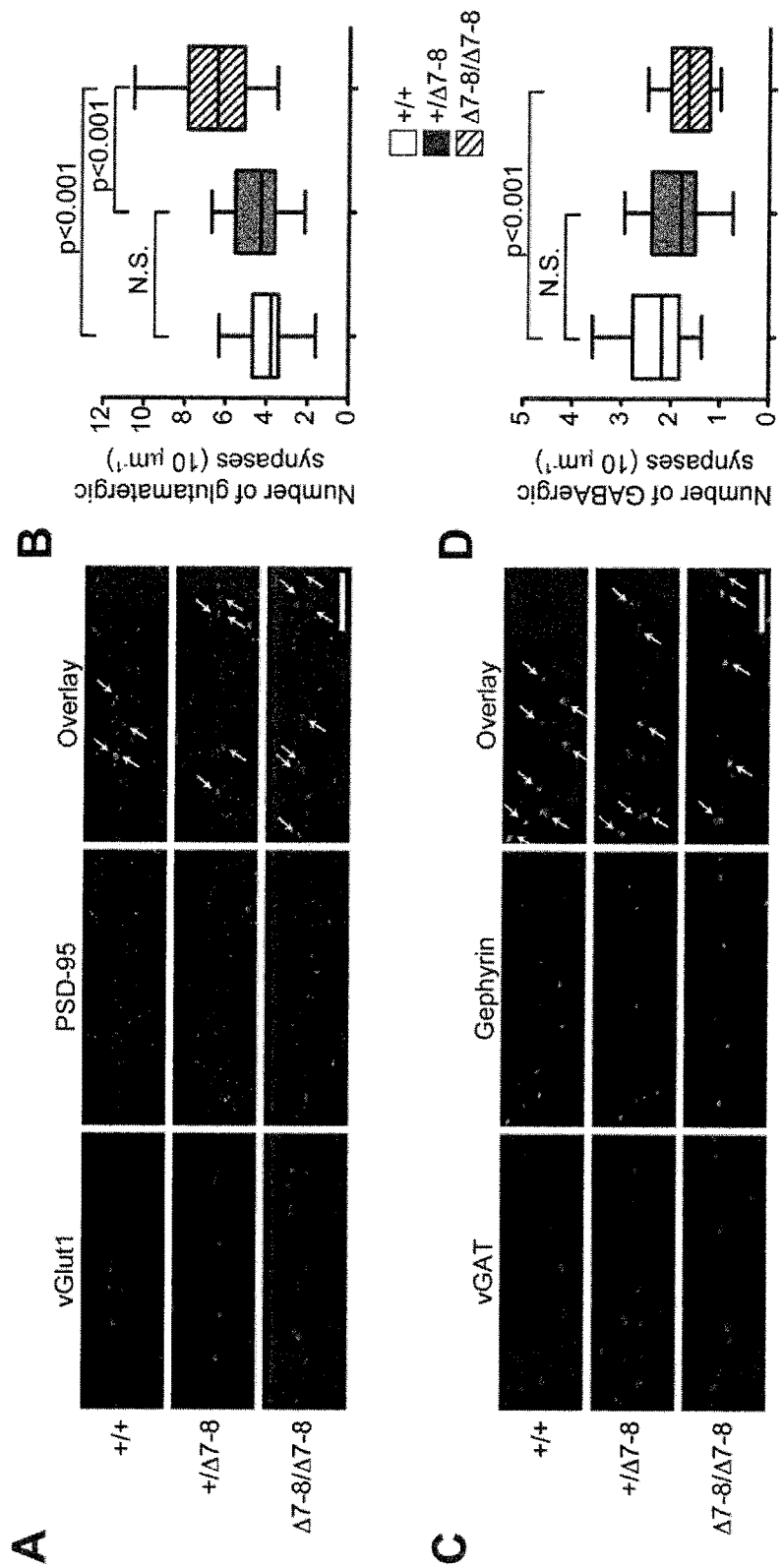

FIG. 40 shows an increase in the number of excitatory and a decrease in the number of inhibitory synapses in cultured cortical neurons lacking nSR100. A-B) Immunostaining with vGlut1, PSD-95 and MAP-2 was performed to highlight (A) and quantify (B) glutamatergic synapses. C-D) Immunostaining with vGAT, gephyrin and MAP-2 was performed to highlight (A) and quantify (B) GABAergic synapses. Synapses were quantified on 40 to 48 dendrites from DIV16 cortical neurons cultured from 3 embryos for each genotype. Scale bar: 5 µm. Kruskal-Wallis test with Dunn's post hoc multiple comparison test. Whiskers: $10^{th}$-$90^{th}$ percentiles.

Figure 41:
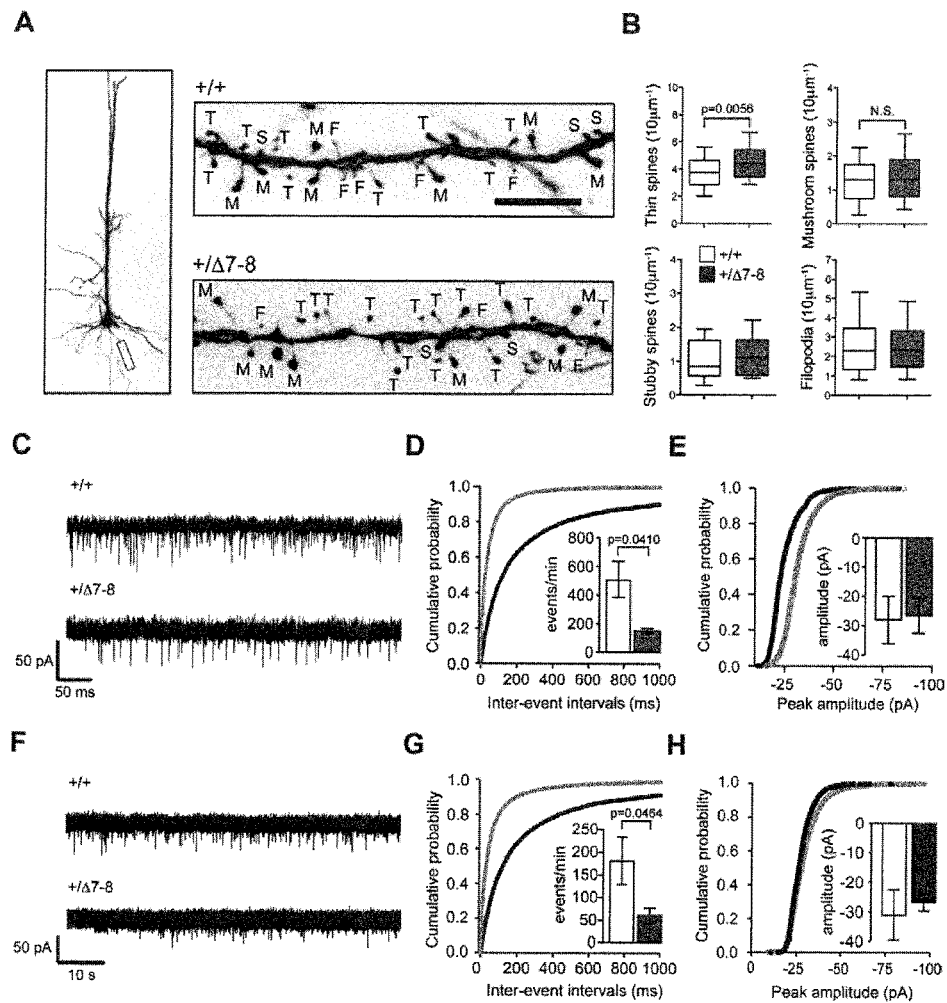

FIG. 41 shows that nSR100$^{+/\Delta7\text{-}8}$ neurons have impaired excitatory synaptic transmission. A) The number and morphology of spines was characterized from GFP$^+$ pyramidal neurons of the somatosensory cortex from mice bearing the Thy1-GFP transgene in a region of the dendritic arbor corresponding to the boxed area in the left panel. Spines were assessed as mushroom ("M"), thin ("T"), stubby ("S") or filopodia ("F"). B) nSR100$^{+/\Delta7\text{-}8}$ mice have a higher number of thin spines. N=3 mice for each genotype, 21-27 dendrites each mouse. Two-tailed Mann-Whitney test. Whiskers: $10^{th}$-$90^{th}$ percentiles. C-H) nSR100$^{+/\Delta7\text{-}8}$ mice have a dramatically lower frequency but unaltered amplitude of spontaneous and miniature EPSCs. Representative traces of spontaneous (C) or miniature (F) EPSCs in VVT and mutant neurons from the somatosensory cortex of adult mice are shown, and the frequency of firing (spontaneous, D; miniature, G) and amplitude (spontaneous, E; miniature, H) were quantified.

Figure 42:
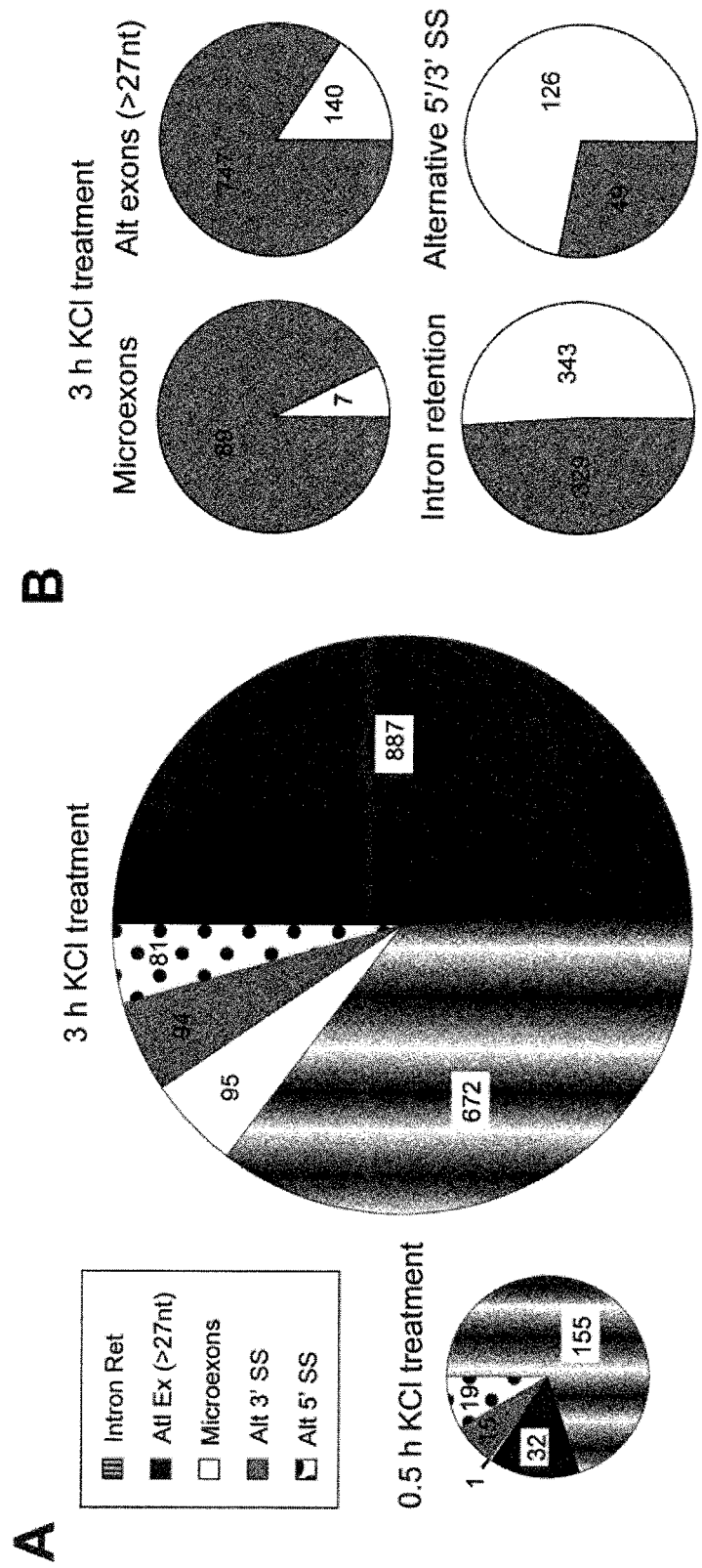
Figure 42:
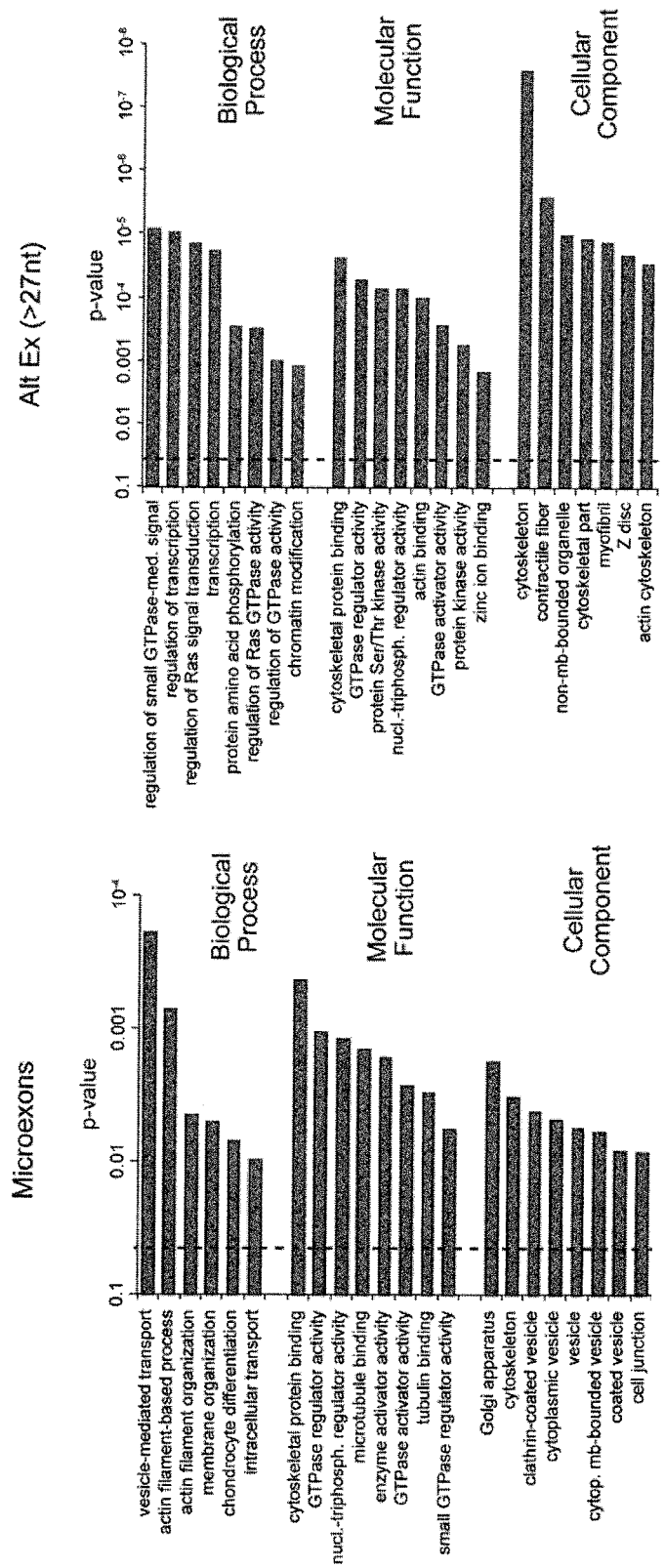

FIG. 42 shows that neuronal activity causes microexons skipping. A) Number of alternative splicing events with PSI, percent intron retention (PIR) or percent splice site usage (PSU) changes of at least 15, 30 minutes and 3 hours after neuronal depolarization. B) Microexons and cassette exons are preferentially skipped following neuronal depolarization, whereas retained introns show no directionality. C) Gene ontology analysis of microexons and cassettes exons with $\Delta PSI \geq 15$ during neuronal depolarization.

Figure 43:
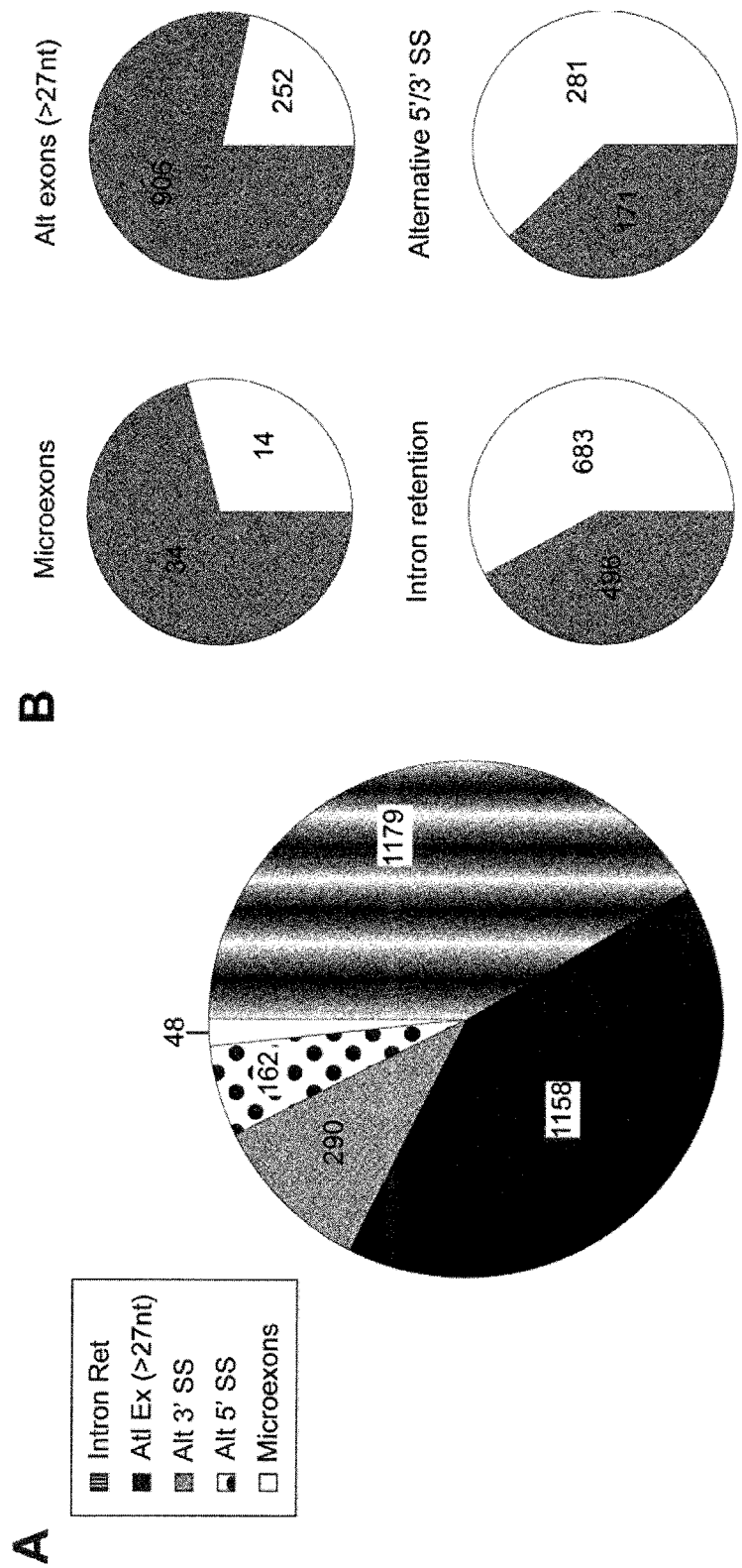

FIG. 43 shows RNA-Seq analysis revealing that a large program of alternative splicing events is regulated by neuronal activation (related to FIG. 42). A) RNA-Seq data generated from DIV8 cortical neurons treated with 57 mM KCl for 5 hours by Maze et al. (Maze et al., Neuron, 2015) was analyzed using VAST-TOOLS. Shown is the number of alternative splicing events with PSI, PIR or PSU changes of at least 15. B) Relative proportion of events undergoing inclusion and skipping after KCl treatment for each class of alternative splicing events.

Figure 44:
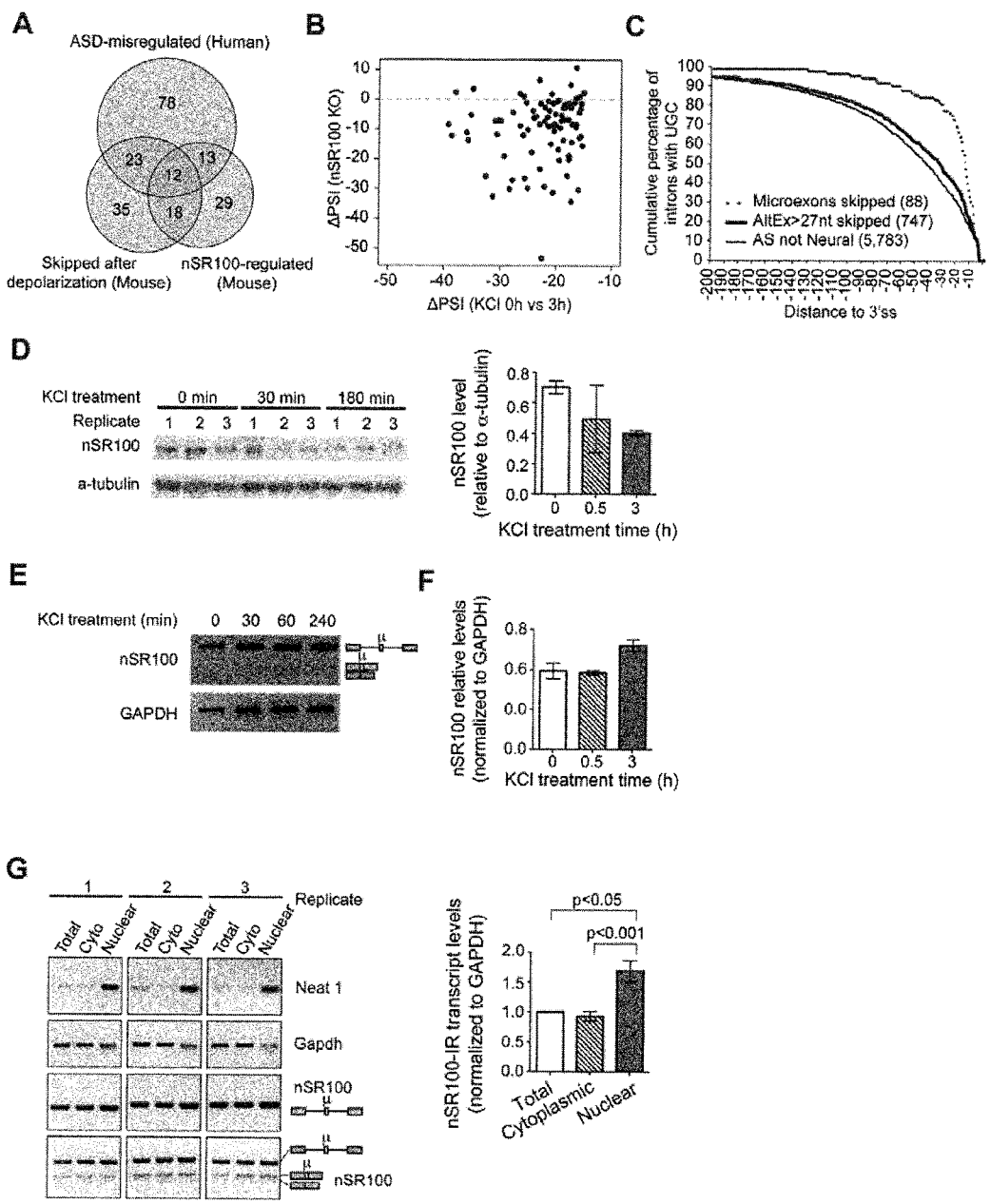

FIG. 44 shows that nSR100$^{+/\Delta7\text{-}8}$ neurons mirror the molecular signature of depolarized neurons. A) Overlap between microexons that are skipped in humans with ASD (upper set), skipped upon neuronal depolarization (lower left set) and nSR100-regulated microexons (lower right set). B) Microexons were plotted based on their PSI difference between depolarized and resting wild-type neurons (X-axis), and between nSR100$^{\Delta7\text{-}8/\Delta7\text{-}8}$ and nSR100$^{+/+}$ mice (Y-axis). C) Cumulative distribution plots indicating the position of the first UGC motif within 200 nt upstream of neuronal activity-regulated microexons (dashed curve) or longer cassette exons (thick solid curve) vs. non-neural alternative cassette exons (light solid curve). The number of exons used to analyze each subgroup is shown in parentheses. D) Western blot on KCl-treated DIV11 cortical neurons (left panel) and quantification of nSR100 protein level (right panel). E) RT-PCR showing increased intron retention and microexon inclusion in nSR100 transcripts early after depolarization of DIV11 cortical neurons. F) qRT-PCR on KCl-treated DIV11 cortical neurons for nSR100 normalized to GAPDH (see also FIG. 45). G) Representative RT-PCRs on nuclear and cytosolic fractions (left panel) to assess localization of nSR100 transcripts in three replicates of cultured DIV4 cortical neurons with qRT-PCR quantification of the abundance of nSR100 isoforms harboring the retained intron, normalized to GAPDH levels in the correspondent cell fractions from six replicates (right panel). Kruskal-Wallis test with Dunn's post hoc multiple comparison test. Error bars: S.D.

Figure 45:
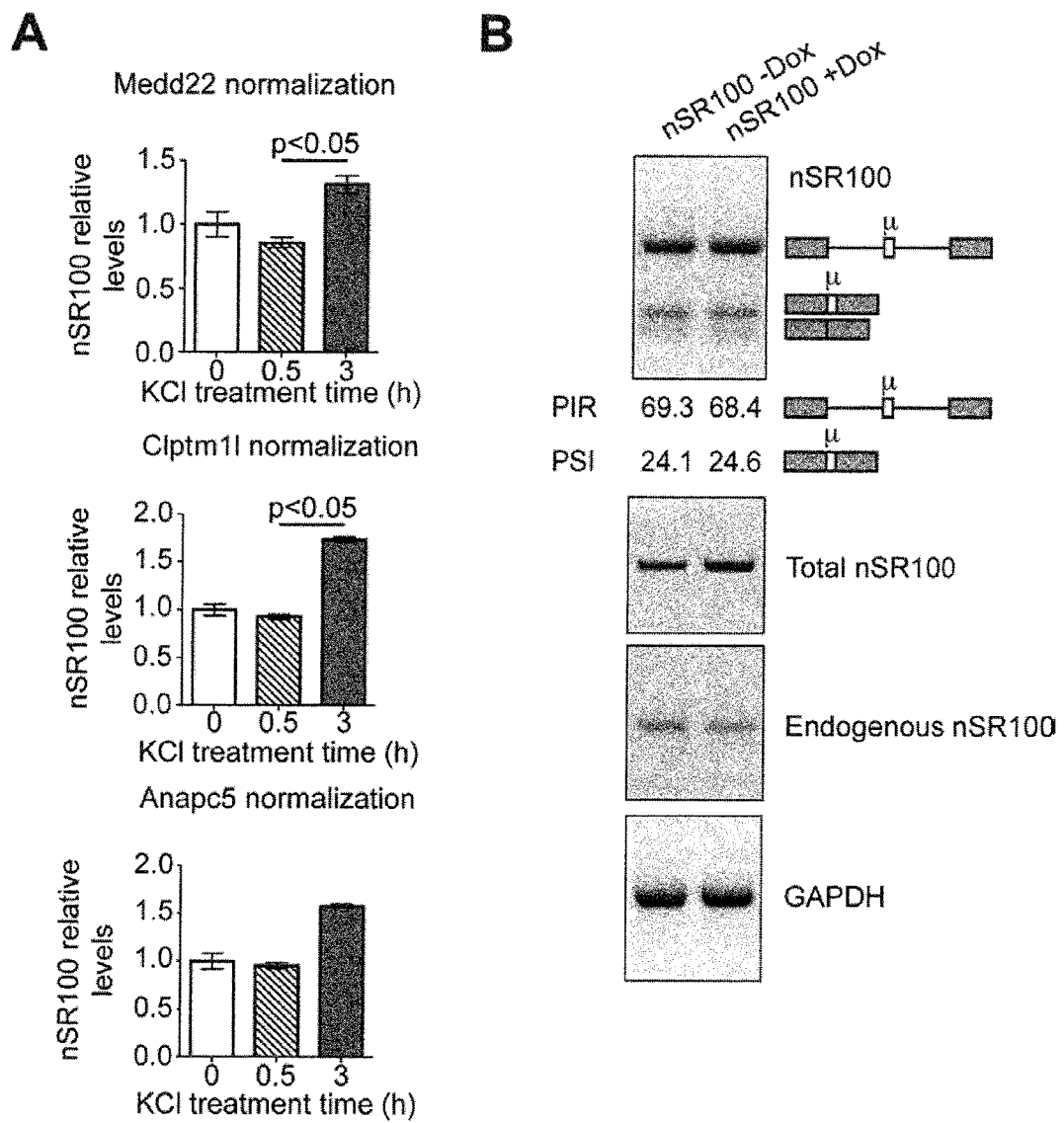

FIG. 45 shows that the shift in nSR100 transcript splicing is not self-regulatory and does not affect transcript stability (related to FIG. 44). A) Additional qRT-PCR validations for nSR100 transcript levels upon neuronal depolarization with normalization to Medd22, Clptm11 and Anapc5. Kruskal-Wallis test with Dunn's post hoc multiple comparison test. Error bars: S.D. B) Dox-inducible nSR100 N2A cells were left untreated (left lane) or treated with Dox (right lane) and nSR100 isoform abundance was assessed by semi-quantitative RT-PCR. The ratio of nSR100 isoforms containing the microexon or the retained intron is not affected by increased nSR100 expression.

Figure 46:
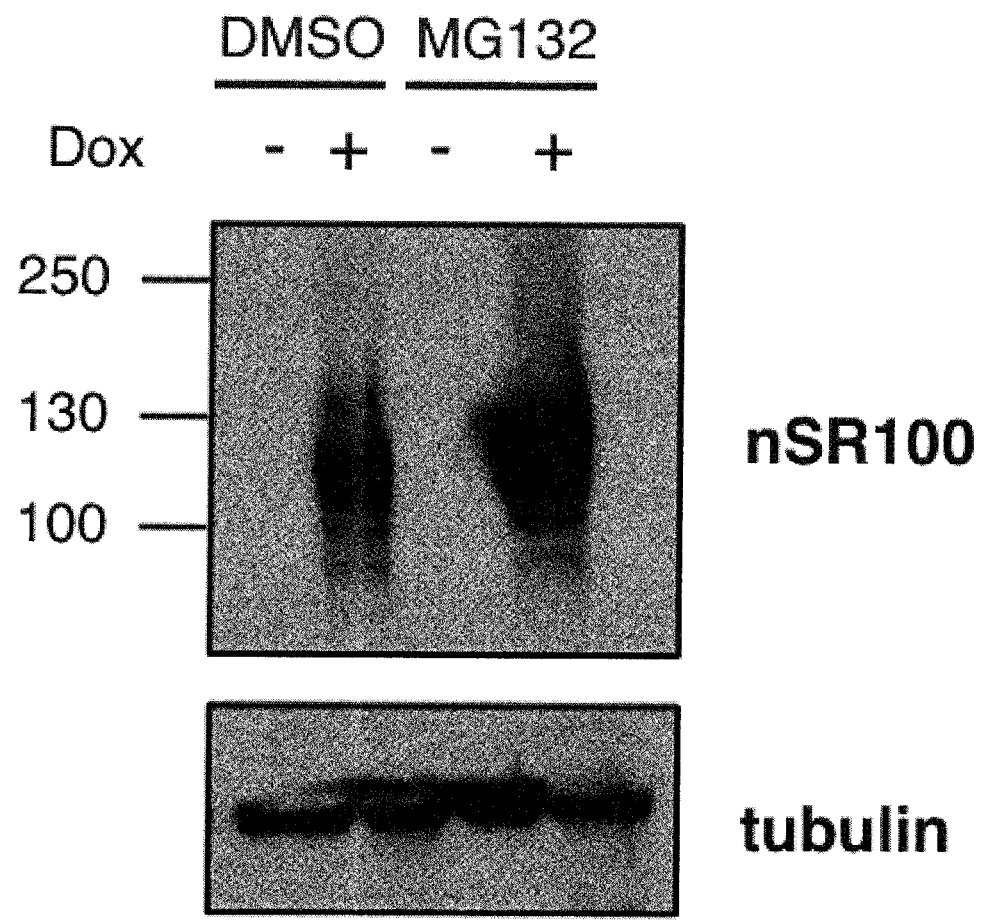

FIG. 46 shows dox-inducible, nSR100-expressing 293T cells treated with DMSO or the proteasome inhibitor MG132. nSR100 protein levels were monitored using a western blot. Tubulin detection was used as loading control.

Figure 47:
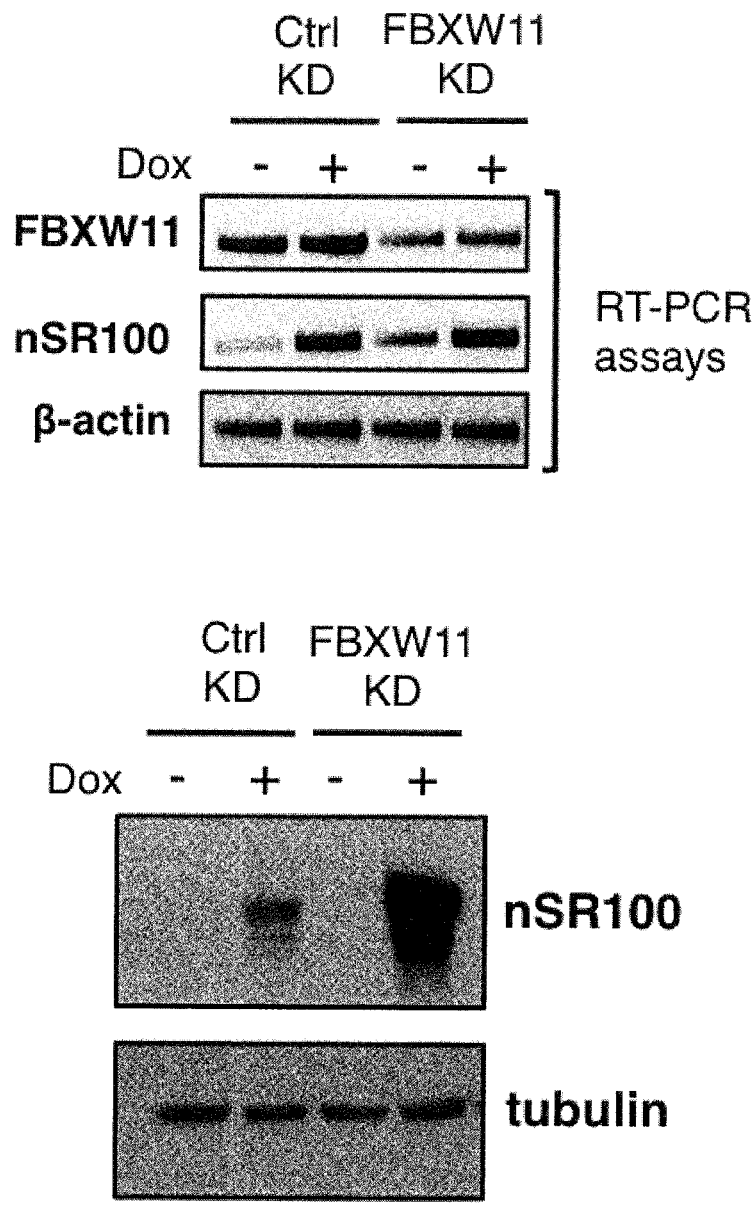

FIG. 47 shows dox-inducible, nSR100-expressing 293T cells transfected with control or FBXW11 siRNAs. RT-PCR assays were used to confirm FBXW11 knockdown. nSR100 protein levels were monitored using a western blot. Tubulin and 1-actin detection was used to control for loading.

Figure 48:
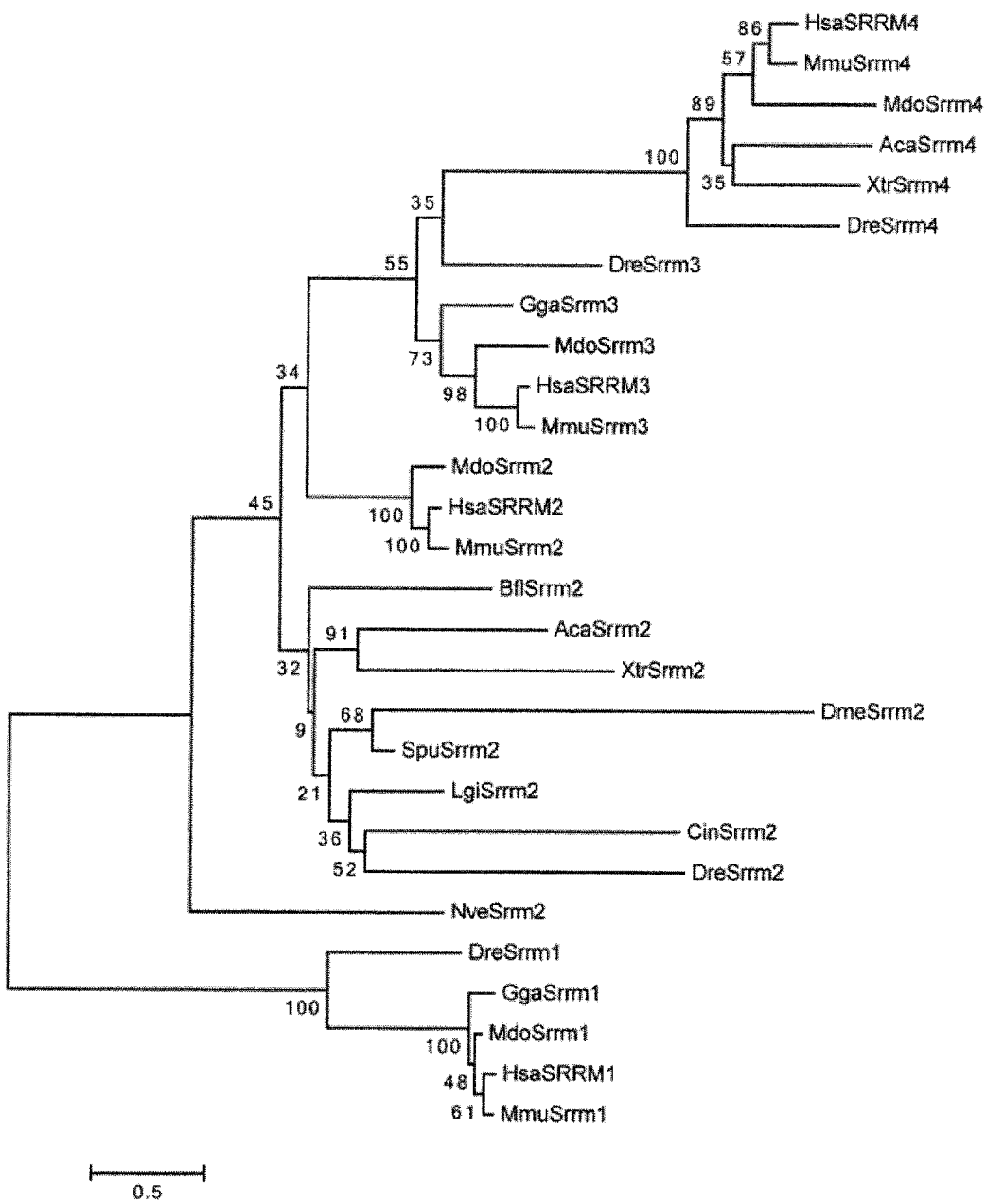
Figure 48:
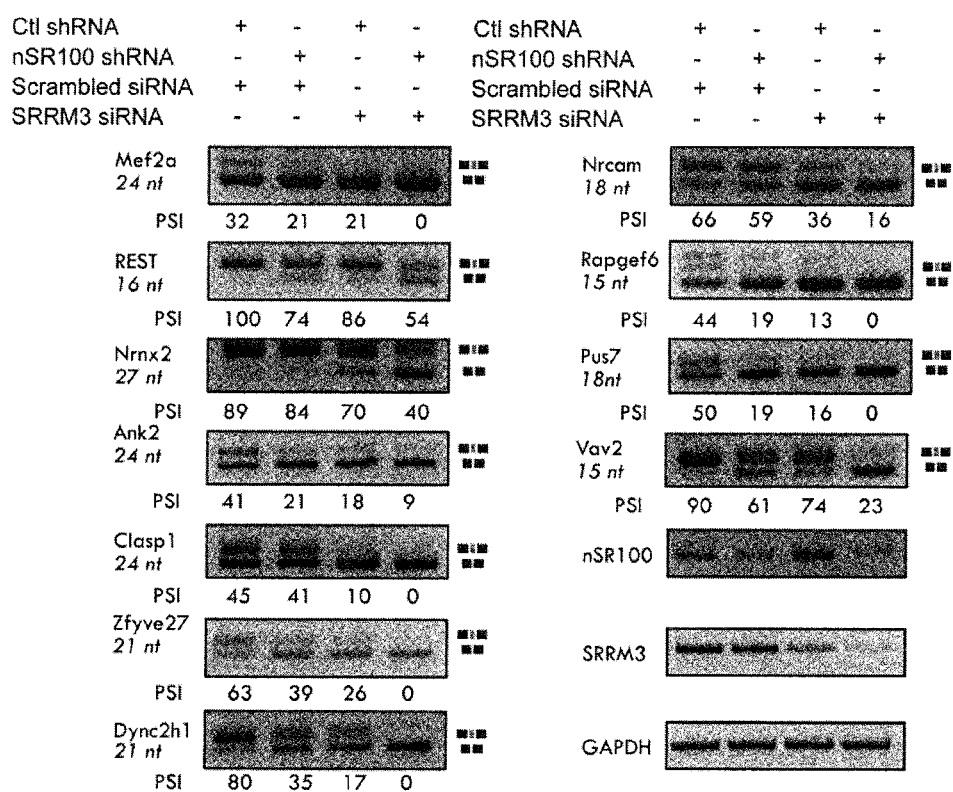

FIG. 48 shows that the alternative splicing regulatory program of the nSR100/Srrm4 paralog Srrm3 overlaps with that of nSR100. A) Phylogenetic analysis for SRm160/Srrm1, SRm300/Srrm2, Srrm3 and nSR100/Srrm4 (neighbor-joining method). The amino acid sequence identity between nSR100/Srrm4 and Srrm3 is 27.0% (168/622 amino acid residues are identical). B) Srrm3 was knocked down in Neuro2a cells expressing a control shRNA, or nSR100-targeting shRNA, and inclusion levels for known nSR100 target microexons and cassette exons was assessed by semi-quantitative RT-PCR.

DETAILED DESCRIPTION OF THE DISCLOSURE (A) Definitions

The term "neurological disorder or disease" as used herein refers to a disorder, disease or condition which directly or indirectly affects the normal functioning or anatomy of a subject's nervous system, including, but not limited to, the brain. In one embodiment, the neurological disorder or disease is a neurodevelopmental disorder.

An example of a neurological disorder or disease is autism. Another example of a neurological disorder or disease is autism spectrum disorder. In other examples, the neurological disorder or disease is epilepsy, schizophrenia or mental retardation.

Autism spectrum disorder (ASD) is a range of complex neurodevelopment disorders, characterized by social impairments, communication difficulties, and restricted, repetitive, and stereotyped patterns of behavior. Autism (also known as autistic disorder or classical ASD) is the most severe form of ASD. Other conditions along the spectrum include Asperger syndrome, childhood disintegrative disorder and pervasive developmental disorder not otherwise specified (also referred to as PDD-NOS), and Chromosome 15q11.2-13.1 duplication syndrome (dup15q syndrome).

The phrase "treating a neurological disorder or disease" as used herein includes, but is not limited to, reversing, alleviating or inhibiting the progression of a neurological disorder or disease or conditions associated with a neurological disorder or disease. As used herein, and as well understood in the art, "to treat" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "neurological function" as used herein refers to the functioning and/or activity of a subject's nervous system.

The term "improving neurological function" as used herein refers to improving the structure, function and/or activity of a subject's nervous system. In one embodiment, improving neurological function includes improving neurodevelopment and/or improving behavior.

The term "microexon" as used herein refers to an exon 3-27 nucleotides in length. An exon is a nucleotide sequence encoded by a gene that remains present within the final mature RNA product of that gene after introns have been removed by RNA splicing. The term exon refers to both the DNA sequence within a gene and to the corresponding sequence in RNA transcripts.

The term "subject" as used herein refers to any member of the animal kingdom, such as a mammal. In one embodiment, the subject is a human. In another embodiment, the subject is a mouse.

The term "a cell" includes a single cell as well as a plurality or population of cells. Administering a modulator or an agent to a cell includes both in vitro and in vivo administrations.

(B) Methods of Treatment and Uses

Modulation of nSR100/SRRM4 and/or SRRM3

The present inventors have demonstrated that a set of neuronal microexons is misregulated in individuals with autism spectrum disorder (ASD). They have also shown that at least half of all detected microexons are controlled by the alternative splicing (AS) regulator nSR100/SRRM4, and that microexon levels correlate significantly with SRRM4 expression levels in the brains of human subjects. They have further shown that microexons regulated by SRRM4 are also regulated by SRRM3. Consistent with these findings, the present inventors have shown that microexons are misregulated in mice deficient of SRRM4, and that these mice display autistic-like behaviors. Further, the inventors have shown that exogenous expression of an Unc13b microexon-containing splice variant, or of expression of increased levels of SRRM4 protein, rescues the phenotype of reduced neurite length in cultures of neurons obtained from SRRM4 deficient mice.

Accordingly, the disclosure provides methods of treating a neurological disorder or disease or improving neurological function comprising administering a modulator of SRRM4 and/or a modulator of SRRM3 to a subject in need thereof.

Also disclosed is use of a modulator of SRRM4 and/or a modulator of SRRM3 for treating a neurological disorder or disease or improving neurological function. Further disclosed is use of a modulator of SRRM4 and/or a modulator of SRRM3 for preparing a medicament for treating a neurological disorder or disease or improving neurological function. Even further disclosed is a modulator of SRRM4 and/or a modulator of SRRM3 for use in treating a neurological disorder or disease or improving neurological function.

SRRM4 is a neuronal-specific, alternative splicing regulator. It is also referred to herein as neuronal specific Ser/Arg-related protein of 100 kDa or nSR100. The SRRM4 protein is encoded by the SRRM4 gene (human mRNA accession # NM_194286.3, mouse mRNA accession # NM_026886.3; human protein accession # NP_919262.2, mouse protein accession # NP_081162.1).

SRRM3 is a Ser/Arg-related protein that shares sequence similarities with other SRRM family proteins, including SRRM4. The SRRM3 protein is encoded by the SRRM3 gene (human mRNA accessions # NM_001110199.2 and NM_001291831.1; mouse mRNA accession # NM_021403.3); human protein accession # A6NNA2.4, NP_001278760.1, NP_001103669.1; mouse protein accession # NP_067378.2).

As used herein, the terms "modulator of SRRM4" and "modulator of SRRM3" includes any agent that directly or indirectly increases, or up-regulates, the expression of SRRM4 and/or SRRM3 in a subject, sample and/or cell. In one embodiment, the modulator directly or indirectly increases, or up-regulates, the protein expression of SRRM4 and/or SRRM3 and includes the addition of exogenous SRRM4 and/or SRRM3 protein. In another embodiment, the modulator directly or indirectly increases, or up-regulates, the expression of the gene encoding SRRM4 and/or SRRM3 and includes the addition of nucleic acid molecules encoding SRRM4 and/or SRRM3. In another embodiment, the modulator directly or indirectly decreases, or down-regulates, the protein expression of SRRM4 and/or SRRM3. In another embodiment, the modulator directly or indirectly decreases, or de-regulates, the expression of the gene encoding SRRM4 and/or SRRM3.

An increase or decrease in expression can be assayed by any method known in the art. In one embodiment, a modulator that increases the expression of SRRM4 and/or SRRM3 is a modulator that when contacted with a cell, sample or subject, results in at least a 5, 10, 25, 50 or 200% increase in expression (or amount) of SRRM4 and/or SRRM3 protein or mRNA compared to a subject, sample or cell that has not been contacted with the agent. In another embodiment, a modulator that decreases the expression of SRRM4 and/or SRRM3 is a modulator that when contacted with a cell, sample or subject, results at least a 5, 10, 25, 50 or 200% decrease in expression (or amount) of SRRM4 and/or SRRM3 protein or mRNA compared to a subject, sample or cell that has not been contacted with the agent.

Modulators of SRRM4 and/or SRRM3, include, but are not limited to, chemical compounds, small molecules, biologics (including antibodies, lipids, polysaccharides, proteins, peptides, nucleic acids, aptamers) and combinations thereof.

Other methods of modulating SRRM4 and/or SRRM3 include genome targeting strategies. Accordingly, modulators of SRRM4 and/or SRRM3 include, without limitation, modified or unmodified endonucleases such as CRISPR-Cas9 and TALEN nucleases targeting the SRRM4 and/or SRRM3 gene loci. In one embodiment, a modified endonuclease is a mutant inactive Cas9 fused to an effector domain such as a transcriptional activation domain.

In one embodiment, the agent is a nucleic acid molecule, optionally a nucleic acid corresponding to, or encoding, SRRM4 and/or SRRM3. In another embodiment, the agent is a cDNA molecule encoding SRRM4 and/or SRRM3. The nucleic acid molecule can be contained on an expression construct. Various expression molecules are well known in the art. In one embodiment, the expression construct promotes overexpression of the nucleic acid molecule.

The inventors have shown that SRRM4 is subject to proteasomal degradation. Accordingly, in one embodiment, a modulator of SRRM4 and/or SRRM3 directly or indirectly prevents or decreases degradation of SRRM4 and/or SRRM3. In another embodiment, a modulator of SRRM4 and/or SRRM3 directly or indirectly increases or decreases expression of a protein associated with SRRM4 and/or SRRM3 stability or activity.

As used herein, a "protein associated with SRRM4 and/or SRRM3 stability or activity" is a protein that directly or indirectly increases or decreases SRRM4 and/or SRRM3 stability or activity. In one embodiment, protein stability is defined as the ability of a protein to retain its structural conformation or its activity when subjected to biological, physical or chemical manipulations. "Activity" includes the biological activity of a protein, including, but not limited to, enzyme activity. Methods of assaying stability or activity of proteins are well known in the art. In one embodiment, a "protein associated with SRRM4 and/or SRRM3 stability or activity" is a protein that promotes or increases degradation of SRRM4 and/or SRRM3.

As used herein, a modulator that "increases or decreases expression of a protein associated with SRRM4 and/or SRRM3 stability or activity" includes any agent that increases, decreases, up-regulates or down-regulates the expression of protein associated with SRRM4 and/or SRRM3 stability in a subject, sample and/or cell. In one embodiment, the agent increases, decreases, up-regulates or down-regulates, the protein expression of a protein associated with SRRM4 and/or SRRM3 stability or activity. In another embodiment, the agent increases, or up-regulates, the expression of the gene encoding a protein associated with SRRM4 and/or SRRM3 stability or activity. In another embodiment, the agent decreases or down-regulates the expression of the gene encoding a protein associated with SRRM4 and/or SRRM3 stability or activity. In one embodiment, the agent decreases the expression or activity of the transcriptional repressor REST/NSRF. REST/NSRF is a negative regulator of SRRM4 expression (Raj et al. 2011).

In one embodiment, the modulator of SRRM4 and/or SRRM3 is an antibody or peptide or nucleic acid-derived aptamer to the protein associated with SRRM4 and/or SRRM3 stability or activity, antisense RNA or small interfering RNA that increases or decreases the expression of the protein associated with SRRM4 and/or SRRM3 stability or activity, or a compound that inhibits the expression or function of the protein associated with SRRM4 and/or SRRM3 stability or activity.

As used herein, the term "compound that inhibits the expression or function of the protein associated with SRRM4 and/or SRRM3 stability or activity" includes, but is not limited to, chemical compounds, small molecules, biologics (including antibodies, lipids, polysaccharides, proteins, peptides, nucleic acids, aptamers) and combinations thereof.

An increase or decrease in expression can be assayed by any method known in the art. In one embodiment, an agent that induces an increase or decrease in the expression of a protein associated with SRRM4 and/or SRRM3 stability is an agent that when contacted with a cell, sample or subject, results at least a 5, 10, 25, 50 or 200% increase or decrease in expression of a protein associated with SRRM4 and/or SRRM3 stability compared to a subject, sample or cell that has not been contacted with the agent.

The inventors identified a number of SRRM4 interaction partners in human and mouse cells (Tables 4 and 5, respectively), including the F-box protein FBXW11 (also known as 1TRCP2 and BTRC). The Skp-Cullin-F-box (SCF) complex is a multiprotein complex that regulates cellular protein levels via ubiquin mediated proteolysis. FBXW11 is an E3 ubiqutin ligase that confers specifity to the SCF complex by recognizing a particular phosphodegron on targets. Treatment of cells with siRNA directed to FBXW11 resulted in increased levels of SRRM4.

Accordingly, in one embodiment, the protein associated with SRRM4 and/or SRRM3 stability or activity is an SRRM4 interaction partner selected from Table 4 or 5. In another embodiment, the protein is FBXW11.

In another embodiment, the modulator of SRRM4 and/or SRRM3 is an interfering RNA molecule (for example, siRNA or shRNA) directed at FBXW11 that decreases expression of FBXW11.

The inventors have also shown that treatment of cells with the proteasome inhibitor MG132 results in increased levels of SRRM4. Thus, in another embodiment, a modulator of SRRM4 and/or SRRM3 is a proteasome inhibitor. Proteasome inhibitors include, but are not limited to MG132, lactacystin, bortezomib, disulfiram, epigallocatechin-3-gallate, salinosporamide A, carfilzomib, ONX 0912, CEP-18770, MLN9708, and poxomicin.

Modulation of Splice Variants

The present inventors have demonstrated a set of highly conserved, neuronal-specific, 3-27 nucleotide microexons that are misregulated in individuals with autism spectrum disorder (ASD). As one example, an SRRM4-regulated 6 nucleotide microexon in the Unc13b gene promotes neurite growth in mouse primary neurons. The inventors have shown that cortical neurons from SRRM4$^{+/\Delta 7-8}$ mice display a neurogenesis defect, and expression of Unc13b transcripts including the microexon, but not transcripts lacking the microexon, is sufficient to rescue the mutant phenotype. The 6 nucleotide microexon in Unc13b transcripts is regulated by SRRM4 in mouse (N2A) cells (Table 2) and in human (293T) cells. However the magnitude of regulation in 293T cells is not large enough to meet the minimum threshold (PSI≥10) requirement for annotation as "YES" under the "regulation by nSR100 column" in Table 1. In this regard, "NO" in the columns in Table 1 and Table 2 indicates that regulation may occur but does not meet a miminal threshold change of PSI≥10.

Accordingly, the disclosure provides methods of treating a neurological disorder or disease or improving neurological function comprising administering an agent that modulates the expression of at least one, at least two, at least three, at least 5, at least 10 or at least 20 microexon splice variants listed in Table 1 or 2 to a subject in need thereof.

Also disclosed is use of an agent that modulates the expression of at least one, at least two, at least three, at least 5, at least 10 or at least 20 microexon splice variants listed in Table 1 or 2 for treating a neurological disorder or disease or improving neurological function. Further disclosed is use of an agent that modulates the expression of at least one, at least two, at least three, at least 5, at least 10 or at least 20 microexon splice variants listed in Table 1 or 2 for preparing a medicament for treating a neurological disorder or disease or improving neurological function. Even further disclosed is an agent that modulates the expression of at least one, at least two, at least three, at least 5, at least 10 or at least 20 microexon splice variants listed in Table 1 or 2 for use in treating a neurological disorder or disease or improving neurological function.

As used herein, the term "microexon splice variant listed in Table 1 or 2" refers to the splice variants (genes) listed in Table 1 or 2, respectively, wherein each of the splice variants includes the specified microexon. For example, the splice variant of Unc13b listed in Table 1 includes the 6 nucleotide microexon having the genomic coordinates chr9:35371931-35371936. The genomic coordinates in Table 1 refer to human genome build 19 (hg19) (hg19 released February, 2009, Genome Reference Consortium GRCh37).

In one embodiment, the microexon splice variant includes a microexon 3-15 nucleotides in length. In another embodiment, the microexon splice variant includes a microexon 16-27 nucleotides in length.

In one embodiment, the subject is human and the microexon splice variant is from Table 1. In another embodiment, the subject is mouse and the microexon splice variant is from Table 2.

In one embodiment, the microexon splice variant is regulated by SRRM4 and/or SRRM3. As used herein, the term "regulated by SRRM4 and/or SRRM3" means that the inclusion or exclusion of the splice variant in neural tissues or cells is dependent upon the expression of SRRM4 and/or SRRM3.

As used herein, the term "agent that modulates the expression of at least one microexon splice variant listed in Table 1 or 2" includes an agent that directly or indirectly increases, or up-regulates, the expression of at least one microexon splice variant listed in Table 1 or 2, respectively, in a subject, sample and/or cell that is typically upregulated in neural tissue/cells. In one embodiment, the modulator directly or indirectly increases, or up-regulates, the protein expression of at least one microexon splice variant listed in Table 1 or 2 in a subject, sample and/or cell that is typically upregulated in neural tissue/cells. In another embodiment, the agent directly or indirectly decreases, or down-regulates, the expression of at least one microexon splice variant listed in Table 1 or 2 in a subject, sample and/or cell that is typically downregulated in neural tissue/cells. In one embodiment, the agent directly or indirectly decreases, or down-regulates, the protein expression of at least one microexon splice variant listed in Table 1 or 2 in a subject, sample and/or cell that is typically downregulated in neural tissue/cells.

The term "microexon splice variant" and "splice variant" may be used herein interchangeably when referring to the splice variants of Table 1 and/or Table 2.

An increase or decrease in expression can be assayed by any method known in the art. In one embodiment, an agent that increases the expression of at least one microexon splice variant listed in Table 1 is an agent that when contacted with a cell, sample or subject, results in at least a 5, 10, 25, 50 or 200% increase in expression compared to a subject, sample or cell that has not been contacted with the agent. In another embodiment, an agent that decreases the expression of at least one microexon splice variant listed in Table 1 is an agent that when contacted with a cell, sample or subject, results at least a 5, 10, 25, 50 or 200% decrease in expression compared to a subject, sample or cell that has not been contacted with the agent.

Agents that modulate the expression of at least one microexon splice variant listed in Table 1, include, but are not limited to, chemical compounds, small molecules, biologics (including antibodies, lipids, polysaccharides, proteins, peptides, nucleic acids, aptamers) and combinations thereof.

In one embodiment, the agent is a nucleic acid molecule, optionally a nucleic acid corresponding to, or encoding, the microexon splice variant. In another embodiment, the agent is a nucleic acid molecule corresponding to, or encoding a nucleic acid molecule of a splice variant that skips the microexon. In another embodiment, the agent is a cDNA molecule encoding the microexon splice variant or the splice variant that skips the microexon. The nucleic acid molecule can be contained on an expression construct. Various expression molecules are well known in the art. In one embodiment, the expression construct promotes overexpression of the nucleic acid molecule. In yet another embodiment, the agent is the microexon splice variant encoded protein or protein encoded by the splice variant that skipped the microexon.

In one embodiment, the at least one microexon splice variant is of a gene that is associated with neuronal differentiation, neurite outgrowth, axon guidance and/or one or more neuronal functions including synaptic activity.

In one embodiment, the splice variant is the Unc13b splice variant containing the microexon with coordinates chr9:35371931-35371936 (hg19) and the modulator is a nucleic acid molecule encoding the Unc13b splice variant or is the protein itself.

In another embodiment, the splice variant is the Slit2 splice variant containing the microexon with coordinates chr4:20492426-20492437 (hg19) and the modulator is a nucleic acid encoding the Slit2 splice variant or is the protein itself.

In yet another embodiment, the splice variant is the Apbb1 splice variant containing the microexon with coordinates chr11:6423207-6423212 (hg19) and the modulator is a nucleic acid encoding the Apbb1 splice variant or is the protein itself.

In a further embodiment, the splice variant is the AP1S2 splice variant containing the microexon with coordinates chrX:15846315-15846323 (hg19) and the modulator is a nucleic acid encoding the AP1S2 splice variant or is the protein itself.

Modulators, Agents and Pharmaceutical Compositions

The modulators and agents described herein may be formulated into pharmaceutical compositions for administration to subjects and/or use in subjects in a biologically compatible form suitable for administration in vivo. The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20$^{th}$ ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

In one embodiment, the modulators and agents described herein are formulated into pharmaceutical compositions for administration to the brain or central nervous system of a subject. Modulators, agents and pharmaceutical compositions which cannot penetrate the blood-brain barrier can be effectively administered by an intraventricular route or other appropriate delivery system suitable for administration to the brain.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Proteins may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethyl-amino ethanol, histidine, procaine, etc.

The modulators, agents and/or pharmaceutical compositions described herein may be administered to, or used in, living organisms including humans, and animals. The term "subject" or "animal" as used herein refers to any member of the animal kingdom, in one embodiment a mammal such as a human being.

Administration of an "effective amount" of the modulators, agents and/or pharmaceutical compositions is defined as an amount effective, at dosages and for periods of time necessary to achieve the desired result. For example, an effective amount of a substance may vary according to factors such as the disease state, age, sex, and weight of the individual, and the ability of the recombinant protein to elicit a desired response in the individual. Dosage regime may be adjusted to provide the optimum therapeutic response. For example, several divided doses may be administered daily or the dose may be proportionally reduced as indicated by the exigencies of the therapeutic situation.

(C) Methods of Detecting and/or Screening

The present inventors have demonstrated a set of highly conserved, neuronal-specific microexons that is misregulated in individuals with autism spectrum disorder.

Accordingly, the present disclosure is also directed to a method of detecting and/or screening for a neurological disorder or disease, in a subject, comprising:

a. determining a sample neuronal alternative splicing profile from a sample from said subject, said sample profile comprising the level of at least one, optionally at least 5, at least 10, at least 25, at least 50, at least 100, at least 150, at least 200, at least 250, at least 300, or all microexon splice variants from Table 1 or 2; and b. determining the level of similarity of said sample profile to one or more control profiles, wherein (i) a high level of similarity of the sample profile to a neurological disorder or disease-specific control profile; (ii) a low level of similarity to a non-neurological disorder or disease control profile; and/or (iii) a higher level of similarity to a neurological disorder or disease control profile than to a non-neurological disorder or disease control profile indicates the presence of, or an increased likelihood of a neurological disorder or disease.

The present disclosure is further directed to a method of detecting and/or screening for autism or autism spectrum disorder, in a subject, comprising:

a. determining a sample neuronal alternative splicing profile from a sample from said subject, said sample profile comprising the level of at least one, optionally at least 5, at least 10, at least 25, at least 50, at least 100, at least 150, at least 200, at least 250, at least 300, or all microexon splice variants from Table 1 or 2; and b. determining the level of similarity of said sample profile to one or more control profiles, wherein (i) a high level of similarity of the sample profile to an autism or autism spectrum disorder-specific control profile; (ii) a low level of similarity to an autism or autism spectrum disorder control profile; and/or (iii) a higher level of similarity to an autism or autism spectrum disorder control profile than to a non-autism or autism spectrum disorder control profile indicates the presence of, or an increased likelihood of autism or autism spectrum disorder.

In one embodiment, the methods of detecting and/or screening further comprise obtaining a sample prior to determining a sample neuronal alternative splicing profile from a sample from said subject. In one embodiment, the sample is a RNA sample. The RNA sample can be obtained, for example, from tissue or cells. In one embodiment, the tissue or cells are neural or neuronal tissues or cells. In another embodiment, the sample is obtained from neurons, optionally neurons from subject iPS cells.

In an embodiment, the subject is human and the microexon splice variants are from Table 1. In another embodiment, the subject is mouse and the microexon splice variants are from Table 2.

As used herein, the phrase "detecting and/or screening" for a condition refers to a method or process of determining if a subject has or does not have said condition. Where the condition is a likelihood or risk for a disease or disorder, the phrase "detecting and/or screening" will be understood to refer to a method or process of determining if a subject is at an increased or decreased likelihood for the disease or disorder.

As used herein, the term "neuronal alternative splicing profile" refers to the gene or protein expression level of each of the splice variants listed in Table 1 or Table 2, or a subset thereof in a cell, tissue or subject.

In some embodiments, the sample neuronal alternative splicing profile is compared to one or more control profiles. The control profile may be a reference value and/or may be derived from one or more samples, optionally from histori- cal data for a patient or pool of patients who are known to have, or not have, a neurological disorder or disease. In such cases, the historical neuronal alternative splicing data can be a value that is continually updated as further samples are collected and individuals are identified as having a neurological disease or not. It will be understood that the control profile represents an average of the gene or protein expression level of selected splice variants as described herein. Average expression values may, for example, be the mean values or median values.

For example, a "neurological disease or disorder control profile" may be generated by measuring the gene expression level of selected splice variants in genomic DNA or mRNA from an individual subject, or population of subjects, who are known to have a neurological disease or disorder. Similarly, a "non-neurological disease or disorder control profile" may be generated by measuring the gene expression level of selected splice variants in tissues or cells from an individual subject or population of subjects who are known to not have a neurological disease or disorder. In certain embodiments, the tissue source from which the sample profile and control profile are derived is matched, so that they are both derived from the same or similar tissue. In some embodiment, the tissue is neural tissue.

Methods of determining expression levels of genes are generally known in the art. For example, levels of mRNA can be quantitatively measured by northern blotting. mRNA levels can also be measured by RT-qPCR. In this technique, reverse transcription is followed by quantitative PCR. Microarrays can be used for high-throughput analysis of many genes within a sample. For example, a single array or "chip" may contain probes to determine transcript levels for numerous genes. Alternatively, "tag based" technologies like Serial analysis of gene expression (SAGE) and RNA-Seq, which can provide a relative measure of the cellular concentration of different mRNAs, can be used.

High-throughput RNA sequencing (RNA-Seq) is a technology that uses massively parallel sequencing (also referred to as 'next generation sequencing' of cDNA fragments to reveal a snapshot of RNA presence and quantity from a genome at a given moment in time.

Methods of determining the similarity between neuronal alternative splicing profile profiles are well known in the art. Methods of determining similarity may in some embodiments provide a non-quantitative measure of similarity, for example, using visual clustering. In another embodiment, similarity may be determined using methods which provide a quantitative measure of similarity. For example, in an embodiment, similarity may be measured using hierarchical clustering.

In another embodiment, similarity may be measured by computing a "correlation coefficient", which is a measure of the interdependence of random variables that ranges in value from −1 to +1, indicating perfect negative correlation at −1, absence of correlation at zero, and perfect positive correlation at +1. It will be appreciated that any "correlation value" which provides a quantitative scaling measure of similarity between neuronal alternative splicing profile profiles may be used to measure similarity.

A sample profile may be identified as belonging to an individual with a neurological disease or disorder, or an increased likelihood of a neurological disease or disorder, where the sample profile has high similarity to a neurological disease or disorder profile, low similarity to a non-neurological disease or disorder profile, or higher similarity to a neurological disease or disorder profile than to a non-neurological disease or disorder profile. Conversely, a sample profile may be identified as belonging to an individual without a neurological disease or disorder, or a decreased likelihood of a neurological disease or disorder, where the sample profile has high similarity to a non-neurological disease or disorder profile, low similarity to a neurological disease or disorder profile, or higher similarity to a non-neurological disease or disorder profile than to the neurological disease or disorder profile.

Another aspect of the disclosure provides a method of assigning a course of management for an individual with a neurological disorder or disease, or an increased likelihood of a neurological disorder or disease, comprising:

a) identifying an individual with a neurological disorder or disease or an increased likelihood of a neurological disorder or disease, according to the methods described herein; and b) assigning a course of management for a neurological disorder or disease and/or symptoms of a neurological disorder or disease.

As used herein, the term "a course of management" refers to the any testing, treatment, medical intervention and/or therapy applied to an individual with a neurological disorder or disease and/or symptoms of a neurological disorder or disease.

(D) Mouse Models and Uses Thereof

The present inventors generated mice carrying an exon deletion in the SRRM4 (nSR100) gene that results in widespread loss of the full length protein. SRRM4$^{+/\Delta 7-8}$ mice display an aversion for the company of other mice and a preference to interact with an inert object over stranger mice. These are atypical behaviours in the mouse and similar phenotypes have consistently been identified in mouse models of ASD-associated genes.

Accordingly, the present disclosure provides a transgenic mouse having increased or decreased expression of SRRM4 and/or SRRM3 compared to a wild-type control mouse. The present disclosure also provides a transgenic mouse cell wherein the mouse cell has increased or decreased expression of SRRM4 and/or SRRM3 compared to a wild-type control mouse cell.

As used herein, the term "wild-type control mouse" or "wild-type control mouse cell" refers to mouse or mouse cell, for example a non-transgenic mouse or mouse cell, that does not have altered expression of SRRM4 and/or SRRM3.

In one embodiment, the transgenic mouse or mouse cell has increased or decreased expression of the gene encoding SRRM4 and/or the gene encoding SRRM3 compared to a wild-type control mouse. In another embodiment, the transgenic mouse or mouse cell has increased or decreased expression of SRRM4 protein and/or SRRM3 protein compared to a wild-type control mouse.

The expression of SRRM4 and/or SRMM3 may be altered by any method known in the art.

For example, in one embodiment, at least one copy of the gene encoding SRRM4 and/or SRRM3 is overexpressed to provide increased expression of SRRM4 and/or SRRM3.

In another embodiment, the mouse or mouse cell comprises a disruption in at least one copy of the gene encoding SRRM4 and/or the gene encoding SRRM3. In one embodiment, the mouse or mouse cell comprises a heterozygous disruption of the gene encoding SRRM4 and/or SRRM3. In another embodiment, the mouse or mouse cell comprises a homozygous disruption of the gene encoding SRRM4 and/or SRRM3.

As used herein, the term "disruption" refers to any direct or indirect method such that expression of the genes encoding SRRM4 and/or SRRM3 is reduced compared to a wild-type control mouse. For example, interfering RNA directed to SRRM4 and/or SRRM3 may be introduced into the mouse or mouse cell resulting in decreased expression of SRRM4 and/or SRRM3.

In one embodiment, a transgene is introduced into the mouse or mouse cell, wherein the transgene encodes a non-functional or partially functional version of SRRM4 and/or SRRM3. In one embodiment, the transgene encodes SRRM4 lacking exons 7 and 8.

In another embodiment, the mouse or mouse cell is genetically engineer such that at least one copy of the gene encoding for SRRM4 and/or SRRM3 is completely deleted or "knocked-out".

Various methods of introducing transgenes are known in the art. The nucleic acid is introduced into the cell, directly or indirectly, by introduction into a precursor of the cell, by way of deliberate genetic manipulation, such as by microinjection or by infection with a recombinant virus. This molecule may be integrated within a chromosome, or it may be extrachromosomally replicating DNA.

The term "transgene" as used herein refers to a construct for introducing, for example, SRRM4 lacking exons 7 and 8, to a mouse to prepare a transgenic mouse. The transgene will be integrated into the genome of the animal so that SRRM4 lacking exons 7 and 8 is capable of being expressed in all cells. The transgene will also contain the necessary regulatory sequences to allow for expression of the transgene. In one embodiment, by introducing the transgene, the transgenic animal will express SRRM4 in its cells at a level that is lower than non-transgenic or wild type animals.

To produce a transgenic mouse, any method known in the art for introducing a recombinant construct or transgene into an embryo or embryonic stem cell, such as microinjection, cell gun, transfection, liposome fusion, electroporation, and the like, may be used.

The present disclosure includes any and all uses of the transgenic mice and mouse cells described herein. In one embodiment, the transgenic animals are useful models in studying neurological disorders and diseases such as autism and autism spectrum disorder. The animals can assist in studying the role of SRRM4 and/or SRRM3 in these diseases.

As shown in Examples 2 and 3, SRRM4$^{+/\Delta 7-8}$ mice demonstrate behaviours associated with autism and autism spectrum disorder.

In another embodiment, the transgenic mice and mouse cells described herein are useful as animal models for testing potential agents that can modulate the effect of increases or decreases in expression of SRRM4 and/or SRRM3.

Under expression of SRRM4 is shown herein to be associated with autism. Therefore, finding agents that can increase expression of SRRM4 and/or SRRM3 and lead to new therapies for autism and autism spectrum disorder.

Accordingly, the disclosure also provides a method for identifying agents for treating a neurological disorder or disease, wherein the method comprises:

a) contacting the mouse or mouse cell as described above with at least one test agent, and b) determining the effect of the test agent on the mouse or mouse cell.

In another embodiment, the disclosure provides a use of the mouse or mouse cell above for identifying agents for treating a neurological disorder or disease.

In one embodiment, a test agent is identified as a putative therapeutic for a neurological disorder or disease wherein the test agent improves the neurological function and/or behavior of the mouse. In another embodiment, a test agent is identified as a putative therapeutic for a neurological disorder or disease wherein the test agent improves a neurological-associated phenotype of the mouse cell.

The test agents in the screening assays can be generated by methods well known to those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds, including antibodies, also can be obtained from commercial sources. Combinatorial libraries of molecules can be prepared using well known combinatorial chemistry methods (Gordon et al., J. Med. Chem. 37: 1233-1251 (1994); Gordon et al., J. Med. Chem. 37: 1385-1401 (1994); Gordon et al., Acc. Chem. Res. 29:144-154 (1996); Wilson and Czarnik, eds., Combinatorial Chemistry: Synthesis and Application, John Wiley & Sons, New York (1997)).

In one embodiment, the mouse cell is a neuron and determining the effect of the test agent comprises measuring neurite outgrowth length.

(E) Human Cells and Uses Thereof

The present disclosure also provides a human cell, wherein the human cell has decreased or increased expression of at least one copy of the gene encoding SRRM4 and/or at least one copy of the the gene encoding SRRM3 compared to a wild type control mouse cell.

In one embodiment, the human cell comprises a homozygous disruption of the gene encoding SRRM4 and/or SRRM3. In another embodiment, the human cell comprises a heterozygous disruption of the gene encoding SRRM4 and/or SRRM3. Optionally, the gene encoding SRRM4 lacks exons 7 and 8.

The human cell is optionally a neural or neuronal cell, for example a neuron.

Method of increasing or decreasing expression of particular genes in human cells are known in the art. For example, genome targeting strategies such as CRISPR may be used to modulate the expression or activity of SRRM4 and/or SRRM3 in human ES/iPS cells. The ES/iPS cells may then be differentiated into neurons.

Further provided is a use of the human cell described herein as a model for a neurological disorder or disease.

In one embodiment, the human cells described herein are used in a method for identifying agents to treating a neurological disorder or disease, wherein the method comprises:
 a. contacting the human cell with at least one test agent, and
 b. determining the effect of the test agent on the human cell.

In an embodiment, the human cell is a neuron and determining the effect of the test agent comprises measuring neurite length.

The following non-limiting examples are illustrative of the present disclosure:

EXAMPLES

Example 1: A Global Regulatory Mechanism for Activating an Exon Network Required for Neurogenesis Summary A new RNA-Seq pipeline was developed for the systematic discovery and analysis of all classes of alternative splicing (AS), including microexons. By applying this pipeline to deep RNA-Seq datasets from more than 50 diverse cell and tissue types, as well as developmental stages, from human and mouse, a large program of neural-regulated AS was defined. Strikingly, neural-included microexons represent the most highly conserved and dynamically-regulated component of this program, and the corresponding genes are highly enriched in neuronal functions. These microexons are enriched on the surfaces of protein interaction domains and are under strong selection pressure to preserve reading frame. It was observed that microexons are frequently misregulated in the brains of autistic individuals, and that this misregulation is linked to the reduced expression of the neural-specific Ser/Arg-related splicing factor of 100 kDa, SRRM4/nSR100. Collectively, the results reveal that alternative microexons represent the most highly conserved component of developmental AS regulation identified to date, and that they function in domain surface "microsurgery" to control interaction networks associated with neurogenesis.

Global Features of Neural-Regulated AS

Figure 1:
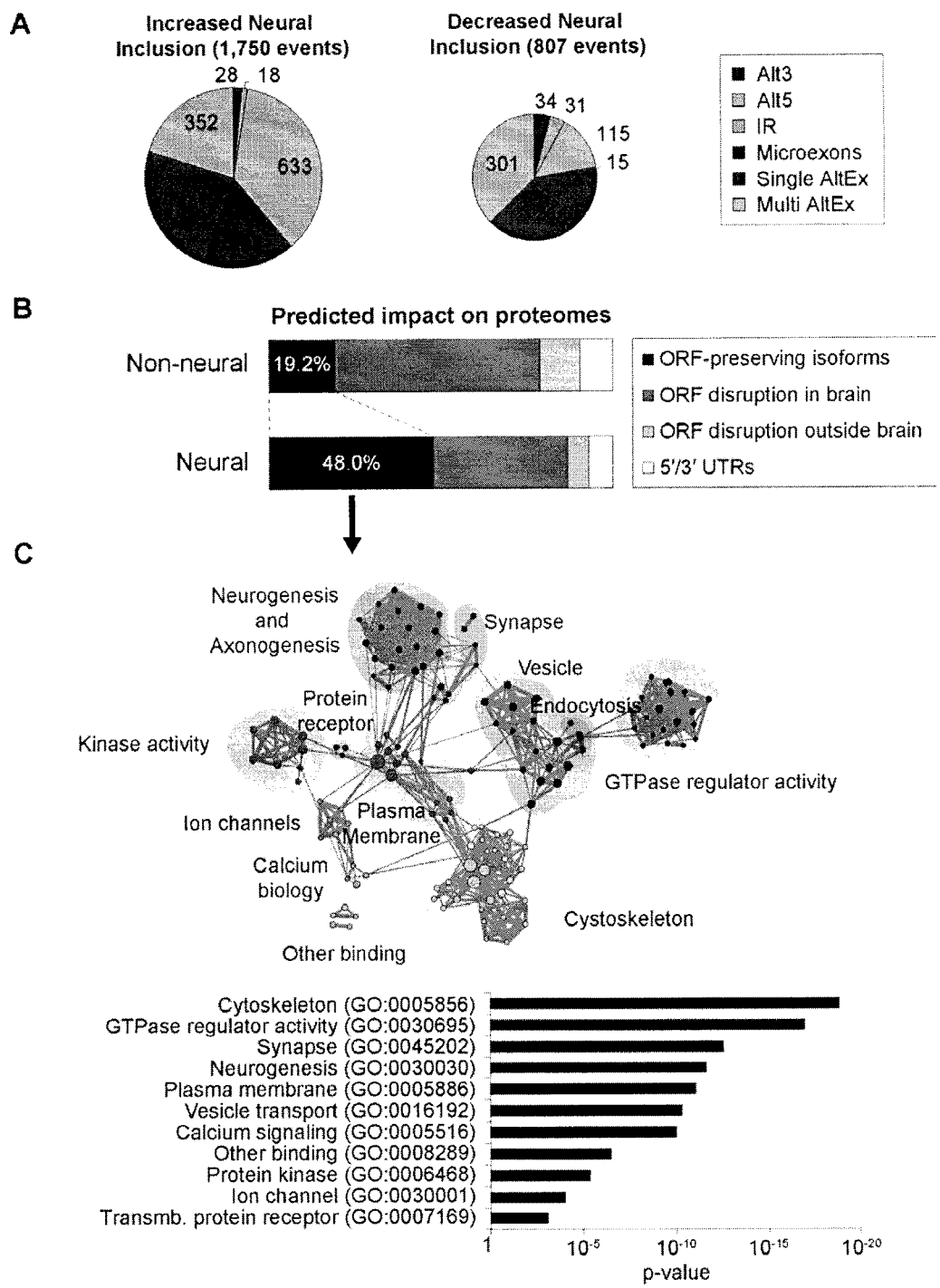
FIG. 1 shows an extensive program of neural-regulated alternative splicing (AS). A) Distribution by type of human AS events with increased/decreased neural inclusion of the alternative sequence. Alt3/5, alternative splice site acceptor/donor selection; IR, intron retention; Microexons, 3-27 nt exons; Single/Multi AltEx, single/multiple cassette exons. B) Predicted impact of non-neural and neural-regulated AS events on proteomes. Neural-regulated events are more often predicted to generate isoforms preserving open reading frame (ORF) when the alternative sequence is included and excluded ("ORF-preserving isoforms", black), than to disrupt ORFs (i.e. the exon leads to a frame shift and/or introduces a premature termination codon) specifically in neural samples ("ORF disruption in brain", dark grey) or in non-neural samples ("ORF preservation in brain", light grey). C) Enrichment map for GO and KEGG categories in genes with neural-regulated AS that are predicted to generate alternative protein isoforms (top), and representative GO terms and their associated enrichment p-value for each subnetwork (bottom). The node size is proportional to the number of genes associated with the GO category, and the width of the edges to the number of genes shared between GO categories.

An RNA-Seq analysis pipeline was developed to detect and quantify all AS event classes involving all hypothetically possible splice junctions formed by the usage of annotated and unannotated splice sites, including those that demarcate microexons. By applying this pipeline to more than 50 diverse cell and tissue types each from human and mouse identified ~2,500 neural-regulated AS events in each species (FIG. 1A). A list of 308 human AS events involving microexons are listed in Table 1. A list of 333 mouse AS events involving microexons are listed in Table 2. "Regulation by nSR100" in Tables 1 and 2 indicates a change in the inclusion level (PSI≥10) of a microexon in human 293T cells overexpressing nSR100, and in mouse N2A cells depleted of nSR100, respectively. "Misregulation in ASD" in Tables 1 and 2 indicates a change in microexon inclusion level of PSI≥10.

Figure 2:
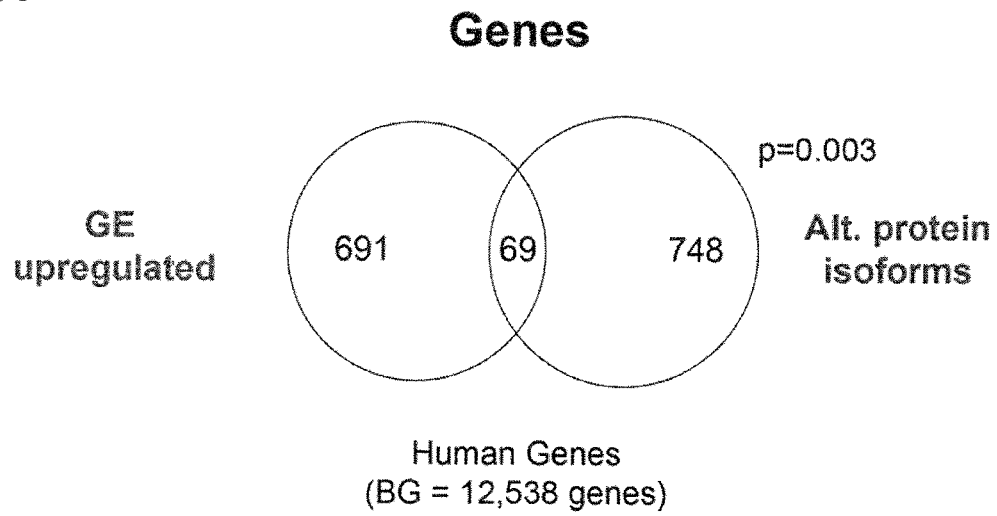
FIG. 2 shows the relationship between neural regulation at the AS and gene-expression levels (related to FIG. 1). A) Overlap between differentially regulated genes at each level of regulation (gene expression [GE] and AS). Only 8.5% of the genes undergoing neural-regulated AS also display neural regulation at the GE level. B) Overlap of significantly enriched GO terms (Benjamini corrected p value <0.01) for genes that are significantly differentially upregulated at the mRNA steady state levels in neural samples ("GE upregulated") and genes that harbor AS events that are differentially regulated in neural versus non-neural samples and are predicted to generate alternative ORF-preserving isoforms ("Alt. protein isoforms"). Over 40% of the GO categories enriched among the genes with neural regulated AS are shared with those of genes upregulated at the GE level in neural tissues. p values correspond to hypergeometric tests.
Figure 2:
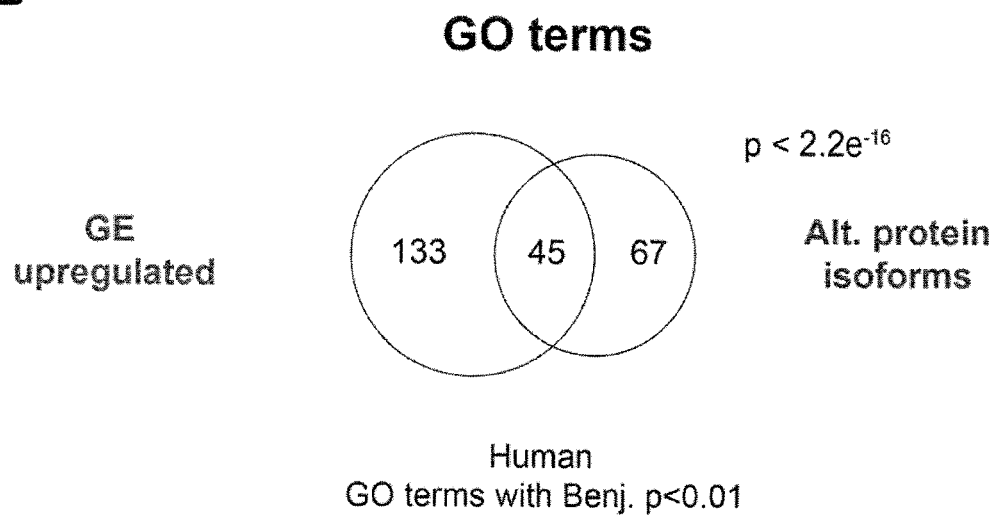

Nearly half of the neural-regulated AS events, including alternative retained introns, are predicted to generate protein isoforms both when the alternative sequence is included and skipped. In contrast, only ~20% of AS events not subject to neural regulation (hereafter 'non-neural' events) have the potential to generate alternative protein isoforms (FIG. 1B; $p=2.7 \times 10^{-248}$, proportion test). Gene Ontology (GO) analysis shows that genes with neural-regulated AS events predicted to generate alternative protein isoforms form highly interconnected networks based on functions associated with neuronal biology, signaling pathways, structural components of the cytoskeleton and the plasma membrane (FIG. 1C). Consistent with previous results (Fagnani et al., 2007; Pan et al., 2004), there is little overlap (8.5%) between genes with neural-regulated AS and mRNA expression, although these subsets of genes are highly enriched in overlapping GO terms (40% in common; FIG. 2). These data reveal the largest program of neural-regulated AS events defined to date, and that this program is associated with a broader range of functional processes and pathways linked to nervous system biology than previously detected (Boutz et al., 2007; Fagnani et al., 2007; Ule et al., 2005).

Highly Conserved Microexons are Frequently Neural Specific

Figure 3:
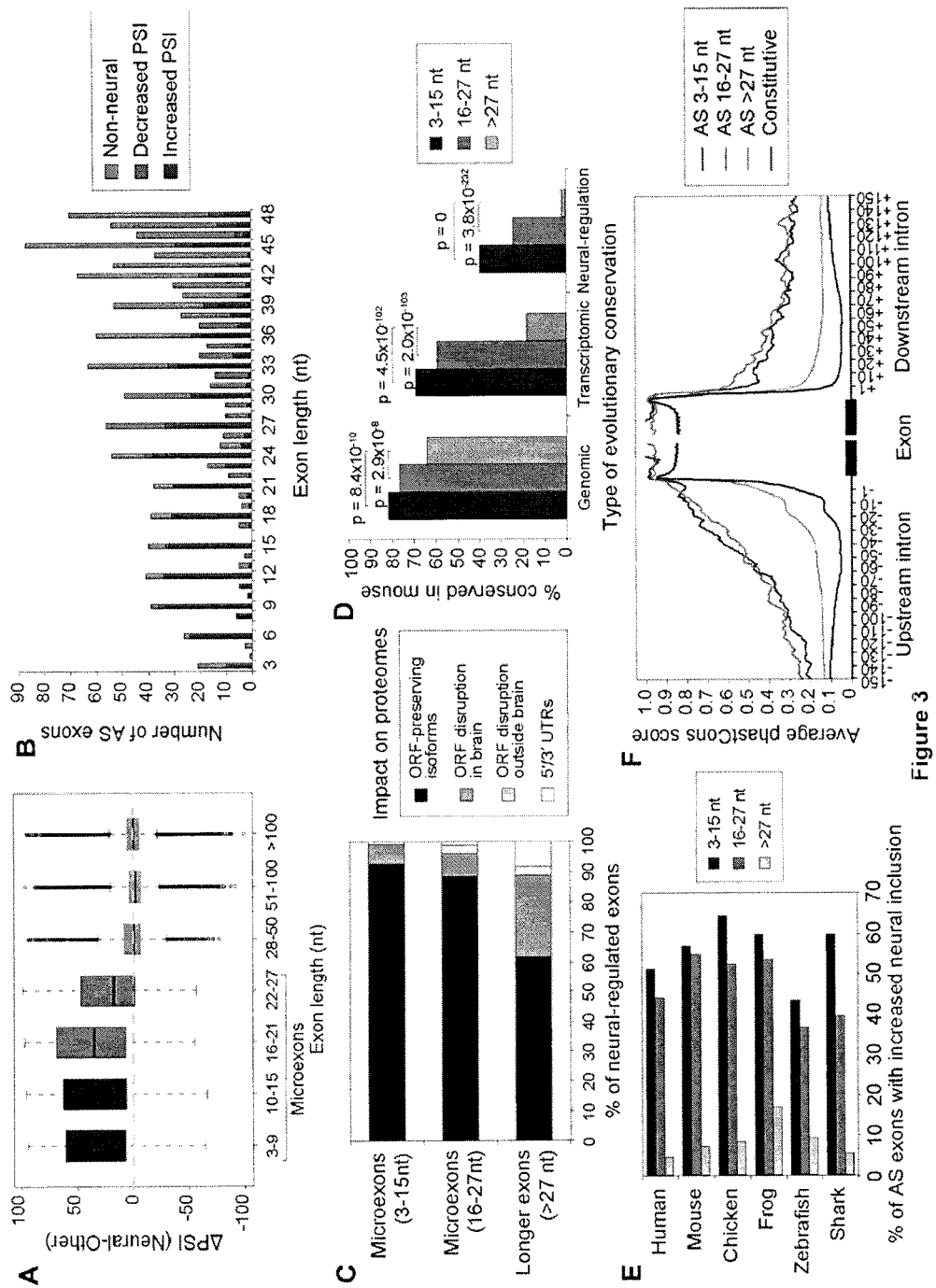
FIG. 3 shows a landscape of highly conserved neural microexons. A) Difference in exon inclusion level (ΔPSI) between the average PSIs for neural samples and non-neural samples (Y-axis) for bins of increasing exon lengths (X-axis). Microexons are defined as exons with lengths of 3-27 nt. Restricting the analysis to alternative exons with a PSI range across samples of >50 showed a similar pattern. B) Number of exons by length whose inclusion level is higher, lower or not different in neural compared to non-neural samples, are indicated. Short exons tend to be multiple of 3 nts and have higher inclusion in neural samples. C) Percent of neural-regulated microexons (of lengths of 3-15 and 16-27 nt) and longer exons that are predicted to generate alternative ORF-preserving isoforms (black), disrupt the ORF in/outside neural tissues (dark/light grey), or overlap non-coding sequences (white). D) Higher evolutionary conservation of alternative microexons compared to longer alternative exons at the genomic, transcriptomic (i.e. whether the exon is alternatively spliced in both species), and neural-regulatory level. Y-axis shows the percent of conservation at each specific level between human and mouse. p-values correspond to two-sided proportion tests. E) Percent of alternative microexons and longer exons that are detected as neural-regulated (average absolute ΔPSI>25) in each vertebrate species. F) Alternative 3-15 and 16-27 nt microexons show higher average phastCons scores at their intronic boundaries than longer alternative and constitutive exons. See also FIG. 4.
Figure 4:
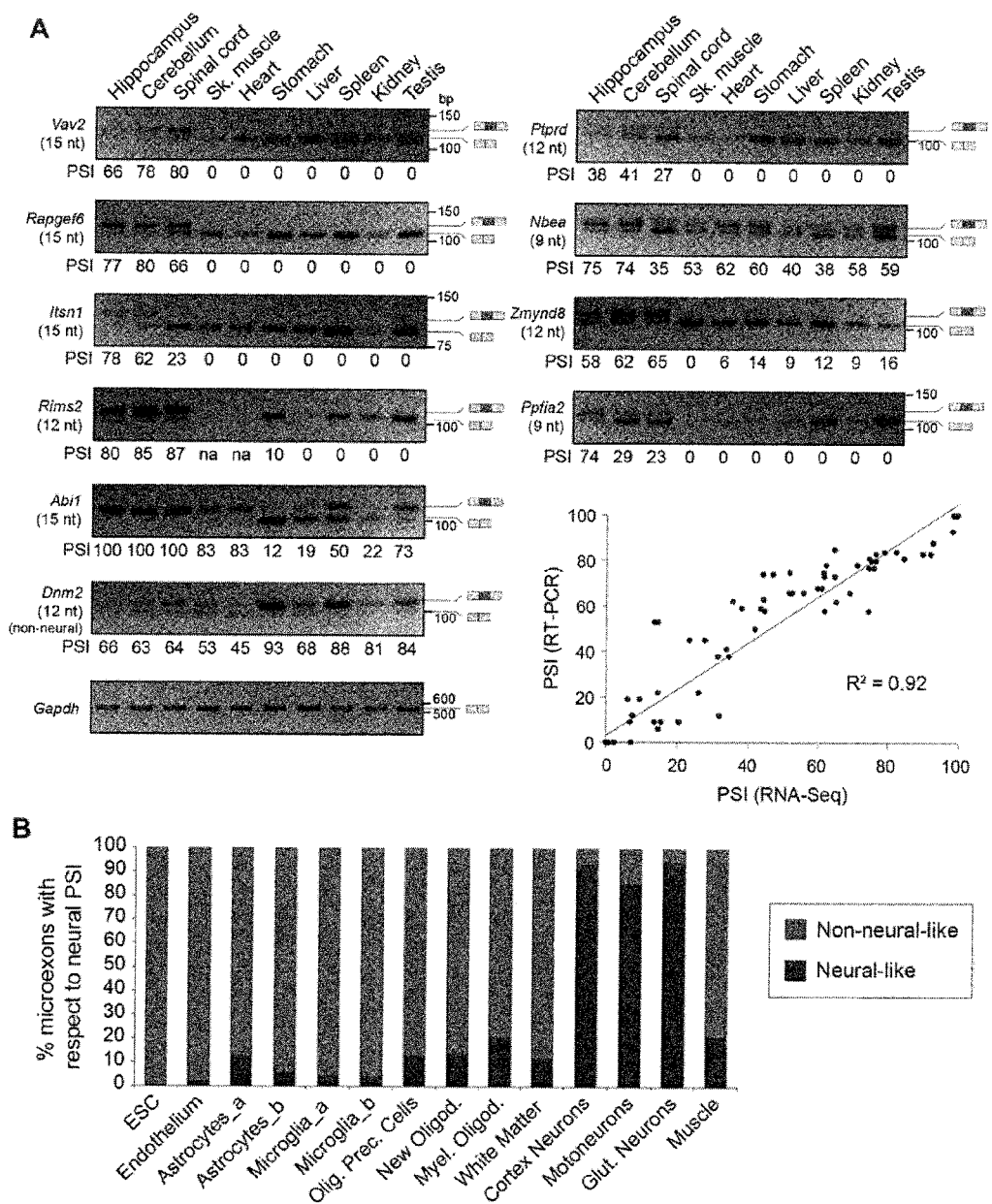
FIG. 4 shows the impact on protein and evolutionary conservation of neural-regulated exons (related to FIG. 3). A) Representative RT-PCR assays monitoring AS patterns of microexons in Vav2, Rapgef6, Itsn1, Rims2, Abi1, Ptprd, Nbea, Zmynd8, Ppfia2, and Dnm2 (nonneural) in mouse neural (hippocampus, cerebellum, and spinal cord), muscle-related (heart and skeletal muscle), and other (stomach, liver, spleen, kidney and testis) tissues. Molecular weight markers are indicated. B) For each sample, proportion of neural-regulated microexons that show inclusion levels similar to neural or non-neural samples. C) PSI distributions for neural-regulated microexons with increased neural inclusion for different classes of cell and tissue types. For clarity, outliers are not shown. D) Heatmap of PSI changes (ΔPSIs) between time points during differentiation of C2C12 myoblasts to myotubes in vitro (Trapnell et al., 2010). Shades or grey indicate increased/decreased PSI at a given transition (T1 to T3). Unsupervised clustering detects a cluster of 17 microexons with increased PSI during differentiation, particularly at T1. Right inset: PSIs for each microexon (gray lines) in the highlighted cluster; dark line shows the median PSI at each time point. E) Higher evolutionary conservation of human neural 3-15 nt and 16-27 nt microexons compared to longer neural exons at the genomic, transcriptomic and neural regulatory level. y axis shows the percent of conservation between human and mouse. p values correspond to proportion tests. F) Contribution of each type of AS to events with conserved neural regulation between human and mouse, according to their predicted impact on proteomes. Microexons comprise approximately one-third of all conserved neural-regulated events predicted to generate alternative protein isoforms. G) Distributions of average phastCons scores for exonic sequences of alternative microexons and long exons, as well as constitutive exons. H) Distributions of average phastCons scores for exonic sequences of neural-regulated microexons and long exons, as well as non-neural alternative exons and constitutive exons. p values for (G) and (H) correspond to Wilcoxon rank-sum tests. I) Average phastCons scores for neighboring intronic sequences of neural-regulated microexons and longer exons, as well as non-neural alternative exons and constitutive exons. Only exons conserved at the genomic level between human and mouse were used for this analysis.
Figure 4:
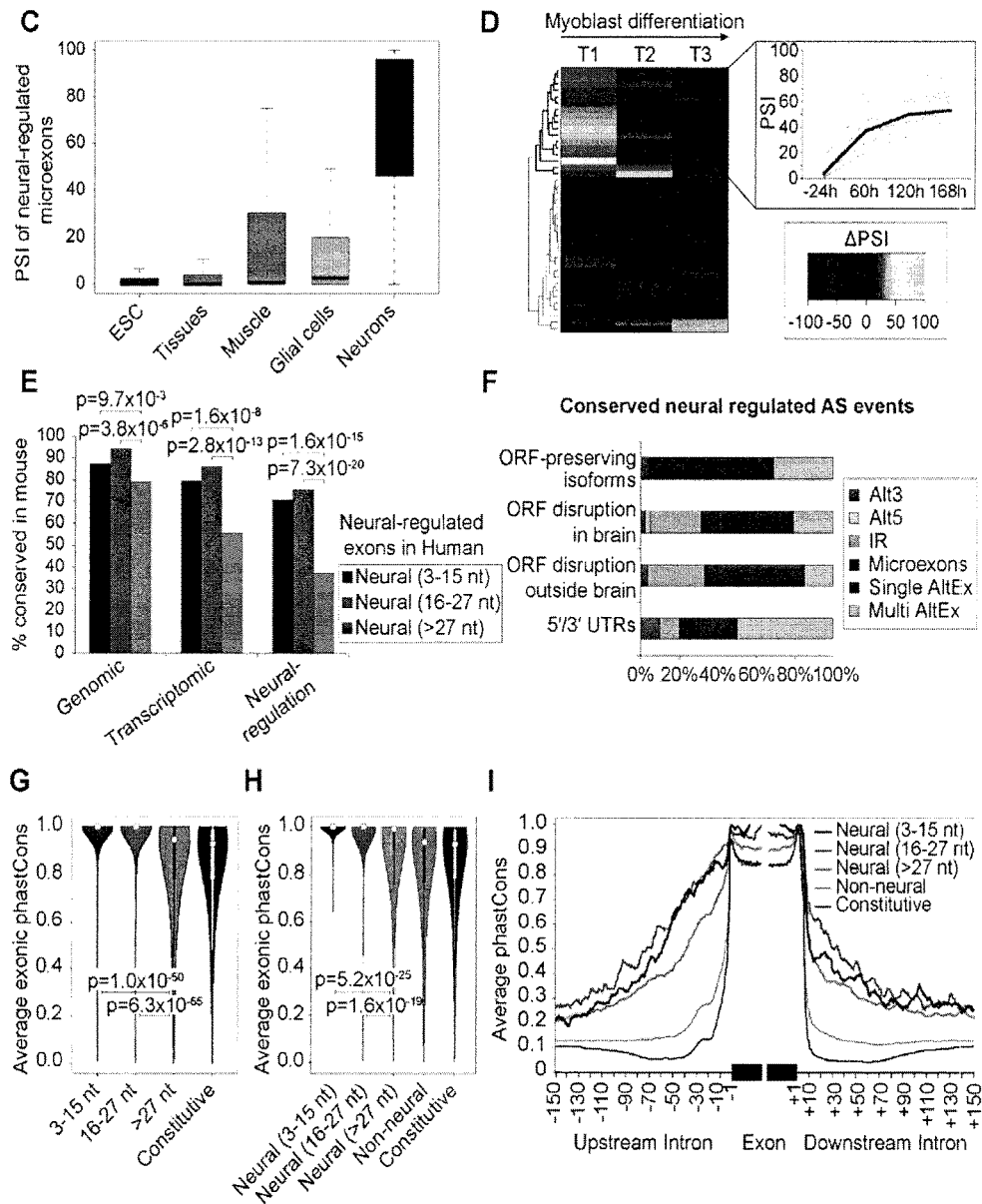

Further analysis of the neural-regulated AS program revealed a striking inverse relationship between the length of an alternative exon and its propensity to be specifically included in neural tissues. Increased neural-specific inclusion was detected for the majority of microexons (length≤27 nt, FIG. 3A); 60.7% of alternative microexons show increased neural 'percent spliced in' (PSI) (ΔPSI>15) versus 9.5% of longer (average ~135 nt) alternative exons (p=1.9× $10^{-220}$, proportion test). This trend extends to microexons as short as 3 nt. RT-PCR validation experiments confirmed the RNA-Seq-detected regulatory profiles and inclusion levels of all (10/10) microexons analyzed across ten diverse tissues ($R^2$=0.92, n=107; FIG. 4A). To further investigate the cell and tissue type specificity of microexon regulation, RNA-Seq data (Sofueva et al., 2013; Zhang et al., 2014; Zhang et al., 2013) was used to compare their inclusion levels in major glial cell types (astrocytes, microglia and oligodendrocytes), isolated neurons, and in muscle cells and tissues. While up to ~20% of the detected neural-regulated microexons showed increased PSIs in one or more glial cell types, and/or in muscle, compared to other non-neural tissues, the vast majority (>90%) of neural-regulated microexons display highest PSIs in neurons compared to all other cell and tissue types analyzed (FIGS. 4B-D). These results indicate that tissue-regulated microexons are predominately neuronal-specific.

Relative to longer alternative exons, microexons, in particular those that are 3-15-nt long and neural-specifically included, are strongly enriched in multiple features indicative of functionally important AS. They are highly enriched for lengths that are multiples of three nts (FIG. 3B), and a significantly larger fraction are predicted to generate alternative protein isoforms upon inclusion and exclusion, compared with longer exons (FIG. 3C; p<$10^{-10}$, proportion test). They are also significantly more often conserved at the levels of genomic sequence, detection in alternatively spliced transcripts, and neural-differential regulation (FIGS. 3D and 4E, neural-regulated exons; p<0.001 for all pairwise comparisons, proportion tests. Similar results were obtained when comparing neural-regulated microexons and longer exons that have matching distributions of neural versus non-neural ΔPSI values). Of 308 neural-regulated microexons in human, 225 (73.5%) are neural-differentially spliced in mouse, compared to only 527 of 1390 (37.9%) longer neural-regulated exons. While microexons represent only ~1% of all AS events, they comprise approximately one third of all neural-regulated AS events conserved between human and mouse that are predicted to generate alternative protein isoforms (FIG. 4F). Moreover, of ~150 analyzed mammalian, neural-regulated, 3-15-nt microexons, at least 55 are deeply conserved in vertebrate species spanning 400-450 million years of evolution, from zebrafish and/or shark to human. This is in marked contrast to the generally low degree of evolutionary conservation of other types of AS across vertebrate species (Barbosa-Morais et al., 2012; Braunschweig et al., 2014; Merkin et al., 2012). Furthermore, comparable numbers of alternative microexons were detected in all analyzed vertebrate species, the majority of which are also strongly neural-specifically included (FIG. 3E). Consistent with their regulatory conservation, sequences overlapping microexons, including both the upstream and downstream flanking intronic regions, are more highly conserved than sequences surrounding longer alternative exons (FIGS. 3F and 4G), including longer exons with a similar distribution of neural versus non-neural ΔPSI values (FIGS. 4H and 4I).

Dynamic Regulation of Microexons During Neuronal Differentiation

Figure 5:
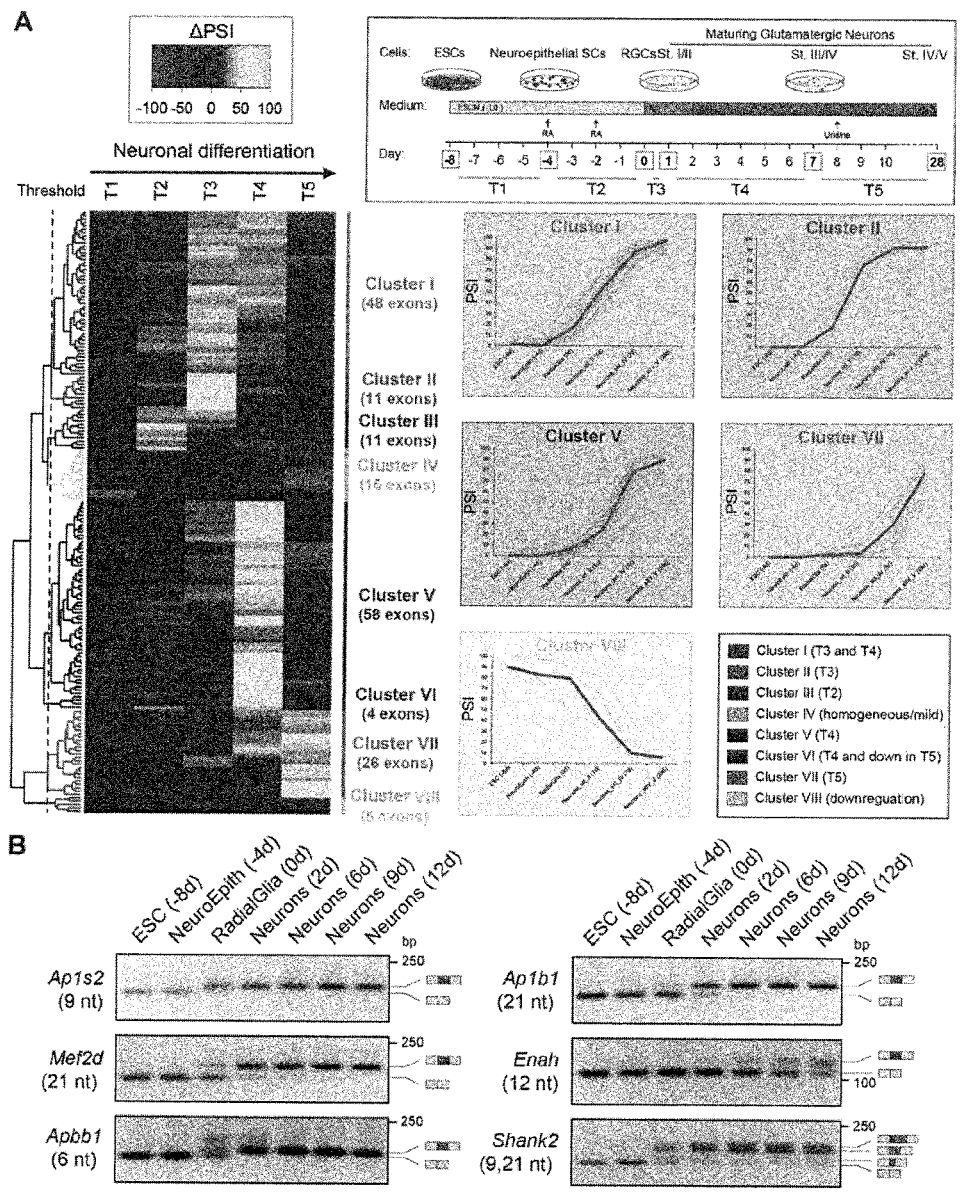
FIG. 5 shows switch-like regulation of microexons during neuronal differentiation. A) Heatmap of PSI changes ($\Delta$PSIs) between time points during differentiation of ESCs to glutamatergic neurons in vitro (Hubbard et al., 2013). Y Increased/decreased PSIs at a given transition (T1 to T5) are indicated. Unsupervised clustering detects eight clusters of exons based on their dynamic PSI regulation (clusters I-VIII, legend). Right, top: scheme of the neuronal differentiation assay time points of sample collection, and analyzed transitions. Right, bottom: PSIs for each microexon (grey lines) in five selected clusters; dark grey lines show the median for the cluster at each time point. B) Representative RT-PCR assays monitoring AS patterns of microexons during neuronal differentiation in Ap1s2 (9 nt), Mef2d (21 nt), Apbb1 (6 nt), Ap1b1 (21 nt), Enah (12 nt) and Shank2 (9 and 21 nt). See also FIG. 6.
Figure 6:
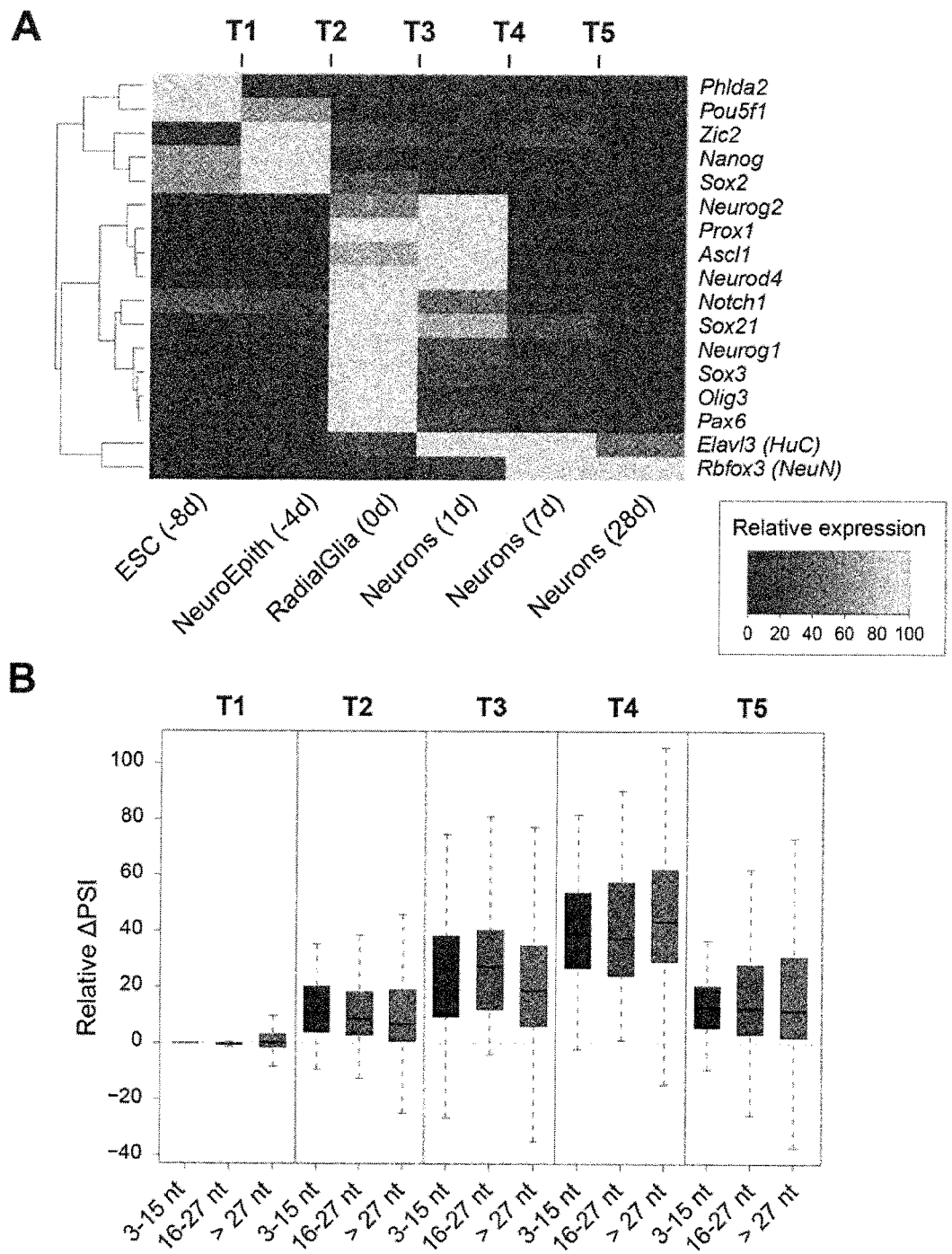
FIG. 6 shows switch-like regulation of microexons during neuronal differentiation (related to FIG. 5). A) Heatmap showing relative gene expression levels for key ESC and neural markers, including proneural genes (Neurog2 to Pax6) and postmitotic neuronal markers (Elavl3/HuC and Rbfox3/NeuN). B) Distribution of relative $\Delta$PSI ($\Delta$PSI divided by the PSI range across the six time points) for neural microexons and longer exons at each transition.
Figure 7:
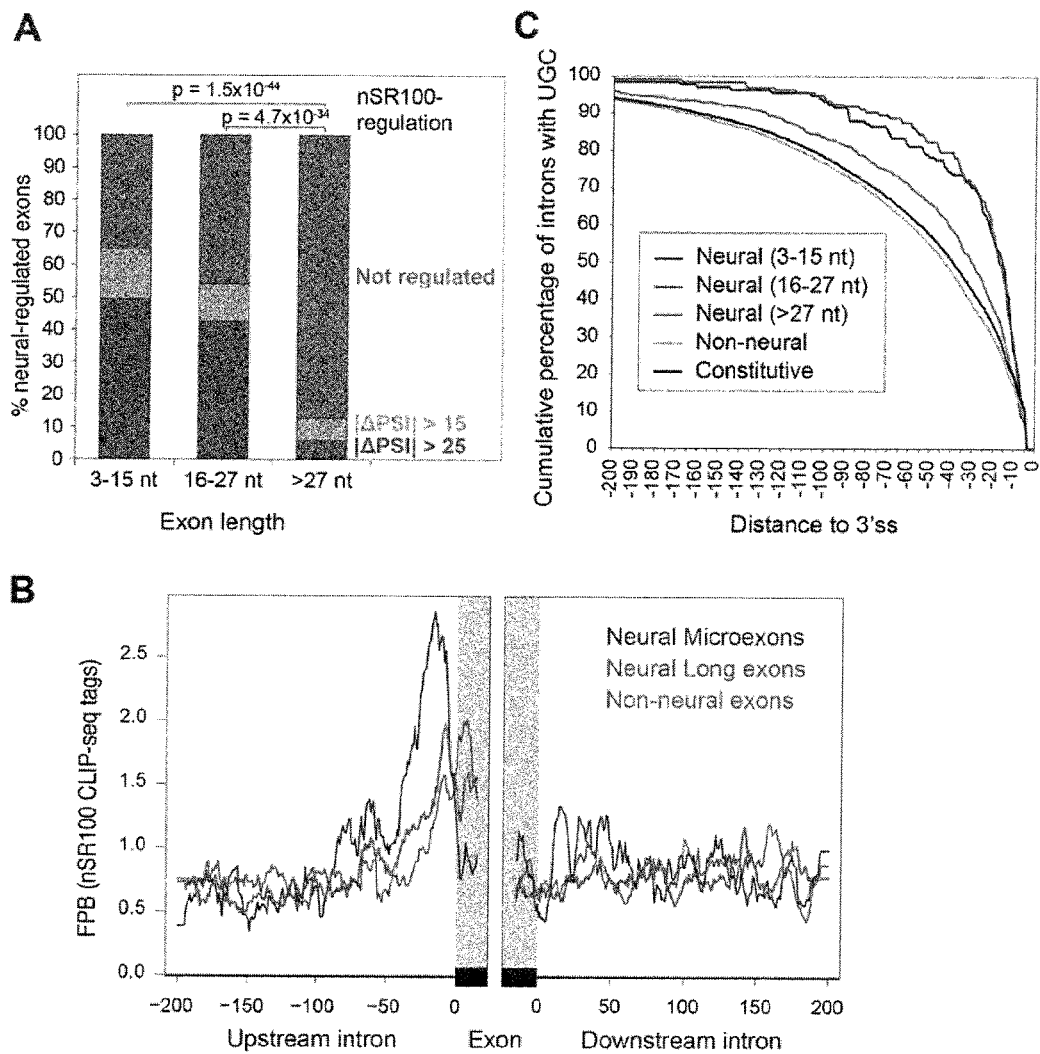
FIG. 7 shows SRRM4/nSR100 is a positive, direct regulator of most microexons. A) Percent of neural-regulated exons within each length class that is affected by nSR100 expression in human 293T kidney cells (absolute $\Delta$PSI>15, light grey or absolute $\Delta$PSI>25, dark grey). p-values correspond to two-sided proportion tests of affected vs. non-affected events. B) Average normalized density of nSR100 cross-linked sites in 200 nt windows encompassing neural-regulated exons of different length classes. FPB, Fragments Per Billion. C) Cumulative distribution plots indicating the position of the first UGC motif within 200 nts upstream of neural-regulated microexons and longer exons, as well as non-neural and constitutive exons. p<0.0001 for all comparisons against microexons, Wilcoxon Sum Rank test. See also FIG. 8.
Figure 8:
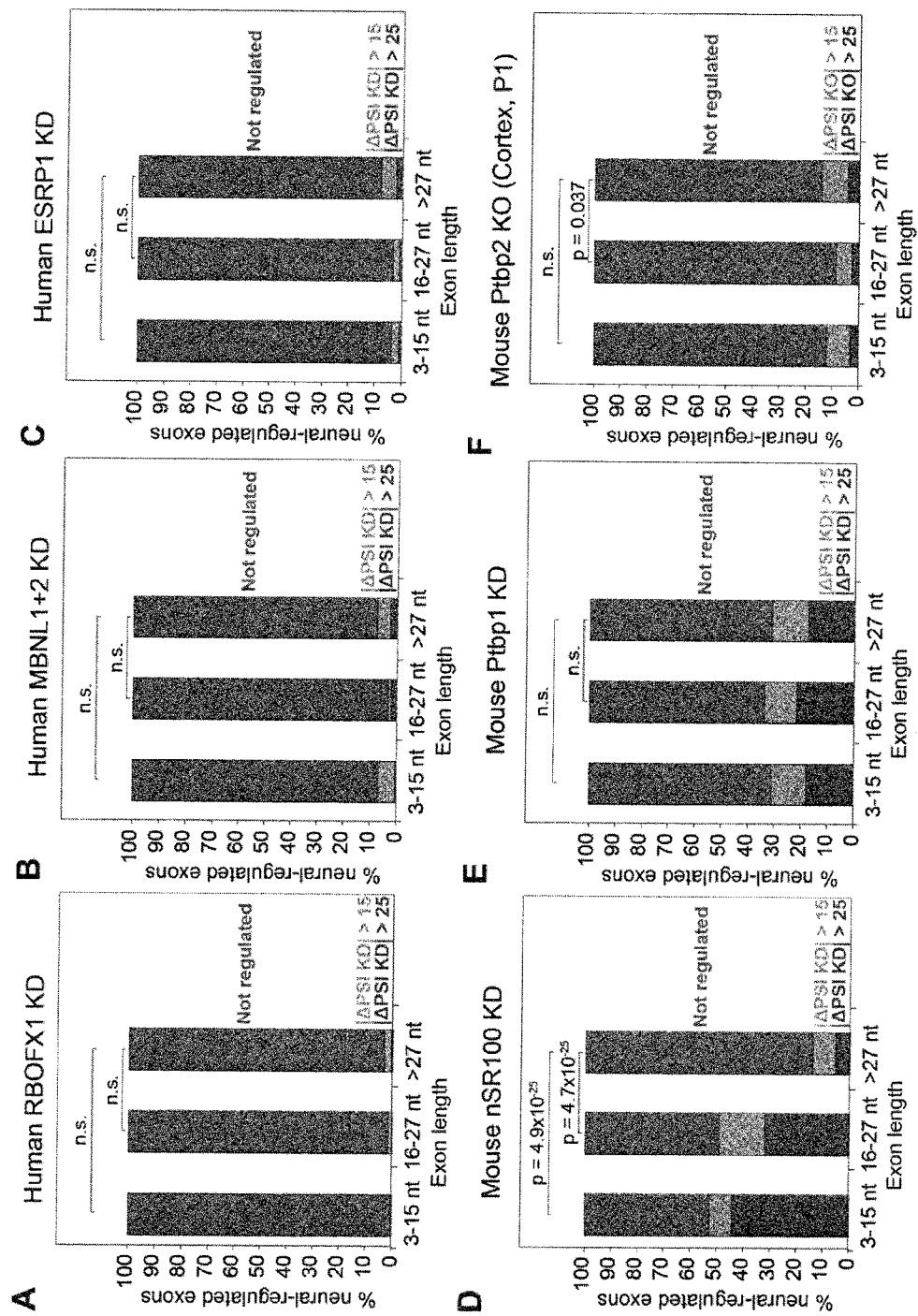
FIG. 8 shows regulation of neural-regulated exons and microexons by splicing factors (related to FIG. 7). A-H) Percent of neural-regulated exons within each length class that is affected at 15<|$\Delta$PSI|<25 and |$\Delta$PSI|>25 by (A) RBFOX1 knockdown in human neural precursor cells; (B) MBNL1 and MBNL2 double knockdown in human HeLa cells; (C) ESRP1 knockdown in human PNT2 cells; (D) nSR100/Srrm4 knockdown in mouse N2A cells; (E) Ptbp1 knockdown in mouse N2A cells; (F) Ptbp2 knockout in mouse cortex (P1 stage); (G) Ptbp2 knockout in mouse embryonic brain (18.5 days post-conception); and (H) Rbfox1 knockout. p values correspond to two-sided proportion tests of regulated versus non-regulated events. I) Expression of nSR100 in different isolated brain cell types (Zhang et al., 2014). Error bars indicate SEM. J) Box plots comparing the 30 and 50 splice site strengths of neural 3-15 nt and 16-27 nt microexons, longer (>27 nt,) exons, non-neural alternative exons, and constitutive exons.
Figure 8:
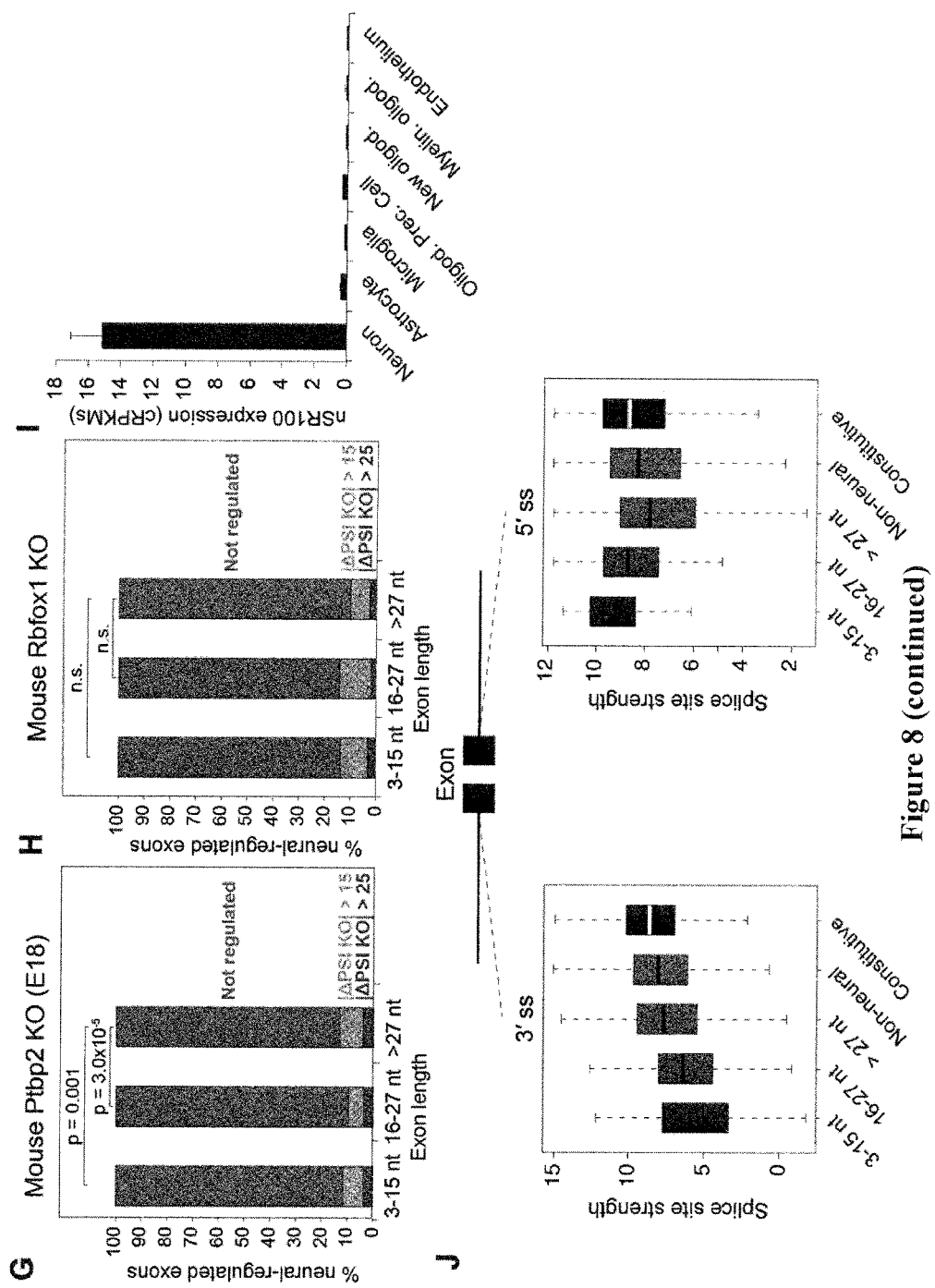

To further investigate the functional significance of neural-regulated microexons, RNA-Seq data was used to analyze their regulation across six time points of differentiation of mouse embryonic stem (ES) cells into cortical glutamatergic neurons (FIG. 5). Of 219 neural-regulated microexons with sufficient read coverage across time points, 151 (69%) displayed a PSI switch ≥50 between ES cells and mature neurons, and 65 (30%) a switch of ≥90 (FIG. 5). Unsupervised hierarchical clustering of PSI changes between consecutive time points (transitions T1 to T5) revealed several temporally-distinct regulatory patterns (FIG. 5A). Most microexons show sharp PSI switches at late (T3 to T5) transitions during differentiation. These stages correspond to maturing post-mitotic neurons when pan-neuronal markers are already expressed, and are subsequent to the expression of most neurogenic transcription factors (FIG. 6A). This pattern of late activation (FIG. 6B) suggests enrichment for functions for microexons in terminal neurogenesis (FIG. 1C). Despite the small number of genes representing clusters of kinetically-distinct sets of regulated microexons, each cluster revealed significant enrichment of specific GO terms including "regulation of GTPase activity" (Cluster I), "glutamate receptor binding" and "actin cytoskeleton organization" (Cluster V). These observations indicate that the dynamic switch-like regulation of microexons is intimately associated with the maturation of neurons.

The Neural-Specific Splicing Factor nSR100/SRRM4 Regulates Most Neural Microexons Among several analyzed splicing regulators, knockdown and overexpression of nSR100 had the strongest effect on microexon regulation, with more than half of the profiled microexons displaying a pronounced change in inclusion level compared to controls (FIGS. 7A and 8A-8H). Moreover, an analysis of RNA-Seq data from different neural cell types (Zhang et al., 2014) revealed that nSR100 has the strongest neuronal-specific expression relative to the other splicing regulators (FIG. 8I), which is also consistent with its immunohistochemical detection in neurons but not glia (Calarco et al., 2009). Recently, it was shown that nSR100 promotes the inclusion of a subset of (longer) neural exons via binding to intronic UGC motifs proximal to suboptimal 3' splice sites (Raj et al., 2014). Consistent with these results, and supporting a direct role for nSR100 in microexon regulation, RNA sequence tags cross-linked to nSR100 in vivo are also highly enriched in intronic sequences containing UGC motifs, located adjacent to the 3' splice sites of nSR100-regulated microexons (FIG. 7B, C; p<0.0001 for all comparisons, Wilcoxon Rank Sum test). Relative to longer exons, it was additionally observed that neural-regulated microexons are associated with weak 3' splice sites and strong 5' splice sites (FIG. 8J). nSR100 thus has a direct and extensive role in the regulation of the neural microexon program.

Distinct Protein Regulatory Properties of Microexons

Figure 9:
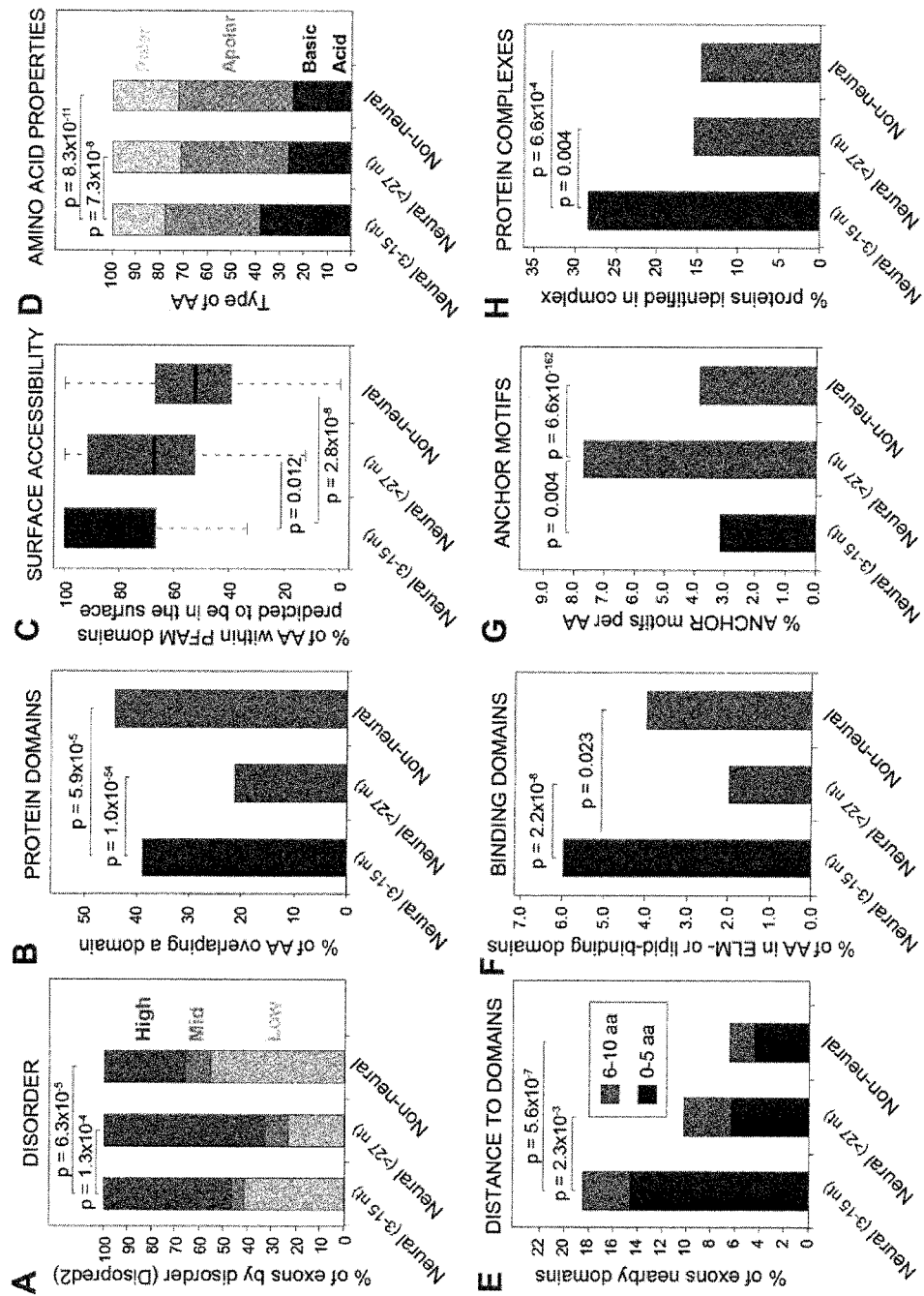
FIG. 9 shows microexons possess distinct protein-coding features. For each analysis, values are shown for neural-regulated, 3-15 nt microexons and longer (>27 nt) exons, as well as non-neural AS exons (see FIG. 10 for other types of exons). A) Percent of exons with a high average (>0.67), mid-range (0.33 to 0.67) and low disorder rate (<0.33). B) Fraction of amino acids (AA) that overlap a PFAM protein domain. C) Percent of AA within PFAM domains predicted to be on the protein surface. D) Percent of AA types based on their properties; p-values correspond to the comparison of charged (acid and basic) versus uncharged (polar and apolar) AAs. E) Percent of exons that are adjacent to a domain (within 0-5 (black) or 6-10 AAs (grey)); p-values correspond to the comparison of exons within 0-5 AAs. F) Percent of residues overlapping PFAM domains involved in linear motif or lipid binding. G) Percent of residues overlapping binding motifs predicted by ANCHOR. H) Percent of exons with proteins identified as belonging to one or more protein complexes (data from (Havugimana et al., 2012)). All p-values correspond to proportion tests except for A (3-way Fisher test) and C (Wilcoxon Sum Ranks test). See also FIG. 10.
Figure 10:
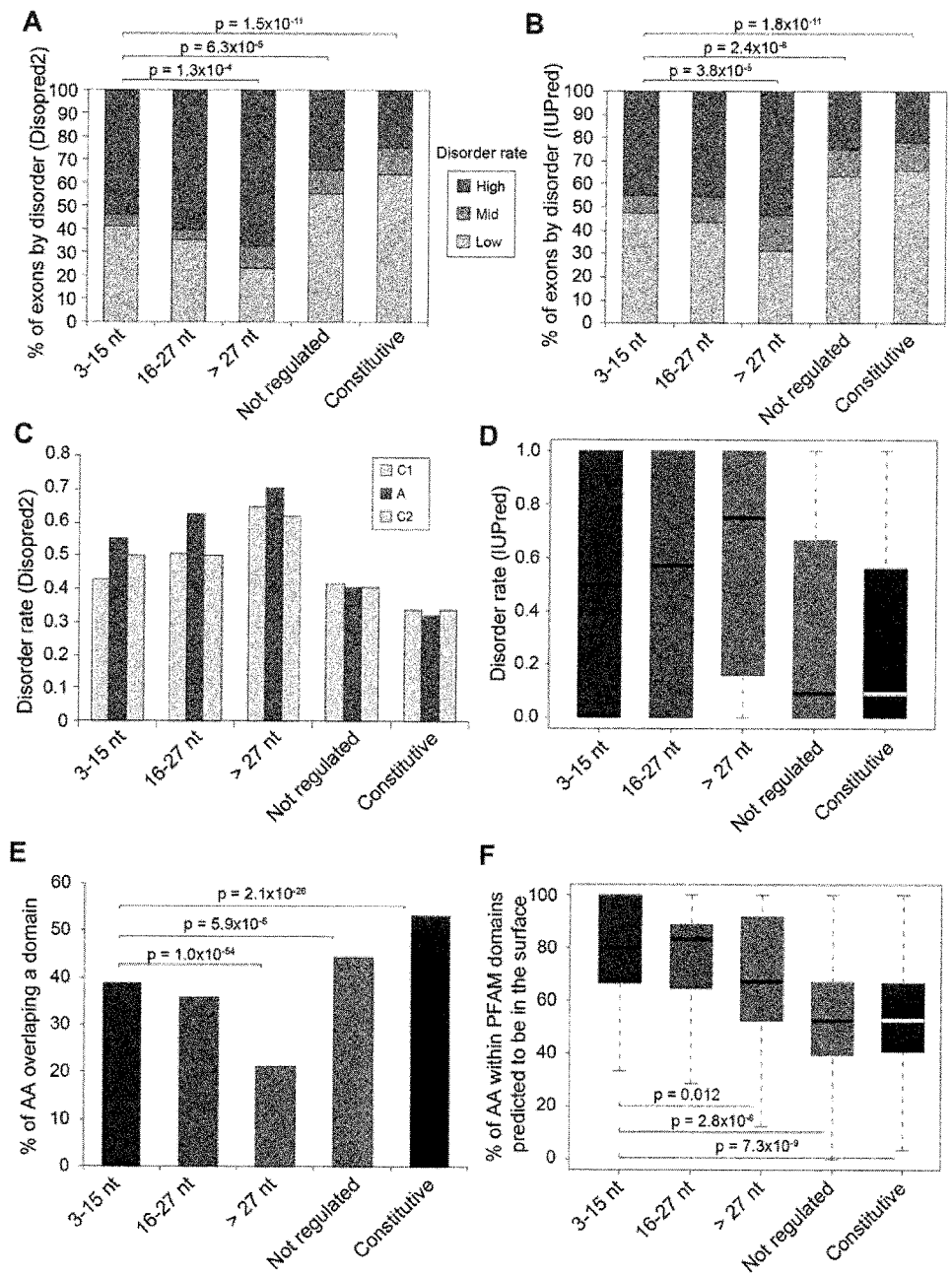
FIG. 10 shows protein features of different exon classes (related to FIG. 9). For each analysis, values are shown for neural 3-15 nt and 16-27 nt microexons and longer (>27 nt,) exons, as well as non-neural AS exons and constitutive exons. A and B) Percent of exons with high (average disorder rate>0.67), mid (between 0.33 and 0.67), and low (<0.33) disorder calculated using Disopred2 (A) or IUPred (B); p values correspond to three-way Fisher tests. C) Average disorder rate calculated using Disopred2 for each group of exons, as well as their neighboring upstream (C1, left) and downstream (C2, right) exons. D) Distribution of disorder rate across exon groups, calculated by IUPred. E) Percent of residues that overlap a PFAM protein domain. p values correspond to proportion tests. F) Percent of AA within PFAM domains predicted to be in the protein surface using NetSurfP; p values correspond to Wilcoxon rank-sum test. G) Accessible surface area score, based on the subset of exons with available crystal structures in PDB; p values correspond to Wilcoxon rank-sum test. H) Percent of AA groups based on their properties; p values correspond to proportion tests for the comparison of charged (acid and basic) versus uncharged (polar and apolar) AAs. I) Significantly enriched (Glu, Lys, Arg) or depleted (Pro, Thr) AAs in microexons compared to other exon types. Asterisks correspond to different levels of statistical significance (*p<0.05; p<0.01; *p<0.001) in a proportion test. J) Percent of exons that fall nearby PFAM protein domains, without overlap. Black, within 0-5 AAs; gray, within 6-10 AAs. p values correspond to proportion tests for exons within 0-5 AAs of a domain. K) Cumulative distance of exons that do not overlap domains with the nearest protein domain. Exons in proteins with no predicted PFAM domain are excluded. L) Percent of residues overlapping PFAM domains involved in linear motif or lipid binding; p values correspond to proportion tests. M) PFAM protein domains enriched in genes containing microexons. N) Percent of residues overlapping ANCHOR binding motifs; p values correspond to proportion tests. O) Degree (number of interactors in PPI networks) of proteins containing different types of exons. Degree values obtained from Ellis et al. (2012). p values correspond to Wilcoxon rank-sum test. P) Percent of exons in which the containing proteins have been identified as part of protein complexes (data from Havugimana et al., 2012); p values correspond to proportion tests.
Figure 10:
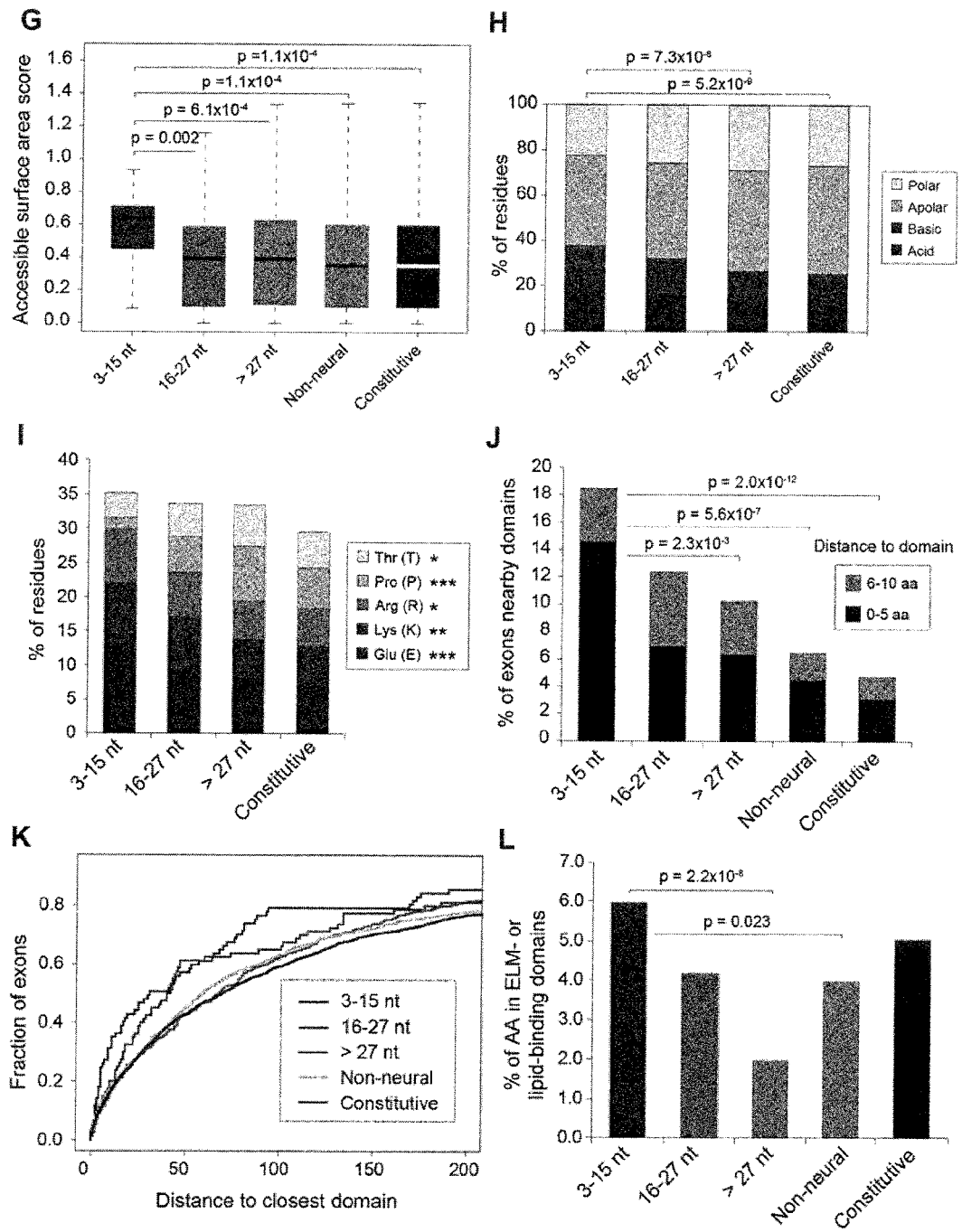
Figure 10:
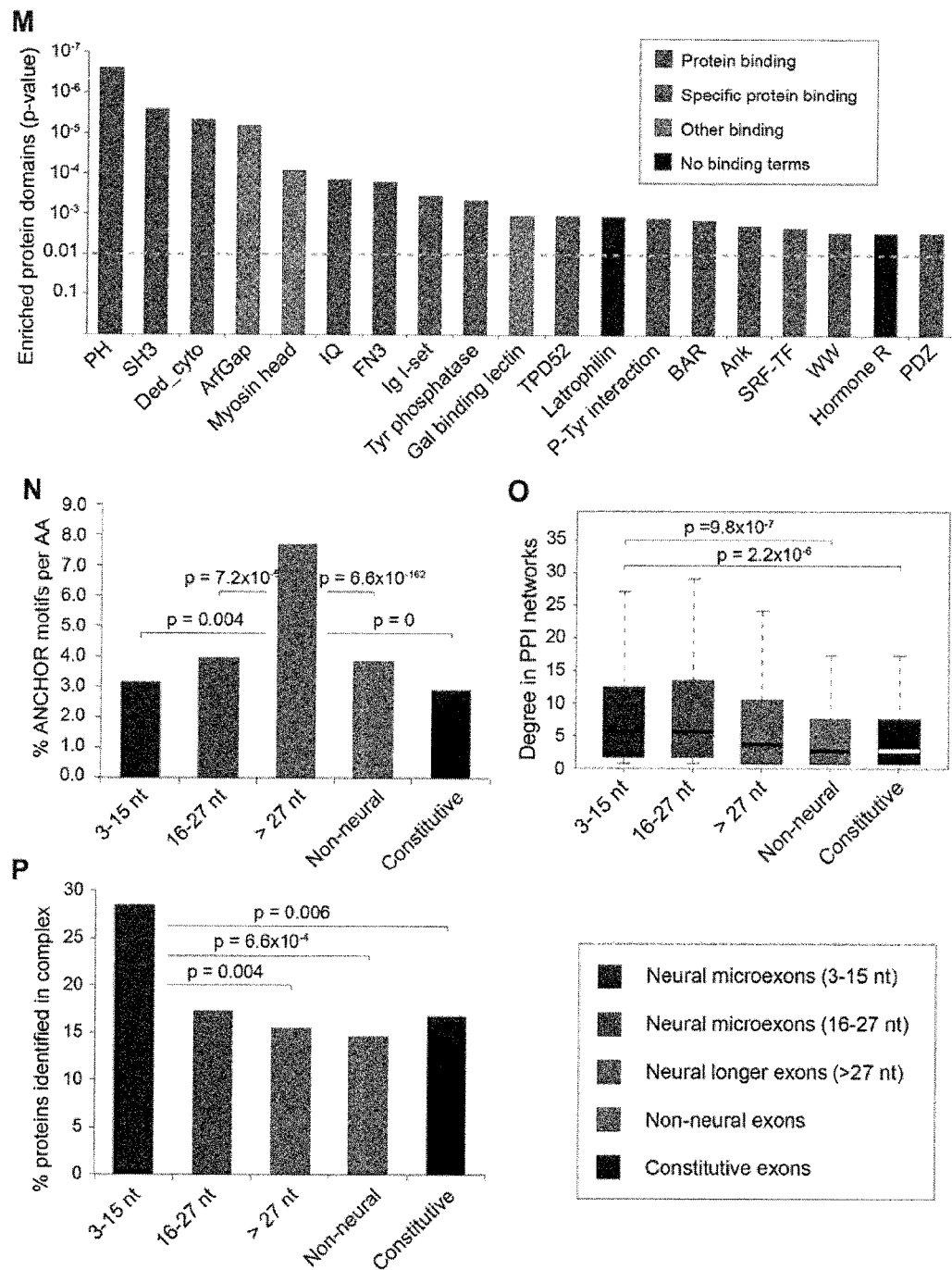
Figure 11:
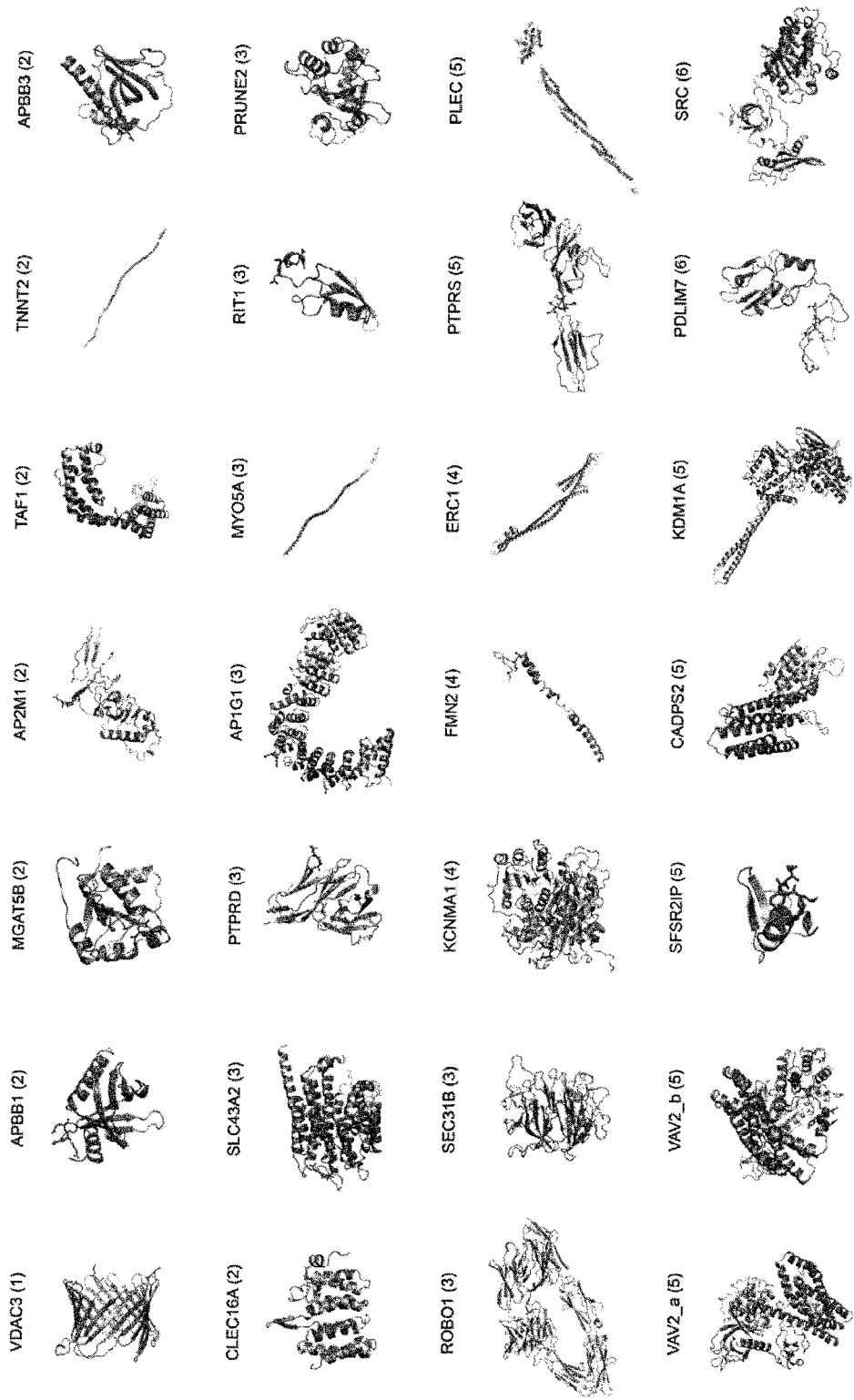
FIG. 11 shows location of microexons in protein structures (related to FIG. 12). A) Selection of available protein structures from PDB and SWISS-MODEL, and modeled structures using Phyre2 containing neural-regulated microexons. The number of residues of each microexon is indicated in parenthesis. B and D) 293T cells were transfected with HA-tagged Apbb1 (B) or AP1S2 (D) constructs, with or without the microexon, together with 3Flag-tagged App (B) or AP1B1 (D), as indicated. Immunoprecipitation was performed with anti-Flag antibody or anti-HA antibody, as indicated. C) Quantification of LUMIER-normalized luciferase intensity ratio (NLIR) values for RL-tagged Apbb1, with or without the microexon, coimmunoprecipitated with 3Flag-tagged App. p values in (B) and (C) correspond to t tests for three replicates, respectively; error bars indicate SEM.
Figure 11:
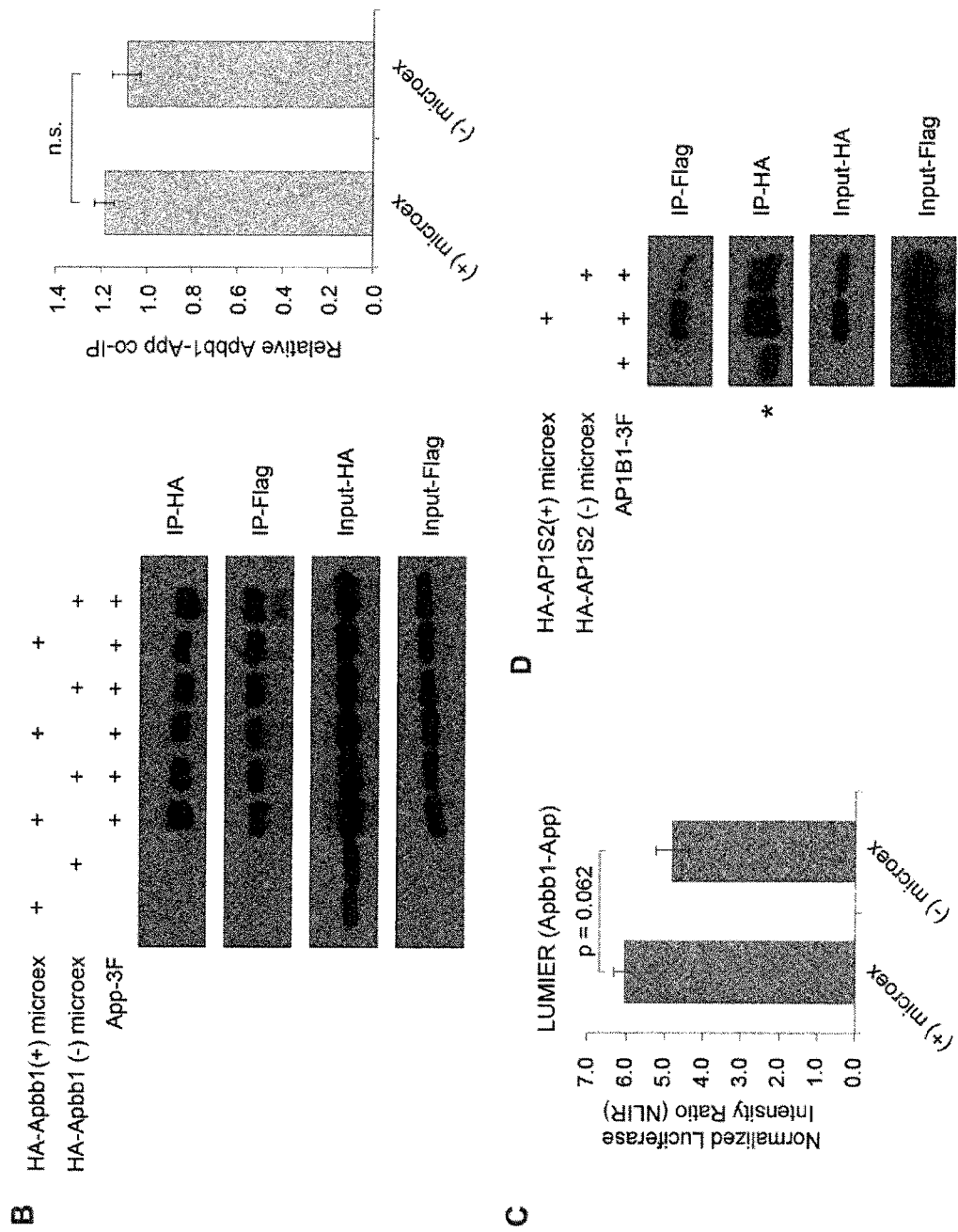

Neural-regulated microexons, in particular those that are 3-15-nt long, possess multiple properties that distinguish them from longer neural-regulated exons (FIGS. 9 and 10). A significantly smaller fraction overlap predicted disordered amino acid residues (FIGS. 9A and 10A-D; p<$1.3\times10^{-4}$; 3-way Fisher Exact tests), whereas a significantly higher fraction overlap modular protein domains (FIGS. 9B and 10E; ~2-fold increase, p=1.0×10⁻⁵⁴, proportion test). In contrast, microexon residues overlapping protein domains are significantly more often surface-accessible and enriched in charged residues (FIGS. 9C, 9D, and 10F-I; p<10⁻⁷ for all comparisons, proportion test) than are residues overlapping longer neural or non-neural exons. Moreover, when not overlapping protein domains, microexons are significantly more often located immediately adjacent (i.e. within 5 amino acids) to folded protein domains (FIGS. 9E and 10J,K). Without being bound by theory, these results suggest that a common function of microexons may be to modulate the activity of overlapping or adjacent protein domains. Supporting this view, among 49 available and de novo-modeled tertiary protein structures containing microexons, the corresponding residues are largely surface accessible and unlikely to significantly affect the folding of the overlapping or adjacent protein domains (FIG. 11A).

Microexons Modulate the Function of Interaction Domains

Figure 13:
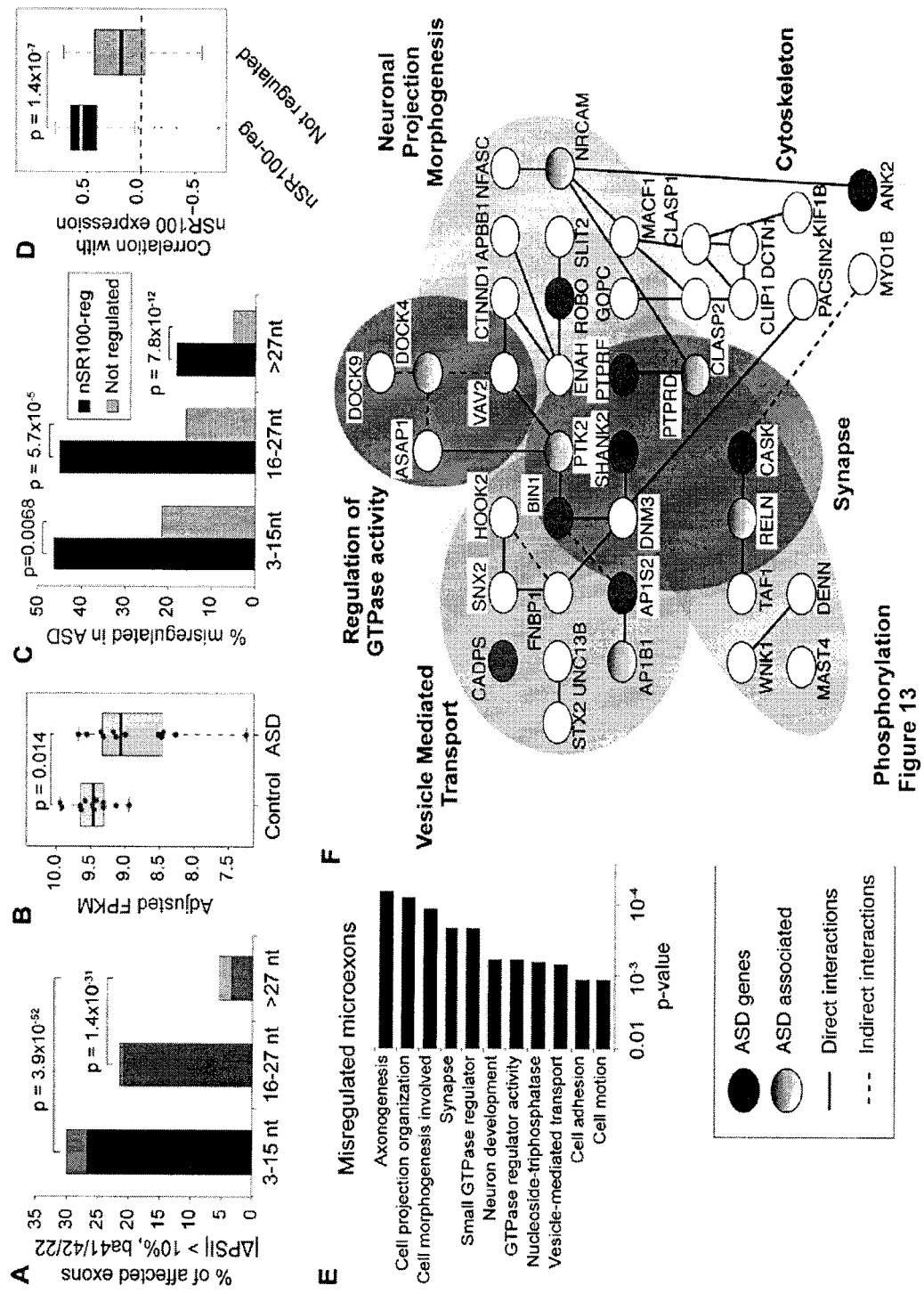
FIG. 13 shows microexons are often misregulated in autism spectrum disorder (ASD). A) Percent of alternative exons of each length class that are misregulated in ASD (absolute ΔPSI>10 between PSI-averaged ASD and control groups) in ba41/42/22 brain regions. Dark shading, lower inclusion in ASD; light shading, higher inclusion in ASD; p-values correspond to proportion tests. B) Expression of nSR100 across the 12 control and 12 ASD individuals, Adjusted Fragments Per Kilobase Of Exon Per Million Fragments Mapped (FPKMs) were calculated using a regression analysis that accounts for variation derived from differences in RNA integrity, brain sample batch, sequencing depth, and 5'-3' bias in measurements of gene-level FPKM values. C) Percent of exons within each length class misregulated in autistic compared to control brains (average absolute ΔPSI>10) for nSR100-regulated (ΔPSI>25 in the nSR100-overexpressing compared to control 293T cells) and non-nSR100-regulated (absolute ΔPSI<5) exons. D) Distribution of correlation coefficients between PSIs and nSR100 expression values across stratified ASD and control samples for microexons that are (n=59) or are not (n=69) regulated by nSR100. Only microexons with sufficient read coverage to derive accurate PSI quantifications in at least 9 ASD and 9 control ba41/42/22 samples were included. p-value correspond to Wilcoxon Sum Rank test. E) GO categories significantly enriched in genes with microexons that are misregulated in ASD. F) A protein-protein interaction network involving genes with ASD misregulated microexons (ΔPSI>10) in ba41/42/22 brain regions. Genes with major effect mutations, and smaller effect risk genes, are indicated in shaded ovals. Genes grouped by functional category are indicated. See also FIG. 14.

Neural-regulated microexons are significantly enriched in domains that function in peptide and lipid-binding interactions (FIGS. 9F and 13L; p=1.7×10⁻⁶, proportion test). Overall, genes with microexons are highly enriched in modular domains involved in cellular signaling, such as SH3 and PH domains (FIG. 11M). Conversely, unlike longer neural exons (Buljan et al., 2012; Ellis et al., 2012), they are depleted of linear binding motifs (FIG. 9G and S5N, p<0.005, proportion tests for all comparisons). Moreover, proteins containing microexons are significantly more often central in protein-protein interaction networks and detected in protein complexes compared to proteins with other types of alternative exons (FIGS. 9H and 11O,P, p≤0.004 for all comparisons, Wilcoxon Rank Sum test). Taken together with the data in FIG. 1, these results suggest that microexons may often regulate interaction domains to facilitate the remodeling of protein interaction networks associated with signaling and other aspects of neuronal maturation and function.

Figure 12:
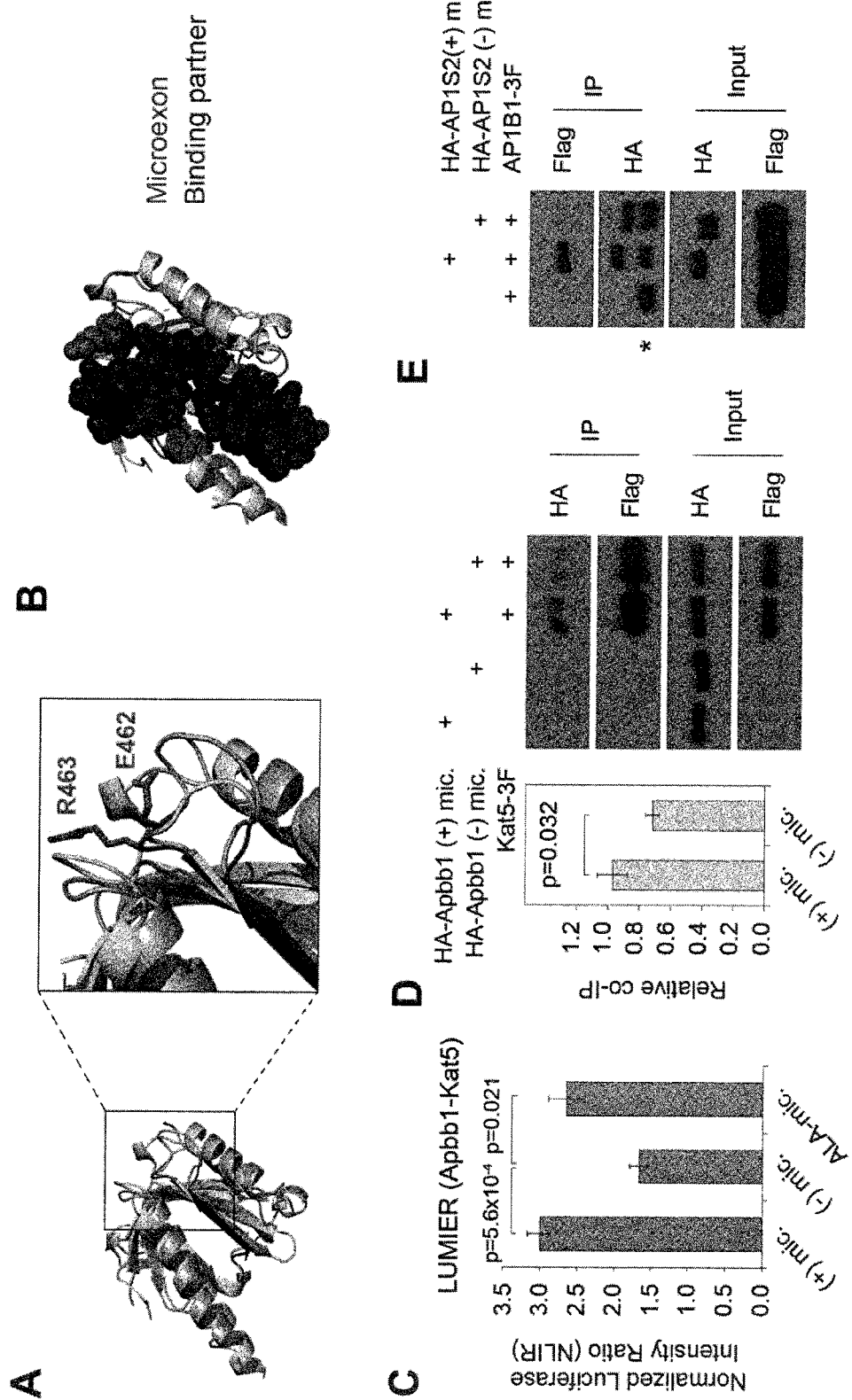
FIG. 12 shows microexons regulate protein-protein interactions. A) Structural alignment of APBB1-PTB1 and APBB1-PTB2 domains. Residues located at the protein-binding interface of APBB1-PTB2 are shown. Inset shows the microexon residues in APBB1-PTB1 (E462-R463). B) Upon superimposition of APBB1-PTB1 and APBB1-PTB2 domains, the microexon is located close to the APBB1-PTB2 binding partner (APP protein fragment), suggesting the microexon in PTB1 may affect protein binding. C) Quantification of LUMIER-normalized luciferase intensity ratio (NLIR) values for RL-tagged Apbb1, with or without the microexon, or with a mutated version consisting of two Alanine substitutions (ALA-mic.), coimmunoprecipitated with 3Flag-tagged Kat5. D, E) 293T cells were transfected HA-tagged Apbb1 (D) or AP1S2 (E) constructs, with or without the respective microexon, together with 3Flag-tagged Kat5 (D) or AP1B1 (E), as indicated. Immunoprecipitation was performed with anti-Flag (D) or anti-HA (E) antibody, and the immunoprecipitates were blotted with anti-HA or anti-Flag antibody, as indicated. Results shown in (E) were confirmed in a biological replicate experiment (FIG. 11D). p-values in C and D correspond to t-tests for four and three replicates, respectively; error bars indicate standard error. Asterisk in panel E indicates a band corresponding to the light chain of the HA antibody.

To test this hypothesis, luminescence-based mammalian interactome mapping (LUMIER; (Barrios-Rodiles et al., 2005; Ellis et al., 2012)) and co-immunoprecipitation-western blot assays were employed to investigate whether the insertion of a highly conserved, neural-regulated 6-nt microexon in the nuclear adaptor Apbb1 affects its known interactions with the histone acetyltransferase Kat5/Tip60, and amyloid precursor protein App (FIG. 12A-D). Previous genetic and functional studies have revealed multiple functions for the Apbb1-Kat5 complex (Cao and Sudhoff, 2001; Stante et al., 2009), and that the loss of Kat5 activity is associated with developmental defects that impact learning and memory (Pirooznia et al., 2012; Wang et al., 2004; Wang et al., 2009) (see Discussion, below). Apbb1 contains two phosphotyrosine binding domains, PTB1 and PTB2, which bind Kat5 and App, respectively (Cao and Sudhoff, 2001). Exemplifying the distinct protein features of neural microexons described above (FIG. 9), the Apbb1 microexon adds two charged residues (Arg and Glu) to the PTB1 domain near its predicted interaction surface (FIGS. 12A and 12B). LUMIER and co-immunoprecipitation-western analysis reveals that inclusion of the microexon significantly enhances the interaction with Kat5, whereas there is little to no effect on the interaction with App (FIGS. 12C, 12D, 11B and 11C). Substitution of both microexon residues with alanine also enhanced the Kat5 interaction, although to a lesser extent than the presence of Arg and Glu (FIG. 12C). Without being bound by theory, this suggests that the primary function of this microexon is to extend the interface with which Apbb1 binds its partner proteins.

The function of a 9-nt microexon in the AP1S2 subunit of the adaptor-related protein complex 1 (AP1) was also examined. The AP1 complex functions in the intracellular transport of cargo proteins between the trans-Golgi apparatus and endosomes by linking clathrin to the cargo proteins during vesicle membrane formation (Kirchhausen, 2000), and is important for the somatodendritic transport of proteins required for neuronal polarity (Farias et al., 2012). Interestingly, mutations in AP1S2 have been previously implicated in phenotypic features associated with ASD and X-linked mental retardation (Borck et al., 2008; Tarpey et al., 2006). Co-immunoprecipitation-western analyses reveal that the microexon in AP1S2 strongly promotes its interaction with another AP1 subunit, AP1B1 (FIGS. 12E and 11D). This observation thus provides additional evidence supporting an important role for microexons in the control of protein interactions that function in neurons.

Microexons are Misregulated in Individuals with Autism Spectrum Disorder

Figure 14:
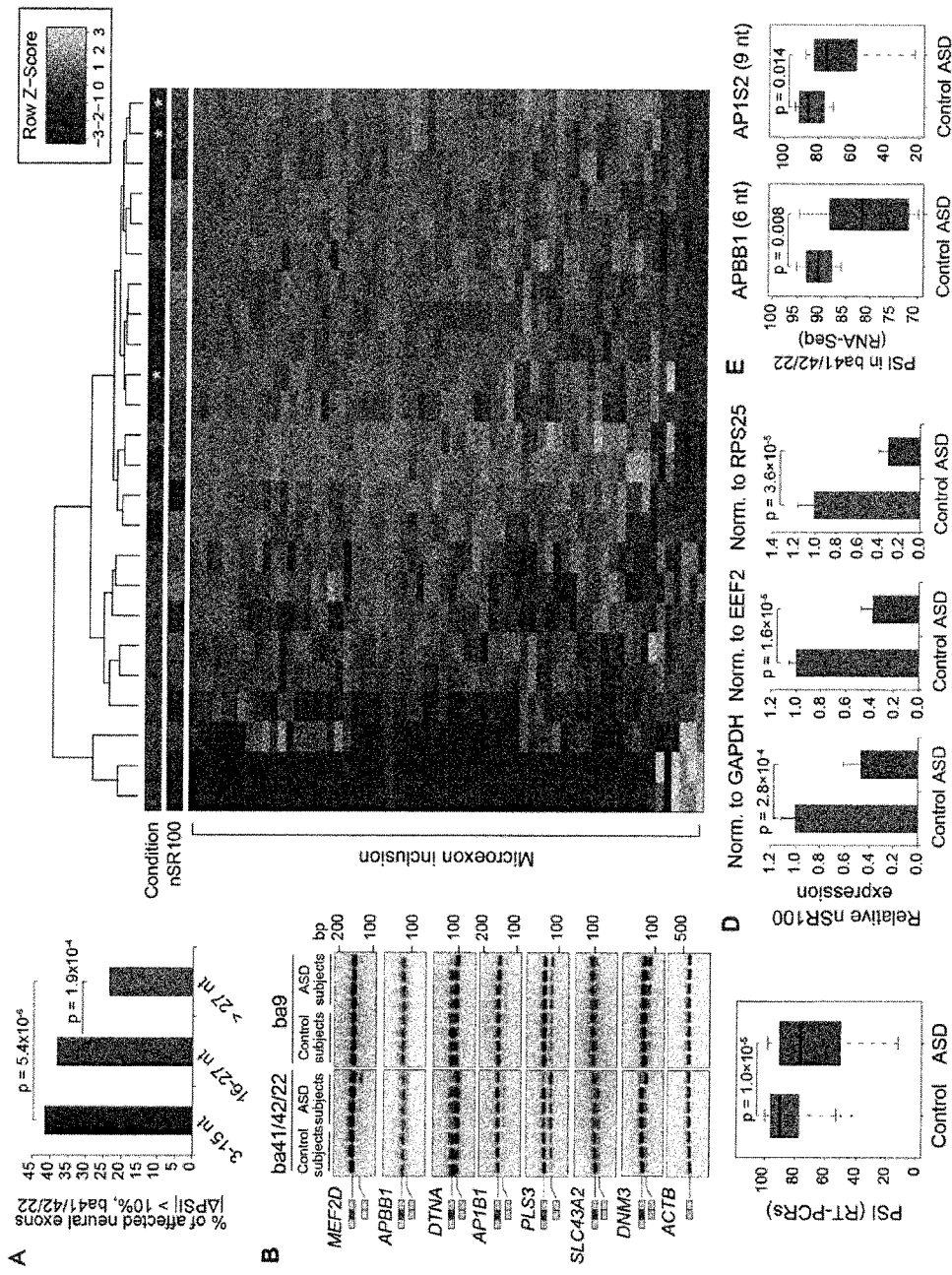
FIG. 14 shows microexons are often misregulated in ASD (related to FIG. 13). A) Percent of neural-regulated exons by length groups that are misregulated in ASD (|ΔPSI|>10 between averaged ASD and control groups) in ba41/42/22 brain region. p values correspond to proportion tests. B) Representative RT-PCRs for microexons misregulated in ba41/42/22 and ba9 regions from ASD versus control individuals. Bottom: boxplot of isoform quantifications from RT-PCR assays for 10 microexons in control (n=70 data points) and ASD (n=80 data points) individuals. p value from Wilcoxon ranksum test. C) Heatmap and unsupervised clustering of z scores of PSIs for microexons misregulated in ASD individuals with sufficient read coverage in at least 9 ASD and 9 control samples (n=64), and of nSR100 expression values. Conditions: ASD, control. Asterisks indicate individual samples used in RTPCR and qRT-PCR analyses (panels B and D). D) qRT-PCR quantifications of nSR100 expression in four ASD and three control samples (see panel C) normalized for three different housekeeping genes. p values correspond to two-sided t tests. Error bars indicate SEM. E) PSI distributions of the 6 nt and 9 nt microexons in APBB1 and AP1S2, respectively, in control and ASD individuals; p values from Wilcoxon ranksum test.

The properties of microexons described above suggest that their misregulation could be associated with neurological disorders. To investigate this possibility, RNA-Seq data was analyzed from the superior temporal gyrus (Brodmann areas ba41/42/22) from post-mortem samples from individuals with ASD and control subjects, matched for age, gender and other variables (Experimental Procedures). These samples were stratified based on the strength of an ASD-associated gene expression signature (Voineagu et al., 2011), and subsets of 12 ASD samples with the strongest ASD-associated differential gene expression signatures and 12 controls were selected for further analysis. Within these samples, 126 of 504 (30%) detected alternative microexons display a mean ΔPSI>10 between ASD and control subjects (FIG. 13A), of which 113 (90%) also display neural-differential regulation. By contrast, only 825 of 15,405 (5.4%) longer (i.e. >27 nt) exons show such misregulation (FIG. 13A), of which 285 (35%) correspond to neural-regulated exons. Significant enrichment for misregulation among microexons compared to longer exons was also observed when restricting the analysis to neural-regulated exons, including subsets of neural-regulated microexons and longer exons with similar distributions of neural versus non-neural ΔPSI values (FIG. 14A; p<2×10⁻⁴, proportion test). Similar results were observed when analyzing data from a different brain region (Brodmann area ba9) from the same individuals. RT-PCR experiments on a representative subset of profiled tissues confirmed increased misregulation of microexons in autistic versus control brain samples (FIG. 14B). Analysis of the proportions of microexons displaying coincident misregulation revealed that the vast majority (81.3%) have a ΔPSI>10 in at least half of the ASD stratified brain samples (FIG. 14C). However, only 26.9% (32/119) of the genes containing misregulated microexons overlapped with the 2,519 genes with significant ASD-associated misregulation at the level of gene expression. This reveals that largely distinct subsets of genes are misregulated at the levels of expression and microexon splicing in the analyzed ASD subjects. In contrast, a comparison of autistic subjects that possessed a weaker ASD-related differential gene expression signature did not reveal significant misregulation of microexons, or of longer exons. These data reveal frequent misregulation of microexon splicing in the brain cortices of some individuals with ASD.

Consistent with a widespread and important role for nSR100 in the regulation of microexons (FIG. 7), nSR100 mRNA expression is, on average, significantly downregulated in the brains of the analyzed ASD versus control subjects, and to an even greater extent in brain samples with the strongest ASD-associated signature compared to the controls (~10%, p=0.014, FDR<0.1, FIG. 13B). These differences were confirmed by qRT-PCR assays for a representative subset of individuals (p<$2.8 \times 10^{-4}$ for all normalizations; two-sided T-test; FIG. 14D). Moreover, relative to other exons, nSR100-dependent microexons are significantly more often misregulated in brain tissues from ASD compared to control subjects (FIG. 13C; p<0.01 for all comparisons, proportion test). Notably, significantly higher correlations between microexon inclusion and nSR100 mRNA expression levels across the stratified ASD samples and controls, for those microexons regulated by nSR100 relative to those microexons that are not regulated by this factor (FIG. 13D; p=$1.4 \times 10^{-7}$, Wilcoxon Sum Rank test) were also observed.

A GO analysis of genes with ASD-associated misregulation of microexons reveals significant enrichment of terms related to axonogenesis and synapse biology (FIG. 13E), processes that have been previously implicated in autism (Gilman et al., 2011; Parikshak et al., 2013; Voineagu et al., 2011). Many of the corresponding genes act in common pathways and/or physically interact through protein-protein interactions (FIG. 13F). Moreover, misregulated microexons are also significantly enriched in genes that have been genetically linked to ASD (p<0.0005, Fisher exact test), including many relatively well-established examples such as DNTA, ANK2, ROBO1, SHANK2, AP1S2. Other genes with misregulated microexons have been linked to learning or intellectual disability (e.g. APBB1, TRAPPC9, RAB3GAP1). In this regard, it is noted that the microexons analyzed in APBB1 and AP1S2 are significantly misregulated in the brain samples from ASD subjects (p<0.05 Wilcoxon Sum Rank test; FIG. 14E). Taken together with data in FIGS. 9 and 12, without being bound by theory, the results suggest that the misregulation of microexons, as well as of longer alternative exons (Corominas et al., 2014; Voineagu et al., 2011), may impact protein interaction networks that are required for normal neuronal development and synaptic function. Disruption of microexon-regulated protein interaction networks is therefore a potential mechanism underlying ASD and likely other neurodevelopmental disorders.

Discussion

In this study, it is shown that alternative microexons display the highest degrees of genomic sequence conservation, tissue-specific regulatory conservation, and frame-preservation potential, relative to all other classes of AS detected to date in vertebrate species. Unlike longer neural-regulated exons, neural microexons are significantly enriched in surface-accessible, charged amino acids that overlap or lie in close proximity to protein domains, including those that bind linear motifs. Together with their dynamic regulation, these observations show that microexons contribute important and complementary roles to longer neural exons in the remodeling of protein interaction networks that operate during neuronal maturation.

Most microexons display high inclusion at late stages of neuronal differentiation in genes (e.g. Src (Black, 1991), Bin1, Agrn, Dock9, Shank2, Robo1) associated with axonogenesis and the formation and function of synapses. Supporting such functions, an alternative microexon overlapping the SH3A domain of Intersectin 1 (Itsn1) has been reported to promote an interaction with Dynamin 1, and was proposed to modulate roles of Itsn1 in endocytosis, cell signaling and/or actin-cytoskeleton dynamics (Dergai et al., 2010). A neural-specific microexon in Protrudin/Zfyve27 was recently shown to increase its interaction with the vesicle-associated membrane protein-associated protein (VAP), and to promote neurite outgrowth (Ohnishi et al., 2014). Similarly, in the present study, it is shown that a 6 nt neural microexon in Apbb1/Fe65 promotes an interaction with Kat5/Tip60. Apbb1 is an adapter protein that functions in neurite outgrowth (Cheung et al., 2014; Ikin et al., 2007) and synaptic plasticity (Sabo et al., 2003), processes that have been linked to neurological disorders including ASD (Hussman et al., 2011). Consistent with these findings, the present inventors have previously shown that nSR100 promotes neurite outgrowth (Calarco et al., 2009). In the present study it is further demonstrated that it controls the switch-like regulation of most neural microexons, and that its reduced expression is linked to the altered splicing of microexons in the brains of subjects with ASD. In most cases, decreased inclusion or splicing of microexons is seen in the brains of subject with ASD but in a few cases increased inclusion is observed.

Many of the conserved, neural-regulated microexons identified in this study are misregulated in ASD individuals, including the microexon in AP1S2 that strongly promotes an interaction with the AP1B1 subunit of the AP1 intracellular transport complex. Intriguingly, several other genes containing microexons are genetically linked to ASD, intellectual disability and/or functions in memory and learning (see Results). Another link to ASD is the observation that nSR100 is strongly co-expressed in the developing human brain in a gene network module, M2, which is enriched for rare de novo ASD-associated mutations (Parikshak et al., 2013). Furthermore, additional genes containing microexons may have as yet undiscovered roles in ASD and or other neuropsychiatric disorders. For example, the microexon in APBB1 is also significantly misregulated in brain tissues from ASD subjects (FIGS. 14B and 14E). Without being bound by theory, it is possible that the misregulation of microexons, at least in part through altered expression of nSR100, perturbs protein interaction networks required for proper neuronal maturation and function, thus contributing to ASD as well as other neurodevelopmental disorders. Consistent with this view, recent reports have begun to link individual microexons with neurodevelopmental disorders, including ASD (Zhu et al., 2014), schizophrenia (Ovadia and Shifman, 2011) and epilepsy (Rusconi et al., 2014). The discovery and characterization of widespread, neural-regulated microexons in the present study thus enables a systematic investigation of new and highly conserved mechanisms controlling protein interaction networks associated with vertebrate nervous system development and neurological disorders.

Experimental Procedures

RNA-Seq Data and Genomes

Unless stated otherwise, RNA-Seq data was generated from Poly(A)$^+$ RNA. Analyses used the following genome releases: *Homo sapiens*, hg19, *Mus musculus*, mm9; *Gallus gallus*, galGal3; *Xenopus tropicalis*, xenTro3; *Danio rerio*, danRer7; *Callorhinchus milii*, v1.0).

Alternative Splicing Analysis Pipeline

A multi-module analysis pipeline was developed that uses RNA-Seq, expressed sequence tag (EST) and cDNA data, as well as gene annotations and evolutionary conservation, to assemble libraries of exon-exon-junctions (EEJs) for subsequent read alignment to detect and quantify AS events in RNA-Seq data. For cassette exons, three complementary modules were developed for assembling EEJs: (i) A "transcript-based module", employing cufflinks (Trapnell et al., 2010) and alignments of ESTs and cDNAs with genomic sequence (Khare et al., 2012); (ii) A "splice site-based module", utilizing joining of all hypothetically-possible EEJ combinations from annotated and de novo splice sites (Han et al., 2013); and (3) A "microexon module", including de novo searching of pairs of donor and acceptor splice sites in intronic sequence. Alt3 or Alt5 events were quantified based on the fraction of reads supporting the usage of each alternative splice site. Intron retention was analyzed as recently described (Braunschweig et al., 2014).

LUMIER Assay

HEK-293T cells were transiently transfected using Polyfect (Qiagen) with *Renilla* Luciferase (RL)-tagged Apbb1, with or without inclusion of the microexon, or with a version consisting of two alanine substitutions, together with 3Flag-tagged Kat5. Subsequent steps were performed essentially as described previously (Ellis et al., 2012).

Immunoprecipitation and Immunoblotting

HEK-293T cells were transiently transfected using Lipofectamine 2000 (Life Technologies). Cells were lysed in 0.5% TNTE. After pre-clearing with protein G-Sepharose, lysates were incubated with anti-Flag M2 antibody (Sigma) or anti-Hemagglutinin (HA)-antibody (Roche) bound to Protein-G Dynabeads (Life Technologies™) for 2 hours at 4° C. Immunoprecipitates were washed 5 times with 0.1% TNTE, subjected to SDS-PAGE, transferred onto nitrocellulose and immunoblotted with the anti-Hemagglutinin (HA)-antibody (Roche) or anti-Flag M2 antibody (Sigma). Detection was achieved using horseradish peroxidase-conjugated rabbit anti-rat (Sigma) or sheep anti-mouse secondary antibodies (GE Healthcare) and chemiluminescence. ImageJ was used for quantification of band intensities.

Analysis of Microexon Regulation

Available RNA-Seq Data from Splicing Factor-Deficient or -overexpressing systems were used to identify misregulated exons and microexons. To investigate regulation by nSR100, PAR-iCLIP data and motif enrichments analyses, as recently described (Raj et al., 2014) was used.

Comparison of ASD and Control Brain Samples 24 autistic individuals and 24 controls matched by age and gender were analyzed. Samples from superior temporal gyrus (Brodmann areas ba41/42/22) were dissected retaining grey matter from all cortical layers, and RNA was isolated using the miRNeasy kit (Qiagen). Ribosomal RNA was depleted from 2 µg total RNA with the Ribo-Zero Gold kit (Epicentre), and then size-selected with AMPure XP beads (Beckman Coulter). An average of 64 million, 50 bp paired-end reads were generated for each sample. The 12 samples with the strongest ASD-associated differential gene expression signature and 12 control samples with a signal that is closest to the median of all controls were selected for downstream analyses. Sample selection was independent of any information on splicing changes.

Example 2. Essential Roles for the Splicing Regulator nSR100/SRRM4 During Nervous System Development Summary To investigate the functions of nSR100 and microexons in vivo, mice carrying a conditional exon deletion in the nSR100 (Srrm4) gene that results in widespread loss of the full-length protein were generated. It was observed that nSR100 is essential for early postnatal survival of a large majority of mutant animals, with the few surviving animals displaying balance defects similar to those seen in bv/by mice, but also exhibiting persistent tremors. Additionally, loss of nSR100 in mice results in impaired neurite outgrowth in the diaphragm, defective cortical layering, and a failure of callosal axons to cross the midline in the forebrain. Using a RNA-Seq analysis pipeline, all classes of AS, including alternative microexons, that are controlled by nSR100 in vivo are defined. A large fraction of alternative cassette exons and microexons positively regulated by nSR100 are neurally enriched, which is not the case for other classes of nSR100-dependent splicing events. Moreover, a higher proportion of neural microexons are affected by disruption of nSR100 than are other neural-regulated AS events. These include highly conserved exons with the potential to insert only one or two amino acids in proteins of key functional relevance to neuronal maturation. An nSR100-regulated 6-nucleotide microexon in the Unc13b gene promotes neurite growth in mouse primary neurons. Cortical neurons from nSR100$^{\Delta 7-8/\Delta 7-8}$ mice display a neuritogenesis defect, and expression of Unc13b transcripts including the microexon, but not transcripts lacking the microexon, is sufficient to rescue the mutant phenotype.

Results

Perinatal Mortality in nSR100 Mutant Mice

Figure 15:
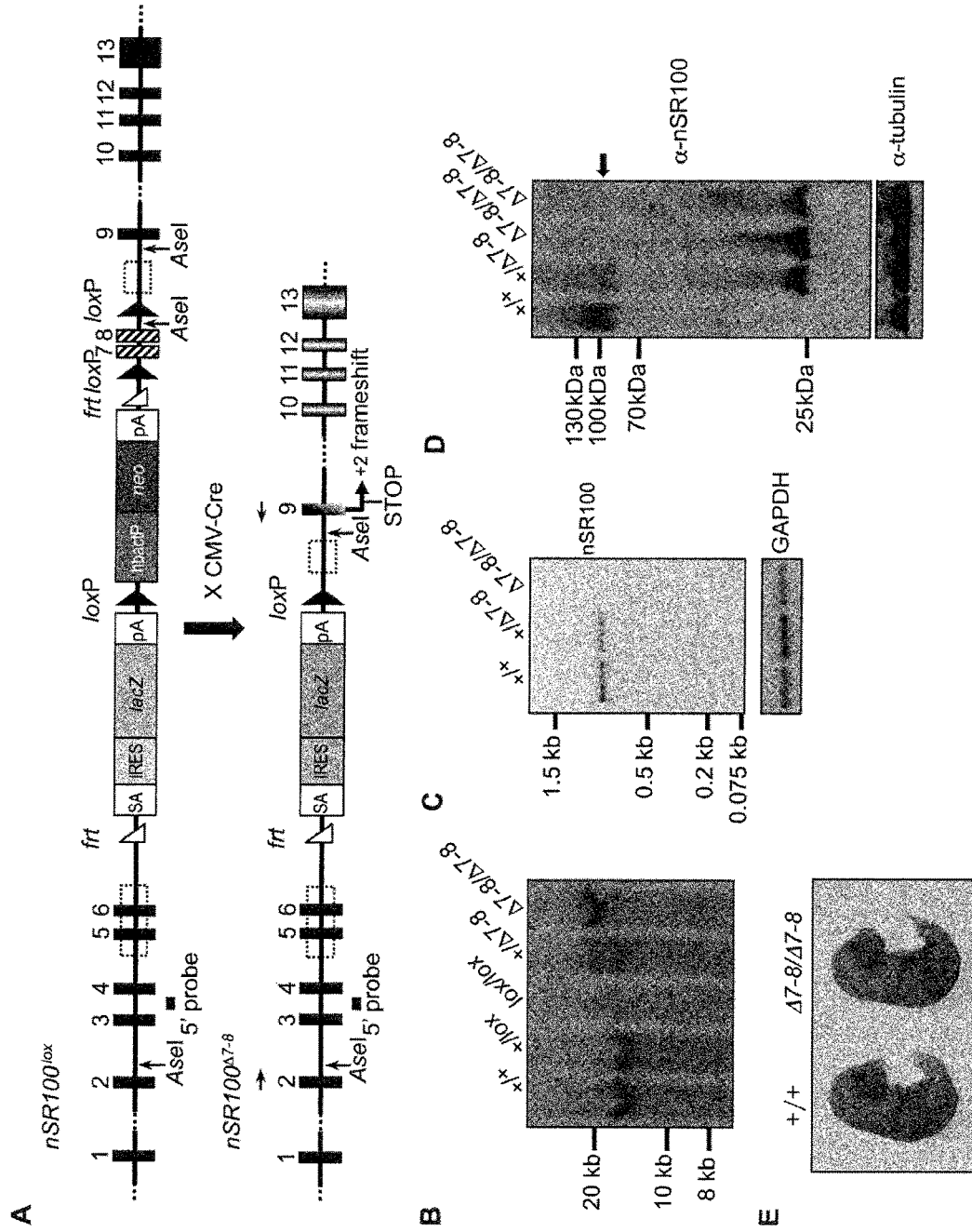
FIG. 15 shows the loss of full-length nSR100 protein in nSR100$^{\Delta7-8/\Delta7-8}$ mutant mice. A) Upper panel: map of the conditional nSR100/SRRM4 allele showing position of exons, Frt (open triangles) and LoxP (solid triangles) recombination sites, homology arms (dashed boxes), and cutting sites for the AseI restriction enzyme (vertical arrows) and the probe (solid bar) used for Southern blot analysis (see B). Lower panel: map of the KO allele following crossing of the conditional nSR100$^{frt-lox}$ mouse with a CMV-Cre transgenic line. Cre-LoxP recombination drives the loss of nSR100 exons 7 and 8 and results in a +2 frameshift and the introduction of several premature termination codons downstream of the deletion. The positions of AseI sites and probe used for Southern blot analysis (see B) and primers used for RT-PCR (horizontal arrows—see C) are indicated. Homozygous nSR100$^{lox/lox}$ mice do not display any overt phenotype. B) Southern blot analysis on tail DNA from wild-type (+/+), conditional (lox) and KO mice (Δ7-8). DNA was digested with AseI and hybridized with a probe binding upstream of the 5' homology arm on the conditional allele in intron 3. Predicted band size is 15.4 kb in wild-type, 16.4 kb in conditional and 19.4 kb in KO alleles, respectively. C) RT-PCR on E16.5 whole brain total RNA using primers amplifying exon 2 to exon 9. No transcript could be detected in homozygous mutants. D) Western blotting on E17.5 whole brain lysates using an antibody to nSR100. Full-length nSR100 protein is completely lost in homozygous mutants (arrow), but a 25 kDa fragment is expressed from the Δ7-8 allele. E) E17.5 mutant embryos display normal morphology.
Figure 16:
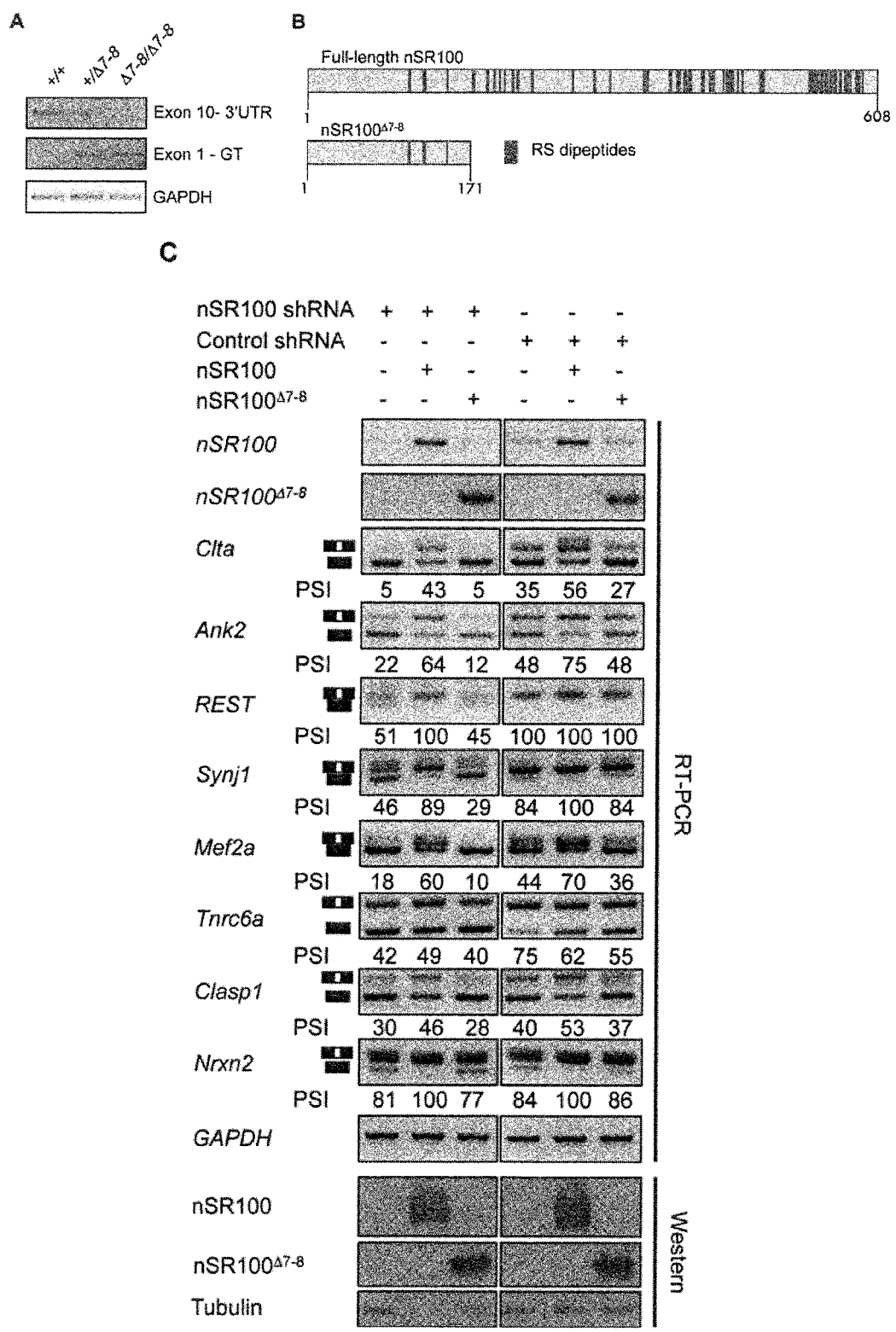
FIG. 16 shows that the N-terminal nSR100 fragment expressed in nSR10$^{Δ7-8}$ mice has no splicing activity. A) RT-PCR showing the presence of a hybrid transcript between nSR100 exons 1 to 6 and the gene trap (GT) included in the targeting construct in heterozygous and homozygous mutant mice. Primers were located downstream of the deletion (exon10-3'UTR) or overlapping upstream exons and the gene trap (exon1-GT). B) Protein domain comparison between full-length nSR100 and the 25 kD N-terminal fragment produced in mutant mice. The N-terminal fragment only contains 171 of the 608 total residues of nSR100 and lacks most nSR100 RS repeats. C) Splicing complementation assay. Full-length nSR100 or the 25 kD N-terminal fragment were transfected in Neuro2A cells expressing control or nSR100-targeting shRNA. Splicing patterns of 8 known nSR100 targets were assayed by RT-PCR.

Previous studies using in vivo knockdown of nSR100 in the zebrafish and mouse embryo suggested that nSR100 may play a role in several aspects of nervous system development (Calarco et al. 2009; Raj et al. 2011). To address the full extent of nSR100 functions in the developing nervous system, mice carrying a conditional KO nSR100$^{lox}$ allele from embryonic stem cells obtained from EUCOMM were generated. The nSR100$^{lox}$ allele includes a LacZ reporter and LoxP sites framing nSR100 exons 7 and 8 (FIG. 15A). Southern blotting confirmed the integrity of the integration site in nSR100$^{lox}$ mice (FIG. 15B). By crossing nSR100$^{lox/+}$ mice with mice carrying the widely expressed CMV-Cre recombinase transgene, nSR100$^{\Delta 7-8}$ mice, in which exons 7 and 8 have been deleted throughout the animal and in the germline, were obtained. This deletion introduces a +2 frameshift in downstream exons and causes complete loss of full-length nSR100 transcript and protein in homozygous nSR100$^{\Delta 7-8}$ mice (FIGS. 15C and 15D). Western blotting revealed that a 25 kD protein fragment could be detected in homozygous and heterozygous mutant mice using an antibody to the N-terminus of nSR100. RT-PCR confirmed that a transcript encompassing nSR100 exons 1 to 6 was preserved in the mutant mouse (FIG. 16A). This N-terminal fragment lacks the RS-rich domain of nSR100 (FIG. 16B), which, based on previous studies of nSR100 and other SR proteins, is predicted to function in the formation of protein-protein and/or protein-RNA interactions required for splicing complex formation (Wu and Maniatis 1993; Shen and Green 2004; Raj et al. 2014). In contrast to full-length protein, overexpression of the truncated protein in Neuro2a cells depleted of endogenous nSR100 fails to restore nSR100-dependent splicing (FIG. 16C, lanes 1-3). Moreover, when co-expressed with full-length nSR100 in Neuro2a cells, the truncated mutant does not interfere with splicing of nSR100 target exons (FIG. 16C, lanes 4-6). Thus, the nSR100$^{\Delta 7-8/\Delta 7-8}$ mice likely represent functionally null nSR100 mutants.

It was observed that over 85% of nSR100$^{\Delta 7-8/\Delta 7-8}$ mice died in the first few hours after birth. Although these mice present no gross morphological phenotype at late embryonic stages or at birth (FIG. 15E), they show signs of respiratory defects, including irregular breathing and heavy gasping, and become cyanotic soon after birth. This phenotype contrasts sharply with the previously described nSR100 mutant by mouse, in which only the last 103 amino acids from the C-terminus of nSR100 are lost. Homozygous by mice are viable and display a phenotype limited to the degeneration of the inner hair cells of the inner ear (Deol and Gluecksohn-Waelsch 1979; Nakano et al. 2012). Interestingly, the few homozygous nSR100$^{\Delta 7-8/\Delta 7-8}$ survivors obtained from crossing heterozygous parents display a head tilting and circling behavior, reminiscent of the balancing defect observed for the by mutant strain. However, in contrast to the by mutant, all surviving nSR100$^{\Delta 7-8/\Delta 7-8}$ individuals additionally display pronounced tremors, a phenotype that is often associated with neurobiological defects. Embryos harvested at E17.5 and E18.5 were found at Mendelian ratios, indicating that loss of nSR100 does not cause early embryonic lethality. The extensive perinatal mortality observed in nSR100$^{\Delta 7-8/\Delta 7-8}$ mice thus reflects the indispensable nature of nSR100 during embryonic development.

Loss of nSR100 Impairs Diverse Neuronal Processes

Figure 17:
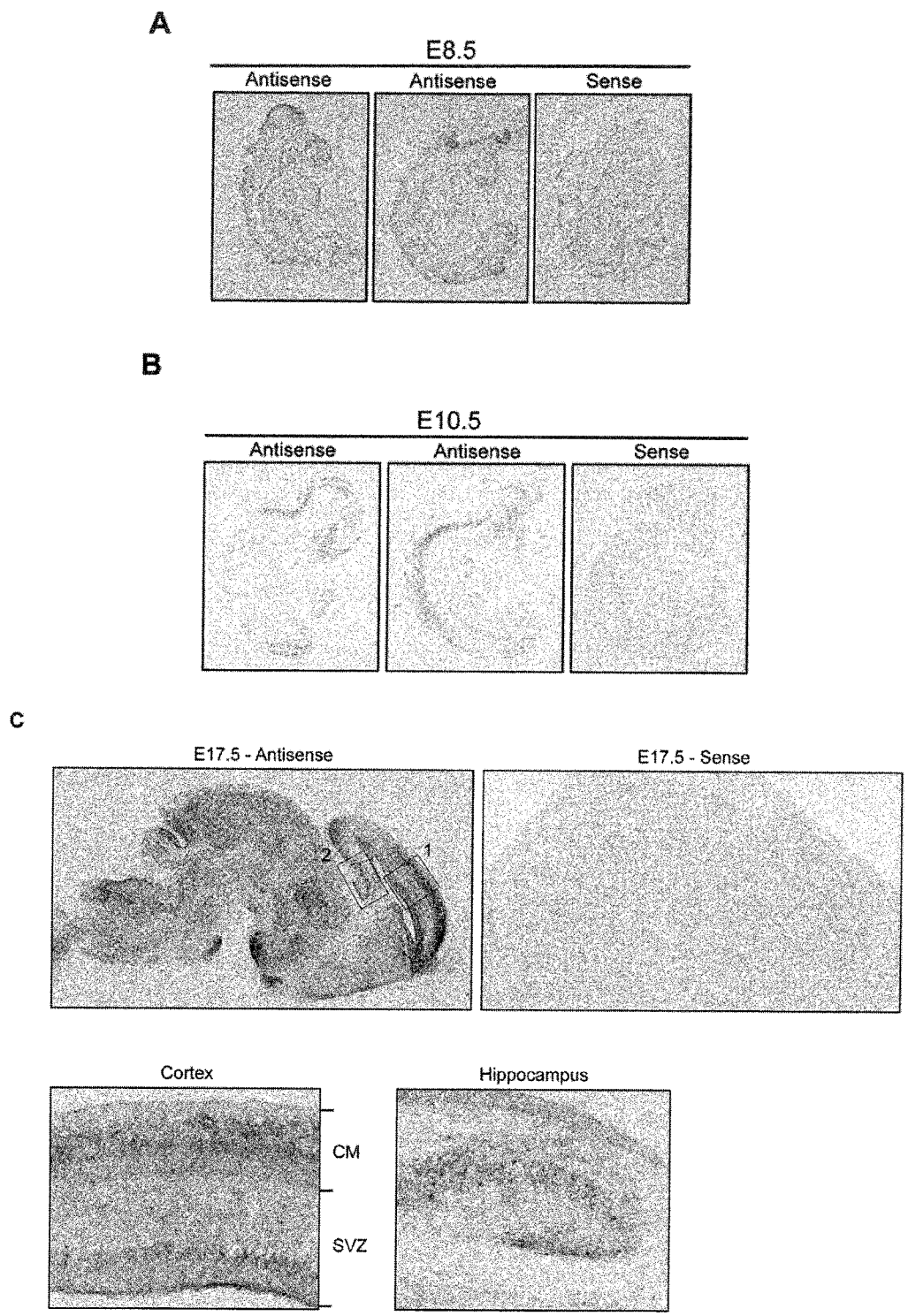
FIG. 17 shows in situ hybridization for nSR100 transcripts with neural-specific expression of nSR100 during mouse development. A) In situ hybridization on sagittal sections of wild-type embryos at E8.5 and (B) E10.5 using an antisense (two left panels) or sense (right panel, negative control) probe to exons 9 to 13 of nSR100 confirms that nSR100 expression is restricted to the nervous system during development. Sagittal sections of the same embryos are shown. C) In situ hybridization on a sagittal section of wild-type embryonic brain at E17.5 shows widespread nSR100 expression in the brain, including strong expression in the cerebral cortex (boxed area 1 and lower left panel) and hippocampus (boxed area 2 and lower right panel). Top right panel shows absence of signal when a sense probe is hybridized. CM: cortical mantle, SVZ: subventricular zone.
Figure 18:
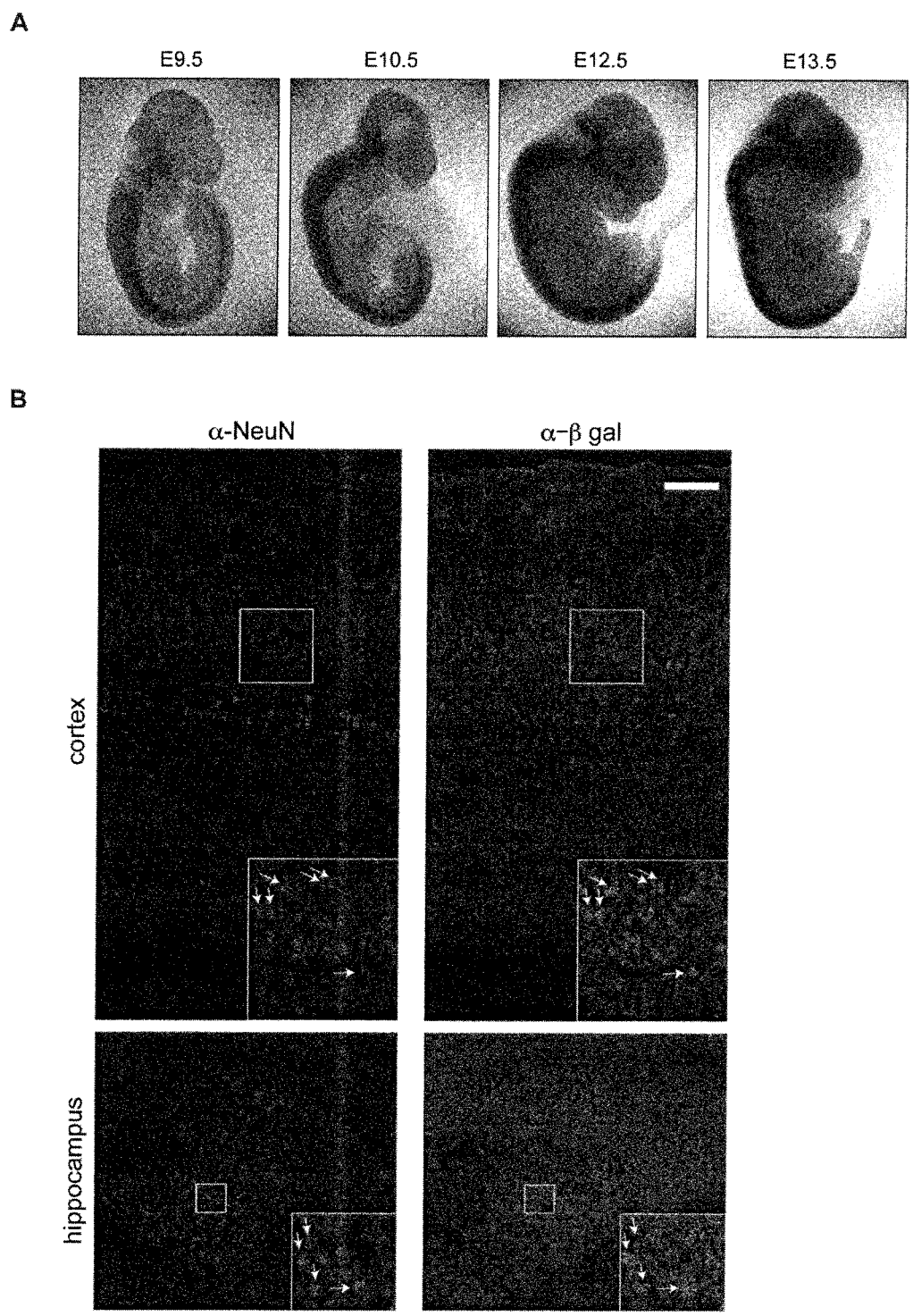
FIG. 18 shows LacZ reporter expression in conditional nSR100$^{lox}$ allele revealing neuronal-specific expression of nSR100 during mouse development. A) X-Gal staining was performed on whole nSR100$^{+/lox}$ embryos at different time points and shows β-galactosidase expression from E9.5 in both the brain and neural tube. B) A coronal section of a heterozygous E18.5 nSR100$^{+/lox}$ brain bearing the conditional allele was stained with antibodies to β-galactosidase (right panels) and NeuN (left panels). Co-staining reveals that all β-gal$^+$ cells also express NeuN (arrows). Upper panels show cortex with inset showing co-localization of NeuN and β-gal signals (arrows). Bottom panels show hippocampus with inset showing co-localization of NeuN and β-gal signals. Scale bars: 50 µm; insets: 10 µm.

The respiratory problems accompanying perinatal mortality in nSR100$^{\Delta 7-8/\Delta 7-8}$ mice suggested that the innervation of the diaphragm might be impaired by loss of nSR100 protein. It was asked if nSR100 is expressed in the peripheral nervous system where motor neurons innervating the diaphragm are located. nSR100 expression was surveyed at different time points during development using both the LacZ cassette in the nSR100$^{lox}$ mouse as a reporter for nSR100 gene expression and in situ RNA hybridization in wild-type mice. X-Gal staining and in situ hybridization show that nSR100 is expressed in both the brain and the neural tube during early neurogenesis, with the reporter being detectable as early as E9.5 and nSR100 mRNA expressed as early as E8.5 (FIGS. 17A and 17B). In situ hybridization at E18 shows that nSR100 expression is maintained in the brain during development, with high expression in the cerebral cortex and hippocampus late in embryogenesis (FIG. 17C). Using a marker for post-mitotic neurons along with an antibody to β-galactosidase in nSR100$^{+/lox}$ mice reveals that most neurons express nSR100 (FIGS. 18A and 18B). These results corroborate analyses of RNA-Seq data from different neural cell types, a neuronal differentiation time series, as well as from different tissue samples (Raj et al. 2014), showing that nSR100 expression is neuron-specific, occurs in the brain and dorsal root ganglia, and increases in the brain through embryogenesis from E11 to E18, before decreasing in the adult. Taken together, these experiments confirm that nSR100 is neuronal-specific and is expressed in both the central and peripheral nervous system in the developing mouse.

Figure 19:
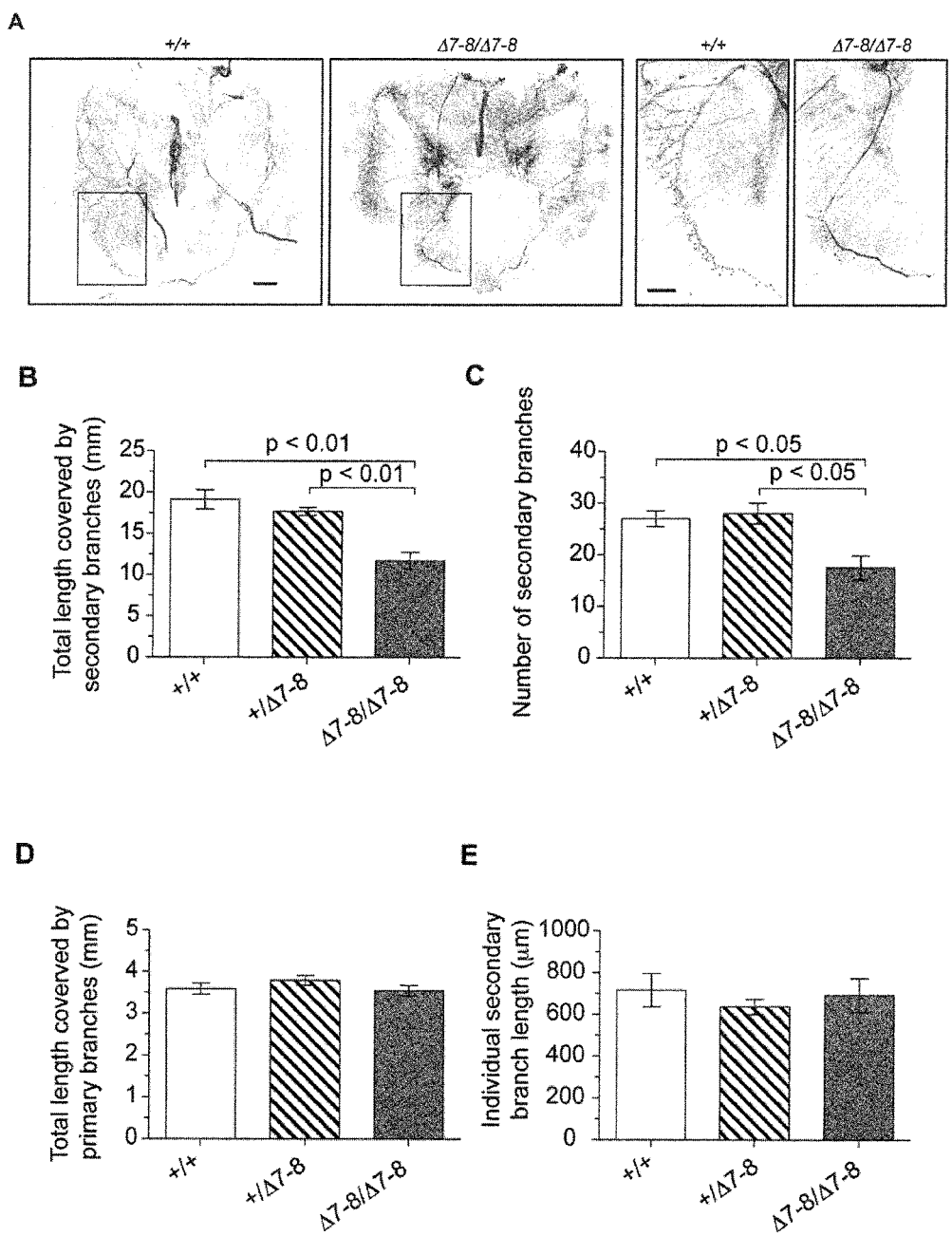
FIG. 19 shows that loss of nSR100 impairs neurite outgrowth in motor neurons. A) Whole-mount staining of E18.5 diaphragms with anti-neurofilament antibody to highlight innervation. Small dots mark secondary branches in insets. Scale bars: 1,000 µm in left panels, 500 µm in inset. B) The total distance covered by all secondary axons and (C) the number of secondary branches present on the right ventral primary branch of the phrenic nerve were quantified on 3 or 4 individuals for each genotype. The total distance covered by secondary neurites and the number of secondary branches formed is significantly lower in homozygous mutants. One-tailed Mann-Whitney test. D) The total length covered by primary branches is not affected in homozygous mutants. E) The average length of each individual secondary branch in the mutant is the same as wild-type and heterozygous littermates. n=3 diaphragms for wild-type and heterozygous embryos and n=4 diaphragms for homozygous mutants. One-tailed Mann-Whitney test. Whiskers indicate 10$^{th}$ and 90$^{th}$ percentiles in all box plots.
Figure 20:
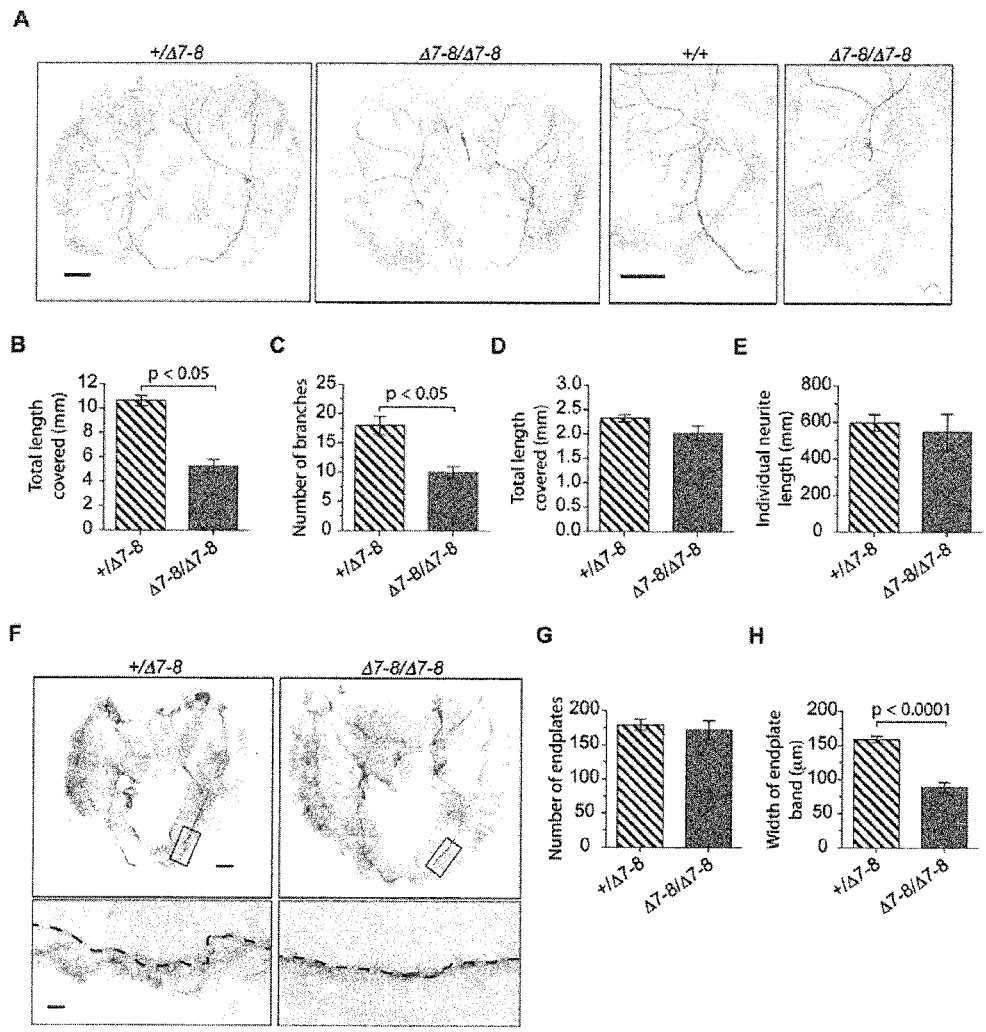
FIG. 20 shows that loss of nSR100 affects sprouting of secondary neurites but not the formation of neuromuscular junctions. A) Whole-mount immunofluorescence of E16.5 diaphragms from heterozygous and homozygous mutant embryos using an antibody to neurofilament highlights defective innervation in homozygous mutants. B) The length covered by secondary branches and (C) their number are already defective in homozygous mutants at E16.5. n=3 diaphragms for each genotype. One-tailed Mann-Whitney test. D) The total length covered by primary branches is not affected at E16.5. E) The average length of individual secondary branches in the mutants is the same as wild-type and heterozygous littermates at E16.5. n=3 diaphragms for each genotype. One-tailed Mann-Whitney test. F) Whole-mount staining of E18.5 diaphragms from heterozygous and homozygous mutant mice using an anti-neurofilament antibody to highlight innervation. Lower panels show higher magnification of boxed regions with neurofilament and Alexa-594-labelled α-bungarotoxin staining to highlight innervation (dashed line) and motor endplates (small points distributed around nerve branch). Scale bars: 1000 µm in upper panel, 100 µm in inset. G) The number of endplates found on a 475 µm-long segment was quantified on the left ventrally-projecting nerve of the diaphragm and (H) the distance between endplates and the primary branch was measured (right). 4 or 5 diaphragms were analyzed per genotype. One-tailed Mann-Whitney test. Whiskers indicate 10$^{th}$ and 90$^{th}$ percentiles in all box plots.
Figure 21:
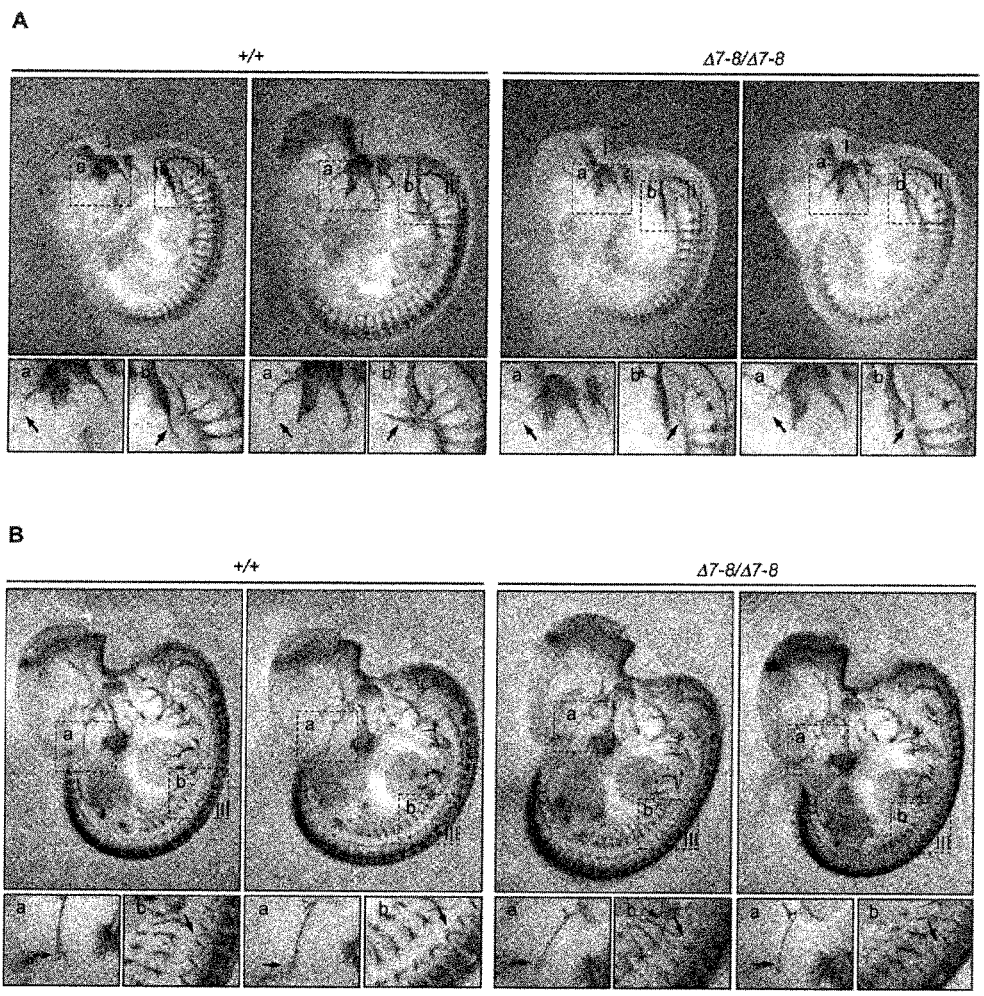
FIG. 21 shows early innervation defects in nSR100$^{Δ7-8}$ mutant mice. A) Whole E10.5 and B) E12.5 embryos were stained with an antibody to neurofilament. Two embryos of each genotype and at each time point are shown. Arrows highlight innervation defects. Insets show higher magnification of boxed regions "a" and "b" in each panel. I: trigeminal nerves; II: hypoglossal nerves; III: spinal nerves

Next the innervation of the diaphragm just before birth at E18.5 using an antibody to neurofilament on whole-mount preparations was visualized. This staining revealed that primary branches deriving from the phrenic nerve appear thinner in nSR1000$^{\Delta 7-8/\Delta 7-8}$ mice (FIG. 19A). In addition, it was observed that the total length covered by secondary motor axons is greatly reduced, and that the number of secondary axons is decreased by almost two-fold in homozygous mutants, a phenotype not seen in heterozygotes (FIGS. 19B and 19C). These defects are already present at E16.5 (FIG. 20A-C), suggesting that the lack of secondary branches does not stem from degeneration or pruning but rather from deficient sprouting in the mutant mice. The overall distance covered by primary axons was not affected at either E16.5 or E18.5 (FIGS. 20D and 20E). Each individual secondary branch forming in mutants projects as far as its wild-type counterpart (FIGS. 20F and 20G), and motor endplates form in the same numbers in the diaphragm of nSR100 homozygous and heterozygous mutant mice, although at higher density in the homozygous mutant most likely due to a lack of secondary branching (FIG. 20H). The diminished axon sprouting capacities of motor neurons in the diaphragm of nSR100$^{\Delta 7-8/\Delta 7-8}$ mice likely contributes to nSR100-dependent respiratory defects and early postnatal death. These axon guiding or branching defects are not limited to phrenic nerve innervation as defective formation of the trigeminal, hypoglossal and spinal nerves was detected in whole-mount staining of E10.5 and E12.5 embryos (FIG. 21).

Figure 22:
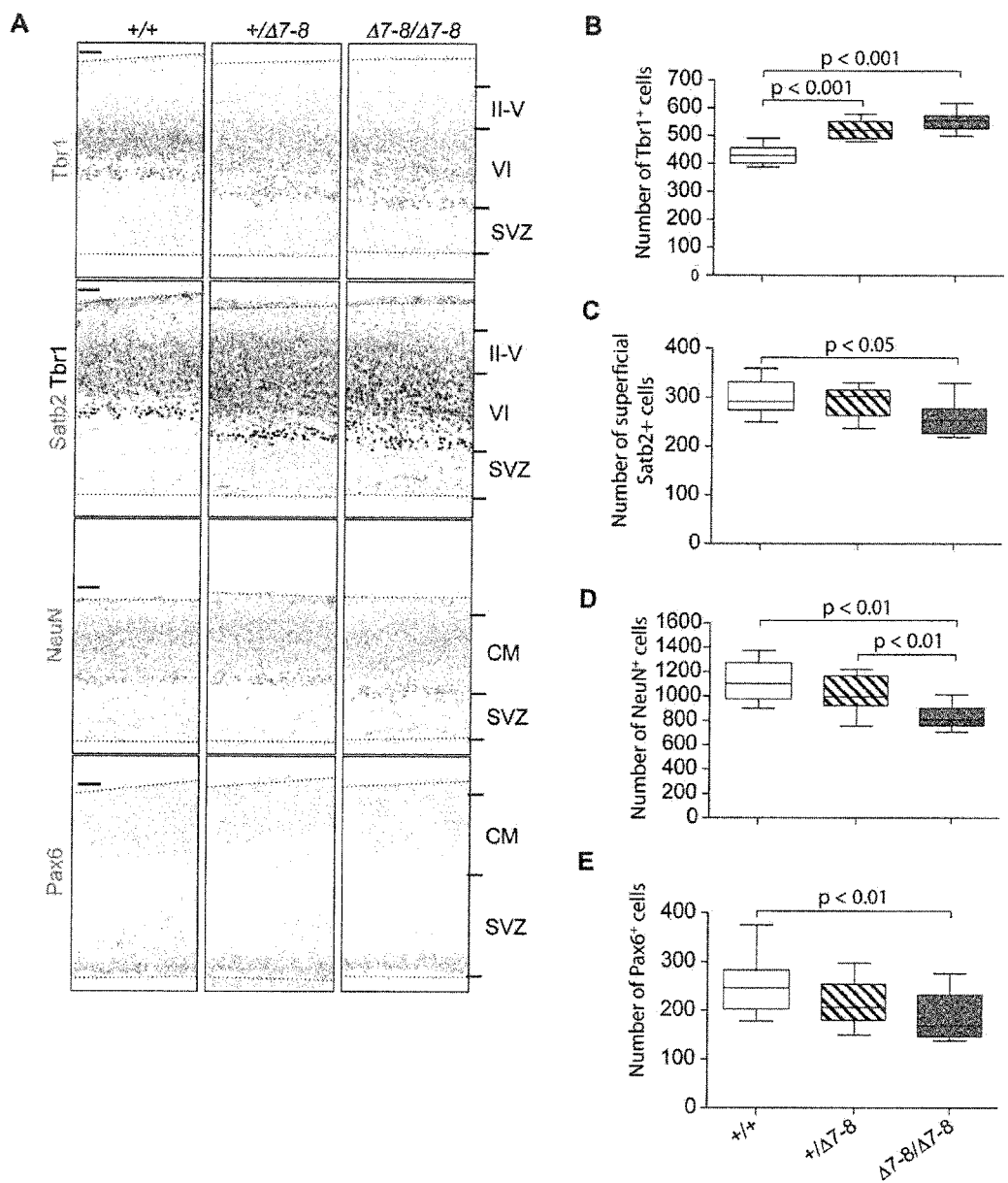
FIG. 22 shows that nSR100 mutant mice display aberrant cortical layering and premature neurogenesis. A) Immunofluorescence using antibodies to Tbr1, Satb2, NeuN and Pax6 to label deep layer VI, superficial layers II-V, postmitotic neurons and neural progenitors, respectively, on coronal sections of E18.5 embryonic brains. Scale bars: 50 µm. SVZ: subventricular zone; I-VI: cortical layers I-VI; CM: cortical mantle. Dashed white lines highlight ventral and dorsal cortical boundaries. B-E) Number of Tbr1$^-$ (B), layer II-V Satb2$^+$ (C), NeuN$^+$ (D) and Pax6$^+$ cells were quantified for 3 to 5 individuals per genotype and on 3 sections for each individual. These stainings highlight an increase in the number of deep, early born Tbr1+ neurons and a corresponding decrease in superficial Satb2+ neurons total number of neurons (NeuN+) and neural progenitors (Pax6+). One-way ANOVA with Tukey-Kramer post-hoc test. F) EdU-labeling was performed at E12.5 (black), and brains were harvested at E18.5 and stained with an antibody to Tbr1 (light grey). Scale bar: 100 µm. G-I) The number of EdU+ cells (black) was counted in deep layer VI (G), superficial layers II-V (H) and the subventricular zone (I). One-way ANOVA with Tukey-Kramer post-hoc test. J) The thickness of the subventricular zone was measured from the pre-plate to the lateral ventricle and relative to the total thickness of the cortex measured from the surface of layer I to the lateral ventricle. One-way ANOVA with Tukey-Kramer post-hoc test. Whiskers indicate 10$^{th}$ and 90$^{th}$ percentiles in all box plots.
Figure 22:
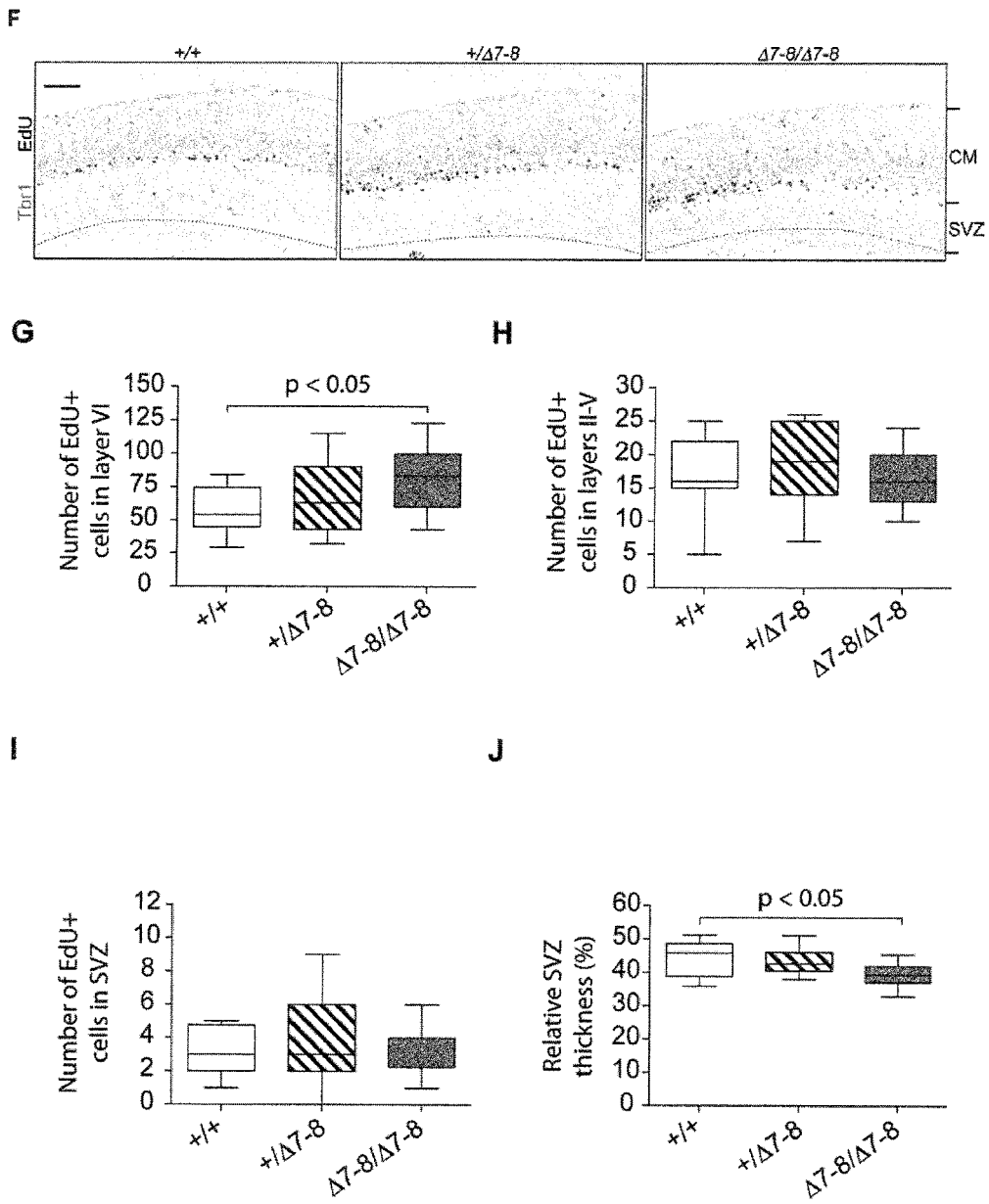

Because nSR100 is expressed at the highest level in the brain and in utero knockdown of nSR100 resulted in defects in neuronal differentiation in the cortex (Raj et al. 2011), it was investigated whether cortical anatomy was modified in nSR100 mutants. The establishment of defined cortical layers is an important and conserved step in mammalian brain development. Overall thickness of the cortex was not significantly different in nSR100$^{\Delta 7-8/\Delta 7-8}$ mice, but immunofluorescence using layer-specific markers revealed that the deep, Tbr1-positive cortical layer VI is enlarged and comprised of more cells in the homozygous mutant, a phenotype also seen to a lesser extent in heterozygotes (FIGS. 22A and 22B). The definition of the preplate was also altered in homo- and heterozygotes. Staining with an antibody to Satb2 to highlight cortical layers II to IV revealed a decrease in the number of superficial neurons (FIGS. 22A and 22C) and staining with antibodies to NeuN and Pax6 revealed a decrease in the overall number of post-mitotic neurons (FIGS. 22A and 22D) and neural progenitors (FIGS. 22A and 22E), respectively. Pulse-chase labeling of dividing cells at embryonic day 12.5 using the 5-ethynyl-2'-deoxyuridine (EdU) nucleoside analog further showed that loss of nSR100 results in premature neurogenesis (FIG. 22F-J). Without being bound by theory, this suggests that nSR100 may contribute to the rate and timing at which new neurons are born from progenitors and/or to the migration of newly born neurons.

Figure 23:
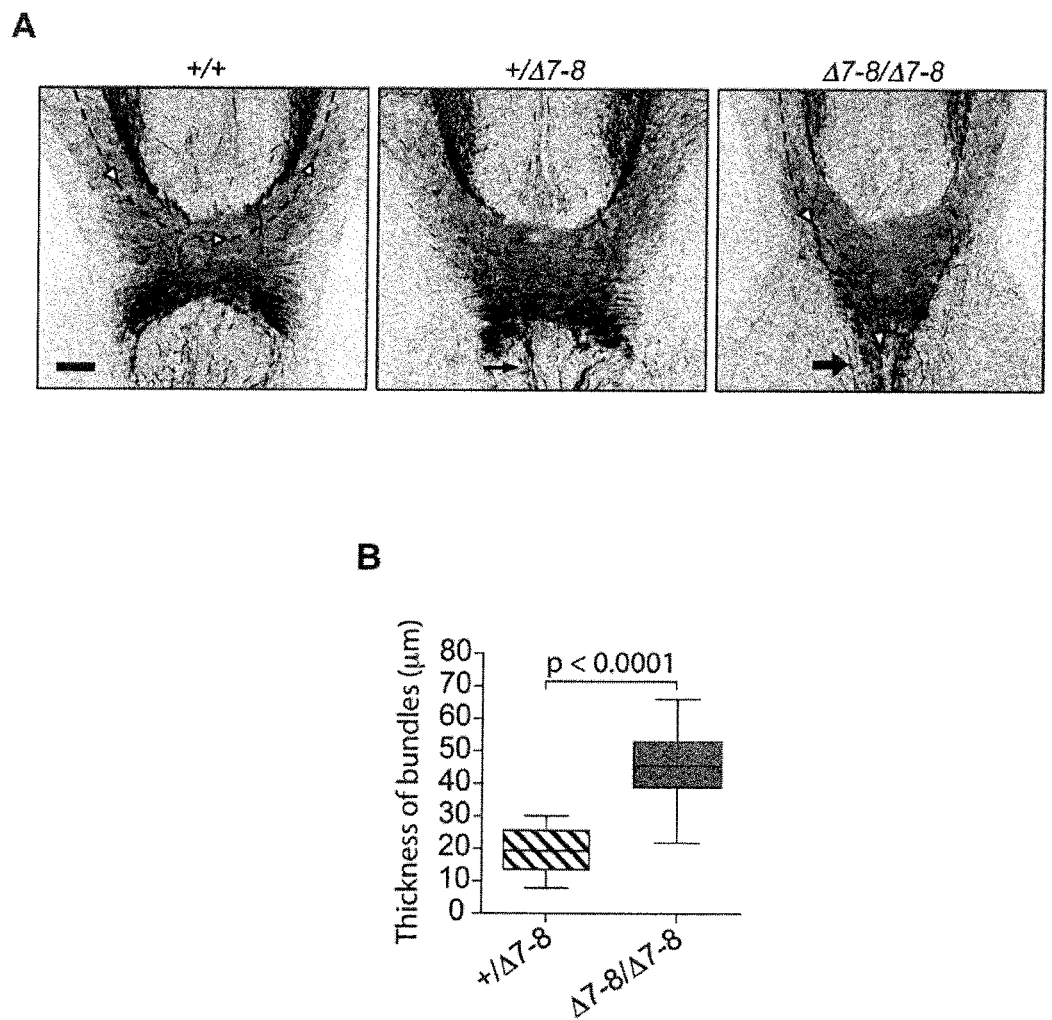
FIG. 23 shows midline crossing defects in nSR100 mutant mice. A) Negative gray scale images of immunofluorescence using an antibody to neurofilament on coronal sections of the rostral part of the corpus callosum of E18.5 embryos. Dashed lines with arrowheads show either the prototypical tracts of callosal axons in the wild-type (+/+) or the ectopic ventral projections in the homozygous mutant ($\Delta 7$-8/$\Delta 7$-8). Arrows point at ectopic bundles in the heterozygous and homozygous mutants. Scale bar: 100 μm. B) The thickness of ventrally projecting bundles was measured at 3 levels on each side of the corpus callosum for 3 or 4 individuals per genotype and on 3 sections for each individual. Whiskers indicate $10^{th}$ and $90^{th}$ percentiles. One-tailed Mann-Whitney test.

While analyzing cortical layering, it was noticed that the morphology of the rostral part of the corpus callosum in nSR100$^{\Delta 7-8/\Delta 7-8}$ mice differed from its stereotypical shape. The corpus callosum consists mostly of cortical axons crossing the midline to contact neurons of the opposite hemisphere. This interconnection between hemispheres is essential for the fast processing of information and cognition (Paul et al. 2007). Neurofilament immunostaining revealed that several callosal axons are misguided in the absence of nSR100 and form thick ectopic fascicles similar to Probst bundles, projecting ventrally instead of crossing the midline (FIG. 23A). This phenotype is never observed in wild-type mice, but is important enough in homozygous mutants to alter the shape of the corpus callosum. Although the corpus callosum of nSR100$^{+/\Delta 7-8}$ mice does not appear grossly misshapen, it also contains ectopic ventrally-projecting bundles (FIG. 23B). These observations represent the first example of a midline crossing defect as a consequence of the knockout of an alternative splicing regulator. Overall, the phenotypic survey so far shows that nSR100 controls a diverse array of neuronal functions in both the central and peripheral nervous system, including cortical layering, axon guidance, and midline crossing.

An In Vivo nSR100-Regulated Splicing Program

Figure 24:
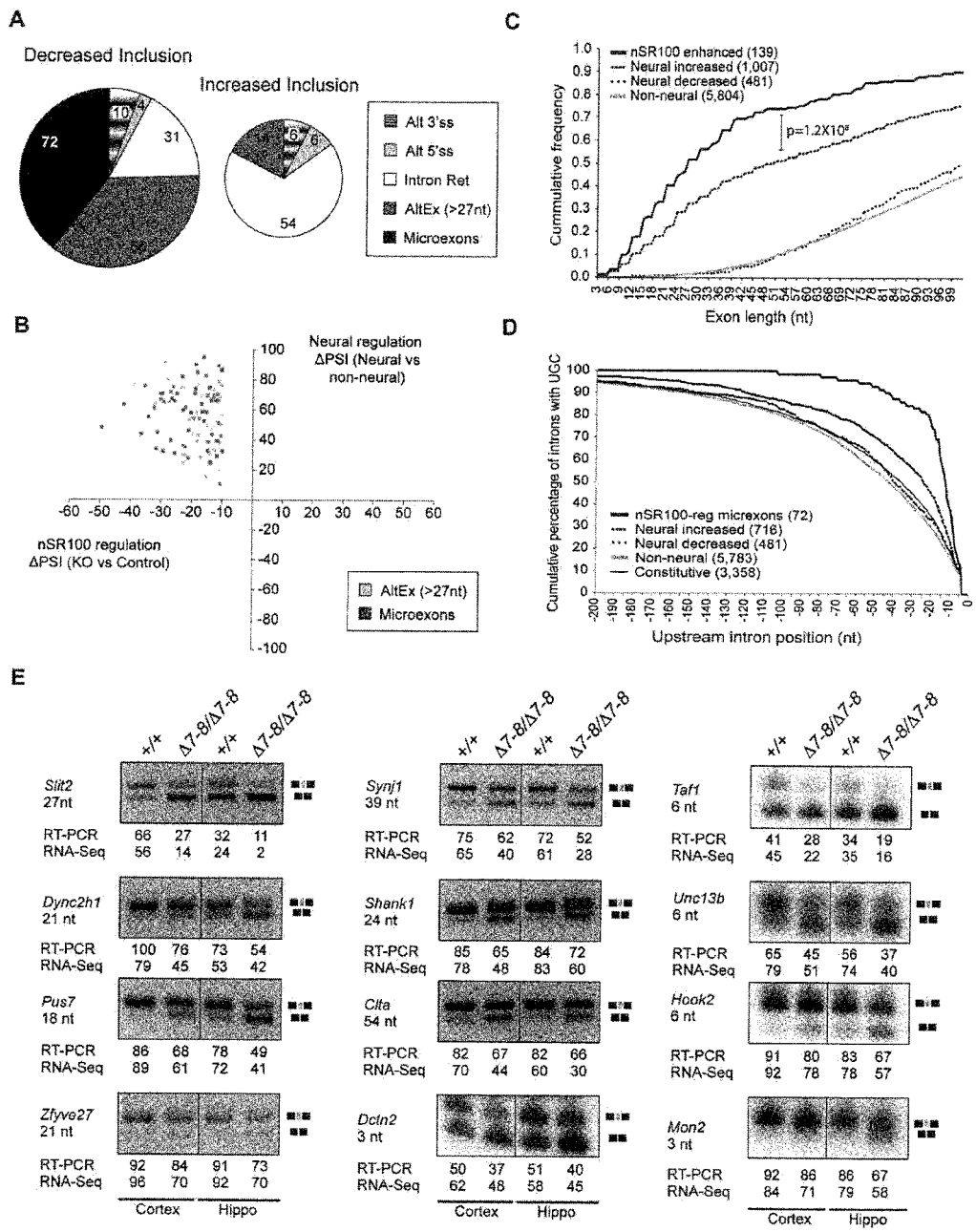
FIG. 24 shows a nSR100-regulatory program in the mouse brain. A) Number of AS events showing significantly decreased (left) or increased (right) inclusion upon nSR100 depletion in the mouse brain, plotted by class. AltEx, alternative cassette exons. B) Microexons (dark squares) and longer cassette exons (light squares) were plotted based on their PSI difference between nSR10$^{\Delta 7\text{-}8/\Delta 7\text{-}8}$ and wild-type samples (x-axis) and their $\Delta$PSI between the average of neural vs. non-neural tissues (y-axis) (Irimia et al. 2014). C) Cumulative distribution of exon lengths for different groups of alternative exons, including events that show decreased inclusion in nSR100$^{\Delta 7\text{-}8/\Delta 7\text{-}8}$ compared to control (nSR100-enhanced), all alternative exons with increased neural PSI (Neural increased), all alternative exons with decreased neural PSI (Neural decreased) and non-neural alternative exons (Non-neural). D) Cumulative distribution plots indicating the position of the first UGC motif within 200 nt upstream of nSR100-regulated microexons, longer exons (>27 nt) with increased neural inclusion, exons with decreased neural inclusion as well as non-neural and constitutive exons. The number of exons used in the analysis for each subgroup is indicated in parentheses. E) RT-PCR validations of nSR100-regulated cassette exons in cortical (left two lanes) and hippocampal (right two lanes) samples. PSI values calculated from semi-quantitative RT-PCR or RNA-Seq analysis are showed below the gel for each event. Primers were located in flanking constitutive exons.
Figure 25:
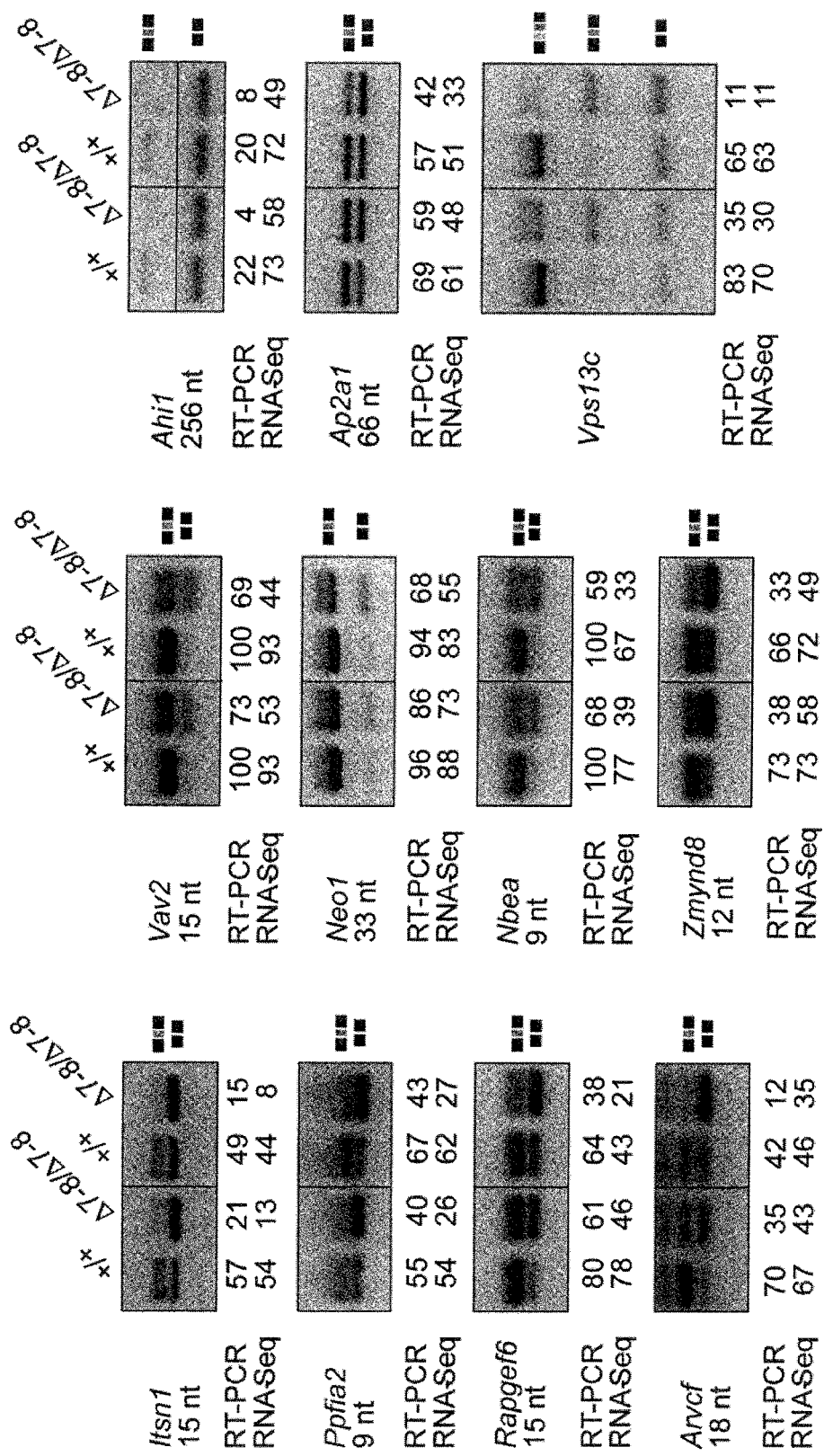
FIG. 25 shows additional RT-PCR validation of RNA-Seq predictions. RT-PCRs were run as previously described for cassette exons and microexons in cortical (left two lanes) and hippocampal (right two lanes) samples. PSI values calculated from semi-quantitative RT-PCR or RNA-Seq analysis are shown below the gel for each event.
Figure 26:
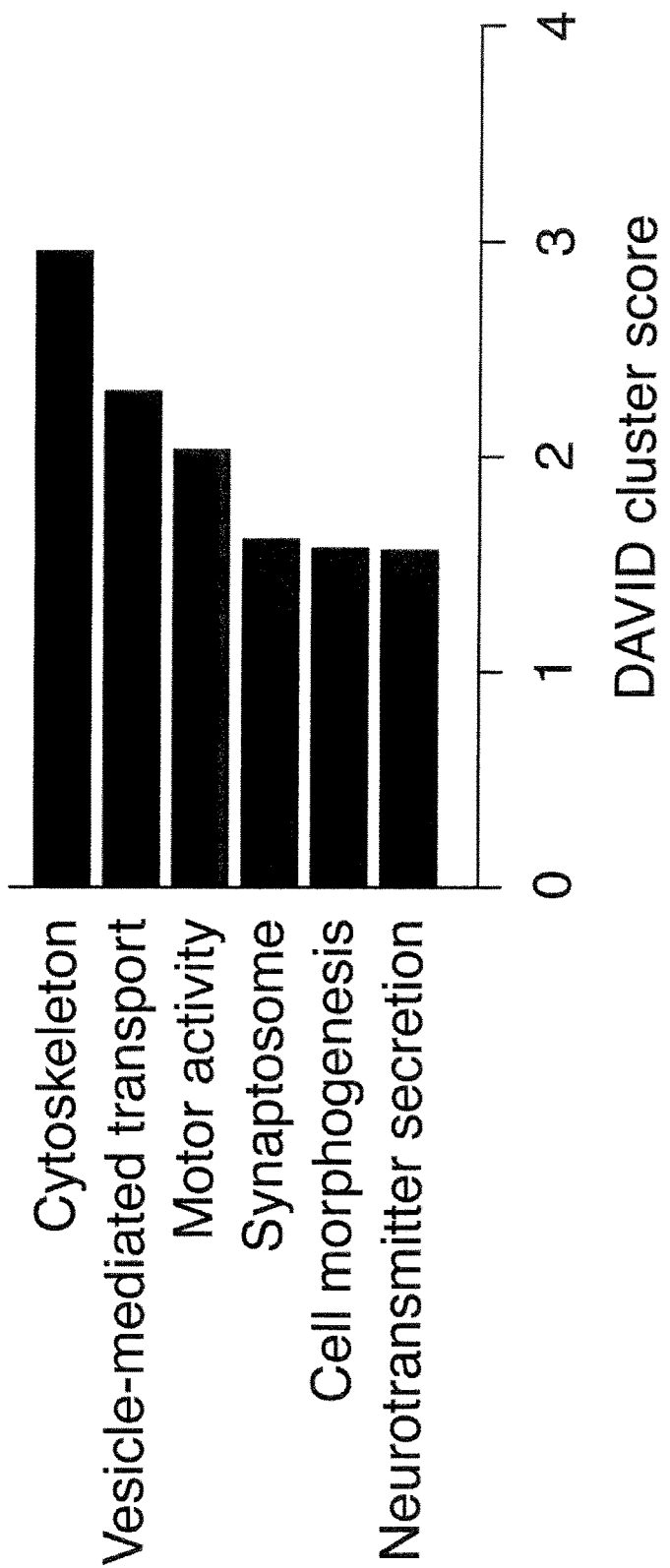
FIG. 26 shows DAVID gene enrichment analysis. Gene ontology terms with a p-value<0.01 are listed.

To identify AS events that contribute to the aforementioned neurodevelopmental deficits, RNA-Seq analyses were performed on two sets of biological replicate samples, each consisting of pooled E18.5 mouse cortical or hippocampal tissue from wild-type and nSR100$^{\Delta 7-8/\Delta 7-8}$ mice (eight samples in total). A new RNA-Seq analysis pipeline was employed that generates quantitative estimates for "percent spliced in" (PSI) values for alternative cassette exons, "percent splice-site usage" (PSU) values for sequences formed by alternative 5'13' splice site selection, as well as "percent intron retained" (PIR) values for intron retention events (Braunschweig et al. 2014). This pipeline also identifies and quantifies PSI values for 3-27 nt microexons (Irimia et al., 2014). To identify which AS events were differentially spliced between wild-type and nSR100$^{\Delta 7-8/\Delta 7-8}$ brains, a paired t-test was performed between the four pairs of samples and required an average ΔPSI/PIR/PSU between pairs of samples of ≥10. Of the 263 AS events displaying differential splicing according to these criteria, cassette alternative exons, including microexons, represented the largest class, comprising 58% of the total (FIG. 24A). A large number of retained introns as well as a few alternative 3' and 5' alternative splice sites were also misregulated in nSR100$^{\Delta 7-8/\Delta 7-8}$ brain tissues. Of the alternative cassette exons and microexons that displayed changes, 66 (83%) and 72 (100%), respectively, displayed decreased PSI levels in nSR100$^{\Delta 7-8/\Delta 7-8}$ mouse brains. Furthermore, 70% of cassette and 96% of microexons positively regulated by nSR100 were defined by RNA-Seq profiling of multiple wild-type mouse tissues (Irimia et al., 2014) as having increased neural inclusion compared to other tissues (FIG. 24B). Other classes of AS events displaying differential splicing in nSR100$^{\Delta 7-8/\Delta 7-8}$ mice did not display enrichment for neural-specific regulation or nSR100-dependent inclusion. An analysis of the cumulative distributions of exon lengths for cassette exons shows that nSR100-regulated exons are significantly shorter than the full set of neurally-regulated exons, either with increased or decreased neural PSI, as well as non-neural alternative exons (FIG. 24C; $p<10^{-7}$ for all comparisons with nSR100-regulated exons; Wilcoxon Rank-Sum tests). Moreover, consistent with recent results from analyzing nSR100-dependent, neural-regulated exons in cell lines (Raj et al. 2014), nSR100-regulated microexons show very strong enrichment for UGC motifs in the first several nucleotides upstream of microexons regulated by nSR100 in vivo (FIG. 24D). Of 22 analyzed differential splicing events involving alternative cassette and microexons, which were detected by RNA-Seq to undergo reduced inclusion as a consequence of the loss of nSR100, all were validated by semi-quantitative RT-PCR assays (FIG. 24E and FIG. 25). Expression analysis based on cRPKMs revealed only nine genes, other than nSR100, with an average mRNA expression difference of ≥1.5-fold between both replicates of wild-type and nSR100$^{\Delta 7-8/\Delta 7-8}$ tissues and $p<0.05$ (paired t-test). Analysis of genes with alternative cassette and microexons exons affected by loss of nSR100 revealed significant enrichment ($p<0.01$) for Gene Ontology (GO) terms essential to many aspects of neuronal cell biology, such as "vesicle-mediated transport", "neurotransmitter secretion", "synaptosome", and "cell projection morphogenesis" (FIG. 26). Collectively, these observations suggest that multiple neural cassette exons, in particular highly conserved microexons that display marked decreases in inclusion levels as a consequence of the loss of nSR100, may underlie mutant phenotypes detected in nSR100$^{\Delta 7-8/\Delta 7-8}$ mice.

Functions of nSR100-Regulated Microexons

Based on previous and present analyses of the in vivo mutant phenotypes of zebrafish and mice lacking nSR100, and also the known functions of genes that harbor nSR100-dependent exons, a major function of the nSR100-regulated splicing program is likely to control different aspects of neurite outgrowth. Consistent with this proposal, it was found that that hippocampal neurons cultured from nSR100$^{\Delta 7-8/\Delta 7-8}$ mice have significantly shorter neurites compared to neurons from wild-type animals (FIGS. 27A and 27B; $p<0.0001$, two-tailed Mann-Whitney test). To investigate whether nSR100-regulated microexons may be responsible for neurite outgrowth, a previously uncharacterized, highly conserved nSR100 target microexon of 6 nt in Unc13b/Munc13 (FIG. 24E), a gene that has previously been shown to contribute to early neuritogenesis in primary mouse neurons (Broeke et al. 2010) was focused on. Since the RNA-Seq analysis can only locate this microexon in the context of its immediate flanking constitutive exons due to short read length, Sanger sequencing of RT-PCR products from mouse brain was performed. This revealed that the Unc13b microexon, located between exons 13 and 14, is spliced in transcripts that contain at least exons 5 to 14 and exons 11 to 20.

Figure 27:
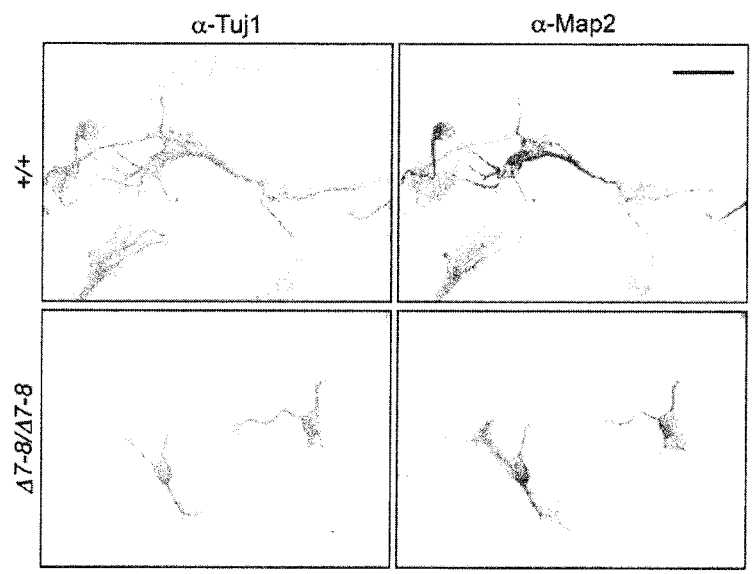
FIG. 27 shows functional regulation of a neural microexon by nSR100. A) Representative images of primary hippocampal neurons from wild-type (+/+) and nSR100$^{\Delta 7\text{-}8/\Delta 7\text{-}8}$ mice cultured for 2 days and then stained with antibodies to Tuj1 (left panels) and Map2 (right panels). Scale bar: 25 μm. B) The length of the longest neurite was measured for each neuron. n=451 cells from 4 embryos and 425 cells from 3 embryos for wild-type and mutant samples, respectively. C) Immunoblotting with an antibody to RFP on Neuro2A lysates transfected with increasing amounts of the same constructs that were used for experiments in D-F showing Unc13b-skp-RFP (skp) and Unc13b-inc-RFP (inc) protein expression. D) RT-PCR showing inclusion levels of the Unc13b microexon, and RFP, nSR100 and GAPDH expression in transfected nSR100$^{++}$ and nSR100$^{\Delta 7\text{-}8/\Delta 7\text{-}8}$ cortical neuronal cultures. E) Representative images of primary cortical neurons from nSR100$^{++}$ and nSR10$^{\Delta 7\text{-}8/\Delta 7\text{-}8}$ mice transfected with RFP, Unc13b-skp-RFP (skp), Unc13b-inc-RFP (inc) or nSR100, cultured for 2 days and then stained with an antibody to Tuj1 (right panels). Cell body is highlighted with an asterisk and the tip of the longest neurite is shown with an arrow. Scale bar: 25 μm. F) nSR100$^{++}$ primary cortical neurons were transfected with RFP, Unc13b-skp-RFP or Unc13b-inc-RFP (three left groups) and nSR100$^{\Delta 7\text{-}8/\Delta 7\text{-}8}$ primary cortical neurons were transfected with the same constructs and nSR100-RFP (four right groups). The longest neurites were measured in RFP-expressing cells. Whiskers indicate $10^{th}$ and $90^{th}$ percentiles. Kruskal-Wallis test with Dunn's multiple comparison test.
Figure 27:
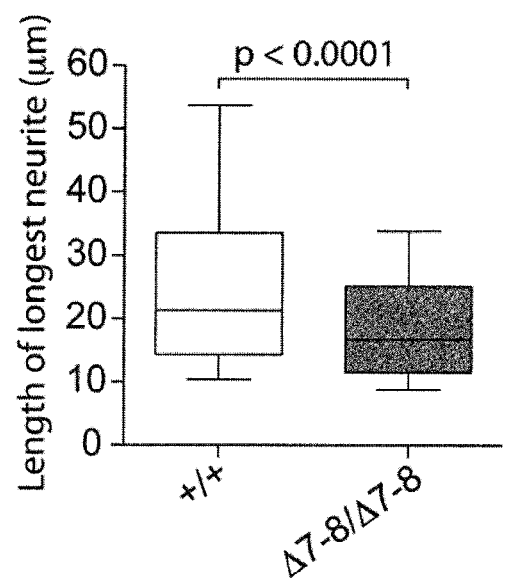
Figure 27:
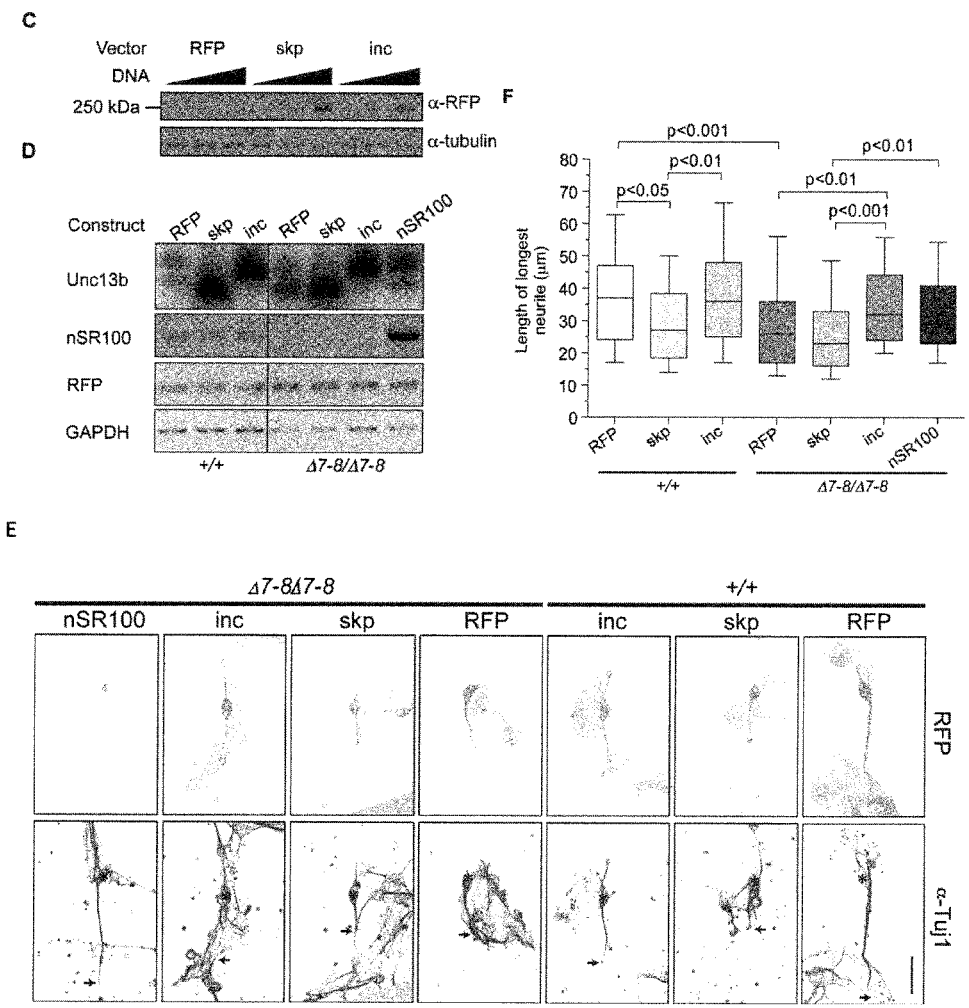

To address whether increased skipping of the Unc13b microexon may contribute to the neuritogenesis defect in nSR100$^{\Delta 7-8/\Delta 7-8}$ neurons, cortical neurons were harvested from wild-type and mutant E18.5 embryos and transfected them with red fluorescence protein (RFP)-Unc13b expression constructs that either include (Unc13b-inc) or skip (Unc13b-skp) the microexon (FIGS. 27C and 27D). At day in vitro 2 (DIV2), the cellular distribution and expression levels of Unc13b-inc-RFP and Unc13b-skp-RFP appear similar (FIGS. 27D and 27E). Control RFP-expressing mutant cortical neurons display the same neuritogenesis defect as hippocampal neurons (FIG. 27F). Wild-type neurons expressing Unc13b-skp-RFP produce neurites that are as short as mutant neurons expressing control RFP, and significantly shorter than control wild-type neurons (FIGS. 27E and 27F; $p<0.0001$, two-tailed Mann-Whitney test). Expression of the skipped Unc13b isoform does not further affect neurite growth in mutant neurons. Strikingly, however, while expression of Unc13-inc-RFP does not affect neurite growth in wild-type neurons, inclusion of the microexon in mutant cells restores the neuritogenesis phenotype to the level of wild-type neurons (FIGS. 27E and 27F). The phenotypes observed in nSR100$^{\Delta 7-8/\Delta 7-8}$ mice may therefore be attributed, at least in part, to the reduced inclusion of neuronal microexons.

Rescue of nSR100 Mutant Phenotype in Primary Neurons

Figure 28:
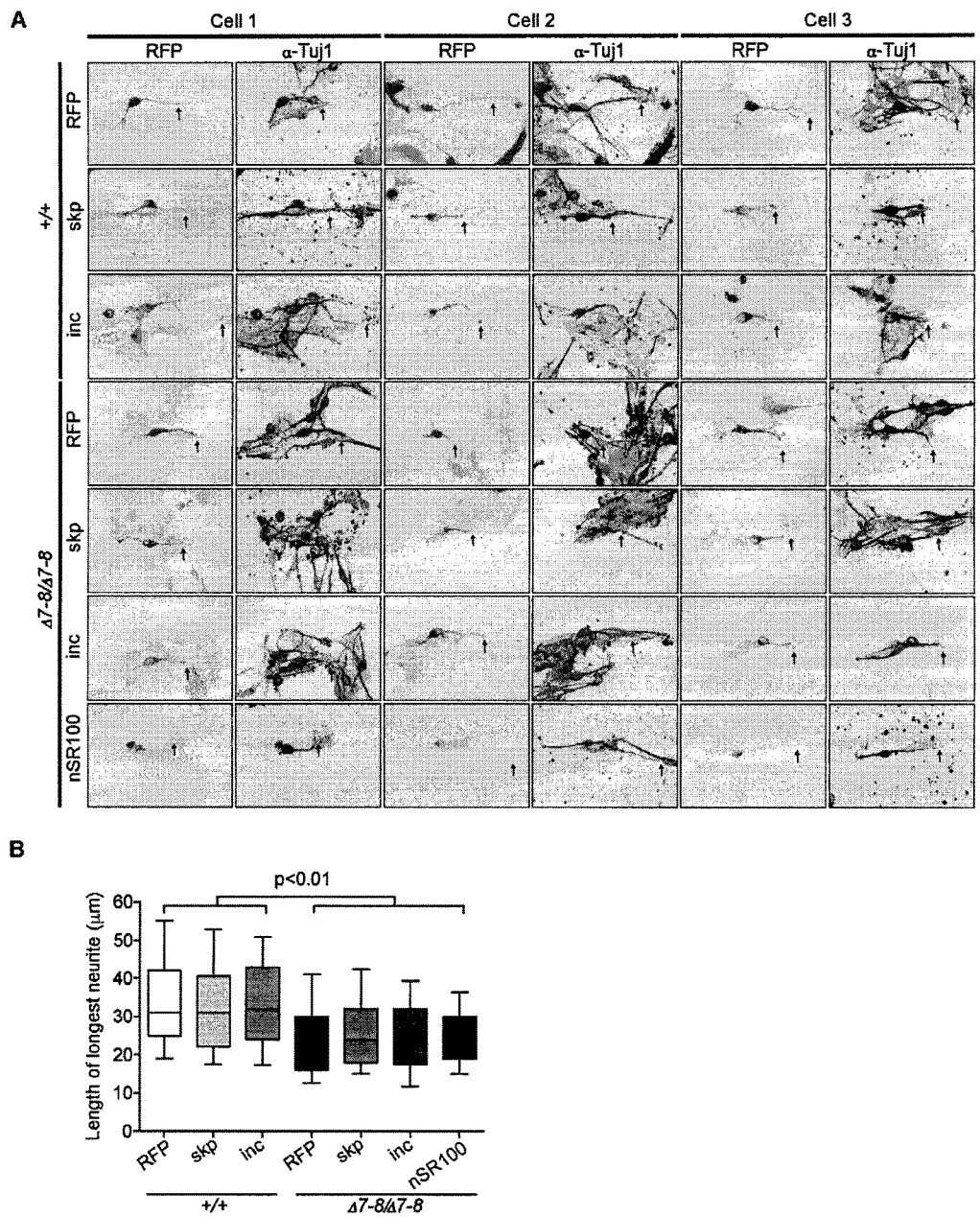
FIG. 28 shows validation of primary neuronal cultures (related to FIG. 27). A) Supplementary pictures of transfected primary cortical neurons. The cells were plated at low density and only 10-20% of neurons in culture express transfected constructs. RFP, Unc13b-skp-RFP and Unc13b-inc-RFP are all distributed over the total length of processes, allowing for unequivocal length measurements even in when transfected cells were seeded in close proximity to other neurons. Only well-isolated nSR100-RFP-transfected neurons were quantified. The tip of the longest neurite is indicated with an arrow. B) The longest neurite of untransfected wild-type and mutant neurons (Tuj1-positive, RFP-negative) growing in the same wells as transfected neurons quantified in FIG. 27F were measured. p<0.001 for all comparisons except +/+ Unc13b-skp ($2^{nd}$ group) vs. $\Delta 7$-8/$\Delta 7$-8 Unc13b-skp ($5^{th}$ group) where p<0.01, one-way ANOVA with Tukey-Kramer post-hoc test. Whiskers indicate $10^{th}$ and $90^{th}$ percentiles.

Transfection of nSR100 in nSR100$^{\Delta 7-8/\Delta 7-8}$ mutant neurons also results in the growth of significantly longer neurites than mutant cells transfected with a control vector (FIGS. 27E and 27F; $p<0.05$, two-tailed Mann-Whitney test). Thus, restoring nSR100 levels in mutant nSR100$^{\Delta 7-8/\Delta 7-8}$ neurons results in neurons that are indistinguishable from wildtype neurons and rescues the mutant neuritegenesis phenotype. All untransfected wild-type neurons grown with transfected cells produced similar-sized neurites between wells and shorter neurites were consistently measured in nSR100 mutant neurons (FIG. 28; $p<0.0001$, one-way ANOVA), confirming that the difference in neurite length observed here is dependent on transfection of the nSR100 expression vector and not the quality of the cultures.

Discussion

In this study, mice deficient of nSR100/SRRM4, a vertebrate- and neural-specific splicing factor that regulates approximately 30% of alternative exons with increased neural inclusion, including a large number of highly conserved 3-27 nucleotide microexons were generated and characterized. It was shown that the loss of nSR100 protein in vivo results in numerous neurodevelopmental defects during mouse embryogenesis that lead to early postnatal mortality in the majority of animals. These neurodevelopmental deficiencies were linked to the loss of microexon regulation.

nSR100 Regulates Multiple Neurodevelopmental Processes

Some neurodevelopmental phenotypes observed in mice deficient of nSR100 may relate to altered phenotypes seen in other splicing factor knockouts, while others are unique. Neonatal lethality has been reported as a consequence of loss of the splicing regulator Ptbp2. Ptbp2 is expressed in neurons as well as in skeletal and cardiac muscle (Licatalosi et al. 2012), and mice lacking Ptbp2 are paralyzed at birth (Licatalosi et al. 2012; Li et al. 2014). However, mice lacking Ptbp2 specifically in neurons (Ptbp2 Nestin KO mice) die within an hour of birth, similar to nSR100 mutants, and initiate breathing at a greatly reduced rate (Li et al. 2014). Given that nSR100 promotes the expression of Ptbp2 by activating the inclusion of an alternative exon that prevents nonsense mediated decay of Ptbp2 transcripts (Calarco et al. 2009), it is possible that the requirement for nSR100 for innervation of the diaphragm may relate to Ptbp2 misregulation. However, neural exons directly or indirectly regulated by nSR100 and Ptbp2 (and its paralog Ptbp1) only partially overlap (Calarco et al. 2009; Raj et al. 2014). Therefore, overlapping and distinct exons targeted by these factors may contribute to breathing defects, paralysis and early postnatal death. This conclusion is further supported by the observation of phenotypes that are unique to nSR100$^{\Delta 7-8/\Delta 7-8}$ mice.

Also as in the case of nSR100$^{\Delta 7-8/\Delta 7-8}$ and Ptbp2 knockout mice, mice deficient in both Nova1 and Nova2 proteins (Nova DKO mice) showed muscular paralysis at birth (Ruggiu et al. 2009). While phrenic nerve branching appeared normal, neuromuscular junctions (NMJs) in E18.5 Nova DKO mice had few acetylcholine receptors (AChRs) and only rarely contacted motor axon terminals. By contrast, in nSR100$^{\Delta 7-8/\Delta 7-8}$ mice, motor endplates (sarcolemma folds in which AChRs concentrate) are of similar abundance as those of nSR100$^{+/\Delta 7-8}$ heterozygous littermates, which are fully viable, although AChR distribution is altered due to the phrenic nerve deficits. These phrenic nerve deficits may be a consequence of altered axon branching and/or growth. The deficit in phrenic nerve branching that is reported here, to the present inventors' knowledge, has not been described previously for other splicing regulators.

Another neurodevelopmental aberration in nSR100$^{\Delta 7-8/\Delta 7-8}$ mice that has not been previously observed in other splicing factor knockouts is the axon midline crossing defect in the corpus callosum. Approximately 60 mouse genes are known to be required for the formation of the corpus callosum (Paul et al. 2007; Donahoo and Richards 2009). Interestingly, the present RNA-Seq analysis reveals that transcripts from one of these genes, Slit2, contain one of the most strongly differentially-regulated nSR100-dependent exons. Slit2 is secreted by distinct neuronal populations located at or near the midline. It binds Robo receptors expressed in growing axons to help mediate midline crossing. Its function has been extensively studied in vivo (Chedotal 2007), and a Slit2 KO mouse displays a midline crossing defect that is strikingly similar to the one observed in nSR100$^{\Delta 7-8/\Delta 7-8}$ mice, with bundles of callosal axons projecting ventrally along the midline (Unni et al. 2012). The nSR100-dependent Slit2 exon adds 9 amino acids to the fifth EGF domain in the secreted N-terminal portion of the protein that is responsible for the its repulsive activity during axon guidance. The differential activities of the resulting Slit2 isoforms have not been previously investigated, although an AS event in Robo3 that switches the axonal response to Slit proteins from attraction to repulsion has been reported (Chen et al. 2008). It is interesting to consider that the nSR100-dependent regulation of the alternative Slit2 exon represents a complementary mechanism for controlling axon guidance and that it may contribute to the midline crossing defect observed in the nSR100 mutant mouse.

In addition to the differences observed in the corpus callosum of nSR100 heterozygotes and homozygotes, nSR100 dosage-dependent cortical deficits were observed. It is noteworthy that subtle deficits in the corpus callosum and in cortical layering have been linked to impaired cognitive and behavioral function in humans (Paul et al. 2007). Cortical layer formation and distribution is conserved in mammals and disruption of this pattern has been observed in individuals with schizophrenia and autism (Akbarian et al. 193; Ross et al. 2006; Stoner et al. 2014). It was found that layer VI is significantly expanded in the mutant brain. The cortical layering defects in nSR100 deficient mice could result from the disorganization of several processes involved in brain development, including impaired cell migration, altered neurogenesis or mistiming in neuronal differentiation. While cell migration defects often result in the aberrant positioning of cortical layers (Caviness 1982; Kwan et al. 2008), early production of post-mitotic neurons by cortical progenitors has been shown to result in an expansion of deep cortical layers (Feng and Walsh 2004). Premature production of neurons depletes the pool of progenitors and causes fewer late-born neurons to be generated. In nSR100$^{\Delta 7-8/\Delta 7-8}$ mice, a trend toward the reduction of superficial layers where late-born neurons migrate was seen as well as a trend toward an overall thinning of the cortex at E18.5. These trends show that loss of nSR100 may cause premature neuronal differentiation.

nSR100 Regulates Alternative Splicing Events in Genes with Important Neuronal Functions Loss of nSR100 affected all classes of AS events. In addition to changes in the inclusion levels of a large number of neural cassette exons, of which many are microexons (see below), many retained introns that are misregulated in developing nSR100$^{\Delta 7-8/\Delta 7-8}$ mouse brains were identified. Although a subset of the retained introns introduce premature termination codons, it appears that the corresponding transcripts in most cases are not subject to nonsense-mediated mRNA decay as their steady state levels were not appreciably affected in nSR100$^{\Delta 7-8/\Delta 7-8}$ brain tissue. A small number of nSR100-dependent alternative 5' and 3' splice site selection events, most of which are frame-preserving were also identified.

Collectively, AS events misregulated in nSR100$^{\Delta 7-8/\Delta 7-8}$ mouse brains are enriched in genes involved in neuronal functions, such as genes associated with neuronal differentiation (Zmynd8, Ahi1), neurite outgrowth (Zfyve27, Clasp2), and axon guidance (Slit2, Nrcam, Mycbp2). Many of these genes possess pivotal roles as scaffolding proteins for endo- and exocytosis, cytoskeleton remodeling and vesicle transport, and are associated with defects similar to the ones observed in the mouse model.

Functional Impact of nSR100-Regulated Microexons

Among genes that contain microexons regulated by nSR100, several encode proteins that are known to interact. These proteins form a network that is involved in the trafficking and recycling of vesicles, including Itsn1, Ppfia2, Rims2, Dnm2, Nbea, Abi1, Ptprd and Vav2. 65 of the 72 nSR100-activated microexons are frame-preserving and have the potential to result in the insertion of 1 to 9 amino acid residues in the corresponding protein products. These seemingly modest changes to coding sequence raise interesting questions as to the functional roles of microexons.

It has been observed that amino acid residues encoded by microexons are almost invariably surface accessible and enriched within—or immediately adjacent to—domains involved in protein-protein or protein-lipid interactions (Irimia et al., 2014). Consistent with these observations, the present inventors and others have observed that deletion of microexons reduces interactions with partner proteins. For example, a microexon in the SH3 domain of the Down Syndrome-associated gene Itsn1, which is shown here to be strongly regulated by nSR100 (FIG. 25), promotes interactions with multiple partners (Tsyba et al. 2008). A recent report has demonstrated that an nSR100-regulated microexon in the Zfyve27 transcript (FIG. 24E) promotes interactions with the partner proteins VAP-A and VAP-B (Ohnishi et al. 2014). Consistent with nSR100-associated phenotypes in the present study, an isoform including the microexon, but not one lacking it, promotes polarized neurite outgrowth in primary mouse neurons. Furthermore, the present inventors have shown that neural microexons in the AP1 endocytic transport complex subunit, Ap1s2, and in the Amyloid beta precursor protein-binding family B member 1 (Apbb1), which is also associated with neuritogenesis (Cheung et al. 2014), promote interactions with respective partner proteins (Irimia et al., 2014). These findings are extended by demonstrating that nSR100-dependent inclusion of a 6-nt microexon in Unc13b transcripts is sufficient to promote the increased length of neurites and rescue a neuritogenesis defect in nSR100 mutant neurons. This microexon has the potential to add two amino acids adjacent to a predicted MAPK docking site in the Unc13b. Without being bound by theory, it is possible that the nSR100-dependent regulation of this microexon affects the phosphorylation status of Unc13b in ways that affect interactions required for neurite formation.

Most (~76%) of the microexons affected by the in vivo loss of nSR100 in the present study are conserved in humans, and many (~46%) of these display loss of inclusion in the brain cortices of subjects with ASD (Irimia et al., 2014). Furthermore, this altered pattern of inclusion in ASD subjects affected genes enriched in known genetic associations with ASD, and it was also highly correlated with reduced expression of nSR100. Additional studies have linked microexon misregulation to schizophrenia and epilepsy (Ovadia and Shifman 2011; Rusconi et al. 2014).

Materials and Methods nSR100 Mutant Mouse Generation

Stem cells containing the conditional nSR100$^{lox}$ allele were ordered from EUCOMM (project #71507, clones EPD0538_3_A08 AND EPD0538_3_A09) (Friedel et al. 2007) and aggregated with outbred ICR morula. Following confirmation of germline transmission, mice bearing the nSR100$^{lox}$ allele were maintained on a C57Bl/6N background and crossed with the B6.C-Tg(CMV-cre)1Cgn/J line from the Jackson Laboratory. Excision of exons 7 and 8 in resulting nSR100$^{+/\Delta7-8}$ mice is confirmed by PCR and sequencing.

Southern Blotting

Southern blotting was performed as described elsewhere (Sambrook and Russell 2001). Briefly, 60 µg of mouse genomic tail DNA was digested with AseI and loaded on an agarose gel for each genotype. DNA was transferred to a Hybond XL membrane (GE Healthcare Life Sciences) and hybridized with a $^{32}$P-dCTP-labeled probe encompassing 456 bp of nSR100 intron 3, upstream of the 5' homology arm used for homologous recombination of the nSR100$^{lox}$ allele.

Rt-PCR

Semi-quantitative RT-PCR was performed using the QIAGEN One-Step RT-PCR kit as per the manufacturer's instructions using 15 ng total RNA as template per 10 µl reaction and run on 2% or 4% agarose gels. Radiolabeled reactions included 0.05 µCi of $^{32}$P-dCTP and were run on 6% Sequagel Urea gels (National Diagnostics). Bands were quantified using BioRad or ImageJ.

Antibodies

For immunoblotting a polyclonal rabbit antibody (Calarco et al. 2009) raised against amino acids 1 to 82 of nSR100 was used at 1:5000. Anti-tubulin (T6074, Sigma) was used at 1:5000. For immunostaining, mouse monoclonal anti-neurofilament (2H3 conditioned medium, Iowa Developmental Studies Hybridoma Bank) was diluted to 1:50 for whole-mount diaphragm staining and 1:100 for brain section staining. Mouse anti-NeuN (mab377, Millipore), mouse anti-Satb2 (ab51502, Abcam), rabbit anti-Tbr1 (ab31940, Abcam) and chicken polyclonal anti-β-galactosidase (ab9361, Abcam) were all diluted to 1:500. Chiken anti-MAP2 (ab5392, Abcam) and mouse anti-Tuj1 (MRB-435P, Covance) were diluted to 1:10,000 and 1:750, respectively. For in situ hybridization, an anti-DIG antibody conjugated to alkaline phosphatase (Roche) was diluted to 1:5000.

In Situ Hybridization

In situ hybridization was essentially performed as previously described (Sambrook and Russell 2001). 20 µm brain sections were post-fixed in 4% formaldehyde for 10 minutes at room temperature. Sections were then pre-hybridized for 3 to 6 hours at room temperature, followed by hybridization with sense or antisense DIG-labeled probes to nSR100 exons 9 to 13 diluted to 200 ng/ml overnight at 60° C. Alkaline-phosphatase-conjugated anti-DIG antibody was added to slides for 1 hour at room temperature, washed, and an NBT/BCIP solution (Roche) was applied for 1 hour to overnight at room temperature. Sections were cleared in xylene and mounted in Cytoseal XYL (Thermo Scientific).

Immunofluorescence

For whole-mount diaphragm staining, diaphragms were dissected from E16.5 or E18.5 embryos and fixed overnight in 2% formaldehyde at 4° C. Diaphragms were washed in 0.1 M glycine in PBS and blocked overnight at 4° C. in 0.5% triton X-100, 3% BSA, 5% donkey serum with Alexa-594-coupled α-bungarotoxin diluted at 1:1500 (Life Technologies). Diaphragms were then further permabilized briefly in 100% methanol and fixed again in 0.2% glutaraldehyde and 4% formaldehyde for 20 minutes at room temperature and then incubated overnight at 4° C. in blocking buffer with a monoclonal anti-neurofilament antibody diluted to 1:100. After extensive washes, samples were incubated overnight at 4° C. in blocking buffer with an Alexa-488 anti-mouse antibody diluted to 1:500 (Life Technologies).

Quantification of Phenotypic Data

For neurite length measurements on whole-mount diaphragm, tracings were generated with the NeuronJ plugin for ImageJ. Right branches on the ventral and dorsal parts of the diaphragm were measured and counted. For neuromuscular junctions, a 475 µm-long region of interest was selected over the ventrally-projecting left primary branch and neuromuscular junctions were quantified using the ICTN plugin in ImageJ. The dispersion of neuromuscular junctions was measured as the average width of the neuromuscular junction band at 3 different levels of the same region of interest. Cortical layer thickness was measured relative to the total thickness of the cerebral cortex from the lateral ventricle to the surface of layer I. The number of cells was counted in a 300 µm radial unit region of interest using the ICTN plugin. Cells and layers were quantified on 3 sections from each brain and at least 3 brains per genotype.

RNA-Seq Analysis

A first replicate consisted in total RNA extracted from cerebral cortices and hippocampi dissected from 5 wild-type and 5 nSR100$^{\Delta 7\text{-}8/\Delta 7\text{-}8}$ homozygous mutant brains at E18.5. RNA was pooled by genotype, prepared using the Illumina TruSeq mRNA kit, and cortical and hippocampal samples were sequenced on different runs of Illumina HiSeq2500 (average of ~93 million 100-nt single end and 100-nt paired-end reads for each run, respectively). A second replicate was processed as above and consisted of total RNA pooled from 3 wild-type or 3 mutant brains at E18.5. An average of ~90 million of 100-nt paired-end reads were sequenced for each sample.

Transcriptome-wide AS and gene expression profiling was performed using the described pipeline (vast-tools; Irimia et al., 2014). vast-tools uses reads mapping to exon-exon (or exon-intron) junctions (EEJ or EIJ) only to accurately detect and quantify all types of AS events, including 3-15 nucleotide microexons. Gene expression levels are measured using the cRPKM metric (Labbe et al. 2012).

PSI/PIR/PSU of AS events for the eight samples were paired into four replicates (wild-type and nSR100$^{\Delta 7\text{-}8/\Delta 7\text{-}8}$ for two cortex and two hippocampus samples) and a paired t-test was performed for AS events with enough read coverage in all eight samples. A given AS event was considered to have sufficient read coverage in a particular RNA-Seq sample according to the following criteria (Irimia et al., 2014):

For cassette exons (except for those quantified using the microexon pipeline): (i) ≥10 actual reads (i.e. before mappability correction) mapping to the sum of exclusion EEJs, OR (ii) ≥10 actual reads mapping to one of the two inclusion EEJs, and ≥5 to the other inclusion EEJ.

For microexons: (i) ≥10 actual reads mapping to the sum of exclusion EEJs, OR (ii) ≥10 actual reads mapping to the sum of inclusion EEEJs.

For IR: (i) ≥10 actual reads mapping to the sum of skipping EEJs, OR (ii) ≥10 actual reads mapping to one of the two inclusion EIJs, and ≥5 to the other inclusion EIJ.

For Alt3 and Alt5: ≥10 actual reads mapping to the sum of all EEJs involved in the specific event.

Then, for an AS event to be considered as differentially regulated between wild-type and nSR100$^{\Delta 7\text{-}8/\Delta 7\text{-}8}$ brains, a p-value<0.05 in the t-test and an average ΔPSI (between the 4 paired replicates) of at least 10% was required.

Functional Enrichment Analyses

Ensembl gene IDs for the cassette exons and microexons that showed significantly increased skipping in nSR100$^{\Delta 7\text{-}8/\Delta 7\text{-}8}$ brains (137 genes in total) were uploaded to DAVID (http://david.abcc.ncifcrf.gov) (Huang da et al. 2009) to perform functional enrichment analyses using a stringent background consisting of 10,968 genes with expression of at least cRPKM>2 in one of the brain samples. Only GO_FAT terms and KEGG pathways were used for the clustering analyses.

Primary Neuronal Cultures

Protocols for culturing primary mouse neurons were kindly provided by Drs. Antony Boucard and Thomas Sudhof (Stanford University) (Boucard et al. 2005). Briefly, hippocampal or cortical neurons were harvested from wild-type or nSR100$^{\Delta 7\text{-}8/\Delta 7\text{-}8}$ mice at E18.5 and plated on glass coverslips coated with 2% Matrigel (Corning) in plating medium consisting of MEM medium (51200-038, Life Technologies) supplemented with 0.5% glucose, 0.2 mg/ml NaHCO$_3$, 0.1 mg/ml transferrin (616420, Calbiochem), 10% fetal bovine serum (FBS, SH30396.03, GE life sciences), 2 mM L-glutamine (12403-010, Life Technologies) and 25 µg/ml insulin (1-6634, Sigma). Plating medium was changed at DIV1 to growth medium consisting of MEM medium supplemented with 0.5% glucose, 0.2 mg/ml NaHCO$_3$, 0.1 mg/ml transferrin, 5% FBS, 0.5 mM L-glutamine and 2% B-27 supplement (17504-044, Life technologies). Dissociated neurons were transfected previous to plating using the Amaxa Nucleofector kit (VPG-1001, Lonza) using approximately 5×10^4 cells and 10 µg plasmid DNA per transfection. Unc13_skp, Unc13_inc and nSR100 were cloned upstream of the RFP coding sequence and placed under the control of the CAGGS promoter. The length of neurites was quantified using the NeuronJ plugin for ImageJ.

Example 3. Investigating Behavioral and Neurobiological Characteristics of nSR100-Deficient Mice nSR100 mutant mice were assessed for their utility as a model for studying human neurological disorders, particularly ASD.

Autism spectrum disorder (ASD) affects ~1% of children and is highly heterogeneous with respect to its presentation and contributing genetic factors. By definition, all ASD patients exhibit deficits in socialization and communication. Several genetic syndromes include ASD along with other symptoms, but the majority of ASD cases are of unknown origin. While many genetic variants—some only occurring in a single patient—have been associated with non-syndromic ASD, the genes and genetic programs most strongly contributing to idiopathic ASD have been elusive.

Down-regulation of the neuronal-specific splicing regulator nSR100/Srrm4 and disruption of the nSR100-dependent alternative splicing program described hererin was observed in nine (9) of twenty-two (22) analyzed ASD patient samples (Irimia et al. 2014). In autistic postmortem brain samples predominantly decreased microexon inclusion was observed. These associative findings suggest the existence of a distinct subcategory of ASD patients, in which the affected molecular and/or neurobiological mechanisms converge on nSR100 dependent pathways.

Despite this association between nSR100 downregulation, microexon skipping and ASD, there existed no causative link between reduced nSR100 levels and ASD. Thus, since genetic mouse models for syndromic autism, such as Rett syndrome and Fragile X syndrome, have recapitulated human ASD phenotypes, here the present inventors have examined the effects of reduced nSR100 levels on ASD-related phenotypes in the mouse.

Results

Figure 29:
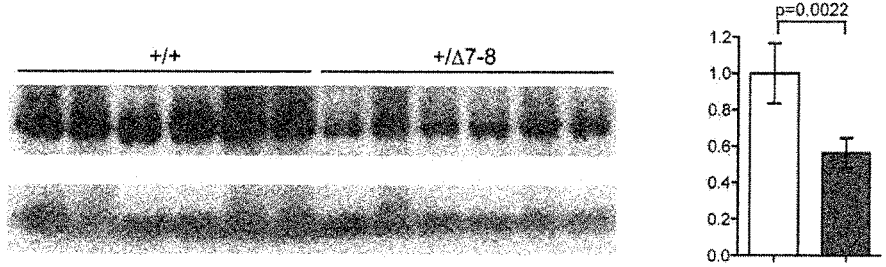
FIG. 29 shows intermediate levels of nSR100 protein and alternative splicing defects in the brain of nSR100$^{+/\Delta 7\text{-}8}$ mutant mice. A) Immunoblotting was performed using an antibody to nSR100 on lysates from wild-type (+/+) and nSR100 mutant (+/$\Delta 7$-8) E18.5 cortex. Error bars: S.D. B) RT-PCR on nSR100 targets in wild-type (+/+), nSR100 heterozygous (+/$\Delta 7$-8) and nSR100 homozygous mutant ($\Delta 7$-8/$\Delta 7$-8) E18.5 cortex. Scatter plot: lines indicate mean with standard deviation.
Figure 29:
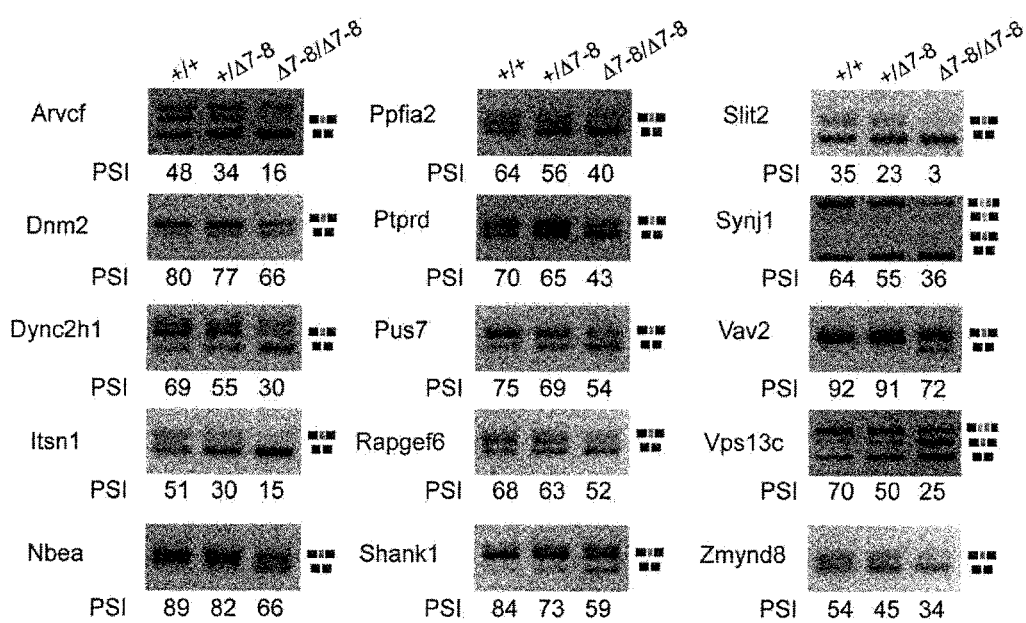
Figure 29:
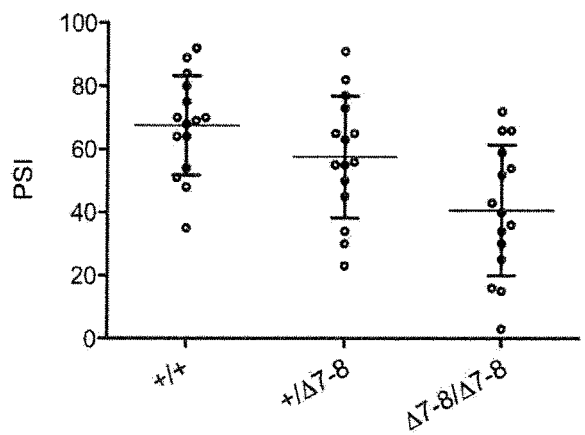

Mutant mice that only lack one copy of the nSR100 gene (nSR100$^{+/\Delta 7\text{-}8}$) express approximately 50% of wild-type protein levels and have intermediate levels of target exon inclusion as compared to wild-type and homozygous mutant (nSR100$^{\Delta 7\text{-}8/\Delta 7\text{-}8}$) animals that entirely lack expression of full length nSR100 protein (FIG. 29). Given that the defining and unifying feature of ASD is its impact on social behaviors, the behaviors of nSR100$^{+/\Delta 7\text{-}8}$ mice were examined.

Figure 30:
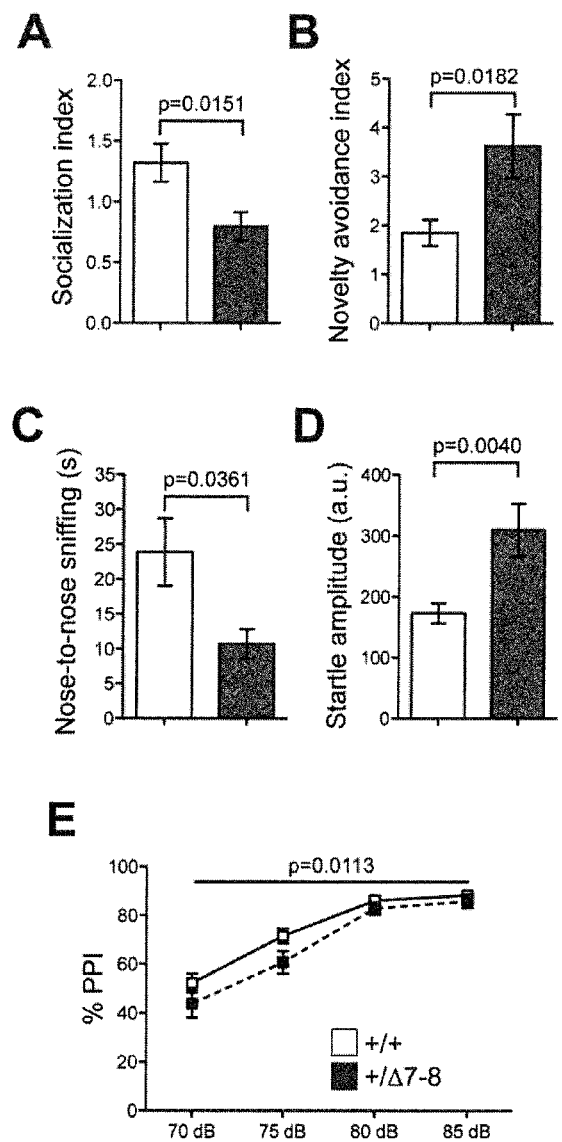
FIG. 30 shows that nSR100$^{+/\Delta 7\text{-}8}$ male mice display autistic-like behaviour. A and B) Social behavior was measured using the 3-chamber apparatus with a sociability index in the social choice test (A; time interacting with stranger/time interacting with object) and as a social novelty avoidance index in the social novelty test (B; time spent in chamber with familiar mouse or neutral chamber/time spent in chamber with stranger mouse). C) The reciprocal social interaction test was used to measure direct nose-to-nose interaction. D) The startle response and E) the PPI were measured in adult mice. A-D, unpaired two-tailed t-test; E, two-way ANOVA, $F(1,115)=6.628$, $p_{genotype}=0.0113$. N=17 WT and 15 nSR100$^{+/\Delta 7\text{-}8}$ for 3-chamber apparatus; N=10 WT and 8 nSR100$^{+/\Delta 7\text{-}8}$ for reciprocal social interaction test; N=13 males per genotype for PPI) Error bars: S.E.M.

Importantly, the main deficit exhibited by nSR100+/− mice is one in social behavior: A three-chamber sociability test uncovered social avoidance in heterozygous nSR100 mutants (FIGS. 30A and 30B). More specifically, nSR100$^{+/\Delta 7\text{-}8}$ mice display an aversion for the company of other mice and a preference to interact with an inert object over stranger mice in the social preference test (FIG. 30A). Similarly, if they had to choose between a known mouse and a stranger (unknown) mouse, they would prefer to interact with the familiar (known) mouse in the social novelty test (FIG. 30B). This decrease in social behaviour was also observed in the reciprocal interaction test where both male and female nSR100 mutants spent significantly less time engaging in direct social behaviour (FIG. 30C). These are atypical behaviors in the mouse and similar phenotypes have consistently been observed in mouse models of ASD-associated genes (Shinoda et al. 2013).

Disruption of "prepulse inhibition" (PPI), the ability to become desensitized to and ultimately ignore an irrelevant external stimulus, is considered a hallmark of ASD and also schizophrenia. Individuals with ASD typically have sensory gating defects that result in hyperacusis (Baranek, 2002) as well as a decrease of the pre-pulse inhibition of the startle response (McAlonan et al. 2002, Perry et al., 2007). Importantly, PPI is a highly conserved phenomenon in mammals and several validated mouse models of ASD, including mice carrying mutations in FMR1 and MeCP2, which model Rett's and Fragile X syndrome, respectively, show decreases in PPI (Lijam et al. 1997; Paylor et al. 2006; Gandal et al. 2012)(Renoux et al, Behav Brain Res. 2014 Jul. 1; 267:42-5; Kron et al.; J Neurosci. Oct. 3, 2012; 32(40): 13860-13872). Consistent with ASD-like symptoms, nSR100$^{+/\Delta 7-8}$ mice showed a significant increase in the amplitude of their startle response (FIG. 30D) as well as a decrease in the pre-pulse inhibition of the startle response (FIG. 30E).

Figure 31:
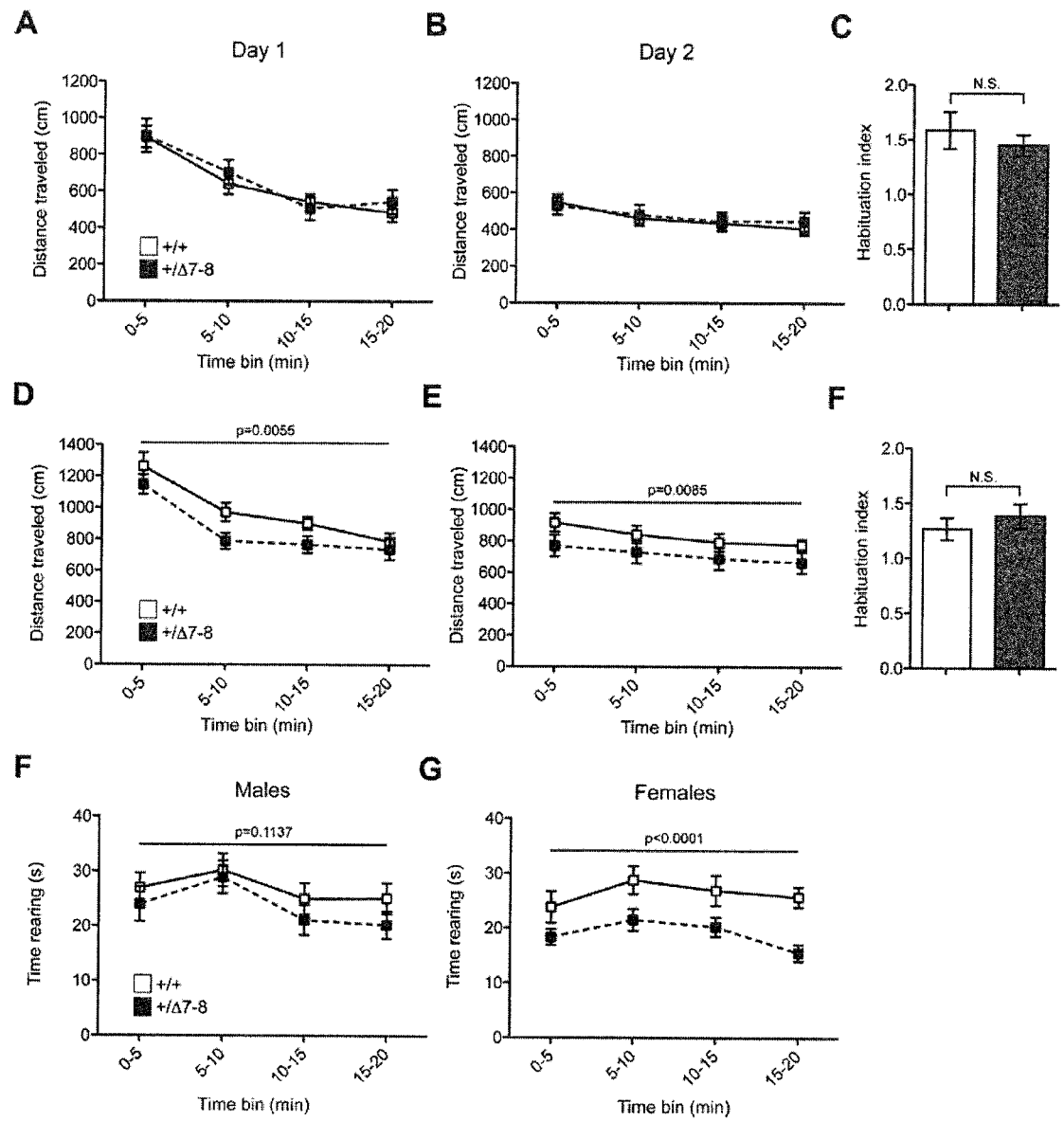
FIG. 31 shows that nSR100 mutant mice have no apparent locomotor or habituation defects. A-C) Open field test in males and (D-F) females. Total distance traveled was measured on two consecutive days (A, B, D and E) and habituation index was calculated as a ratio between total distance traveled on day 1 and total distance traveled on day 2 (C, F). N=23 WT and 18 nSR100$^{+/\Delta 7\text{-}8}$ males; N=22 WT and 25 nSR100$^{+/\Delta 7\text{-}8}$ females. Error bars: S.E.M.
Figure 32:
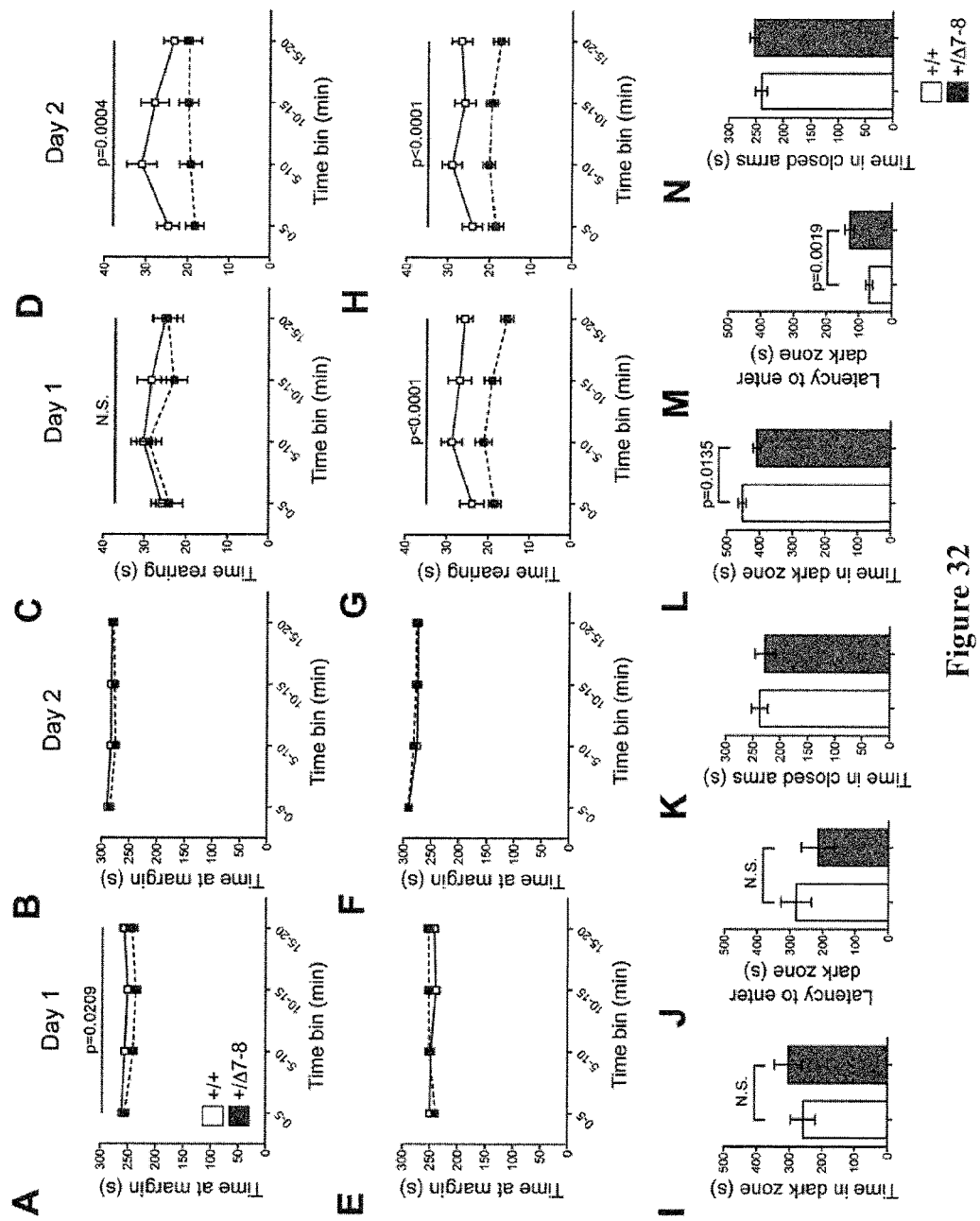
FIG. 32 shows a slight decrease in exploratory behaviour without anxiety in nSR100 mutant mice. A-D) Thigmotaxis (A, B) and rearing (C, D) in males in the open field test. E-H) Thigmotaxis (E, F) and rearing (G, H) in females in the open field test. I-K) Anxious behaviour was measured in males in the light-dark box (I, J) and in the elevated zero-maze (K). L-N) Anxious behaviour was measured in females in the light-dark box (L, M) and in the elevated zero-maze (N).

ASD is almost 5 times more common among boys (1 in 42) than girls (1 in 189), while women are twice more likely to be diagnosed with an anxiety disorder (Centers for Disease Control and Prevention). While gross anomalies in anxiety were not observed (FIGS. 31 and 32), females showed indications of a mild deficit in anxiety. Females also showed social deficits, although not as extensive as males in the 3-chamber apparatus (FIGS. 33A, 33B and 33C), and sensory gating defects (FIGS. 33D and 33E). Only females exhibited a decrease in exploratory behavior, spending less time rearing in the open field (FIG. 31G) and with an increase in the latency to enter the dark zone in the light-dark box (FIG. 32M). This constellation of behaviors is suggestive of possible mild anxiety-like phenotypes even though behavior in the elevated zero-maze was normal (FIG. 32K). Thus, in mice, reducing nSR100 levels produces hallmark ASD social deficits to a degree reflecting the sexually dimorphic distribution of ASD seen in patients.

Additional behavioral observations can also be linked with ASD-like behavior in nSR100$^{+/\Delta 7-8}$ mice. While locomotor activity (as assessed by distance traveled in the open field test), exploration and working memory (Y-maze) were similar in nSR100$^{+/+}$ and nSR100$^{+/\Delta 7-8}$ mice, nSR100$^{+/\Delta 7-8}$ mice displayed a decrease in rearing activity in the open field test. Such a phenotype has been observed in other mouse models with impaired sociability (DeLorey et al. 2008; Peca et al. 2011). Aside from rearing behavior, nSR100$^{+/\Delta 7-8}$ mice were normal with respect to their locomotor, habituation (FIG. 31A-31F), anxiety (FIG. 32), short-term memory (FIG. 34), olfaction (FIG. 35), or hearing (FIG. 36) deficiencies. Compulsive or repetitive behaviour was not significantly affected by reduced nSR100 levels in the marble burying test or when assessing self-grooming and digging (FIG. 37). Both males and females had decreased responses to light stimuli (FIG. 38), although this defect was not severe enough to impair performance in behavioural tests (Ku et al., 2011). Taken together and considering existing mouse models of ASD, these nSR100$^{+/\Delta 7-8}$ phenotypes are consistent with ASD-related aspects of behavior in adult mice. Collectively, the results define new in vivo functions of nSR100 during mouse development and in the control of adult mouse behavior, and they link these functions to the disruption of a conserved program of nSR100-dependent alternative splicing (AS).

These results highlight an aversion of nSR100$^{+/\Delta 7-8}$ mice for the company of other mice and a preference to interact with an inert object over a stranger mouse. These are atypical behaviors in the mouse and similar phenotypes have consistently been observed in mouse models of ASD-associated genes (Shinoda et al. 2013)

Taken together and considering existing mouse models for ASD, these nSR100$^{+/\Delta 7-8}$ phenotypes are consistent with ASD-related aspects of behavior in adult mice.

The development of a mouse model for reduced expression of nSR100 that displays behavioral phenotypes resembling aspects of human ASD represents a tractable system for testing treatments.

Neurobiological Findings in nSR100 Mice Consistent with Findings in ASD Patients:

The biology of ASD is poorly understood. Neurobiological signs previously associated with ASD both in human and in mouse models include:
a. Disruption of cortical layering (Brielmaier et al., 2012; Stoner et al., 2014),
b. Mis-wiring of the brain circuitry (Willsey et al. 2013; Rothwell et al., 2014),
c. Disturbance in the number of parvalbumin-expressing (Pv+) interneurons (Cellot and Cherubini, 2014),
d. A change in synaptic density (Shinoda et al., 2013),
e. Anomalies in dendritic spine development, and
f. Altered synaptic activity (Shinoda et al., 2013).

The present inventors have shown that downregulation of nSR100 in nSR100$^{+/\Delta 7-8}$ mice causes:
a. Aberrant cortical layering (FIG. 22) and
b. Axon guidance defects (mis-wiring defects) (FIG. 23) (Quesnel-Vallières et al. 2015).
c. An increase in the number of interneurons in the cortex of nSR100$^{\Delta 7-8/\Delta 7-8}$ mice (FIG. 39)
d. To address whether a decrease in nSR100 activity affects basic synapse formation and/or density, primary cortical neurons were cultured and it was found that cells lacking nSR100 harbor more glutamatergic and fewer GABAergic synapses than wild-type neurons, as identified by co-immunofluorescence with vGlut1-PSD95 and vGAT-gephryrin, respectively (FIG. 40). These observations lend support for the functional importance of microexons located within genes involved in the dynamics of neurotransmitter release are among those misregulated upon nSR100 loss and/or in ASD individuals (Irimia et al. 2014; Quesnel-Vallières et al. 2015).
e. Using a Thy1-GFP reporter line, it was observed that the in vivo density of dendritic spines was increased in the somatosensory cortex of adult nSR100$^{+/\Delta 7-8}$ mice (FIGS. 41A and 41B). While the overall dendritic spine density correlates well with an increase in excitatory perisynapses in cultured neurons, the increase in dendritic spines, however, was specific to thin spines as the number of mushroom spines, stubby spines and filopodia were unaffected in mutant neurons (FIG. 41B). The observed increase in the number of thin spines in vivo and of glutamatergic perisynapses in culture resemble those reported in many analyses of young mice lacking Fragile X mental retardation protein (Fmr) (He and Portera-Cailiau, 2013) and in autopsy studies of Fragile X Syndrome patients (Rudelli et al., 1985; Hinton et al., 1991) Cortical neurons with abnormally thin, long spines that resemble immature spines have been reported in autopsy studies of Fragile X Syndrome (FXS). Because their morphology resembles that of early immature spines, in the case of FXS, it has been hypothesized that these spines are immature and developmentally delayed.

f. Altered synaptic activity: Agreeing with the notion that thin spines are immature and mostly non-functional synapses, whole-cell recordings from adult nSR100$^{+/\Delta 7-8}$ cortical brain slices revealed a significant decrease in the frequency of both spontaneous and miniature excitatory postsynaptic currents (EPSCs) (FIG. 41C-41H), indicating impairment in glutamatergic synaptic transmission. No significant change in the amplitude of EPSCs was observed (FIGS. 41E and 41H), which suggests that reduced levels of nSR100 do not alter the quantal size of presynaptic vesicles or conductance of postsynaptic receptors. These results suggest that a decrease in nSR100 levels results in a decrease in presynaptic glutamate release. Overall, these data demonstrate that nSR100$^{+/\Delta 7-8}$ neurons have lower excitatory synaptic transmission.

nSR100 Levels and Microexon Splicing are Responsive to Neuronal Activity and May Act as Indicators of Disturbances in Neuronal Activity, Such as Those Seen in ASD.

Synaptogenesis and synaptic activity are highly dynamic processes that are regulated by neuronal stimulation (Katz and Shatz, 1996) and the results show that these processes are directly affected by changes in nSR100 levels. Also as aforementioned, both synaptogenesis and synaptic activity are perturbed in ASD and other neurobiological disorders, such as epilepsy-which often co-occurs with ASD. A prevailing hypothesis in ASD-supported by the observations (a-f) listed above in ASD brains and in the present nSR100 mouse model—is that neuronal activity is disrupted in ASD brains.

These observations prompted the investigation of whether nSR100 controls alternative splicing events that respond to neuronal activity and/or whether nSR100 levels are affected by neuronal activity. Because neuronal stimulation results in depolarization, the effects of neuronal stimulation can be examined in primary neuronal cultures that are depolarized by KCl treatment.

A systematic analysis of alternative splicing events modulated by neuronal activity, including microexons, longer cassette exons, retained introns and alternative 5' and 3' splice sites was first performed. Cultured wild-type hippocampal mouse neurons were depolarized using KCl treatment for thirty minutes or three hours and RNA-Seq analysis was performed on these samples. This analysis revealed that 222 alternative splicing events already display changes as early as 30 minutes after KCl treatment, and that 1,829 events display changes after 3 hours of treatment (FIG. 42A). Of 598 detected microexons, none were found to display increased skipping, after 30 min of treatment whereas 88 microexons (14.7% of all microexons) displayed increased skipping after 3 hours of KCl treatment. Only 7 microexons were found to have higher inclusion levels after 3 hours of treatment (FIG. 42B). Among the additional alternative splicing events affected by neuronal depolarization were 887 (of 10830 detected alternative cassette exons>27 nt; 8.1%) alternative cassette exons and 672 retained introns. Longer alternative cassette exons were also primarily skipped in depolarized neurons (747/887; 84.2%) (FIG. 42B). Genes harboring depolarization-dependent alternative cassette exons have functions related to signal transduction and transcription regulation whereas those with microexons relate primarily to vesicle transport (FIG. 42C). In sharp contrast with the strong directionality displayed by microexons and cassette exons, retained introns comprise a similar number of events that are positively and negatively affected by neuronal depolarization, and 5' and 3' alternative splice sites are increasingly used after neuronal depolarization (FIG. 42B). The analysis of RNA-Seq data from a recent report where primary cortical mouse neurons were treated with KCl for 5 hours (Maze et al., 2015) gave comparable results to these observations, with 70.8% (34/48) microexons and 78.2% (906/1,158) of longer alternative cassette exons undergoing skipping upon depolarization (FIG. 43). These results demonstrate that a large number of alternative splicing events, including a significant fraction of neural microexons enriched for functions related to the synapse, are dynamically regulated by neuronal activity.

Next addressed was whether microexons undergoing skipping during neuronal activity are regulated by nSR100. Surprisingly, 69.3% (61/88) of skipped microexons in depolarized neurons are known nSR100 targets and 39.8% (35/88) of microexons that are skipped after depolarization in mouse neurons were also found to be included at lower levels in human subjects with ASD (FIG. 44A). Furthermore, 63.6% (56/88) of skipped microexons in depolarized neurons are also skipped upon loss of nSR100 in the mouse brain (FIG. 44B; association p-value=$2.402 \times 10^{-13}$). These microexons are significantly enriched in UGC motifs immediately upstream of microexons where nSR100 binds to promote exon inclusion (FIG. 44C) (Raj et al., Mol Cell 2014). Longer exons that are skipped in depolarized neurons only display a slight enrichment in UGC motifs (FIG. 44C). These results suggest a direct role for nSR100 for the inclusion of microexons that are dynamically involved in synaptic functions and respond to external stimuli, and suggest that nSR100 is regulated by neuronal activity.

The analyses demonstrated that nSR100 protein levels are regulated by neuronal activity since a 2-fold decrease in nSR100 protein levels was observed as early as 30 minutes into KCl treatment (FIG. 44D). Interestingly, one of the 7 microexons that is promoted by neuronal depolarization is located in the nSR100 gene itself, and lies within an intron that is increasingly retained upon depolarization (FIG. 44E). Although the 16-nucleotide nSR100 microexon is predicted to lead to nonsense-mediated decay of the alternative isoform, nSR100 mRNA levels remain steady thirty minutes after depolarization (FIGS. 44F and 45A), indicating that the inclusion of the microexon does not affect nSR100 transcript levels. Cell fractionation to assess transcript levels in nucleus vs. cytoplasm of resting neurons indicates that nSR100 isoforms carrying the retained intron are enriched by almost 2-fold in the nucleus (FIG. 44G), which could explain why nSR100 protein levels go down without a change in total nSR100 transcript abundance. These events are not part of a self-regulatory loop, as overexpression of nSR100 in N2A cells does not significantly affect the inclusion levels of the microexon nor intron retention (FIG. 45B).

Thus, nSR100 levels and a subset of its microexon splicing program are responsive to neuronal activity and may be used as indicators or biomarkers of disturbances in neuronal activity, such as those seen in ASD.

Uniqueness of nSR100 Mouse Model

The mutant mouse described herein only shows reduced nSR100 protein levels and therefore represents a physiologically relevant model for the study of autism disorders characterized by the misregulation of microexons as well as longer neural alternative exons. Microexons regulated by nSR100 are highly conserved between human and mouse and the nSR100 heterozygous mutant mouse recapitulates several hallmark features of ASD observed in humans, as well as in other mouse models, including defects in social behaviour, sensory gating and altered synaptic activity. The demonstration that nSR100 mutant neurons have impaired glutamatergic transmission and mirror the molecular signature of depolarized neurons constitutes an important step in the understanding of the neurobiological mechanisms underlying autism. These findings suggest a model, in which different ASD-causing mutations and mechanisms can converge upon nSR100 and its alternative splicing program. ASDs often co-occur with epilepsy, which causes depolarization. So, for example, ASD cases linked to copy number variations (CNVs) of Chromosome 15q can also suffer from epileptic seizures (Battaglia, 2005). Notably, the autistic cohort in which the present inventors showed downregulation of nSR100 and misregulation of its microexon splicing program contained patients with idiopathic ASD (Irimia et al., 2014). Thus, not wishing to be bound by theory, it is conceivable that sometime epileptic seizures can worsen ASD phenotypes and contribute to nSR100 downregulation. The nSR100 pathway may also intersect with that of FXS, since Fmrp has been shown to regulate translation of eIF4E, overexpression of which causes ASD phenotypes in mice (Gkogkas et al., 2013; Santini et al., 2013), and the splicing of the other component of the eIF4F complex, Eif4g, is regulated by both depolarization and nSR100 (Table 3). Moreover defects on cortical neurogenesis, which depends on the repressor element 1-silencing transcription factor (REST), have been observed in many ASD models. Previously, it was shown that REST and nSR100 inhibit each other (Raj et al., 2011). ASD cases with disordered neurogenesis and REST misregulation would be predicted to disrupt nSR100 function.

Example 4. nSR100 Interaction Partners

The mechanism by which nSR100 regulates its target exons was investigated (Raj et al. 2014), as well as mechanisms by which nSR100 expression levels are controlled through its association with different interaction partners. Transcriptional regulation of nSR100 is mediated at least in part by a repressor of neurogenesis genes, REST/NRSF (Raj et al. 2011). This indicates that inhibition of REST activity represents a route for increasing nSR100 expression (Raj et al. 2011). However, depletion of REST in ES cells did not result in significant levels of nSR100 protein expression, even though nSR100 mRNA was detected (Raj et al. 2011). This suggested that additional mechanisms regulate nSR100 concentrations in cells.

By applying affinity purification coupled to mass-spectrometry (AP-MS), several interaction nSR100 partner proteins were detected that provide insight into mechanisms of post-translational regulation of nSR100 levels. For example, AP-MS experiments identified the F-box protein FBXW11 (also known as 1TRCP2) as an nSR100 interaction partner. The Skp-Cullin-F-box (SCF) complex is a multi-protein complex that regulates cellular protein levels via ubiquitin-mediated proteolysis. FBXW11 is an E3 ubiquitin ligase that confers specificity to the SCF complex by recognizing a particular phosphodegron on targets. In addition, Skp1, which is required for recognizing and binding FBXW11, was also detected in nSR100 AP-MS experiments. Phosphorylation of consensus binding sites for F-box proteins, including FBXW11, is typically required for targeting of proteins for degradation by the proteosomal pathway. The set of nSR100 interaction partners identified by AP-MS included several kinases such as PLK1, GSK3B, CSNK2, CSNK1, CDK1 and SRPK1, as well as other kinases that may control nSR100 levels and or activity. Consistent with an important role for FBXW11 and the proteasome in controlling nSR100 levels, treatment of cells with the proteasome inhibitor MG132 and siRNA depletion of FBXW11 both resulted in significant increases in levels of nSR100 (FIG. 46; nSR100 protein is subjected to proteasomal degradation and FIG. 47; nSR100 protein is regulated by FBXW11).

Tables 4 and 5 list high confidence AP-MS nSR100 interaction partners from human 293 and mouse N2A cells, respectively.

These results demonstrate that treatments that affect the expression or activity of specific nSR100 interaction partners, including components of the proteosomal degradation pathway, represent a novel potential approach for correcting the misregulation of nSR100 and its target AS network in the context of neurological disorders and disease.

Example 5. SRRM3 Promotes Splicing of Microexons that are Also Regulated by SRRM4

By analyzing mouse microexons and in the mouse neuro2A cell line, it is shown that knockdown of SRRM3 affects the same microexons as regulated by SRRM4 (FIG. 48).

Neuro2a cells expressing a control shRNA or an SRRM4-targeting shRNA were transfected with control siRNAs or siRNAs targeting SRRM3. The splicing profiles of 11 representative microexons were analyzed by RT-PCR assays using primers specific for sequences in flanking constitutive exons. Inclusion levels (PSI, percent spliced in) are indicated below each event.

While the present disclosure has been described with reference to a number of examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

308 human neural-regulated microexons.
Genomic coordinates refer to human genome build 19 (hg19).

| GENE | Microexon Coordinates (hg19) | Length | Regulation In brain | by nSR100 | Misregulation in ASD |
|---|---|---|---|---|---|
| DCTN2 | chr12: 57932302-57932304 | 3 | NEURAL-UP | YES | NO |
| NCAM1 | chr11: 113125485-113125487 | 3 | NEURAL-UP | NO | NA |
| CYTH2 | chr19: 48980974-48980976 | 3 | NEURAL-UP | YES | NO |
| MON2 | chr12: 62938546-62938548 | 3 | NEURAL-UP | YES | YES |

TABLE 1-continued 308 human neural-regulated microexons.
Genomic coordinates refer to human genome build 19 (hg19).

| GENE | Microexon Coordinates (hg19) | Length | Regulation In brain | by nSR100 | Misregulation in ASD |
|---|---|---|---|---|---|
| NEDD4L | chr18: 56024689-56024691 | 3 | NEURAL-UP | NO | NA |
| RALGAPA1 | chr14: 36011233-36011235 | 3 | NEURAL-UP | NA | NA |
| TBC1D4 | chr13: 75881711-75881713 | 3 | NEURAL-UP | YES | NO |
| TNIP1 | chr5: 150434770-150434772 | 3 | NEURAL-UP | NO | NO |
| VDAC3 | chr8: 42254196-42254198 | 3 | NEURAL-UP | YES | YES |
| CLASP2 | chr3: 33605456-33605458 | 3 | NEURAL-DOWN | NO | YES |
| GIT2 | chr12: 110405119-110405124 | 6 | NEURAL-UP | YES | YES |
| MICU1 | chr10: 74269156-74269161 | 6 | NEURAL-UP | NO | YES |
| AP2M1 | chr3: 183898433-183898438 | 6 | NEURAL-UP | NO | NO |
| APBB1 | chr11: 6423207-6423212 | 6 | NEURAL-UP | YES | YES |
| APBB2 | chr4: 40844387-40844392 | 6 | NEURAL-UP | YES | NO |
| APBB3 | chr5: 139941429-139941434 | 6 | NEURAL-UP | YES | NO |
| CLEC16A | chr16: 11066411-11066416 | 6 | NEURAL-UP | NO | YES |
| CLIP1 | chr12: 122760986-122760991 | 6 | NEURAL-UP | YES | YES |
| DOCK10 | chr2: 225649454-225649459 | 6 | NEURAL-UP | NA | NO |
| DOCK9 | chr13: 99461377-99461382 | 6 | NEURAL-UP | NO | YES |
| HOOK2 | chr19: 12876643-12876648 | 6 | NEURAL-UP | YES | YES |
| HOOK3 | chr8: 42855414-42855419 | 6 | NEURAL-UP | YES | NO |
| MGAT5B | chr17: 74929374-74929379 | 6 | NEURAL-UP | YES | NO |
| MYH9 | chr22: 36704854-36704859 | 6 | NEURAL-UP | NO | NO |
| MYO1B | chr2: 192243993-192243998 | 6 | NEURAL-UP | NO | YES |
| NELF | chr9: 140350081-140350086 | 6 | NEURAL-UP | YES | NO |
| NSFL1C | chr20: 1436359-1436364 | 6 | NEURAL-UP | YES | NO |
| PACSIN2 | chr22: 43276623-43276628 | 6 | NEURAL-UP | YES | YES |
| RELN | chr7: 103118836-103118841 | 6 | NEURAL-UP | NA | YES |
| RUNDC1 | chr17: 41137668-41137673 | 6 | NEURAL-UP | YES | NO |
| TAF1 | chrX: 70674857-70674862 | 6 | NEURAL-UP | YES | YES |
| TNNT2 | chr1: 201331514-201331519 | 6 | NEURAL-UP | NA | NA |
| UNC13B | chr9: 35371931-35371936 | 6 | NEURAL-UP | NO | YES |
| VPS8 | chr3: 184561028-184561033 | 6 | NEURAL-UP | YES | NA |
| DCTD | chr4: 183837034-183837041 | 8 | NEURAL-UP | YES | NO |
| ITSN1 | chr21: 35174741-35174748 | 8 | NEURAL-UP | YES | NO |
| COL18A1 | chr21: 46906466-46906473 | 8 | NEURAL-UP | NO | NA |
| DOCK9 | chr13: 99448460-99448467 | 8 | NEURAL-UP | YES | YES |
| FLNA | chrX: 153594113-153594120 | 8 | NEURAL-UP | NO | NO |
| RIT1 | chr1: 155874394-155874401 | 8 | NEURAL-UP | YES | YES |
| AP1G1 | chr16: 71801780-71801788 | 9 | NEURAL-UP | YES | NO |
| CTB-52I2.8 | chr19: 18103863-18103871 | 9 | NEURAL-UP | YES | NO |
| DTNA | chr18: 32405231-32405239 | 9 | NEURAL-UP | YES | YES |
| MYO5A | chr15: 52641015-52641023 | 9 | NEURAL-UP | YES | NO |
| NBEA | chr13: 35743124-35743132 | 9 | NEURAL-UP | YES | NO |
| PTK2 | chr8: 141679826-141679834 | 9 | NEURAL-UP | YES | NO |
| SHANK2 | chr11: 70348028-70348036 | 9 | NEURAL-UP | NA | YES |
| MACF1 | chr1: 39902154-39902162 | 9 | NEURAL-DOWN | NO | YES |
| AP1B1 | chr22: 29725701-29725709 | 9 | NEURAL-UP | YES | NO |
| AP1S2 | chrX: 15846315-15846323 | 9 | NEURAL-UP | YES | YES |
| ASAP1 | chr8: 131173031-131173039 | 9 | NEURAL-UP | YES | YES |
| ASAP2 | chr2: 9476165-9476173 | 9 | NEURAL-UP | YES | NO |
| CADPS | chr3: 62483821-62483829 | 9 | NEURAL-UP | NA | NO |
| CADPS2 | chr7: 122054122-122054130 | 9 | NEURAL-UP | YES | NO |
| CADPS2 | chr7: 122120906-122120914 | 9 | NEURAL-UP | YES | NO |
| CCDC64 | chr12: 120500559-120500567 | 9 | NEURAL-UP | NO | NO |
| CYLD | chr16: 50809077-50809085 | 9 | NEURAL-UP | NO | NA |
| EMC1 | chr1: 19560674-19560682 | 9 | NEURAL-UP | YES | YES |
| FRY | chr13: 32832101-32832109 | 9 | NEURAL-UP | NA | NO |
| ITPR2 | chr12: 26539151-26539159 | 9 | NEURAL-UP | YES | NO |
| KCNMA1 | chr10: 78767943-78767951 | 9 | NEURAL-UP | NA | NA |
| KCNN2 | chr5: 113826388-113826396 | 9 | NEURAL-UP | NO | NO |
| KIF3A | chr5: 132042143-132042151 | 9 | NEURAL-UP | NO | NO |
| MADD | chr11: 47348095-47348103 | 9 | NEURAL-UP | YES | YES |
| MAP4K4 | chr2: 102484491-102484499 | 9 | NEURAL-UP | NO | NO |
| MAST4 | chr5: 66389985-66389993 | 9 | NEURAL-UP | NO | YES |
| NINL | chr20: 25467375-25467383 | 9 | NEURAL-UP | YES | NA |
| PSAP | chr10: 73583645-73583653 | 9 | NEURAL-UP | YES | YES |
| PTPRD | chr9: 8527345-8527353 | 9 | NEURAL-UP | NA | NO |
| RALGAPB | chr20: 37163028-37163036 | 9 | NEURAL-UP | YES | NO |
| SEC31B | chr10: 102268218-102268226 | 9 | NEURAL-UP | YES | NA |
| SPOCK1 | chr5: 136609065-136609073 | 9 | NEURAL-UP | NA | YES |
| SPOCK3 | chr4: 167983793-167983801 | 9 | NEURAL-UP | YES | NO |
| TACC2 | chr10: 124004580-124004588 | 9 | NEURAL-UP | YES | NO |
| PRUNE2 | chr9: 79256888-79256896 | 9 | NEURAL-DOWN | NA | YES |
| ROBO1 | chr3: 78742498-78742506 | 9 | NEURAL-DOWN | NO | YES |
| EVI5 | chr1: 93001594-93001603 | 10 | NEURAL-UP | YES | NA |

TABLE 1-continued 308 human neural-regulated microexons.
Genomic coordinates refer to human genome build 19 (hg19).

| GENE | Microexon Coordinates (hg19) | Length | Regulation In brain | by nSR100 | Misregulation in ASD |
|---|---|---|---|---|---|
| SYPL1 | chr7: 105736739-105736748 | 10 | NEURAL-UP | YES | NO |
| SNX21 | chr20: 44469087-44469097 | 11 | NEURAL-UP | YES | YES |
| TNNT2 | chr1: 201341273-201341283 | 11 | NEURAL-DOWN | NA | NA |
| GULP1 | chr2: 189454467-189454477 | 11 | NEURAL-UP | YES | NA |
| KIAA0141 | chr5: 141313516-141313526 | 11 | NEURAL-UP | YES | NO |
| WWC3 | chrX: 10088488-10088498 | 11 | NEURAL-UP | NA | NA |
| KCNMA1 | chr10: 78785204-78785215 | 12 | NEURAL-UP | NA | NO |
| KDM1A | chr1: 23392553-23392564 | 12 | NEURAL-UP | NO | NO |
| PTPRD | chr9: 8454580-8454591 | 12 | NEURAL-UP | NA | YES |
| PTPRD | chr9: 8523513-8523524 | 12 | NEURAL-UP | NA | YES |
| PTPRM | chr18: 8252486-8252497 | 12 | NEURAL-UP | YES | NO |
| SPAG9 | chr17: 49086492-49086503 | 12 | NEURAL-UP | NO | YES |
| ACAP2 | chr3: 195046173-195046184 | 12 | NEURAL-UP | YES | NA |
| AGAP1 | chr2: 236627025-236627036 | 12 | NEURAL-UP | NO | NO |
| AGRN | chr1: 986412-986423 | 12 | NEURAL-UP | NO | NO |
| ANK2 | chr4: 114234840-114234851 | 12 | NEURAL-UP | YES | YES |
| CADPS | chr3: 62530523-62530534 | 12 | NEURAL-UP | NA | NO |
| DNM3 | chr1: 172292469-172292480 | 12 | NEURAL-UP | NA | YES |
| ENAH | chr1: 225718748-225718759 | 12 | NEURAL-UP | NO | YES |
| ERC1 | chr12: 1313667-1313678 | 12 | NEURAL-UP | YES | NO |
| EXOC6B | chr2: 72410023-72410034 | 12 | NEURAL-UP | YES | NO |
| FMN2 | chr1: 240343469-240343480 | 12 | NEURAL-UP | YES | NO |
| GRAMD1A | chr19: 35513804-35513815 | 12 | NEURAL-UP | YES | NA |
| GRAMD1B | chr11: 123489053-123489064 | 12 | NEURAL-UP | NO | NO |
| L1CAM | chrX: 153128823-153128834 | 12 | NEURAL-UP | YES | NO |
| LPHN2 | chr1: 82407718-82407729 | 12 | NEURAL-UP | YES | YES |
| LRRC16A | chr6: 25507707-25507718 | 12 | NEURAL-UP | YES | NO |
| MTA1 | chr14: 105934675-105934686 | 12 | NEURAL-UP | YES | NO |
| MYO18A | chr17: 27443462-27443473 | 12 | NEURAL-UP | YES | NO |
| PRDM10 | chr11: 129799305-129799316 | 12 | NEURAL-UP | YES | NA |
| PTPRS | chr19: 5256119-5256130 | 12 | NEURAL-UP | NO | NO |
| RASA2 | chr3: 141308972-141308983 | 12 | NEURAL-UP | YES | NA |
| RPGRIP1L | chr16: 53693127-53693138 | 12 | NEURAL-UP | YES | NO |
| SH3GLB2 | chr9: 131775287-131775298 | 12 | NEURAL-UP | YES | YES |
| SIDT2 | chr11: 117057706-117057717 | 12 | NEURAL-UP | YES | NO |
| SLC43A2 | chr17: 1490243-1490254 | 12 | NEURAL-UP | YES | YES |
| SLIT2 | chr4: 20492426-20492437 | 12 | NEURAL-UP | YES | YES |
| SNX2 | chr5: 122162333-122162344 | 12 | NEURAL-UP | YES | YES |
| SUPT5H | chr19: 39948934-39948945 | 12 | NEURAL-DOWN | NO | YES |
| GRAMD1A | chr19: 35513804-35513815 | 12 | NEURAL-UP | YES | NA |
| ARL6 | chr3: 97510797-97510809 | 13 | NEURAL-UP | YES | NO |
| KIF21A | chr12: 39709031-39709045 | 15 | NEURAL-UP | NO | YES |
| FNBP1L | chr1: 94006599-94006613 | 15 | NEURAL-UP | NO | NA |
| SFRS2IP | chr12: 46355091-46355105 | 15 | NEURAL-UP | NO | NO |
| TPD52L1 | chr6: 125573168-125573182 | 15 | NEURAL-UP | YES | NO |
| ATL1 | chr14: 51096713-51096727 | 15 | NEURAL-UP | YES | NO |
| ERGIC3 | chr20: 34142143-34142157 | 15 | NEURAL-UP | YES | YES |
| FNBP1 | chr9: 132678245-132678259 | 15 | NEURAL-UP | NO | YES |
| INPP4A | chr2: 99165418-99165432 | 15 | NEURAL-UP | NO | NO |
| NFASC | chr1: 204960420-204960434 | 15 | NEURAL-UP | NA | NO |
| SPAG9 | chr17: 49085198-49085212 | 15 | NEURAL-UP | YES | NO |
| ABI1 | chr10: 27060004-27060018 | 15 | NEURAL-UP | YES | NO |
| CELSR3 | chr3: 48687708-48687722 | 15 | NEURAL-UP | YES | NO |
| DCTN1 | chr2: 74590741-74590755 | 15 | NEURAL-UP | YES | YES |
| DNAJC13 | chr3: 132191401-132191415 | 15 | NEURAL-UP | YES | YES |
| EDEM3 | chr1: 184670664-184670678 | 15 | NEURAL-UP | YES | YES |
| GDPD5 | chr11: 75150385-75150399 | 15 | NEURAL-UP | NO | NA |
| L1CAM | chrX: 153138683-153138697 | 15 | NEURAL-UP | NA | NO |
| LPHN1 | chr19: 14277828-14277842 | 15 | NEURAL-UP | YES | NO |
| LPHN3 | chr4: 62596340-62596354 | 15 | NEURAL-UP | YES | NO |
| MACF1 | chr1: 39925490-39925504 | 15 | NEURAL-UP | YES | NO |
| PLEC | chr8: 145012569-145012583 | 15 | NEURAL-UP | NO | YES |
| PORCN | chrX: 48372515-48372529 | 15 | NEURAL-UP | YES | NA |
| RAPGEF6 | chr5: 130805494-130805508 | 15 | NEURAL-UP | YES | NO |
| SH3GLB2 | chr9: 131771732-131771746 | 15 | NEURAL-UP | YES | YES |
| SMAP1 | chr6: 71507520-71507534 | 15 | NEURAL-UP | NO | NO |
| SPTAN1 | chr9: 131371930-131371944 | 15 | NEURAL-UP | YES | NO |
| SSR1 | chr6: 7295321-7295335 | 15 | NEURAL-UP | YES | YES |
| UGGT2 | chr13: 96646181-96646195 | 15 | NEURAL-UP | YES | YES |
| VAV2 | chr9: 136652368-136652382 | 15 | NEURAL-UP | YES | YES |
| VAV2 | chr9: 136675313-136675327 | 15 | NEURAL-UP | YES | NA |
| CADPS2 | chr7: 122026349-122026363 | 15 | NEURAL-DOWN | YES | NO |
| ATL2 | chr2: 38523828-38523842 | 15 | NEURAL-UP | YES | YES |

TABLE 1-continued 308 human neural-regulated microexons.
Genomic coordinates refer to human genome build 19 (hg19).

|  |  |  |  | Regulation | Misregulation in |
| --- | --- | --- | --- | --- | --- |
| GENE | Microexon Coordinates (hg19) | Length | In brain | by nSR100 | ASD |
| DOCK7 | chr1: 62953069-62953083 | 15 | NEURAL-UP | YES | YES |
| PDLIM7 | chr5: 176918405-176918421 | 17 | NEURAL-UP | NO | NA |
| ARHGAP44 | chr17: 12876619-12876636 | 18 | NEURAL-UP | YES | NO |
| ARL15 | chr5: 53581171-53581188 | 18 | NEURAL-UP | YES | NO |
| CADPS | chr3: 62498426-62498443 | 18 | NEURAL-UP | NA | NO |
| ABI2 | chr2: 204246912-204246929 | 18 | NEURAL-UP | YES | NO |
| ATP6V0A1 | chr17: 40660590-40660607 | 18 | NEURAL-UP | YES | YES |
| CACNA2D3 | chr3: 54850880-54850897 | 18 | NEURAL-UP | NO | NA |
| CASK | chrX: 41481870-41481887 | 18 | NEURAL-UP | YES | YES |
| CD99L2 | chrX: 149940278-149940295 | 18 | NEURAL-UP | NO | NO |
| CTNND1 | chr11: 57573933-57573950 | 18 | NEURAL-UP | NO | YES |
| DOCK11 | chrX: 117819483-117819500 | 18 | NEURAL-UP | YES | NA |
| FMNL1 | chr17: 43312199-43312216 | 18 | NEURAL-UP | NA | NA |
| FRY | chr13: 32862004-32862021 | 18 | NEURAL-UP | NA | NO |
| FRYL | chr4: 48504845-48504862 | 18 | NEURAL-UP | YES | NO |
| KIF1B | chr1: 10333072-10333089 | 18 | NEURAL-UP | YES | YES |
| LRRC16A | chr6: 25577204-25577221 | 18 | NEURAL-UP | YES | NO |
| MAPKBP1 | chr15: 42105528-42105545 | 18 | NEURAL-UP | NO | YES |
| MED23 | chr6: 131936464-131936481 | 18 | NEURAL-UP | NO | NA |
| NCKAP1 | chr2: 183889706-183889723 | 18 | NEURAL-UP | YES | YES |
| NRCAM | chr7: 107878196-107878213 | 18 | NEURAL-UP | YES | YES |
| PLEKHA5 | chr12: 19423122-19423139 | 18 | NEURAL-UP | NO | NA |
| PORCN | chrX: 48371223-48371240 | 18 | NEURAL-UP | YES | NA |
| PPP6R3 | chr11: 68377079-68377096 | 18 | NEURAL-UP | NO | YES |
| PTK2 | chr8: 141779674-141779691 | 18 | NEURAL-UP | YES | YES |
| PTPRF | chr1: 44041581-44041598 | 18 | NEURAL-UP | NO | NO |
| PTPRK | chr6: 128316394-128316411 | 18 | NEURAL-UP | NO | NO |
| PUS7 | chr7: 105137401-105137418 | 18 | NEURAL-UP | YES | NA |
| RAPGEF2 | chr4: 160164926-160164943 | 18 | NEURAL-UP | YES | NO |
| SRC | chr20: 36014863-36014880 | 18 | NEURAL-UP | YES | NA |
| TBC1D24 | chr16: 2547711-2547728 | 18 | NEURAL-UP | NO | NO |
| C5orf44 | chr5: 64951463-64951480 | 18 | NEURAL-DOWN | YES | NO |
| ARVCF | chr22: 19964229-19964246 | 18 | NEURAL-UP | YES | YES |
| PKD1 | chr16: 2163042-2163060 | 19 | NEURAL-UP | YES | NA |
| CACNB1 | chr17: 37341384-37341403 | 20 | NEURAL-UP | YES | NO |
| INPP5F | chr10: 121579032-121579051 | 20 | NEURAL-UP | NO | YES |
| DDHD1 | chr14: 53569749-53569769 | 21 | NEURAL-UP | YES | YES |
| EIF4G3 | chr1: 21308881-21308901 | 21 | NEURAL-UP | NO | YES |
| TRRAP | chr7: 98543553-98543573 | 21 | NEURAL-UP | YES | NO |
| AP1B1 | chr22: 29735743-29735763 | 21 | NEURAL-UP | NO | YES |
| C1orf9 | chr1: 172546679-172546699 | 21 | NEURAL-UP | YES | NO |
| C6orf162 | chr6: 88040410-88040430 | 21 | NEURAL-UP | YES | NA |
| CACNA2D1 | chr7: 81612630-81612650 | 21 | NEURAL-UP | YES | NO |
| CADPS | chr3: 62479320-62479340 | 21 | NEURAL-UP | NA | YES |
| CADPS2 | chr7: 122076414-122076434 | 21 | NEURAL-UP | YES | NO |
| CAMTA1 | chr1: 7809831-7809851 | 21 | NEURAL-UP | YES | NO |
| CAMTA2 | chr17: 4872795-4872815 | 21 | NEURAL-UP | YES | NO |
| DCTN1 | chr2: 74600055-74600075 | 21 | NEURAL-UP | NO | NO |
| DCTN4 | chr5: 150111448-150111468 | 21 | NEURAL-UP | YES | NO |
| DTNB | chr2: 25642384-25642404 | 21 | NEURAL-UP | YES | NO |
| DYNC2H1 | chr11: 103112256-103112276 | 21 | NEURAL-UP | YES | NO |
| EPRS | chr1: 220191468-220191488 | 21 | NEURAL-UP | NO | YES |
| EXOC1 | chr4: 56733038-56733058 | 21 | NEURAL-UP | NO | YES |
| FMNL2 | chr2: 153479051-153479071 | 21 | NEURAL-UP | NO | YES |
| KIF21A | chr12: 39724044-39724064 | 21 | NEURAL-UP | NO | NO |
| MEF2D | chr1: 156446286-156446306 | 21 | NEURAL-UP | YES | YES |
| MPP3 | chr17: 41894045-41894065 | 21 | NEURAL-UP | YES | NA |
| ODZ3 | chr4: 183665296-183665316 | 21 | NEURAL-UP | YES | NO |
| PHLDB2 | chr3: 111677122-111677142 | 21 | NEURAL-UP | NO | NA |
| PLEKHC1 | chr14: 53327732-53327752 | 21 | NEURAL-UP | YES | NO |
| PTK2 | chr8: 141772467-141772487 | 21 | NEURAL-UP | YES | YES |
| RAB3GAP1 | chr2: 135925263-135925283 | 21 | NEURAL-UP | NO | YES |
| SHANK2 | chr11: 70335433-70335453 | 21 | NEURAL-UP | NA | NO |
| VTI1A | chr10: 114293289-114293309 | 21 | NEURAL-UP | YES | YES |
| ZFYVE27 | chr10: 99512614-99512634 | 21 | NEURAL-UP | NO | YES |
| MYO1D | chr17: 31054617-31054637 | 21 | NEURAL-UP | NO | NO |
| RPS24 | chr10: 79799962-79799983 | 22 | NEURAL-UP | NO | NO |
| ARHGAP23 | chr17: 36655174-36655196 | 23 | NEURAL-UP | NA | NO |
| FSD1L | chr9: 108241635-108241657 | 23 | NEURAL-UP | YES | NO |
| POC1B | chr12: 89853793-89853815 | 23 | NEURAL-UP | YES | NA |
| PHF21A | chr11: 45967627-45967649 | 23 | NEURAL-UP | YES | YES |
| C2orf67 | chr2: 210891104-210891126 | 23 | NEURAL-UP | NA | NA |
| KIF1C | chr17: 4923144-4923166 | 23 | NEURAL-UP | YES | NO |

TABLE 1-continued 308 human neural-regulated microexons.
Genomic coordinates refer to human genome build 19 (hg19).

| GENE | Microexon Coordinates (hg19) | Length | Regulation In brain | by nSR100 | Misregulation in ASD |
|---|---|---|---|---|---|
| PFKFB3 | chr10: 6270159-6270181 | 23 | NEURAL-UP | NO | YES |
| UNC13B | chr9: 35364542-35364564 | 23 | NEURAL-UP | NO | YES |
| PTS | chr11: 112100931-112100953 | 23 | NEURAL-DOWN | NO | NO |
| STX2 | chr12: 131283713-131283735 | 23 | NEURAL-UP | NO | YES |
| CPEB3 | chr10: 93917806-93917829 | 24 | NEURAL-UP | YES | NO |
| SH3GLB1 | chr1: 87195771-87195794 | 24 | NEURAL-UP | YES | YES |
| TBC1D4 | chr13: 75894150-75894173 | 24 | NEURAL-UP | NO | YES |
| PROM1 | chr4: 15981504-15981527 | 24 | NEURAL-DOWN | NA | NA |
| CPEB4 | chr5: 173370029-173370052 | 24 | NEURAL-UP | YES | YES |
| BIN1 | chr2: 127810998-127811021 | 24 | NEURAL-UP | YES | YES |
| NRG2 | chr5: 139239474-139239497 | 24 | NEURAL-UP | NA | NA |
| TRIM9 | chr14: 51449660-51449683 | 24 | NEURAL-UP | YES | YES |
| CLASP1 | chr2: 122202515-122202538 | 24 | NEURAL-UP | YES | NO |
| ACVR2A | chr2: 148669106-148669129 | 24 | NEURAL-UP | YES | NO |
| AGRN | chr1: 987373-987396 | 24 | NEURAL-UP | YES | YES |
| ANK1 | chr8: 41557949-41557972 | 24 | NEURAL-UP | NO | NA |
| ANK2 | chr4: 114158755-114158778 | 24 | NEURAL-UP | YES | NO |
| ARRB1 | chr11: 74982745-74982768 | 24 | NEURAL-UP | YES | NO |
| C9orf5 | chr9: 111848277-111848300 | 24 | NEURAL-UP | NO | NO |
| CLASP1 | chr2: 122166600-122166623 | 24 | NEURAL-UP | YES | NO |
| CLASP2 | chr3: 33615965-33615988 | 24 | NEURAL-UP | YES | YES |
| CPEB2 | chr4: 15042088-15042111 | 24 | NEURAL-UP | YES | NO |
| CSNK1G3 | chr5: 122941033-122941056 | 24 | NEURAL-UP | YES | NO |
| GOPC | chr6: 117898611-117898634 | 24 | NEURAL-UP | YES | YES |
| GULP1 | chr2: 189434347-189434370 | 24 | NEURAL-UP | YES | NO |
| HERC4 | chr10: 69718870-69718893 | 24 | NEURAL-UP | YES | YES |
| LASS6 | chr2: 169622832-169622855 | 24 | NEURAL-UP | YES | NO |
| MEF2A | chr15: 100243567-100243590 | 24 | NEURAL-UP | YES | YES |
| MEF2C | chr5: 88026028-88026051 | 24 | NEURAL-UP | YES | NO |
| MINK1 | chr17: 4796581-4796604 | 24 | NEURAL-UP | YES | YES |
| NAV1 | chr1: 201759682-201759705 | 24 | NEURAL-UP | YES | NO |
| NRBP1 | chr2: 27658590-27658613 | 24 | NEURAL-UP | NO | NO |
| OCRL | chrX: 128718321-128718344 | 24 | NEURAL-UP | YES | NO |
| PPP1R9A | chr7: 94916422-94916445 | 24 | NEURAL-UP | YES | NO |
| PRKACB | chr1: 84640716-84640739 | 24 | NEURAL-UP | NO | YES |
| RAPGEF2 | chr4: 160265188-160265211 | 24 | NEURAL-UP | YES | NO |
| RAPGEF6 | chr5: 130785716-130785739 | 24 | NEURAL-UP | NO | NO |
| RYR2 | chr1: 237906900-237906923 | 24 | NEURAL-UP | NA | NO |
| SHANK3 | chr22: 51150043-51150066 | 24 | NEURAL-UP | YES | NO |
| SLC22A23 | chr6: 3285170-3285193 | 24 | NEURAL-UP | NO | YES |
| SLC38A10 | chr17: 79223870-79223893 | 24 | NEURAL-UP | YES | YES |
| SYNJ1 | chr21: 34048642-34048665 | 24 | NEURAL-UP | YES | NO |
| TNIK | chr3: 170824972-170824995 | 24 | NEURAL-UP | YES | NO |
| PDE1A | chr2: 183032994-183033017 | 24 | NEURAL-DOWN | NA | NO |
| SLIT2 | chr4: 20526772-20526795 | 24 | NEURAL-DOWN | YES | NO |
| CD47 | chr3: 107769425-107769449 | 25 | NEURAL-UP | YES | YES |
| LRRC16A | chr6: 25612605-25612629 | 25 | NEURAL-UP | NO | NO |
| TCF7L2 | chr10: 114921338-114921362 | 25 | NEURAL-UP | YES | NA |
| MFSD6 | chr2: 191364558-191364582 | 25 | NEURAL-UP | YES | YES |
| ZYX | chr7: 143084855-143084880 | 26 | NEURAL-UP | NO | NO |
| LYSMD4 | chr15: 100271378-100271403 | 26 | NEURAL-UP | YES | NA |
| FBXO16 | chr8: 28286895-28286920 | 26 | NEURAL-UP | YES | NA |
| FAM168A | chr11: 73136067-73136093 | 27 | NEURAL-UP | NO | NO |
| PPFIA1 | chr11: 70212047-70212073 | 27 | NEURAL-UP | NO | YES |
| PTPRS | chr19: 5229327-5229353 | 27 | NEURAL-UP | YES | NO |
| TPD52 | chr8: 80962680-80962706 | 27 | NEURAL-UP | NO | NO |
| PTPRD | chr9: 8497242-8497268 | 27 | NEURAL-DOWN | NA | NO |
| CLASP2 | chr3: 33630197-33630223 | 27 | NEURAL-UP | NO | NO |
| TPD52L2 | chr20: 62517369-62517395 | 27 | NEURAL-UP | YES | YES |
| WNK1 | chr12: 1015483-1015509 | 27 | NEURAL-UP | NO | NA |
| ANK3 | chr10: 61841908-61841934 | 27 | NEURAL-UP | YES | NO |
| AXL | chr19: 41745599-41745625 | 27 | NEURAL-UP | NA | YES |
| CLASP1 | chr2: 122184980-122185006 | 27 | NEURAL-UP | YES | YES |
| DENND4A | chr15: 65957537-65957563 | 27 | NEURAL-UP | NO | YES |
| DOCK3 | chr3: 51370432-51370458 | 27 | NEURAL-UP | YES | YES |
| DOCK4 | chr7: 111424153-111424179 | 27 | NEURAL-UP | YES | YES |
| FBXO25 | chr8: 417720-417746 | 27 | NEURAL-UP | YES | YES |
| FIP1L1 | chr4: 54306749-54306775 | 27 | NEURAL-UP | NO | NO |
| GIT1 | chr17: 27905980-27906006 | 27 | NEURAL-UP | YES | NO |
| KCNQ5 | chr6: 73834209-73834235 | 27 | NEURAL-UP | YES | NO |
| LCP1 | chr13: 46722917-46722943 | 27 | NEURAL-UP | NA | NA |
| LPHN3 | chr4: 62894573-62894599 | 27 | NEURAL-UP | NO | NO |
| MYO6 | chr6: 76621389-76621415 | 27 | NEURAL-UP | NO | NO |

TABLE 1-continued 308 human neural-regulated microexons.
Genomic coordinates refer to human genome build 19 (hg19).

| GENE | Microexon Coordinates (hg19) | Length | Regulation In brain | by nSR100 | Misregulation in ASD |
|---|---|---|---|---|---|
| ODZ3 | chr4: 183632728-183632754 | 27 | NEURAL-UP | YES | NO |
| PLS3 | chrX: 114874422-114874448 | 27 | NEURAL-UP | YES | YES |
| PPFIA3 | chr19: 49649423-49649449 | 27 | NEURAL-UP | YES | NO |
| PPFIA4 | chr1: 203030780-203030806 | 27 | NEURAL-UP | NA | NO |
| PRPF18 | chr10: 13639645-13639671 | 27 | NEURAL-UP | NO | YES |
| PTPRA | chr20: 2955861-2955887 | 27 | NEURAL-UP | NO | NO |
| PTPRF | chr1: 44067742-44067768 | 27 | NEURAL-UP | YES | YES |
| PTPRM | chr18: 8248148-8248174 | 27 | NEURAL-UP | NO | NO |
| SNX14 | chr6: 86248556-86248582 | 27 | NEURAL-UP | YES | NO |
| SORBS1 | chr10: 97181947-97181973 | 27 | NEURAL-UP | YES | NO |
| ACO19 | chrX: 23752458-23752484 | 27 | NEURAL-DOWN | YES | NO |
| SGCE | chr7: 94229009-94229035 | 27 | NEURAL-DOWN | NO | NO |

TABLE 2

333 mouse neural-regulated microexons.
Genomic coordinates refer to mouse genome build mm9.

| GENE | Microexon Coordinates (mm9) | Length | Regulation in Brain | by nSR100 | Mis-regulation KO brain | ASD (ortholog) |
|---|---|---|---|---|---|---|
| Dctn2 | chr10: 126709498-126709500 | 3 | NEURAL-UP | YES | YES | NO |
| Cltc | chr11: 86548688-86548690 | 3 | NEURAL-UP | NO | NO | NA |
| Mon2 | chr10: 122460142-122460144 | 3 | NEURAL-UP | YES | YES | YES |
| Psd3 | chr8: 70425707-70425709 | 3 | NEURAL-UP | NA | NO | NA |
| Ralgapa1 | chr12: 56706687-56706689 | 3 | NEURAL-UP | YES | NO | NA |
| Tbc1d4 | chr14: 101859916-101859918 | 3 | NEURAL-UP | YES | YES | NO |
| Asap2 | chr12: 21220228-21220231 | 4 | NEURAL-UP | YES | NO | NO |
| Yap1 | chr9: 7939042-7939046 | 5 | NEURAL-UP | NA | NO | NA |
| Micu1 | chr10: 59229832-59229837 | 6 | NEURAL-UP | NO | NO | YES |
| Vps8 | chr16: 21451429-21451434 | 6 | NEURAL-UP | YES | YES | NA |
| Apbb1 | chr7: 112714460-112714465 | 6 | NEURAL-UP | YES | NO | YES |
| Clec16a | chr16: 10573011-10573016 | 6 | NEURAL-UP | NO | NO | YES |
| Clip1 | chr5: 124031601-124031606 | 6 | NEURAL-UP | YES | NO | YES |
| Dock9 | chr14: 121959617-121959622 | 6 | NEURAL-UP | NO | NO | YES |
| Git2 | chr5: 115203157-115203162 | 6 | NEURAL-UP | YES | NO | YES |
| Hook2 | chr8: 87522285-87522290 | 6 | NEURAL-UP | YES | YES | YES |
| Hook3 | chr8: 27156378-27156383 | 6 | NEURAL-UP | YES | NO | NO |
| Macf1 | chr4: 123177996-123178001 | 6 | NEURAL-UP | NO | NO | NA |
| Myh9 | chr15: 77613338-77613343 | 6 | NEURAL-UP | NO | NO | NO |
| Myo1b | chr1: 51843417-51843422 | 6 | NEURAL-UP | NO | NO | YES |
| Nelf | chr2: 24913485-24913490 | 6 | NEURAL-UP | YES | NO | NO |
| Pacsin2 | chr15: 83214053-83214058 | 6 | NEURAL-UP | YES | YES | YES |
| Pkd1 | chr17: 24708360-24708365 | 6 | NEURAL-UP | YES | YES | NA |
| Reln | chr5: 21397380-21397385 | 6 | NEURAL-UP | NA | NO | YES |
| Rundc1 | chr11: 101289680-101289685 | 6 | NEURAL-UP | YES | NO | NO |
| Taf1 | chrX: 98786073-98786078 | 6 | NEURAL-UP | YES | YES | YES |
| Unc13b | chr4: 43246776-43246781 | 6 | NEURAL-UP | YES | YES | YES |
| Dock9 | chr14: 121943798-121943805 | 8 | NEURAL-UP | YES | NO | YES |
| Flna | chrX: 71486155-71486162 | 8 | NEURAL-UP | YES | YES | NO |
| Madd | chr2: 90980966-90980974 | 9 | NEURAL-UP | NO | NO | YES |
| Cadps2 | chr6: 23304194-23304202 | 9 | NEURAL-UP | NA | NO | NO |
| Tacc2 | chr7: 137899411-137899419 | 9 | NEURAL-UP | NO | NO | NO |
| Macf1 | chr4: 123063792-123063800 | 9 | NEURAL-DOWN | NO | NO | YES |
| Robo1 | chr16: 72956520-72956528 | 9 | NEURAL-DOWN | NA | NO | YES |
| 6330403A02Rik | chr1: 182369237-182369245 | 9 | NEURAL-UP | YES | YES | NO |
| Ap1b1 | chr11: 4940924-4940932 | 9 | NEURAL-UP | YES | NO | NO |
| Ap1g1 | chr8: 112354513-112354521 | 9 | NEURAL-UP | NO | NO | NO |
| Ap1s2 | chrX: 160369295-160369303 | 9 | NEURAL-UP | YES | NO | YES |
| Asap1 | chr15: 63985406-63985414 | 9 | NEURAL-UP | YES | NO | YES |
| C230096C10Rik | chr4: 138920246-138920254 | 9 | NEURAL-UP | YES | NO | YES |
| Casq2 | chr3: 101937013-101937021 | 9 | NEURAL-UP | NA | NA | NA |
| Cyld | chr8: 91242189-91242197 | 9 | NEURAL-UP | NO | NO | NA |
| Dtna | chr18: 23758904-23758912 | 9 | NEURAL-UP | NA | NO | YES |
| Eml6 | chr11: 29664950-29664958 | 9 | NEURAL-UP | YES | YES | NA |
| Fry | chr5: 151263964-151263972 | 9 | NEURAL-UP | NA | NO | NO |
| Fryl | chr5: 73442106-73442114 | 9 | NEURAL-UP | YES | YES | NO |
| Kcnn1 | chr8: 73370663-73370671 | 9 | NEURAL-UP | NO | NO | NO |
| Kcnn2 | chr18: 45840127-45840135 | 9 | NEURAL-UP | NO | NO | NO |

TABLE 2-continued 333 mouse neural-regulated microexons.
Genomic coordinates refer to mouse genome build mm9.

| GENE | Microexon Coordinates (mm9) | Length | Regulation in Brain | by nSR100 | Mis-regulation KO brain | ASD (ortholog) |
|---|---|---|---|---|---|---|
| Mast4 | chr13: 103596231-103596239 | 9 | NEURAL-UP | NO | NO | YES |
| Myo5a | chr9: 75035329-75035337 | 9 | NEURAL-UP | YES | NO | NO |
| Nav1 | chr1: 137354438-137354446 | 9 | NEURAL-UP | NO | NO | NO |
| Nbea | chr3: 55797970-55797978 | 9 | NEURAL-UP | YES | YES | NO |
| Nphp3 | chr9: 103936300-103936308 | 9 | NEURAL-UP | YES | YES | NA |
| Phc1 | chr6: 122288490-122288498 | 9 | NEURAL-UP | YES | YES | NA |
| Psap | chr10: 59760285-59760293 | 9 | NEURAL-UP | YES | NO | YES |
| Ptk2 | chr15: 73042417-73042425 | 9 | NEURAL-UP | YES | NO | NO |
| Ptprd | chr4: 75785198-75785206 | 9 | NEURAL-UP | YES | YES | NO |
| Ralgapb | chr2: 158275225-158275233 | 9 | NEURAL-UP | YES | YES | NO |
| Shank2 | chr7: 151582543-151582551 | 9 | NEURAL-UP | YES | NO | YES |
| Spock3 | chr8: 65592231-65592239 | 9 | NEURAL-UP | YES | YES | NO |
| Sypl | chr12: 33653499-33653508 | 10 | NEURAL-UP | YES | NO | NO |
| Fndc3b | chr3: 27389055-27389065 | 11 | NEURAL-UP | YES | YES | NA |
| Gulp1 | chr1: 44847541-44847551 | 11 | NEURAL-UP | YES | YES | NA |
| N4bp2 | chr5: 66193620-66193630 | 11 | NEURAL-UP | NO | NO | NA |
| Paxip1 | chr5: 28106802-28106812 | 11 | NEURAL-UP | NO | NO | NA |
| Snx21 | chr2: 164617058-164617068 | 11 | NEURAL-UP | YES | YES | YES |
| St5 | chr7: 116679545-116679555 | 11 | NEURAL-UP | NA | NO | NA |
| Atp2c1 | chr9: 105395873-105395884 | 12 | NEURAL-UP | YES | YES | NA |
| Zmynd8 | chr2: 165678368-165678379 | 12 | NEURAL-UP | YES | YES | NA |
| Lama2 | chr10: 26741267-26741278 | 12 | NEURAL-DOWN | NA | NO | NA |
| Dnm3 | chr1: 164005906-164005917 | 12 | NEURAL-UP | NA | NO | YES |
| Kdm1a | chr4: 136119353-136119364 | 12 | NEURAL-UP | YES | YES | NO |
| Ptprd | chr4: 75781449-75781460 | 12 | NEURAL-UP | NA | NO | YES |
| Ptprm | chr17: 67159709-67159720 | 12 | NEURAL-UP | NA | NO | NO |
| Spag9 | chr11: 93940513-93940524 | 12 | NEURAL-UP | YES | NO | YES |
| Tnnt2 | chr1: 137738592-137738603 | 12 | NEURAL-UP | NO | NA | NA |
| Acap2 | chr16: 31129700-31129711 | 12 | NEURAL-UP | YES | NO | NA |
| Agap1 | chr1: 91506859-91506870 | 12 | NEURAL-UP | NO | NO | NO |
| Agrn | chr4: 155543655-155543666 | 12 | NEURAL-UP | YES | NO | NO |
| Ank2 | chr3: 126682174-126682185 | 12 | NEURAL-UP | YES | NO | YES |
| Ank3 | chr10: 69392195-69392206 | 12 | NEURAL-UP | YES | NO | NO |
| Ccdc64 | chr5: 116122153-116122164 | 12 | NEURAL-UP | YES | NO | NO |
| Dnm1 | chr2: 32178699-32178710 | 12 | NEURAL-UP | YES | NO | NO |
| Enah | chr1: 183861305-183861316 | 12 | NEURAL-UP | NO | NO | YES |
| Erc1 | chr6: 119684099-119684110 | 12 | NEURAL-UP | YES | NO | NO |
| Gramd1a | chr7: 31918239-31918250 | 12 | NEURAL-UP | NO | NO | NA |
| Gramd1b | chr9: 40108025-40108036 | 12 | NEURAL-UP | NO | NO | NO |
| Idh3g | chrX: 71027637-71027648 | 12 | NEURAL-UP | NO | NO | NA |
| L1cam | chrX: 71100991-71101002 | 12 | NEURAL-UP | YES | NO | NO |
| Lphn2 | chr3: 148523391-148523402 | 12 | NEURAL-UP | YES | NO | YES |
| Lrrc16a | chr13: 24193941-24193952 | 12 | NEURAL-UP | NA | NO | NO |
| Macf1 | chr4: 123046064-123046075 | 12 | NEURAL-UP | NO | NO | NO |
| Mta1 | chr12: 114373012-114373023 | 12 | NEURAL-UP | YES | YES | NO |
| Nrcam | chr12: 45698769-45698780 | 12 | NEURAL-UP | NO | NO | NA |
| Prdm10 | chr9: 31150840-31150851 | 12 | NEURAL-UP | YES | YES | NA |
| Ptprd | chr4: 75700493-75700504 | 12 | NEURAL-UP | YES | YES | YES |
| Ptprf | chr4: 117894176-117894187 | 12 | NEURAL-UP | YES | NO | NA |
| Ptprf | chr4: 117917895-117917906 | 12 | NEURAL-UP | NO | NO | NO |
| Ptprk | chr10: 28283901-28283912 | 12 | NEURAL-UP | NA | NO | NO |
| Ptprs | chr17: 56585322-56585333 | 12 | NEURAL-UP | NO | NO | NO |
| Rpgrip1l | chr8: 93799924-93799935 | 12 | NEURAL-UP | YES | YES | NO |
| Scyl2 | chr10: 89117080-89117091 | 12 | NEURAL-UP | YES | YES | NA |
| Sh3glb2 | chr2: 30204746-30204757 | 12 | NEURAL-UP | YES | NO | YES |
| Sidt2 | chr9: 45755624-45755635 | 12 | NEURAL-UP | YES | NO | NO |
| Slc43a2 | chr11: 75379906-75379917 | 12 | NEURAL-UP | YES | YES | YES |
| Slit2 | chr5: 48582242-48582253 | 12 | NEURAL-UP | YES | NO | YES |
| Arl6 | chr16: 59618492-59618504 | 13 | NEURAL-UP | NO | NO | NO |
| Pde3b | chr7: 121660835-121660847 | 13 | NEURAL-UP | YES | YES | NA |
| Cdon | chr9: 35283315-35283328 | 14 | NEURAL-UP | YES | NO | NA |
| Fnbp1l | chr3: 122255054-122255068 | 15 | NEURAL-UP | NO | NO | NA |
| Kif21a | chr15: 90778755-90778769 | 15 | NEURAL-UP | NA | NO | YES |
| Myo9b | chr8: 73861102-73861116 | 15 | NEURAL-UP | YES | NO | NA |
| Snap91 | chr9: 86693665-86693679 | 15 | NEURAL-UP | YES | NO | NO |
| Tpd52l1 | chr10: 31062818-31062832 | 15 | NEURAL-UP | YES | YES | NO |
| Cadps2 | chr6: 23270933-23270947 | 15 | NEURAL-DOWN | NA | NO | NO |
| Ncam1 | chr9: 49349993-49350007 | 15 | NEURAL-UP | NO | NO | NA |
| Abi1 | chr2: 22818734-22818748 | 15 | NEURAL-UP | YES | YES | NO |
| Atl1 | chr12: 71061535-71061549 | 15 | NEURAL-UP | NO | NO | NO |
| Bbs9 | chr9: 22452464-22452478 | 15 | NEURAL-UP | YES | YES | NA |
| Chchd3 | chr6: 32843392-32843406 | 15 | NEURAL-UP | YES | YES | NA |
| Dctn1 | chr6: 83147313-83147327 | 15 | NEURAL-UP | YES | YES | YES |

TABLE 2-continued 333 mouse neural-regulated microexons.
Genomic coordinates refer to mouse genome build mm9.

| GENE | Microexon Coordinates (mm9) | Length | Regulation in Brain | by nSR100 | Mis-regulation KO brain | ASD (ortholog) |
|---|---|---|---|---|---|---|
| Dnajc13 | chr9: 104112199-104112213 | 15 | NEURAL-UP | NO | NO | YES |
| Edem3 | chr1: 153659884-153659898 | 15 | NEURAL-UP | NO | NO | YES |
| Eea1 | chr10: 95462985-95462999 | 15 | NEURAL-UP | YES | NO | NA |
| Ergic3 | chr2: 155841113-155841127 | 15 | NEURAL-UP | YES | YES | YES |
| Fnbp1 | chr2: 30900402-30900416 | 15 | NEURAL-UP | NO | NO | YES |
| Gdpd5 | chr7: 106605507-106605521 | 15 | NEURAL-UP | NO | NO | NA |
| Inpp4a | chr1: 37431120-37431134 | 15 | NEURAL-UP | NO | NO | NO |
| Itsn1 | chr16: 91842873-91842887 | 15 | NEURAL-UP | YES | YES | NO |
| L1cam | chrX: 71112361-71112375 | 15 | NEURAL-UP | YES | NO | NO |
| Lphn1 | chr8: 86450161-86450175 | 15 | NEURAL-UP | YES | NO | NO |
| Nfasc | chr1: 134489928-134489942 | 15 | NEURAL-UP | YES | NO | NO |
| Pcca | chr14: 123127293-123127307 | 15 | NEURAL-UP | NO | NO | NA |
| Plec | chr15: 76024989-76025003 | 15 | NEURAL-UP | YES | NO | YES |
| Porcn | chrX: 7778784-7778798 | 15 | NEURAL-UP | NA | NO | NA |
| Rapgef6 | chr11: 54465251-54465265 | 15 | NEURAL-UP | YES | YES | NO |
| Ryr1 | chr7: 29841253-29841267 | 15 | NEURAL-UP | NO | NO | NO |
| Sh3glb2 | chr2: 30201579-30201593 | 15 | NEURAL-UP | YES | NO | YES |
| Sidt1 | chr16: 44256080-44256094 | 15 | NEURAL-UP | NA | NA | NA |
| Slc12a5 | chr2: 164822364-164822378 | 15 | NEURAL-UP | YES | NO | NA |
| Spna2 | chr2: 29869678-29869692 | 15 | NEURAL-UP | YES | NO | NO |
| Ssr1 | chr13: 38074964-38074978 | 15 | NEURAL-UP | YES | YES | YES |
| Vav2 | chr2: 27155950-27155964 | 15 | NEURAL-UP | YES | YES | NA |
| Vav2 | chr2: 27140359-27140373 | 15 | NEURAL-UP | YES | YES | YES |
| Atl2 | chr17: 80250227-80250241 | 15 | NEURAL-UP | YES | NO | YES |
| Dock7 | chr4: 98620557-98620571 | 15 | NEURAL-UP | YES | NO | YES |
| Pcgf2 | chr11: 97561093-97561108 | 16 | NEURAL-UP | NA | NA | NA |
| Mapk14 | chr17: 28877689-28877704 | 16 | NEURAL-UP | NO | NO | NA |
| Col11a1 | chr3: 113841089-113841104 | 16 | NEURAL-UP | YES | YES | NA |
| Pdlim7 | chr13: 55609225-55609241 | 17 | NEURAL-UP | NO | NO | NA |
| Col4a1 | chr8: 11204536-11204552 | 17 | NEURAL-UP | YES | NO | NA |
| Clasp2 | chr9: 113769238-113769255 | 18 | NEURAL-UP | YES | YES | NA |
| Lrrfip1 | chr1: 92969901-92969918 | 18 | NEURAL-UP | NA | NO | NO |
| 2410002O22Rik | chr13: 104942245-104942262 | 18 | NEURAL-DOWN | NO | NO | NO |
| Arhgap44 | chr11: 64826409-64826426 | 18 | NEURAL-UP | NA | NO | NO |
| Arvcf | chr16: 18400874-18400891 | 18 | NEURAL-UP | YES | YES | YES |
| Ash2l | chr8: 26940847-26940864 | 18 | NEURAL-UP | NO | NO | NA |
| Atp6v0a1 | chr11: 100910773-100910790 | 18 | NEURAL-UP | YES | NO | YES |
| Cacna2d3 | chr14: 29937852-29937869 | 18 | NEURAL-UP | NA | NO | NA |
| Cd99l2 | chrX: 68678590-68678607 | 18 | NEURAL-UP | NA | NO | NO |
| Ctnnd1 | chr2: 84452689-84452706 | 18 | NEURAL-UP | YES | NO | YES |
| Dock11 | chrX: 33615912-33615929 | 18 | NEURAL-UP | YES | NO | NA |
| Fmnl1 | chr11: 103044330-103044347 | 18 | NEURAL-UP | NO | NO | NA |
| Fry | chr5: 151291536-151291553 | 18 | NEURAL-UP | NA | NO | NO |
| Fryl | chr5: 73416010-73416027 | 18 | NEURAL-UP | YES | YES | NO |
| Gyk | chrX: 82984561-82984578 | 18 | NEURAL-UP | NA | NO | NA |
| Kif1b | chr4: 148639454-148639471 | 18 | NEURAL-UP | YES | NO | YES |
| Limk2 | chr11: 3252903-3252920 | 18 | NEURAL-UP | NO | NO | NA |
| Lrrc16a | chr13: 24141512-24141529 | 18 | NEURAL-UP | YES | YES | NO |
| Mapkbp1 | chr2: 119839037-119839054 | 18 | NEURAL-UP | YES | YES | YES |
| Med23 | chr10: 24603010-24603027 | 18 | NEURAL-UP | NO | NO | NA |
| Mon2 | chr10: 122446969-122446986 | 18 | NEURAL-UP | YES | NO | NO |
| Nrcam | chr12: 45636044-45636061 | 18 | NEURAL-UP | YES | YES | YES |
| Plekha5 | chr6: 140485527-140485544 | 18 | NEURAL-UP | NO | NO | NA |
| Ppp6r3 | chr19: 3459747-3459764 | 18 | NEURAL-UP | YES | NO | YES |
| Ptk2 | chr15: 73112648-73112665 | 18 | NEURAL-UP | YES | YES | YES |
| Ptprf | chr4: 117924681-117924698 | 18 | NEURAL-UP | NO | NO | NO |
| Ptprk | chr10: 28289980-28289997 | 18 | NEURAL-UP | NA | NO | NO |
| Ptpru | chr4: 131341658-131341675 | 18 | NEURAL-UP | YES | NO | NA |
| Pus7 | chr5: 23269152-23269169 | 18 | NEURAL-UP | YES | YES | NA |
| Src | chr2: 157284579-157284596 | 18 | NEURAL-UP | YES | NO | NA |
| Tbc1d24 | chr17: 24321326-24321343 | 18 | NEURAL-UP | YES | NO | NO |
| Trappc8 | chr18: 21014322-21014339 | 18 | NEURAL-UP | YES | YES | NA |
| Dync1i2 | chr2: 71065884-71065901 | 18 | NEURAL-UP | NO | NO | YES |
| Fam178a | chr19: 45017411-45017429 | 19 | NEURAL-UP | YES | YES | NA |
| Pkd1 | chr17: 24708347-24708365 | 19 | NEURAL-UP | YES | NO | NA |
| Cacnb1 | chr11: 97871941-97871960 | 20 | NEURAL-UP | YES | NO | NO |
| Cacnb3 | chr15: 98471390-98471409 | 20 | NEURAL-UP | NO | NO | NO |
| Pfas | chr11: 68816694-68816713 | 20 | NEURAL-UP | NO | NO | NA |
| Aifm3 | chr16: 17506992-17507012 | 21 | NEURAL-UP | NA | NO | YES |
| Ddhd1 | chr14: 46248529-46248549 | 21 | NEURAL-UP | YES | YES | YES |
| Eif4g3 | chr4: 137651824-137651844 | 21 | NEURAL-UP | YES | YES | YES |
| Trrap | chr5: 145571201-145571221 | 21 | NEURAL-UP | NO | NO | NO |
| AI848100 | chr1: 163775691-163775711 | 21 | NEURAL-UP | YES | NO | NO |

TABLE 2-continued 333 mouse neural-regulated microexons.
Genomic coordinates refer to mouse genome build mm9.

| GENE | Microexon Coordinates (mm9) | Length | Regulation in Brain | by nSR100 | Mis-regulation KO brain | ASD (ortholog) |
|---|---|---|---|---|---|---|
| Ap1b1 | chr11: 4933245-4933265 | 21 | NEURAL-UP | NO | NO | YES |
| Cacna2d1 | chr5: 15847808-15847828 | 21 | NEURAL-UP | NA | NO | NO |
| Cadps2 | chr6: 23331057-23331077 | 21 | NEURAL-UP | NA | NO | NO |
| Camta1 | chr4: 150450686-150450706 | 21 | NEURAL-UP | NA | NO | NO |
| Camta2 | chr11: 70484393-70484413 | 21 | NEURAL-UP | YES | YES | NO |
| Dctn4 | chr18: 60705011-60705031 | 21 | NEURAL-UP | YES | NO | NO |
| Dtnb | chr12: 3754096-3754116 | 21 | NEURAL-UP | YES | NO | NO |
| Dync2h1 | chr9: 7045349-7045369 | 21 | NEURAL-UP | YES | YES | NO |
| Eif4g1 | chr16: 20674859-20674879 | 21 | NEURAL-UP | YES | NO | NA |
| Eprs | chr1: 187211236-187211256 | 21 | NEURAL-UP | YES | NO | YES |
| Exoc1 | chr5: 76969772-76969792 | 21 | NEURAL-UP | YES | NO | YES |
| Fam92a | chr4: 12097105-12097125 | 21 | NEURAL-UP | YES | YES | NA |
| Fmnl2 | chr2: 52971311-52971331 | 21 | NEURAL-UP | NO | NO | YES |
| Kdm1b | chr13: 47153046-47153066 | 21 | NEURAL-UP | YES | YES | NA |
| Kif21a | chr15: 90795406-90795426 | 21 | NEURAL-UP | NA | NO | NO |
| Mast2 | chr4: 116006018-116006038 | 21 | NEURAL-UP | YES | NO | NA |
| Mef2d | chr3: 87965703-87965723 | 21 | NEURAL-UP | YES | NO | YES |
| MPP7 | chr18: 7430393-7430413 | 21 | NEURAL-UP | NA | NO | NA |
| Odz3 | chr8: 49372487-49372507 | 21 | NEURAL-UP | YES | NO | NO |
| Odz4 | chr7: 104003227-104003247 | 21 | NEURAL-UP | NO | NO | NA |
| Ptk2 | chr15: 73106051-73106071 | 21 | NEURAL-UP | YES | NO | YES |
| Rab3gap1 | chr1: 129838171-129838191 | 21 | NEURAL-UP | NO | NO | YES |
| Senp6 | chr9: 79946693-79946713 | 21 | NEURAL-UP | YES | NO | NA |
| Shank2 | chr7: 151593961-151593981 | 21 | NEURAL-UP | NO | NO | NO |
| Stk3 | chr15: 35044693-35044713 | 21 | NEURAL-UP | YES | YES | NA |
| Tmem184b | chr15: 79194088-79194108 | 21 | NEURAL-UP | YES | NO | NA |
| Vti1a | chr19: 55461679-55461699 | 21 | NEURAL-UP | YES | YES | YES |
| Arhgap21 | chr2: 20775585-20775605 | 21 | NEURAL-UP | NO | NO | NA |
| Dlg1 | chr16: 31854754-31854774 | 21 | NEURAL-UP | NO | NO | NA |
| Gabbr1 | chr17: 37186722-37186742 | 21 | NEURAL-UP | YES | NO | NO |
| Zfyve27 | chr19: 42260110-42260130 | 21 | NEURAL-UP | YES | YES | YES |
| Poc1b | chr10: 98627220-98627241 | 22 | NEURAL-UP | NO | NO | NA |
| Cep63 | chr9: 102523603-102523624 | 22 | NEURAL-UP | NO | NO | NA |
| Sft2d1 | chr17: 8510715-8510736 | 22 | NEURAL-UP | NO | NO | NO |
| Kif1c | chr11: 70537406-70537427 | 22 | NEURAL-UP | YES | NO | NO |
| Plekhg3 | chr12: 77664487-77664508 | 22 | NEURAL-UP | NA | NO | NA |
| Pfkfb3 | chr2: 11399663-11399685 | 23 | NEURAL-UP | NO | NO | YES |
| Phf21a | chr2: 92191766-92191788 | 23 | NEURAL-UP | YES | NO | YES |
| Arhgap23 | chr11: 97352958-97352980 | 23 | NEURAL-UP | YES | NO | NO |
| Mll3 | chr5: 24809915-24809937 | 23 | NEURAL-UP | NO | NO | NA |
| Phf21b | chr15: 84624326-84624348 | 23 | NEURAL-UP | NO | NO | NA |
| Agrn | chr4: 155542655-155542678 | 24 | NEURAL-UP | NO | NO | YES |
| Clasp1 | chr1: 120409282-120409305 | 24 | NEURAL-UP | YES | YES | NO |
| Rhbdl3 | chr11: 80116166-80116189 | 24 | NEURAL-UP | NO | NO | NA |
| Tbc1d4 | chr14: 101870645-101870668 | 24 | NEURAL-UP | NO | NO | YES |
| Ttc7b | chr12: 101684166-101684189 | 24 | NEURAL-UP | NO | NO | NA |
| Slc38a10 | chr11: 119969781-119969804 | 24 | NEURAL-UP | YES | NO | YES |
| Cpeb4 | chr11: 31818801-31818824 | 24 | NEURAL-UP | YES | YES | YES |
| Nrg1 | chr8: 32941677-32941700 | 24 | NEURAL-UP | YES | NO | NA |
| Nrg2 | chr18: 36187047-36187070 | 24 | NEURAL-UP | YES | YES | NA |
| Prkd1 | chr12: 51520840-51520863 | 24 | NEURAL-UP | NA | NO | YES |
| Srcin1 | chr11: 97403848-97403871 | 24 | NEURAL-UP | NA | NO | NA |
| Gnas | chr2: 174153609-174153632 | 24 | NEURAL-UP | NO | NO | NA |
| Bin1 | chr18: 32589354-32589377 | 24 | NEURAL-UP | YES | NO | YES |
| Kif1a | chr1: 94923409-94923432 | 24 | NEURAL-UP | NA | NO | NO |
| Map3k5 | chr10: 19739364-19739387 | 24 | NEURAL-DOWN | NO | NO | NA |
| 4933424B01Rik | chr6: 146510116-146510139 | 24 | NEURAL-UP | NO | NO | NA |
| Acvr2a | chr2: 48742194-48742217 | 24 | NEURAL-UP | NO | NO | NO |
| Ank1 | chr8: 24220819-24220842 | 24 | NEURAL-UP | NA | NO | NA |
| Ank2 | chr3: 126755144-126755167 | 24 | NEURAL-UP | YES | NO | NO |
| Ank3 | chr10: 69285826-69285849 | 24 | NEURAL-UP | NO | NO | NA |
| Arrb1 | chr7: 106745546-106745569 | 24 | NEURAL-UP | YES | NO | NO |
| Atp11a | chr8: 12851633-12851656 | 24 | NEURAL-UP | NA | NO | NA |
| Ckap5 | chr2: 91439761-91439784 | 24 | NEURAL-UP | YES | NO | NA |
| Clasp1 | chr1: 120438252-120438275 | 24 | NEURAL-UP | YES | NO | NO |
| Clasp2 | chr9: 113767699-113767722 | 24 | NEURAL-UP | YES | NO | NA |
| Clasp2 | chr9: 113787868-113787891 | 24 | NEURAL-UP | YES | YES | YES |
| Cpeb2 | chr5: 43660108-43660131 | 24 | NEURAL-UP | YES | NO | NO |
| Cpeb3 | chr19: 37180281-37180304 | 24 | NEURAL-UP | YES | NO | NO |
| Csnk1g1 | chr9: 65882857-65882880 | 24 | NEURAL-UP | NO | NO | NA |
| Csnk1g3 | chr18: 54108299-54108322 | 24 | NEURAL-UP | NO | NO | NO |
| Cspp1 | chr1: 10049905-10049928 | 24 | NEURAL-UP | YES | YES | NA |
| D730040F13Rik | chr4: 56935259-56935282 | 24 | NEURAL-UP | NO | NO | NO |

TABLE 2-continued 333 mouse neural-regulated microexons.
Genomic coordinates refer to mouse genome build mm9.

| GENE | Microexon Coordinates (mm9) | Length | Regulation in Brain | by nSR100 | Mis-regulation KO brain | ASD (ortholog) |
|---|---|---|---|---|---|---|
| Fina | chrX: 71478306-71478329 | 24 | NEURAL-UP | NO | NO | NO |
| Gopc | chr10: 52077148-52077171 | 24 | NEURAL-UP | YES | NO | YES |
| Herc4 | chr10: 62766593-62766616 | 24 | NEURAL-UP | YES | NO | YES |
| Lass6 | chr2: 68943800-68943823 | 24 | NEURAL-UP | YES | YES | NO |
| Mars | chr10: 126733773-126733796 | 24 | NEURAL-UP | NO | NO | NA |
| Mef2a | chr7: 74389407-74389430 | 24 | NEURAL-UP | YES | NO | YES |
| Mef2c | chr13: 83794203-83794226 | 24 | NEURAL-UP | NA | NO | NO |
| Mink1 | chr11: 70422910-70422933 | 24 | NEURAL-UP | YES | NO | YES |
| Msi2 | chr11: 88181714-88181737 | 24 | NEURAL-UP | NO | NO | NA |
| Nav1 | chr1: 137360492-137360515 | 24 | NEURAL-UP | YES | NO | NO |
| Nrbp1 | chr5: 31548695-31548718 | 24 | NEURAL-UP | NO | NO | NO |
| Ocrl | chrX: 45309387-45309410 | 24 | NEURAL-UP | NO | NO | NO |
| Osbpl6 | chr2: 76407077-76407100 | 24 | NEURAL-UP | NO | NO | NA |
| Ppp1r9a | chr6: 5107004-5107027 | 24 | NEURAL-UP | YES | NO | NO |
| Rapgef2 | chr3: 78886546-78886569 | 24 | NEURAL-UP | YES | NO | NO |
| Sbf1 | chr15: 89137603-89137626 | 24 | NEURAL-UP | YES | NO | NA |
| Sh3glb1 | chr3: 144362818-144362841 | 24 | NEURAL-UP | YES | YES | YES |
| Shank3 | chr15: 89368446-89368469 | 24 | NEURAL-UP | NA | NO | NO |
| Slc22a23 | chr13: 34285118-34285141 | 24 | NEURAL-UP | NA | NO | YES |
| Synj1 | chr16: 90971809-90971832 | 24 | NEURAL-UP | YES | NO | NO |
| Tnik | chr3: 28524121-28524144 | 24 | NEURAL-UP | YES | NO | NO |
| Ttc28 | chr5: 111710900-111710923 | 24 | NEURAL-UP | YES | NO | NA |
| Uggt1 | chr1: 36233621-36233644 | 24 | NEURAL-UP | NO | NO | NO |
| Cd47 | chr16: 49908167-49908191 | 25 | NEURAL-UP | YES | NO | YES |
| 37680 | chr2: 60085545-60085569 | 25 | NEURAL-UP | NO | NO | NA |
| Tcf7l2 | chr19: 56002220-56002244 | 25 | NEURAL-UP | NO | NA | NA |
| Mfsd6 | chr1: 52715543-52715567 | 25 | NEURAL-UP | YES | YES | YES |
| Lysmd4 | chr7: 74369262-74369287 | 26 | NEURAL-UP | YES | YES | NA |
| Antxr1 | chr6: 87220749-87220774 | 26 | NEURAL-UP | YES | YES | NA |
| Chpt1 | chr10: 87944098-87944124 | 27 | NEURAL-UP | YES | NO | NA |
| Lphn2 | chr3: 148490176-148490202 | 27 | NEURAL-UP | YES | YES | NA |
| Tpd52l2 | chr2: 181245209-181245235 | 27 | NEURAL-UP | YES | YES | YES |
| Ppfia1 | chr7: 151674596-151674622 | 27 | NEURAL-UP | YES | NO | YES |
| Ptprs | chr17: 56567214-56567240 | 27 | NEURAL-UP | YES | NO | NO |
| Heatr7a | chr15: 76262802-76262828 | 27 | NEURAL-DOWN | NO | NO | NA |
| Sgce | chr6: 4640469-4640495 | 27 | NEURAL-DOWN | NO | NO | NO |
| Ank3 | chr10: 69443572-69443598 | 27 | NEURAL-UP | YES | YES | NO |
| Baz2b | chr2: 59771469-59771495 | 27 | NEURAL-UP | NO | NO | NO |
| Clasp1 | chr1: 120419898-120419924 | 27 | NEURAL-UP | YES | NO | YES |
| Daam1 | chr12: 73059734-73059760 | 27 | NEURAL-UP | YES | YES | NA |
| Dock4 | chr12: 41521184-41521210 | 27 | NEURAL-UP | YES | NO | YES |
| Fam168a | chr7: 107967250-107967276 | 27 | NEURAL-UP | NO | NO | NO |
| Fbxo25 | chr8: 13938922-13938948 | 27 | NEURAL-UP | YES | NO | YES |
| Fip1l1 | chr5: 74981071-74981097 | 27 | NEURAL-UP | NO | NO | NO |
| Git1 | chr11: 77316331-77316357 | 27 | NEURAL-UP | YES | NO | NO |
| Ipo11 | chr13: 107647579-107647605 | 27 | NEURAL-UP | YES | NO | NA |
| Kcnq5 | chr1: 21456464-21456490 | 27 | NEURAL-UP | YES | NO | NO |
| Kif1a | chr1: 94962129-94962155 | 27 | NEURAL-UP | NA | NO | YES |
| Lphn3 | chr5: 82187011-82187037 | 27 | NEURAL-UP | NA | NO | NO |
| Myo6 | chr9: 80151080-80151106 | 27 | NEURAL-UP | NO | NO | NO |
| Odz3 | chr8: 49398592-49398618 | 27 | NEURAL-UP | YES | NO | NO |
| Odz4 | chr7: 103953615-103953641 | 27 | NEURAL-UP | NO | NO | NA |
| Plch2 | chr4: 154359475-154359501 | 27 | NEURAL-UP | NA | NO | NA |
| Pls3 | chrX: 73045056-73045082 | 27 | NEURAL-UP | YES | YES | YES |
| Ppfia3 | chr7: 52598923-52598949 | 27 | NEURAL-UP | YES | NO | NO |
| Ppfia4 | chr1: 136208106-136208132 | 27 | NEURAL-UP | NA | NO | NO |
| Prom1 | chr5: 44449865-44449891 | 27 | NEURAL-UP | YES | NO | NA |
| Prpf18 | chr2: 4569143-4569169 | 27 | NEURAL-UP | NO | NO | YES |
| Ptpra | chr2: 130335566-130335592 | 27 | NEURAL-UP | NO | NO | NO |
| Ptprf | chr4: 117900424-117900450 | 27 | NEURAL-UP | YES | NO | YES |
| Ptprm | chr17: 67163611-67163637 | 27 | NEURAL-UP | NA | NO | NO |
| Sdccag8 | chr1: 178818892-178818918 | 27 | NEURAL-UP | NO | NO | NA |
| Slit2 | chr5: 48654880-48654906 | 27 | NEURAL-UP | YES | YES | NA |
| Snx14 | chr9: 88295561-88295587 | 27 | NEURAL-UP | YES | NO | NO |
| Sorbs1 | chr19: 40457246-40457272 | 27 | NEURAL-UP | YES | YES | NO |
| Trappc9 | chr15: 72872607-72872633 | 27 | NEURAL-UP | NO | NO | YES |

TABLE 3

95 mouse microexons regulated by neuronal activity. Genomic coordinates refer to mouse genome build mm9

| GENE | Microexon Coordinates (mm9) | Length |
|---|---|---|
| Col11a1 | MmuEX0012118 | 16 |
| Sorbs1 | MmuEX0044374 | 27 |
| Prdm10 | MmuEX0036941 | 12 |
| Itsn1 | MmuEX0024756 | 15 |
| Ergic3 | MmuEX0017296 | 15 |
| Rapgef6 | MmuEX0038816 | 15 |
| Slc43a2 | MmuEX0043333 | 12 |
| Cpeb4 | MmuEX0012543 | 24 |
| Unc13b | MmuEX0050598 | 6 |
| Fryl | MmuEX0019677 | 18 |
| Pus7 | MmuEX0038057 | 18 |
| Phc1 | MmuEX0034681 | 9 |
| Scyl2 | MmuEX0041350 | 12 |
| Stk3 | MmuEX0045422 | 21 |
| Mapkbp1 | MmuEX0027890 | 18 |
| Pacsin2 | MmuEX0033441 | 6 |
| Clasp2 | MmuEX0011515 | 18 |
| Zfyve27 | MmuEX0053823 | 21 |
| Tpd52l2 | MmuEX0048581 | 27 |
| Ssr1 | MmuEX0045072 | 15 |
| Lass6 | MmuEX0026173 | 24 |
| Mon2 | MmuEX0029412 | 3 |
| Lrrc16a | MmuEX0026939 | 25 |
| Pls3 | MmuEX0035876 | 27 |
| Ccdc66 | MmuEX0009873 | 26 |
| Chchd3 | MmuEX0011125 | 15 |
| Mta1 | MmuEX0029871 | 12 |
| Cspp1 | MmuEX0012961 | 24 |
| Kdm1a | MmuEX0025260 | 12 |
| Clasp2 | MmuEX0011532 | 24 |
| Flna | MmuEX0019329 | 8 |
| Sh3glb1 | MmuEX0042195 | 24 |
| Kdm1b | MmuEX0025263 | 21 |
| Ptprm | MmuEX0037946 | 27 |
| Lphn2 | MmuEX0026711 | 12 |
| Clec16a | MmuEX0011633 | 6 |
| Ipo11 | MmuEX0024354 | 27 |
| Mef2a | MmuEX0028559 | 24 |
| Gdpd5 | MmuEX0020267 | 15 |
| Plec | MmuEX0035673 | 15 |
| Kif1b | MmuEX0025502 | 18 |
| Csnk1g1 | MmuEX0012932 | 24 |
| Slc38a10 | MmuEX0043222 | 24 |
| Ralgapa1 | MmuEX0038612 | 3 |
| Sypl | MmuEX0046015 | 10 |
| Git2 | MmuEX0020453 | 6 |
| Pfkfb3 | MmuEX0034574 | 23 |
| Dock4 | MmuEX0015418 | 27 |
| Clasp2 | MmuEX0011514 | 24 |
| Dctn1 | MmuEX0013949 | 21 |
| March7 | MmuEX0027932 | 25 |
| Eif4g1 | MmuEX0016617 | 21 |
| Mast2 | MmuEX0028003 | 21 |
| Mef2d | MmuEX0028570 | 21 |
| Fbxo25 | MmuEX0018852 | 27 |
| Ptprm | MmuEX0037945 | 12 |
| C230096C10 | MmuEX0008514 | 9 |
| Picalm | MmuEX0035018 | 24 |
| Clasp1 | MmuEX0011506 | 27 |
| Trrap | MmuEX0049240 | 21 |
| Dtna | MmuEX0015805 | 9 |
| Ap1g1 | MmuEX0005395 | 9 |
| Snx14 | MmuEX0044238 | 27 |
| Src | MmuEX0044842 | 18 |
| Arhgap21 | MmuEX0005821 | 21 |
| Senp6 | MmuEX0041679 | 21 |
| Fmnl2 | MmuEX0019395 | 21 |
| Eprs | MmuEX0017129 | 21 |
| Rab3gap1 | MmuEX0038343 | 21 |
| Dnajc13 | MmuEX0015182 | 15 |
| AU019823 | MmuEX0002794 | 27 |
| Ppp6r3 | MmuEX0036873 | 18 |
| Senp6 | MmuEX0041673 | 14 |
| Kif21a | MmuEX0025524 | 21 |
| Clasp1 | MmuEX0011511 | 24 |
| Dlg1 | MmuEX0014792 | 21 |
| Cd47 | MmuEX0010235 | 25 |
| Paxip1 | MmuEX0033814 | 11 |
| Cadm2 | MmuEX0008871 | 27 |
| Mapk14 | MmuEX0027827 | 16 |
| Tmem184b | MmuEX0047851 | 21 |
| Acap2 | MmuEX0003401 | 12 |
| Tbc1d24 | MmuEX0046471 | 18 |
| Hook3 | MmuEX0023183 | 6 |
| Myo9b | MmuEX0030590 | 15 |
| Dclre1b | MmuEX0013911 | 27 |
| Gyk | MmuEX0022249 | 18 |
| Unc13b | MmuEX0050596 | 23 |
| Mllt4 | MmuEX0029239 | 21 |
| Max | MmuEX0028056 | 27 |
| Cltc | MmuEX0011807 | 21 |
| Mark3 | MmuEX0027962 | 27 |
| Usp53 | MmuEX0051075 | 25 |
| Srrm4 | MmuEX0044974 | 16 |
| 4933421E11 | MmuEX0001853 | 27 |

TABLE 4

High confidence AP-MS nSR100 interaction partners from human 293 cells. Bait gene name, prey gene name and genbank "prey accession" are according to the NCBI database. The numbers of spectra for the prey in the purifications of the baits are listed ("I" delimits the biological replicates), followed by the average number of spectra per replicate. The number of spectra for the prey in each of the negative controls is also listed, alongside the average of the SAINT scores (the best 2 scores out of the 3 replicates for this dataset), the maximal SAINT score and the Fold Change between the prey Avg spectra of the bait and control purifications (a small value of 0.1 is added to prevent division by 0 in fold change calculations). The calculated FDR (BFDR) is used to determine the reporting cutoffs. Confident interaction partners are those with BFDR ≤1%.

| Bait Gene Name | Prey Protein Accession | Prey Gene Name | Spectra | SpecSum | AvgSpec | Num Replicates | ctrlCounts | AvgP | MaxP | FoldChange | BFDR |
|---|---|---|---|---|---|---|---|---|---|---|---|
| SRRM4 | 118572613 | SRRM2 | 73\|51\|30 | 154 | 51.33 | 3 | 10\|3\|7 | 1 | 1 | 7.7 | 0 |
| SRRM4 | 119226260 | CHERP | 5\|4\|3 | 12 | 4 | 3 | 0\|0\|0 | 1 | 1 | 40 | 0 |
| SRRM4 | 13904870 | RPS5 | 19\|15\|0 | 34 | 11.33 | 3 | 4\|0\|2 | 1 | 1 | 5.67 | 0 |
| SRRM4 | 148727341 | STRAP | 11\|6\|0 | 17 | 5.67 | 3 | 0\|0\|0 | 1 | 1 | 56.67 | 0 |
| SRRM4 | 18379334 | RNPS1 | 12\|7\|5 | 24 | 8 | 3 | 0\|0\|0 | 1 | 1 | 80 | 0 |
| SRRM4 | 193211480 | SKIV2L2 | 15\|13\|7 | 35 | 11.67 | 3 | 2\|4\|2 | 1 | 1 | 4.38 | 0 |
| SRRM4 | 20336290 | DHX30 | 25\|19\|0 | 44 | 14.67 | 3 | 5\|4\|0 | 1 | 1 | 4.89 | 0 |
| SRRM4 | 21536320 | HNRNPUL1 | 5\|2\|3 | 10 | 3.33 | 3 | 0\|0\|0 | 1 | 1 | 33.33 | 0 |

TABLE 4-continued

High confidence AP-MS nSR100 interaction partners from human 293 cells. Bait gene name, prey gene name and genbank "prey accession" are according to the NCBI database. The numbers of spectra for the prey in the purifications of the baits are listed ("I" delimits the biological replicates), followed by the average number of spectra per replicate. The number of spectra for the prey in each of the negative controls is also listed, alongside the average of the SAINT scores (the best 2 scores out of the 3 replicates for this dataset), the maximal SAINT score and the Fold Change between the prey Avg spectra of the bait and control purifications (a small value of 0.1 is added to prevent division by 0 in fold change calculations). The calculated FDR (BFDR) is used to determine the reporting cutoffs. Confident interaction partners are those with BFDR ≤1%.

| Bait Gene Name | Prey Protein Accession | Prey Gene Name | Spectra | SpecSum | AvgSpec | Num Replicates | ctrlCounts | AvgP | MaxP | FoldChange | BFDR |
|---|---|---|---|---|---|---|---|---|---|---|---|
| SRRM4 | 224589071 | BMS1 | 4\|3\|4 | 11 | 3.67 | 3 | 0\|0\|0 | 1 | 1 | 36.67 | 0 |
| SRRM4 | 295842307 | SF1 | 8\|9\|6 | 23 | 7.67 | 3 | 0\|0\|0 | 1 | 1 | 76.67 | 0 |
| SRRM4 | 30795212 | IGF2BP3 | 7\|1\|3 | 11 | 3.67 | 3 | 0\|0\|0 | 1 | 1 | 36.67 | 0 |
| SRRM4 | 33356174 | PNN | 11\|12\|4 | 27 | 9 | 3 | 0\|0\|0 | 1 | 1 | 90 | 0 |
| SRRM4 | 46852388 | CCAR1 | 51\|64\|38 | 153 | 51 | 3 | 9\|0\|0 | 1 | 1 | 17 | 0 |
| SRRM4 | 4759156 | SNRPA | 8\|5\|6 | 19 | 6.33 | 3 | 0\|0\|0 | 1 | 1 | 63.33 | 0 |
| SRRM4 | 48928046 | FBXW11 | 15\|16\|8 | 39 | 13 | 3 | 0\|0\|0 | 1 | 1 | 130 | 0 |
| SRRM4 | 50593002 | SNRPA1 | 33\|23\|6 | 62 | 20.67 | 3 | 6\|4\|2 | 1 | 1 | 5.17 | 0 |
| SRRM4 | 56676371 | CPSF1 | 7\|6\|4 | 17 | 5.67 | 3 | 0\|0\|1 | 1 | 1 | 17 | 0 |
| SRRM4 | 5803036 | HNRNPA0 | 6\|3\|4 | 13 | 4.33 | 3 | 1\|0\|0 | 1 | 1 | 13 | 0 |
| SRRM4 | 5901926 | NUDT21 | 19\|13\|16 | 48 | 16 | 3 | 1\|0\|0 | 1 | 1 | 48 | 0 |
| SRRM4 | 6005926 | U2AF2 | 59\|62\|34 | 155 | 51.67 | 3 | 9\|4\|0 | 1 | 1 | 11.92 | 0 |
| SRRM4 | 116812577 | LUC7L2 | 18\|16\|13 | 47 | 15.67 | 3 | 2\|3\|6 | 1 | 1 | 4.27 | 0 |
| SRRM4 | 122937227 | U2SURP | 20\|16\|8 | 44 | 14.67 | 3 | 3\|6\|4 | 1 | 1 | 3.38 | 0 |
| SRRM4 | 151301228 | PRPF40A | 7\|10\|7 | 24 | 8 | 3 | 0\|0\|0 | 1 | 1 | 80 | 0 |
| SRRM4 | 19923399 | G3BP2 | 4\|5\|2 | 11 | 3.67 | 3 | 0\|0\|0 | 1 | 1 | 36.67 | 0 |
| SRRM4 | 25777713 | SKP1 | 15\|7\|0 | 22 | 7.33 | 3 | 0\|0\|0 | 1 | 1 | 73.33 | 0 |
| SRRM4 | 258645150 | RBMX | 6\|5\|2 | 13 | 4.33 | 3 | 0\|0\|0 | 1 | 1 | 43.33 | 0 |
| SRRM4 | 29570791 | CSNK2A1 | 11\|14\|6 | 31 | 10.33 | 3 | 0\|0\|0 | 1 | 1 | 103.33 | 0 |
| SRRM4 | 47419936 | SRPK1 | 10\|12\|0 | 22 | 7.33 | 3 | 0\|0\|0 | 1 | 1 | 73.33 | 0 |
| SRRM4 | 54112117 | SF3B1 | 42\|48\|37 | 127 | 42.33 | 3 | 14\|12\|11 | 1 | 1 | 3.43 | 0 |
| SRRM4 | 7661920 | EIF4A3 | 6\|15\|0 | 21 | 7 | 3 | 0\|0\|0 | 1 | 1 | 70 | 0 |
| SRRM4 | 76880486 | ASCC3 | 6\|0\|6 | 12 | 4 | 3 | 0\|0\|0 | 1 | 1 | 40 | 0 |
| SRRM4 | 16117783 | BTRC | 4\|6\|0 | 10 | 3.33 | 3 | 0\|0\|0 | 1 | 1 | 33.33 | 0 |
| SRRM4 | 201023339 | FIP1L1 | 7\|4\|7 | 18 | 6 | 3 | 0\|0\|0 | 1 | 1 | 60 | 0 |
| SRRM4 | 20127499 | SRSF6 | 8\|11\|3 | 22 | 7.33 | 3 | 0\|0\|0 | 1 | 1 | 73.33 | 0 |
| SRRM4 | 4557469 | AP2B1 | 3\|5\|0 | 8 | 2.67 | 3 | 0\|0\|0 | 1 | 1 | 26.67 | 0 |
| SRRM4 | 4505343 | NCBP1 | 4\|2\|3 | 9 | 3 | 3 | 0\|0\|0 | 1 | 1 | 30 | 0 |
| SRRM4 | 15431306 | RPL8 | 9\|11\|4 | 24 | 8 | 3 | 2\|0\|2 | 1 | 1 | 6 | 0 |
| SRRM4 | 269847874 | YTHDC2 | 3\|4\|0 | 7 | 2.33 | 3 | 0\|0\|0 | 1 | 1 | 23.33 | 0 |
| SRRM4 | 124028529 | SYMPK | 3\|4\|0 | 7 | 2.33 | 3 | 0\|0\|0 | 1 | 1 | 23.33 | 0 |
| SRRM4 | 54873624 | EIF2A | 3\|4\|0 | 7 | 2.33 | 3 | 0\|0\|0 | 1 | 1 | 23.33 | 0 |
| SRRM4 | 11125770 | AIMP2 | 4\|4\|0 | 8 | 2.67 | 3 | 0\|0\|0 | 1 | 1 | 26.67 | 0 |
| SRRM4 | 14269586 | MRPS26 | 4\|5\|0 | 9 | 3 | 3 | 1\|0\|0 | 1 | 1 | 9 | 0 |
| SRRM4 | 38149981 | SNRPB2 | 5\|8\|6 | 19 | 6.33 | 3 | 0\|1\|0 | 1 | 1 | 19 | 0 |
| SRRM4 | 5803207 | U2AF1 | 13\|9\|7 | 29 | 9.67 | 3 | 0\|0\|0 | 1 | 1 | 96.67 | 0 |
| SRRM4 | 428673536 | KHDRBS1 | 3\|0\|5 | 8 | 2.67 | 3 | 0\|0\|0 | 1 | 1 | 26.67 | 0 |
| SRRM4 | 4506643 | RPL37A | 8\|15\|0 | 23 | 7.67 | 3 | 1\|1\|0 | 1 | 1 | 11.5 | 0 |
| SRRM4 | 18644728 | NOL6 | 3\|9\|0 | 12 | 4 | 3 | 0\|0\|0 | 1 | 1 | 40 | 0 |
| SRRM4 | 154355000 | KHSRP | 3\|3\|6 | 12 | 4 | 3 | 1\|0\|0 | 1 | 1 | 12 | 0 |
| SRRM4 | 162329583 | CPSF6 | 17\|12\|9 | 38 | 12.67 | 3 | 5\|3\|2 | 0.99 | 1 | 3.8 | 0 |
| SRRM4 | 4506725 | RPS4X | 28\|22\|15 | 65 | 21.67 | 3 | 7\|10\|5 | 0.99 | 1 | 2.95 | 0 |
| SRRM4 | 5174449 | H1FX | 13\|7\|0 | 20 | 6.67 | 3 | 2\|0\|0 | 0.99 | 1 | 10 | 0 |
| SRRM4 | 56160512 | 56160512 | 3\|3\|0 | 6 | 2 | 3 | 0\|0\|0 | 0.99 | 0.99 | 20 | 0 |
| SRRM4 | 9558733 | TRA2A | 3\|3\|0 | 6 | 2 | 3 | 0\|0\|0 | 0.99 | 0.99 | 20 | 0 |
| SRRM4 | 10863889 | SART1 | 0\|6\|3 | 9 | 3 | 3 | 1\|0\|0 | 0.99 | 1 | 9 | 0 |
| SRRM4 | 281604136 | PGAM5 | 2\|5\|0 | 7 | 2.33 | 3 | 0\|0\|0 | 0.98 | 1 | 23.33 | 0 |
| SRRM4 | 4502847 | CIRBP | 3\|2\|0 | 5 | 1.67 | 3 | 0\|0\|0 | 0.98 | 0.99 | 16.67 | 0 |
| SRRM4 | 45593130 | GNL3 | 8\|6\|0 | 14 | 4.67 | 3 | 2\|2\|0 | 0.98 | 1 | 3.5 | 0 |
| SRRM4 | 86991438 | SRSF5 | 7\|7\|0 | 14 | 4.67 | 3 | 0\|0\|2 | 0.98 | 0.98 | 7 | 0 |
| SRRM4 | 14589866 | ASPH | 4\|2\|0 | 6 | 2 | 3 | 0\|0\|0 | 0.98 | 1 | 20 | 0 |
| SRRM4 | 5032087 | SF3A1 | 8\|14\|7 | 29 | 9.67 | 3 | 2\|3\|0 | 0.98 | 1 | 5.8 | 0 |
| SRRM4 | 186928854 | MRPS31 | 2\|4\|0 | 6 | 2 | 3 | 0\|0\|0 | 0.98 | 1 | 20 | 0 |
| SRRM4 | 56676330 | HP1BP3 | 2\|5\|0 | 7 | 2.33 | 3 | 0\|0\|0 | 0.98 | 1 | 23.33 | 0 |
| SRRM4 | 4557495 | CSTF3 | 5\|2\|2 | 9 | 3 | 3 | 0\|0\|0 | 0.98 | 1 | 30 | 0 |
| SRRM4 | 14211540 | MOV10 | 5\|2\|0 | 7 | 2.33 | 3 | 0\|0\|0 | 0.98 | 1 | 23.33 | 0 |
| SRRM4 | 375477430 | CCT4 | 1\|2\|4 | 7 | 2.33 | 3 | 0\|0\|0 | 0.98 | 1 | 23.33 | 0 |
| SRRM4 | 4505087 | MAGOH | 8\|2\|0 | 10 | 3.33 | 3 | 0\|0\|0 | 0.98 | 1 | 33.33 | 0 |
| SRRM4 | 164664518 | DDX6 | 2\|6\|0 | 8 | 2.67 | 3 | 0\|0\|0 | 0.98 | 1 | 26.67 | 0 |
| SRRM4 | 118150660 | ZC3H15 | 2\|5\|0 | 7 | 2.33 | 3 | 0\|0\|0 | 0.98 | 1 | 23.33 | 0 |
| SRRM4 | 148612849 | KIF2A | 2\|0\|2 | 4 | 1.33 | 3 | 0\|0\|0 | 0.97 | 0.97 | 13.33 | 0.01 |
| SRRM4 | 170763506 | GTF3C5 | 2\|2\|0 | 4 | 1.33 | 3 | 0\|0\|0 | 0.97 | 0.97 | 13.33 | 0.01 |
| SRRM4 | 19923485 | LUC7L3 | 4\|7\|6 | 17 | 5.67 | 3 | 0\|2\|0 | 0.97 | 0.98 | 8.5 | 0.01 |
| SRRM4 | 259906018 | ACIN1 | 2\|2\|2 | 6 | 2 | 3 | 0\|0\|0 | 0.97 | 0.97 | 20 | 0.01 |
| SRRM4 | 13904866 | RPL28 | 2\|0\|2 | 4 | 1.33 | 3 | 0\|0\|0 | 0.97 | 0.97 | 13.33 | 0.01 |
| SRRM4 | 117938251 | BCLAF1 | 0\|2\|2 | 4 | 1.33 | 3 | 0\|0\|0 | 0.97 | 0.97 | 13.33 | 0.01 |
| SRRM4 | 157694492 | MYBBP1A | 17\|36\|4 | 57 | 19 | 3 | 5\|8\|2 | 0.96 | 1 | 3.8 | 0.01 |

TABLE 4-continued

High confidence AP-MS nSR100 interaction partners from human 293 cells. Bait gene name, prey gene name and genbank "prey accession" are according to the NCBI database. The numbers of spectra for the prey in the purifications of the baits are listed ("I" delimits the biological replicates), followed by the average number of spectra per replicate. The number of spectra for the prey in each of the negative controls is also listed, alongside the average of the SAINT scores (the best 2 scores out of the 3 replicates for this dataset), the maximal SAINT score and the Fold Change between the prey Avg spectra of the bait and control purifications (a small value of 0.1 is added to prevent division by 0 in fold change calculations). The calculated FDR (BFDR) is used to determine the reporting cutoffs. Confident interaction partners are those with BFDR ≤1%.

| Bait Gene Name | Prey Protein Accession | Prey Gene Name | Spectra | SpecSum | AvgSpec | Num Replicates | ctrlCounts | AvgP | MaxP | FoldChange | BFDR |
|---|---|---|---|---|---|---|---|---|---|---|---|
| SRRM4 | 4506605 | RPL23 | 12\|17\|0 | 29 | 9.67 | 3 | 5\|0\|0 | 0.96 | 0.98 | 5.8 | 0.01 |
| SRRM4 | 55741709 | RBM25 | 3\|5\|9 | 17 | 5.67 | 3 | 0\|2\|0 | 0.96 | 0.99 | 8.5 | 0.01 |
| SRRM4 | 4506681 | RPS11 | 7\|4\|5 | 16 | 5.33 | 3 | 2\|0\|1 | 0.95 | 0.99 | 5.33 | 0.01 |
| SRRM4 | 116812575 | YTHDF2 | 6\|4\|5 | 15 | 5 | 3 | 0\|2\|0 | 0.94 | 0.96 | 7.5 | 0.01 |
| SRRM4 | 336176064 | RBM39 | 5\|6\|2 | 13 | 4.33 | 3 | 2\|0\|0 | 0.94 | 0.96 | 6.5 | 0.01 |
| SRRM4 | 10835067 | SSB | 16\|8\|5 | 29 | 9.67 | 3 | 5\|0\|0 | 0.92 | 0.98 | 5.8 | 0.01 |
| SRRM4 | 40556376 | GLYR1 | 8\|4\|3 | 15 | 5 | 3 | 2\|0\|0 | 0.92 | 0.99 | 7.5 | 0.01 |
| SRRM4 | 4506609 | RPL19 | 8\|5\|9 | 22 | 7.33 | 3 | 3\|2\|2 | 0.92 | 0.96 | 3.14 | 0.01 |
| SRRM4 | 156119605 | GTF3C4 | 6\|4\|0 | 10 | 3.33 | 3 | 0\|2\|0 | 0.91 | 0.96 | 5 | 0.01 |
| SRRM4 | 17298690 | PUF60 | 12\|18\|11 | 41 | 13.67 | 3 | 5\|5\|0 | 0.91 | 0.99 | 4.1 | 0.01 |
| SRRM4 | 5032069 | SF3B4 | 13\|5\|0 | 18 | 6 | 3 | 0\|3\|0 | 0.9 | 0.99 | 6 | 0.01 |

TABLE 5

High confidence AP-MS nSR100 interaction partners from mouse N2A cells. Bait gene name, prey gene name and genbank "prey accession" are according to the NCBI database. The numbers of spectra for the prey in the purifications of the baits are listed ("I" delimits the biological replicates), followed by the average number of spectra per replicate. The number of spectra for the prey in each of the negative controls is also listed, alongside the average of the SAINT scores, the maximal SAINT score and the Fold Change between the prey Avg spectra of the bait and control purifications (a small value of 0.1 is added to prevent division by 0 in fold change calculations). The calculated FDR (BFDR) is used to determine the reporting cutoffs. Confident interaction partners are those with BFDR ≤1%.

| Bait Gene Name | Prey Protein Accession | Prey Gene Name | Spectra | SpecSum | AvgSpec | Num Replicates | ctrlCounts | AvgP | MaxP | FoldChange | BFDR |
|---|---|---|---|---|---|---|---|---|---|---|---|
| Srrm4 | 10190660 | Tfip11 | 5\|3 | 8 | 4 | 2 | 0\|0 | 1 | 1 | 40 | 0 |
| Srrm4 | 110625681 | Cwc27 | 6\|11 | 17 | 8.5 | 2 | 0\|0 | 1 | 1 | 85 | 0 |
| Srrm4 | 112420990 | Pnn | 33\|43 | 76 | 38 | 2 | 3\|0 | 1 | 1 | 25.33 | 0 |
| Srrm4 | 115583687 | Prpf8 | 63\|58 | 121 | 60.5 | 2 | 14\|22 | 1 | 1 | 3.36 | 0 |
| Srrm4 | 116256510 | Ap2a1 | 46\|62 | 108 | 54 | 2 | 8\|7 | 1 | 1 | 7.2 | 0 |
| Srrm4 | 118403314 | Rbm39 | 65\|66 | 131 | 65.5 | 2 | 14\|10 | 1 | 1 | 5.46 | 0 |
| Srrm4 | 121674790 | Rnps1 | 26\|25 | 51 | 25.5 | 2 | 1\|2 | 1 | 1 | 17 | 0 |
| Srrm4 | 125988379 | Jmjd6 | 19\|12 | 31 | 15.5 | 2 | 0\|0 | 1 | 1 | 155 | 0 |
| Srrm4 | 126157504 | Srrm2 | 47\|55 | 102 | 51 | 2 | 10\|9 | 1 | 1 | 5.37 | 0 |
| Srrm4 | 128485538 | Plk1 | 43\|43 | 86 | 43 | 2 | 0\|0 | 1 | 1 | 430 | 0 |
| Srrm4 | 133725810 | Snrpn | 38\|30 | 68 | 34 | 2 | 2\|2 | 1 | 1 | 17 | 0 |
| Srrm4 | 13384804 | Cks2 | 4\|7 | 11 | 5.5 | 2 | 0\|0 | 1 | 1 | 55 | 0 |
| Srrm4 | 13878227 | Wdr6 | 13\|19 | 32 | 16 | 2 | 0\|0 | 1 | 1 | 160 | 0 |
| Srrm4 | 153791358 | Sf3b1 | 92\|132 | 224 | 112 | 2 | 29\|36 | 1 | 1 | 3.45 | 0 |
| Srrm4 | 158854005 | Prpf4b | 4\|5 | 9 | 4.5 | 2 | 0\|0 | 1 | 1 | 45 | 0 |
| Srrm4 | 160707945 | Sf1 | 70\|73 | 143 | 71.5 | 2 | 3\|9 | 1 | 1 | 11.92 | 0 |
| Srrm4 | 161086984 | Ap2s1 | 10\|18 | 28 | 14 | 2 | 0\|0 | 1 | 1 | 140 | 0 |
| Srrm4 | 161353449 | Rbm25 | 16\|20 | 36 | 18 | 2 | 0\|0 | 1 | 1 | 180 | 0 |
| Srrm4 | 162287294 | Rbm8a | 12\|8 | 20 | 10 | 2 | 0\|0 | 1 | 1 | 100 | 0 |
| Srrm4 | 163644277 | Ap2a2 | 97\|137 | 234 | 117 | 2 | 18\|20 | 1 | 1 | 6.16 | 0 |
| Srrm4 | 165932270 | Sf3a1 | 20\|30 | 50 | 25 | 2 | 3\|3 | 1 | 1 | 8.33 | 0 |
| Srrm4 | 171906578 | Rad23b | 3\|4 | 7 | 3.5 | 2 | 0\|0 | 1 | 1 | 35 | 0 |
| Srrm4 | 194328715 | Zfp207 | 11\|13 | 24 | 12 | 2 | 0\|0 | 1 | 1 | 120 | 0 |
| Srrm4 | 194440682 | Srrm1 | 25\|36 | 61 | 30.5 | 2 | 5\|4 | 1 | 1 | 6.78 | 0 |
| Srrm4 | 19527174 | Sf3b3 | 90\|105 | 195 | 97.5 | 2 | 28\|28 | 1 | 1 | 3.48 | 0 |
| Srrm4 | 205361112 | Dnaja3 | 4\|4 | 8 | 4 | 2 | 0\|0 | 1 | 1 | 40 | 0 |
| Srrm4 | 21311939 | Ftsjd2 | 4\|4 | 8 | 4 | 2 | 0\|0 | 1 | 1 | 40 | 0 |
| Srrm4 | 21313640 | Ap2b1 | 83\|76 | 159 | 79.5 | 2 | 17\|14 | 1 | 1 | 5.13 | 0 |
| Srrm4 | 215490074 | Sap18 | 17\|28 | 45 | 22.5 | 2 | 0\|0 | 1 | 1 | 225 | 0 |
| Srrm4 | 227330595 | Fip1l1 | 8\|10 | 18 | 9 | 2 | 0\|0 | 1 | 1 | 90 | 0 |
| Srrm4 | 227430367 | Smu1 | 9\|8 | 17 | 8.5 | 2 | 0\|1 | 1 | 1 | 17 | 0 |
| Srrm4 | 227430375 | Snip1 | 5\|9 | 14 | 7 | 2 | 0\|0 | 1 | 1 | 70 | 0 |
| Srrm4 | 22779899 | Cdc5l | 10\|12 | 22 | 11 | 2 | 0\|0 | 1 | 1 | 110 | 0 |
| Srrm4 | 23956110 | Snrpb2 | 6\|5 | 11 | 5.5 | 2 | 0\|0 | 1 | 1 | 55 | 0 |
| Srrm4 | 23956166 | Luc7l3 | 45\|65 | 110 | 55 | 2 | 7\|8 | 1 | 1 | 7.33 | 0 |
| Srrm4 | 254587960 | Pgam5 | 20\|12 | 32 | 16 | 2 | 0\|0 | 1 | 1 | 160 | 0 |
| Srrm4 | 256985211 | Magohb | 10\|11 | 21 | 10.5 | 2 | 0\|1 | 1 | 1 | 21 | 0 |

TABLE 5-continued

High confidence AP-MS nSR100 interaction partners from mouse N2A cells. Bait gene name, prey
gene name and genbank "prey accession" are according to the NCBI database. The numbers of spectra for the
prey in the purifications of the baits are listed ("I" delimits the biological replicates), followed by the average
number of spectra per replicate. The number of spectra for the prey in each of the negative controls is also
listed, alongside the average of the SAINT scores, the maximal SAINT score and the Fold Change between the
prey Avg spectra of the bait and control purifications (a small value of 0.1 is added to prevent division by 0 in
fold change calculations). The calculated FDR (BFDR) is used to determine the reporting cutoffs. Confident
interaction partners are those with BFDR ≤1%.

| Bait Gene Name | Prey Protein Accession | Prey Gene Name | Spectra | SpecSum | AvgSpec | Num Replicates | ctrlCounts | AvgP | MaxP | FoldChange | BFDR |
|---|---|---|---|---|---|---|---|---|---|---|---|
| Srrm4 | 26986581 | Snx8 | 11\|18 | 29 | 14.5 | 2 | 0\|0 | 1 | 1 | 145 | 0 |
| Srrm4 | 270047502 | Ddx41 | 6\|7 | 13 | 6.5 | 2 | 0\|0 | 1 | 1 | 65 | 0 |
| Srrm4 | 27229051 | Necap1 | 12\|13 | 25 | 12.5 | 2 | 0\|0 | 1 | 1 | 125 | 0 |
| Srrm4 | 27229058 | Ddx47 | 3\|4 | 7 | 3.5 | 2 | 0\|0 | 1 | 1 | 35 | 0 |
| Srrm4 | 27881425 | Cwc22 | 37\|40 | 77 | 38.5 | 2 | 0\|0 | 1 | 1 | 385 | 0 |
| Srrm4 | 283135190 | Cdc42bpb | 6\|12 | 18 | 9 | 2 | 0\|0 | 1 | 1 | 90 | 0 |
| Srrm4 | 30519969 | Poldip3 | 7\|6 | 13 | 6.5 | 2 | 0\|0 | 1 | 1 | 65 | 0 |
| Srrm4 | 31560618 | Bub3 | 17\|21 | 38 | 19 | 2 | 1\|3 | 1 | 1 | 9.5 | 0 |
| Srrm4 | 59858549 | Ccdc55 | 5\|10 | 15 | 7.5 | 2 | 0\|0 | 1 | 1 | 75 | 0 |
| Srrm4 | 6753074 | Ap2m1 | 31\|42 | 73 | 36.5 | 2 | 4\|4 | 1 | 1 | 9.12 | 0 |
| Srrm4 | 6753540 | Csnk2a2 | 16\|24 | 40 | 20 | 2 | 2\|2 | 1 | 1 | 10 | 0 |
| Srrm4 | 67846113 | Snrnp70 | 48\|54 | 102 | 51 | 2 | 11\|9 | 1 | 1 | 5.1 | 0 |
| Srrm4 | 7949018 | Cdc37 | 58\|48 | 106 | 53 | 2 | 10\|13 | 1 | 1 | 4.61 | 0 |
| Srrm4 | 9055218 | Prpf40a | 4\|9 | 13 | 6.5 | 2 | 0\|0 | 1 | 1 | 65 | 0 |
| Srrm4 | 94158994 | Api5 | 8\|10 | 18 | 9 | 2 | 0\|1 | 1 | 1 | 18 | 0 |
| Srrm4 | 9790077 | Gsk3b | 6\|7 | 13 | 6.5 | 2 | 0\|0 | 1 | 1 | 65 | 0 |
| Srrm4 | P00761 | P00761 | 15\|15 | 30 | 15 | 2 | 0\|0 | 1 | 1 | 150 | 0 |
| Srrm4 | 114052106 | Snrpa | 38\|40 | 78 | 39 | 2 | 6\|5 | 1 | 1 | 7.09 | 0 |
| Srrm4 | 146231985 | Acin1 | 23\|27 | 50 | 25 | 2 | 0\|0 | 1 | 1 | 250 | 0 |
| Srrm4 | 147898671 | Srsf11 | 38\|62 | 100 | 50 | 2 | 8\|13 | 1 | 1 | 4.76 | 0 |
| Srrm4 | 164565377 | U2af2 | 108\|114 | 222 | 111 | 2 | 23\|23 | 1 | 1 | 4.83 | 0 |
| Srrm4 | 51712358 | Gm5576 | 10\|11 | 21 | 10.5 | 2 | 0\|0 | 1 | 1 | 105 | 0 |
| Srrm4 | 20544149 | Csnk1d | 7\|4 | 11 | 5.5 | 2 | 0\|0 | 1 | 1 | 55 | 0 |
| Srrm4 | 225579033 | Idh2 | 17\|16 | 33 | 16.5 | 2 | 3\|2 | 1 | 1 | 6.6 | 0 |
| Srrm4 | 226874906 | Ywhae | 24\|26 | 50 | 25 | 2 | 7\|7 | 1 | 1 | 3.57 | 0 |
| Srrm4 | 6756039 | Ywhaq | 15\|21 | 36 | 18 | 2 | 0\|0 | 1 | 1 | 180 | 0 |
| Srrm4 | 31560686 | Hspa2 | 41\|37 | 78 | 39 | 2 | 0\|0 | 1 | 1 | 390 | 0 |
| Srrm4 | 254939694 | U2af1 | 22\|24 | 46 | 23 | 2 | 6\|4 | 1 | 1 | 4.6 | 0 |
| Srrm4 | 28195398 | Ccnb1 | 27\|33 | 60 | 30 | 2 | 0\|0 | 1 | 1 | 300 | 0 |
| Srrm4 | 283806681 | Luc7l2 | 35\|43 | 78 | 39 | 2 | 9\|9 | 1 | 1 | 4.33 | 0 |
| Srrm4 | 309262982 | Gm6115 | 21\|9 | 30 | 15 | 2 | 0\|0 | 1 | 1 | 150 | 0 |
| Srrm4 | 31542366 | Cdk1 | 47\|67 | 114 | 57 | 2 | 3\|5 | 1 | 1 | 14.25 | 0 |
| Srrm4 | 31542427 | Csnk2a1 | 44\|55 | 99 | 49.5 | 2 | 11\|9 | 1 | 1 | 4.95 | 0 |
| Srrm4 | 356995868 | Ddx39b | 15\|15 | 30 | 15 | 2 | 0\|0 | 1 | 1 | 150 | 0 |
| Srrm4 | 38372907 | Ddx39 | 12\|10 | 22 | 11 | 2 | 0\|0 | 1 | 1 | 110 | 0 |
| Srrm4 | 6754632 | Mapk1 | 8\|8 | 16 | 8 | 2 | 0\|0 | 1 | 1 | 80 | 0 |
| Srrm4 | 21489933 | Mapk3 | 3\|4 | 7 | 3.5 | 2 | 0\|0 | 1 | 1 | 35 | 0 |
| Srrm4 | 257196183 | Puf60 | 55\|92 | 147 | 73.5 | 2 | 11\|18 | 1 | 1 | 5.07 | 0 |
| Srrm4 | 86198318 | Ccnb2 | 4\|8 | 12 | 6 | 2 | 0\|0 | 1 | 1 | 60 | 0 |
| Srrm4 | 30794464 | Prpf38b | 6\|6 | 12 | 6 | 2 | 0\|0 | 1 | 1 | 60 | 0 |
| Srrm4 | 33468987 | Wdr48 | 3\|6 | 9 | 4.5 | 2 | 0\|0 | 1 | 1 | 45 | 0 |
| Srrm4 | 22095003 | Sf3a3 | 11\|10 | 21 | 10.5 | 2 | 0\|2 | 0.99 | 0.99 | 10.5 | 0 |
| Srrm4 | 56699440 | Dhx8 | 8\|14 | 22 | 11 | 2 | 1\|2 | 0.99 | 1 | 7.33 | 0 |
| Srrm4 | 6755596 | Snrpc | 5\|6 | 11 | 5.5 | 2 | 1\|0 | 0.99 | 1 | 11 | 0 |
| Srrm4 | 7106277 | Csnk2b | 10\|7 | 17 | 8.5 | 2 | 1\|1 | 0.99 | 1 | 8.5 | 0 |
| Srrm4 | 20149756 | Eif4a3 | 18\|24 | 42 | 21 | 2 | 4\|7 | 0.99 | 1 | 3.82 | 0 |
| Srrm4 | 6754994 | Pcbp1 | 16\|18 | 34 | 17 | 2 | 0\|3 | 0.99 | 1 | 11.33 | 0 |
| Srrm4 | 124358955 | Son | 2\|7 | 9 | 4.5 | 2 | 0\|0 | 0.98 | 1 | 45 | 0 |
| Srrm4 | 13384692 | 0610009D07Rik | 10\|19 | 29 | 14.5 | 2 | 3\|2 | 0.98 | 1 | 5.8 | 0 |
| Srrm4 | 83699424 | Rpl18 | 2\|5 | 7 | 3.5 | 2 | 0\|0 | 0.98 | 1 | 35 | 0 |
| Srrm4 | 28849885 | Fam76b | 2\|5 | 7 | 3.5 | 2 | 0\|0 | 0.98 | 1 | 35 | 0 |
| Srrm4 | 13277394 | Grpel1 | 16\|17 | 33 | 16.5 | 2 | 6\|4 | 0.97 | 0.98 | 3.3 | 0 |
| Srrm4 | 13386106 | Nudt21 | 16\|12 | 28 | 14 | 2 | 4\|3 | 0.97 | 1 | 4 | 0 |
| Srrm4 | 227908800 | Wdr11 | 2\|4 | 6 | 3 | 2 | 0\|0 | 0.97 | 1 | 30 | 0 |
| Srrm4 | 78217391 | Sfswap | 2\|3 | 5 | 2.5 | 2 | 0\|0 | 0.97 | 0.99 | 25 | 0 |
| Srrm4 | 83745112 | Clk3 | 2\|3 | 5 | 2.5 | 2 | 0\|0 | 0.97 | 0.99 | 25 | 0 |
| Srrm4 | 113866024 | Rab5c | 3\|2 | 5 | 2.5 | 2 | 0\|0 | 0.97 | 0.99 | 25 | 0 |
| Srrm4 | 33468955 | Ik | 3\|2 | 5 | 2.5 | 2 | 0\|0 | 0.97 | 0.99 | 25 | 0 |
| Srrm4 | 267844920 | Wbp11 | 2\|3 | 5 | 2.5 | 2 | 0\|0 | 0.97 | 0.99 | 25 | 0 |
| Srrm4 | 161016793 | Ddx6 | 2\|4 | 6 | 3 | 2 | 0\|0 | 0.97 | 1 | 30 | 0 |
| Srrm4 | 70906453 | Bcas2 | 2\|3 | 5 | 2.5 | 2 | 0\|0 | 0.97 | 0.99 | 25 | 0 |
| Srrm4 | 158749553 | Sf3a2 | 2\|4 | 6 | 3 | 2 | 0\|0 | 0.97 | 1 | 30 | 0 |
| Srrm4 | 149262567 | Gm11703 | 2\|3 | 5 | 2.5 | 2 | 0\|0 | 0.97 | 0.99 | 25 | 0 |
| Srrm4 | 268837785 | Sf3b2 | 20\|20 | 40 | 20 | 2 | 6\|7 | 0.96 | 0.96 | 3.08 | 0.01 |
| Srrm4 | 27734072 | Rbmx2 | 4\|5 | 9 | 4.5 | 2 | 0\|1 | 0.96 | 0.98 | 9 | 0.01 |
| Srrm4 | 11177922 | Rfc2 | 2\|2 | 4 | 2 | 2 | 0\|0 | 0.95 | 0.95 | 20 | 0.01 |
| Srrm4 | 226437608 | Gcfc1 | 2\|2 | 4 | 2 | 2 | 0\|0 | 0.95 | 0.95 | 20 | 0.01 |

TABLE 5-continued

High confidence AP-MS nSR100 interaction partners from mouse N2A cells. Bait gene name, prey gene name and genbank "prey accession" are according to the NCBI database. The numbers of spectra for the prey in the purifications of the baits are listed ("|" delimits the biological replicates), followed by the average number of spectra per replicate. The number of spectra for the prey in each of the negative controls is also listed, alongside the average of the SAINT scores, the maximal SAINT score and the Fold Change between the prey Avg spectra of the bait and control purifications (a small value of 0.1 is added to prevent division by 0 in fold change calculations). The calculated FDR (BFDR) is used to determine the reporting cutoffs. Confident interaction partners are those with BFDR ≤1%.

| Bait Gene Name | Prey Protein Accession | Prey Gene Name | Spectra | SpecSum | AvgSpec | Num Replicates | ctrlCounts | AvgP | MaxP | FoldChange | BFDR |
|---|---|---|---|---|---|---|---|---|---|---|---|
| Srrm4 | 114158677 | Luc7l | 18\|20 | 38 | 19 | 2 | 6\|6 | 0.95 | 0.99 | 3.17 | 0.01 |
| Srrm4 | 312261233 | Prrc2a | 2\|2 | 4 | 2 | 2 | 0\|0 | 0.95 | 0.95 | 20 | 0.01 |
| Srrm4 | 121583673 | 2510012J08Rik | 2\|2 | 4 | 2 | 2 | 0\|0 | 0.95 | 0.95 | 20 | 0.01 |
| Srrm4 | 226958329 | Gpatch8 | 2\|2 | 4 | 2 | 2 | 0\|0 | 0.95 | 0.95 | 20 | 0.01 |
| Srrm4 | 13385044 | Rpl35 | 2\|2 | 4 | 2 | 2 | 0\|0 | 0.95 | 0.95 | 20 | 0.01 |
| Srrm4 | 13385288 | Crnkl1 | 2\|2 | 4 | 2 | 2 | 0\|0 | 0.95 | 0.95 | 20 | 0.01 |
| Srrm4 | 36031035 | Smc3 | 6\|8 | 14 | 7 | 2 | 2\|0 | 0.91 | 0.96 | 7 | 0.01 |
| Srrm4 | 19527358 | Prpf19 | 11\|29 | 40 | 20 | 2 | 4\|3 | 0.91 | 1 | 5.71 | 0.01 |
| Srrm4 | 31542425 | Csnk1e | 6\|8 | 14 | 7 | 2 | 2\|0 | 0.91 | 0.96 | 7 | 0.01 |
| Srrm4 | 33695123 | Cdk11b | 13\|11 | 24 | 12 | 2 | 3\|4 | 0.9 | 0.98 | 3.43 | 0.01 |
| Srrm4 | 164698474 | Cyfip1 | 7\|15 | 22 | 11 | 2 | 3\|1 | 0.89 | 1 | 5.5 | 0.01 |
| Srrm4 | 13385036 | Rpl15 | 3\|5 | 8 | 4 | 2 | 1\|0 | 0.88 | 0.98 | 8 | 0.01 |
| Srrm4 | 226958349 | Tpi1 | 10\|10 | 20 | 10 | 2 | 3\|3 | 0.87 | 0.87 | 3.33 | 0.01 |
| Srrm4 | 87196334 | Tcerg1 | 1\|7 | 8 | 4 | 2 | 0\|0 | 0.86 | 1 | 40 | 0.01 |

REFERENCES

Akbarian S, Bunney W E, Jr., Potkin S G, Wigal S B, Hagman J O, Sandman C A, Jones E G. 1993. Altered distribution of nicotinamide-adenine dinucleotide phosphate-diaphorase cells in frontal lobe of schizophrenics implies disturbances of cortical development. Arch Gen Psychiatry 50: 169-177.

Baranek G. T. (2002) Efficacy of sensory and motor interventions for children with autism. J Autism Dev Disord, 32:397-422.

Barbosa-Morais, N. L., Irimia, M., Pan, Q., Xiong, H. Y., Gueroussov, S., Lee, L. J., Slobodeniuc, V., Kutter, C., Watt, S., Colak, R., et al. (2012). The evolutionary landscape of alternative splicing in vertebrate species. Science 338, 1587-1593.

Barrios-Rodiles, M., Brown, K. R., Ozdamar, B., Bose, R., Liu, Z., Donovan, R. S., Shinjo, F., Liu, Y., Dembowy, J., Taylor, I. W., et al. (2005). High-throughput mapping of a dynamic signaling network in mammalian cells. Science 307, 1621-1625.

Battaglia A. (2005) The inv dup(15) or idic(15) syndrome: a clinically recognizable neurogenetic disorder. Brain Dev. 27:365-369.

Beachy, P. A., Helfand, S. L., and Hogness, D. S. (1985). Segmental distribution of bithorax complex proteins during Drosophila development. Nature 313, 545-551.

Black, D. L. (1991). Does steric interference between splice sites block the splicing of a short c-src neuron-specific exon in non-neuronal cells? Genes Dev 5, 389-402.

Borck, G., Molla-Herman, A., Boddaert, N., Encha-Razavi, F., Philippe, A., Robel, L., Desguerre, I., Brunelle, F., Benmerah, A., Munnich, A., et al. (2008). Clinical, cellular, and neuropathological consequences of AP1S2 mutations: further delineation of a recognizable X-linked mental retardation syndrome. Hum Mutat 29, 966-974.

Boucard A A, Chubykin A A, Comoletti D, Taylor P, Sudhof T C. 2005. A splice code for trans-synaptic cell adhesion mediated by binding of neuroligin 1 to alpha- and beta-neurexins. Neuron 48: 229-236.

Boutz, P. L., Stoilov, P., Li, Q., Lin, C. H., Chawla, G., Ostrow, K., Shiue, L., Ares, M. J., and Black, D. L. (2007). A post-transcriptional regulatory switch in polypyrimidine tract-binding proteins reprograms alternative splicing in developing neurons. Genes Dev 21, 1636-1652.

Braunschweig, U., Barbosa-Morais, N. L., Pan, Q., Nachman, E. N., Alipanahi, B., Frey, B. J., Irimia, M., and Blencowe, B. J. (2014). Widespread intron retention in mammals functionally tunes transcriptomes. Genome Res, pii: gr.177790.177114.

Braunschweig, U., Gueroussov, S., Plocik, A. M., Graveley, B. R., and Blencowe, B. J. (2013). Dynamic integration of splicing within gene regulatory pathways. Cell 152, 1252-1269.

Brielmaier J., Matteson P. G., Silverman J. L., et al. (2012) Autism-relevant social abnormalities and cognitive deficits in Engrailed-2 knockout mice. PLoS ONE, 7:e40914.

Broeke J H P, Roelandse M, Luteijn M J, Boiko T, Matus A, Toonen R F, Verhage M. 2010. Munc18 and Munc13 regulate early neurite outgrowth. Biology of the Cell 102: 479-488.

Buckanovich R J, Posner J B, Darnell R B. 1993. Nova, the paraneoplastic Ri antigen, is homologous to an RNA-binding protein and is specifically expressed in the developing motor system. Neuron 11: 657-672.

Buljan, M., Chalancon, G., Eustermann, S., Wagner, G. P., Fuxreiter, M., Bateman, A., and Babu, M. M. (2012). Tissue-specific splicing of disordered segments that embed binding motifs rewires protein interaction networks. Mol Cell 46, 871-883.

Calarco, J. A., Superina, S., O'Hanlon, D., Gabut, M., Raj, B., Pan, Q., Skalska, U., Clarke, L., Gelinas, D., van der Kooy, D., et al. (2009). Regulation of vertebrate nervous system alternative splicing and development by an S R-related protein. Cell 138, 898-910.

Calarco, J. A., Zhen, M., and Blencowe, B. J. (2011). Networking in a global world: establishing functional connections between neural splicing regulators and their target transcripts. RNA 17, 775-791.

Cao, X., and Sudhoff, T. C. (2001). A transcriptionally active complex of APP with Fe65 and histone acetyltransferase Tip60. Science 293, 115-120.

Cartegni, L., Chew, S. L., and Krainer, A. R. (2002). Listening to silence and understanding nonsense: exonic mutations that affect splicing. Nat Rev Genet 3, 285-298.

Caviness V S J. 1982. Neocortical histogenesis in normal and reeler mice: a developmental study based upon [3H] thymidine autoradiography. Brain Res 256: 293-302.

Cellot G., and Cherubini E. (2014) GABAergic signaling as a therapeutic target for autism spectrum disorders. Front Pediatr, doi: 10.3389/fped.2014.00070.

Chedotal A. 2007. Slits and their receptors. Adv Exp Med Biol 621: 65-80.

Chen, M., and Manley, J. L. (2009). Mechanisms of alternative splicing regulation: insights from molecular and genomics approaches. Nat Rev Mol Cell Biol 10, 741-754.

Cheung, H. N., Dunbar, C., Morotz, G. M., Cheng, W. H., Chan, H. Y., Miller, C. C., and Lau, K. F. (2014). FE65 interacts with ADP-ribosylation factor 6 to promote neurite outgrowth. FASEB J 28, 337-349.

Coleman, K. G., Poole, S. J., Weir, M. P., Soeller, W. C., and Kornberg, T. (1987). The invected gene of Drosophila: sequence analysis and expression studies reveal a close kinship to the engrailed gene. Genes Dev 1, 19-28.

Corominas, R., Yang, X., Lin, G. N., Kang, S., Shen, Y., Ghamsari, L., Broly, M., Rodriguez, M., Tam, S., Trigg, S. A., et al. (2014). Protein interaction network of alternatively spliced isoforms from brain links genetic risk factors for autism. Nat Commun 5, 3650.

David, C. J., and Manley, J. L. (2010). Alternative pre-mRNA splicing regulation in cancer: pathways and programs unhinged. Genes Dev 24, 2343-2364.

DeLorey T M, Sahbaie P, Hashemi E, Homanics G E, Clark J D. 2008. Gabrb3 gene deficient mice exhibit impaired social and exploratory behaviors, deficits in non-selective attention and hypoplasia of cerebellar vermal lobules: a potential model of autism spectrum disorder. Behav Brain Res 187: 207-220.

Deol M S, Gluecksohn-Waelsch S. 1979. The role of inner hair cells in hearing. Nature 278: 250-252.

Dergai, M., Tsyba, L., Dergai, O., Zlatskii, I., Skrypkina, I., Kovalenko, V., and Rynditch, A. (2010). Microexon-based regulation of ITSN1 and Src SH3 domains specificity relies on introduction of charged amino acids into the interaction interface. Biochem Biophys Res Commun 399, 307-312.

Donahoo A L, Richards L J. 2009. Understanding the mechanisms of callosal development through the use of transgenic mouse models. Semin Pediatr Neurol 16: 127-142.

Ellis, J. D., Barrios-Rodiles, M., Colak, R., Irimia, M., Kim, T., Calarco, J. A., Wang, X., Pan, Q., O'Hanlon, D., Kim, P. M., et al. (2012). Tissue-specific alternative splicing remodels protein-protein interaction networks. Mol Cell 46, 884-892.

Eom, T., Zhang, C., Wang, H., Lay, K., Fak, J., Noebels, J. L., and Darnell, R. B. (2013). NOVA-dependent regulation of cryptic NMD exons controls synaptic protein levels after seizure. Elife 2, e00178.

Fagnani, M., Barash, Y., Ip, J., Misquitta, C., Pan, Q., Saltzman, A., Shai, O., Lee, L., Rozenhek, A., Mohammad, N., et al. (2007). Functional coordination of alternative splicing in the mammalian central nervous system. Genome Biology 8, R108.

Farias, G. G., Cuitino, L., Guo, X., Ren, X., Jarnik, M., Mattera, R., and Bonifacino, J. S. (2012). Signal-mediated, AP-1/clathrin-dependent sorting of transmembrane receptors to the somatodendritic domain of hippocampal neurons. Neuron 75, 810-823.

Feng Y, Walsh C A. 2004. Mitotic spindle regulation by Nde1 controls cerebral cortical size. Neuron 44: 279-293.

Friedel R H, Seisenberger C, Kaloff C, Wurst W. 2007. EUCOMM—the European conditional mouse mutagenesis program. Brief Funct Genomic Proteomic 6: 180-185.

Gandal M J, Anderson R L, Billingslea E N, Carlson G C, Roberts T P, Siegel S J. 2012. Mice with reduced NMDA receptor expression: more consistent with autism than schizophrenia? Genes Brain Behav 11: 740-750.

Gilman, S. R., Iossifov, I., Levy, D., Ronemus, M., Wigler, M., and Vitkup, D. (2011). Rare de novo variants associated with autism implicate a large functional network of genes involved in formation and function of synapses. Neuron 70, 898-907.

Gao P, Sultan K T, Zhang X J, Shi S H. 2013. Lineage-dependent circuit assembly in the neocortex. Development 140: 2645-2655.

Gehman L T, Meera P, Stoilov P, Shiue L, O'Brien J E, Meisler M H, Ares M, Jr., Otis T S, Black D L. 2012. The splicing regulator Rbfox2 is required for both cerebellar development and mature motor function. Genes Dev 26: 445-460.

Gkogkas C. G., Khoutorsky A., Ran I., et al. (2013) Autism-related deficits via dysregulation of elF4E-dependent translational control. Nature. 493:371-377.

Han, H., Irimia, M., Ross, P. J., Sung, H. K., Alipanahi, B., David, L., Golipour, A., Gabut, M., Michael, I. P., Nachman, E. N., et al. (2013). MBNL proteins repress ES-cell-specific alternative splicing and reprogramming. Nature 498, 241-245.

Havugimana, P. C., Hart, G. T., Nepusz, T., Yang, H., Turinsky, A. L., Li, Z., Wang, P. I., Boutz, D. R., Fong, V., Phanse, S., et al. (2012). A census of human soluble protein complexes. Cell 150, 1068-1081.

He C. X., and Portera-Cailliau C. (2013) The trouble with spines in fragile X syndrome: density, maturity and plasticity. Neuroscience 251: 120-128.

Hinton V. J., Brown W. T., Wisniewski K., and Rudelli R. D. (1991) Analysis of neocortex in three males with the fragile X syndrome. Am J Med Genet. 41:289-294.

Huang da W, Sherman B T, Lempicki R A. 2009. Bioinformatics enrichment tools: paths toward the comprehensive functional analysis of large gene lists. Nucleic Acids Res 37: 1-13.

Hubbard, K. S., Gut, I. M., Lyman, M. E., and McNutt, P. M. (2013). Longitudinal RNA sequencing of the deep transcriptome during neurogenesis of cortical glutamatergic neurons from murine ESCs. F1000Res 2, 35.

Hussman, J. P., Chung, R. H., Griswold, A. J., Jaworski, J. M., Salyakina, D., Ma, D., Konidari, I., Whitehead, P. L., Vance, J. M., Martin, E. R., et al. (2011). A noise-reduction GWAS analysis implicates altered regulation of neurite outgrowth and guidance in autism. Mol Autism 2, 1.

Ikin, A. F., Sabo, S. L., Lanier, L. M., and Buxbaum, J. D. (2007). A macromolecular complex involving the amyloid precursor protein (APP) and the cytosolic adapter FE65 is a negative regulator of axon branching. Mol Cell Neurosci 35, 57-63.

Irimia, M., and Blencowe, B. J. (2012). Alternative splicing: decoding an expansive regulatory layer. Curr Opin Cell Biol 24, 323-332.

Irimia M., Weatheritt R. J., Ellis J. D., et al. (2014) A highly conserved program of neuronal microexons is misregulated in autistic brains. Cell, 159:1511-1523.

Jeste S. S., and Geschwind D. H. (2014) Disentangling the heterogeneity of autism spectrum disorder through genetic findings. Nat Rev Neurol. 10:74-81.

Kalsotra, A., and Cooper, T. A. (2011). Functional consequences of developmentally regulated alternative splicing. Nat Rev Genet 12, 715-729.

Katz L. C., and Shatz C. J. (1996) Synaptic activity and the construction of cortical circuits. Science, 274:1133-1138.

Khare, T., Pai, S., Koncevicius, K., Pal, M., Kriukiene, E., Liutkeviciute, Z., Irimia, M., Jia, P., Ptak, C., Xia, M., et al. (2012). 5-hmC in the brain is abundant in synaptic genes and shows differences at the exon-intron boundary. Nat Struct Mol Biol 19, 1037-1043.

Kirchhausen, T. (2000). Clathrin. Annu Rev Biochem 69, 699-727.

Licatalosi, D. D., and Darnell, R. B. (2010). RNA processing and its regulation: global insights into biological networks. Nat Rev Genet 11, 75-87.

Ku C. A., Chiodo V. A., Boye S. L., et al. (2011) Gene therapy using self-complementary Y733F capsid mutant AAV2/8 restores vision in a model of early onset Leber congenital amaurosis. Hum Mol Genet, 20:4569-4581.

Labbe R M, Irimia M, Currie K W, Lin A, Zhu S J, Brown D D, Ross E J, Voisin V, Bader G D, Blencowe B J et al. 2012. A comparative transcriptomic analysis reveals conserved features of stem cell pluripotency in planarians and mammals. Stem Cells 30: 1734-1745.

Li Q, Lee J A, Black D L. 2007. Neuronal regulation of alternative pre-mRNA splicing. Nat Rev Neurosci 8: 819-831.

Li Q, Zheng S, Han A, Lin C H, Stoilov P, Fu X D, Black D L. 2014. The splicing regulator PTBP2 controls a program of embryonic splicing required for neuronal maturation. eLife 3.

Li Y. I., Sanchez-Pulido L., Haerty W., and Ponting C. P. (2015) RBFOX and PTBP1 proteins regulate the alternative splicing of micro-exons in human brain transcripts. Genome Res, 25:1-13.

Licatalosi D D, Yano M, Fak J J, Mele A, Grabinski S E, Zhang C, Darnell R B. 2012. Ptbp2 represses adult-specific splicing to regulate the generation of neuronal precursors in the embryonic brain. Genes Dev 26: 1626-1642.

Lijam N, Paylor R, McDonald M P, Crawley J N, Deng C X, Herrup K, Stevens K E, Maccaferri G, McBain C J, Sussman D J et al. 1997. Social interaction and sensorimotor gating abnormalities in mice lacking Dvl1. Cell 90: 895-905.

Lipscombe D. 2005. Neuronal proteins custom designed by alternative splicing. Curr Opin Neurobiol 15: 358-363.

Lipscombe D, Allen S E, Toro C P. 2013a. Control of neuronal voltage-gated calcium ion channels from RNA to protein. Trends Neurosci 36: 598-609.

Lipscombe D, Andrade A, Allen S E. 2013b. Alternative splicing: functional diversity among voltage-gated calcium channels and behavioral consequences. Biochim Biophys Acta 1828: 1522-1529.

Maze I., Wenderski W., Noh K. M., et al. (2015) Critical role of histone turnover in neuronal transcription and plasticity. Neuron, 87:77-94.

McAlonan G M, Daly E, Kumari V, Critchley H D, van Amelsvoort T, Suckling J, Simmons A, Sigmundsson T, Greenwood K, Russell A et al. 2002. Brain anatomy and sensorimotor gating in Asperger's syndrome. Brain 125: 1594-1606.

Merkin, J., Russell, C. B., Chen, P., and Burge, C. B. (2012). Evolutionary dynamics of gene and isoform regulation in Mammalian tissues. Science 338, 1593-1599.

Nakano Y, Jahan I, Bonde G, Sun X, Hildebrand M S, Engelhardt J F, Smith R J, Cornell R A, Fritzsch B, Banfi B. 2012. A mutation in the Srrm4 gene causes alternative splicing defects and deafness in the Bronx waltzer mouse. PLoS Genet 8: e1002966.

Norris A D, Calarco J A. 2012. Emerging Roles of Alternative Pre-mRNA Splicing Regulation in Neuronal Development and Function. Front Neurosci 6: 122.

Ohnishi, T., Shirane, M., Hashimoto, Y., Saita, S., and Nakayama, K. I. (2014). Identification and characterization of a neuron-specific isoform of protrudin. Genes Cells 19, 97-111.

Ovadia, G., and Shifman, S. (2011). The genetic variation of RELN expression in schizophrenia and bipolar disorder. PLoS One 6, e19955.

Pan, Q., Shai, O., Lee, L. J., Frey, B. J., and Blencowe, B. J. (2008). Deep surveying of alternative splicing complexity in the human transcriptome by high-throughput sequencing. Nat Genet 40, 1413-1415.

Pan, Q., Shai, O., Misquitta, C., Zhang, W., Saltzman, A. L., Mohammad, N., Babak, T., Siu, H., Hughes, T. R., Morris, Q. D., et al. (2004). Revealing global regulatory features of mammalian alternative splicing using a quantitative microarray platform. Mol Cell 16, 929-941.

Parikshak, N. N., Luo, R., Zhang, A., Won, H., Lowe, J. K., Chandran, V., Horvath, S., and Geschwind, D. H. (2013). Integrative functional genomic analyses implicate specific molecular pathways and circuits in autism. Cell 155, 1008-1021.

Paul L K, Brown W S, Adolphs R, Tyszka J M, Richards L J, Mukherjee P, Sherr E H. 2007. Agenesis of the corpus callosum: genetic, developmental and functional aspects of connectivity. Nat Rev Neurosci 8: 287-299.

Paylor R, Glaser B, Mupo A, Ataliotis P, Spencer C, Sobotka A, Sparks C, Choi C H, Oghalai J, Curran S et al. 2006. Tbx1 haploinsufficiency is linked to behavioral disorders in mice and humans: implications for 22q11 deletion syndrome. Proc Natl Acad Sci USA 103: 7729-7734.

Peca J, Feliciano C, Ting J T, Wang W, Wells M F, Venkatraman T N, Lascola C D, Fu Z, Feng G. 2011. Shank3 mutant mice display autistic-like behaviours and striatal dysfunction. Nature 472: 437-442.

Perry W, Minassian A, Lopez B, Maron L, Lincoln A. 2007. Sensorimotor gating deficits in adults with autism. Biol Psychiatry 61: 482-486.

Pirooznia, S. K., Sarthi, J., Johnson, A. A., Toth, M. S., Chiu, K., Koduri, S., and Elefant, F. (2012). Tip60 HAT activity mediates APP induced lethality and apoptotic cell death in the CNS of a Drosophila Alzheimer's disease model. PLoS One 7, e41776.

Polymenidou, M., Lagier-Tourenne, C., Hutt, K. R., Bennett, C. F., Cleveland, D. W., and Yeo, G. W. (2012). Misregulated RNA processing in amyotrophic lateral sclerosis. Brain Res 1462, 3-15.

Quesnel-Vallières M., Irimia M., Cordes S. P., and Blencowe B. J. (2015) Essential roles for the splicing regulator nSR100/SRRM4 during nervous system development. Genes Dev, 29:746-759.

Raj B., O'Hanlon D., Vessey J. P., et al. (2011) Cross-regulation between an alternative splicing activator and a transcriptional repressor controls neurogenesis. Mol Cell. 43:843-850.

Raj B., Irimia M., Brauschweig U., et al. (2014) A global regulatory mechanism for activating an exon network required for neurogenesis. Mol Cell, 56:90-103.

Romero, P. R., Zaidi, S., Fang, Y. Y., Uversky, V. N., Radivojac, P., Oldfield, C. J., Cortese, M. S., Sickmeier, M., LeGall, T., Obradovic, Z., et al. (2006). Alternative splicing in concert with protein intrinsic disorder enables increased functional diversity in multicellular organisms. Proc Natl Acad Sci USA 103, 8390-8395.

Ross C A, Margolis R L, Reading S A, Pletnikov M, Coyle J T. 2006. Neurobiology of schizophrenia. *Neuron* 52: 139-153.

Rothwell P. E., Fuccillo M. V., Maxeiner S., et al. (2014) Autism-associated neuroligin-3 mutations commonly impair striatal circuits to boost repetitive behaviors. Cell, 158:198-212.

Rudelli R. D., Brown W. T., Wisniewski K., et al. (1985) Adult fragile X syndrome. Clinico-neuropathologic findings. Acta Neuropathol (Berl). 67:289-295.

Ruggiu M, Herbst R, Kim N, Jevsek M, Fak J J, Mann M A, Fischbach G, Burden S J, Darnell R B. 2009. Rescuing Z+ agrin splicing in Nova null mice restores synapse formation and unmasks a physiologic defect in motor neuron firing. *Proc Natl Acad Sci USA* 106: 3513-3518.

Rusconi, F., Paganini, L., Braida, D., Ponzoni, L., Toffolo, E., Maroli, A., Landsberger, N., Bedogni, F., Turco, E., Pattini, L., et al. (2014). LSD1 Neurospecific Alternative Splicing Controls Neuronal Excitability in Mouse Models of Epilepsy. Cereb Cortex In press.

Sabo, S. L., Ikin, A. F., Buxbaum, J. D., and Greengard, P. (2003). The amyloid precursor protein and its regulatory protein, FE65, in growth cones and synapses in vitro and in vivo. J Neurosci 23, 5407-5415.

Sambrook J, Russell D W. 2001. *Molecular cloning: a laboratory manual*. Cold Spring Harbor Laboratory Press, New York.

Santini E., Huynh T. N., MacAskill A. F., et al. (2013) Exaggerated translation causes synaptic and behavioural aberrations associated with autism. Nature. 493:411-415.

Shen H, Green M R. 2004. A pathway of sequential arginine-serine-rich domain-splicing signal interactions during mammalian spliceosome assembly. *Mol Cell* 16: 363-373.

Shinoda Y, Sadakata T, Furuichi T. 2013. Animal models of autism spectrum disorder (ASD): a synaptic-level approach to autistic-like behavior in mice. *Exp Anim* 62: 71-78.

Silverman J. L., Yang M., Lord C., and Crawley J. N. (2010) Behavioural phenotyping assays for mouse models of autism. Nat Rev Neurosci, 11:490-502.

Sofueva, S., Yaffe, E., Chan, W. C., Georgopoulou, D., Vietri Rudan, M., Mira-Bontenbal, H., Pollard, S. M., Schroth, G. P., Tanay, A., and Hadjur, S. (2013). Cohesin-mediated interactions organize chromosomal domain architecture. EMBO J 32, 3119-3129.

Stante, M., Minopoli, G., Passaro, F., Raia, M., Vecchio, L. D., and Russo, T. (2009). Fe65 is required for Tip60-directed histone H4 acetylation at DNA strand breaks. Proc Natl Acad Sci USA 106, 5093-5098.

Stoner R., Chow M. L., Boyle M. P, et al. (2014) Patches of disorganization in the neocortex of children with autism. N Engl J Med, 370:1209-1219.

Tarpey, P. S., Stevens, C., Teague, J., Edkins, S., O'Meara, S., Avis, T., Barthorpe, S., Buck, G., Butler, A., Cole, J., et al. (2006). Mutations in the gene encoding the Sigma 2 subunit of the adaptor protein 1 complex, AP1S2, cause X-linked mental retardation. Am J Hum Genet 79, 1119-1124.

Trapnell, C., Williams, B. A., Pertea, G., Mortazavi, A., Kwan, G., van, B.a., M. J, Salzberg, S. L., Wold, B. J., and Pachter, L. (2010). Transcript assembly and quantification by RNA-Seq reveals unannotated transcripts and isoform switching during cell differentiation. Nat Biotechnol 28, 511-515.

Tsyba L, Gryaznova T, Dergai O, Dergai M, Skrypkina I, Kropyvko S, Boldyryev O, Nikolaienko O, Novokhatska O, Rynditch A. 2008. Alternative splicing affecting the SH3A domain controls the binding properties of intersectin 1 in neurons. *Biochem Biophys Res Commun* 372: 929-934.

Ule, J., Ule, A., Spencer, J., Williams, A., Hu, J. S., Cline, M., Wang, H., Clark, T., Fraser, C., Ruggiu, M., et al. (2005). Nova regulates brain-specific splicing to shape the synapse. Nat Genet 37, 844-852.

Unni D K, Piper M, Moldrich R X, Gobius I, Liu S, Fothergill T, Donahoo A L, Baisden J M, Cooper H M, Richards L J. 2012. Multiple Slits regulate the development of midline glial populations and the corpus callosum. *Dev Biol* (NY 1985) 365: 36-49.

Voineagu, I., Wang, X., Johnston, P., Lowe, J. K., Tian, Y., Horvath, S., Mill, J., Cantor, R. M., Blencowe, B. J., and Geschwind, D. H. (2011). Transcriptomic analysis of autistic brain reveals convergent molecular pathology. Nature 474, 380-384.

Volfovsky, N., Haas, B. J., and Salzberg, S. L. (2003). Computational discovery of internal micro-exons. Genome Res 13, 1216-1221.

Wahl, M. C., Will, C. L., and Lührmann, R. (2009). The spliceosome: design principles of a dynamic RNP machine. Cell 136, 701-718.

Wang, B., Hu, Q., Hearn, M. G., Shimizu, K., Ware, C. B., Liggitt, D. H., Jin, L. W., Cool, B. H., Storm, D. R., and Martin, G. M. (2004). Isoform-specific knockout of FE65 leads to impaired learning and memory. J Neurosci Res 75, 12-24.

Wang, E. T., Sandberg, R., Luo, S., Khrebtukova, I., Zhang, L., Mayr, C., Kingsmore, S. F., Schroth, G. P., and Burge, C. B. (2008). Alternative isoform regulation in human tissue transcriptomes. Nature 456, 470-476.

Wang, Y., Zhang, M., Moon, C., Hu, Q., Wang, B., Martin, G., Sun, Z., and Wang, H. (2009). The APP-interacting protein FE65 is required for hippocampus-dependent learning and long-term potentiation. Learn Mem 16, 537-544.

Weatheritt, R. J., Davey, N. E., and Gibson, T. J. (2012). Linear motifs confer functional diversity onto splice variants. Nucleic Acids Res 40, 7123-7131.

Willsey A. J., Sanders S. J., Li M., et al. (2013) Coexpression networks implicate human midfetal deep cortical projection neurons in the pathogenesis of autism. Cell, 155:997-1007.

Wu, J., Anczuków, O., Krainer, A. R., Zhang, M. Q., and Zhang, C. (2013). OLego: fast and sensitive mapping of spliced mRNA-Seq reads using small seeds. Nucleic Acids Res 41, 5149-5163.

Wu J Y, Maniatis T. 1993. Specific interactions between proteins implicated in splice site selection and regulated alternative splicing. *Cell* 75: 1061-1070.

Wu, T. D., and Watanabe, C. K. (2005). GMAP: a genomic mapping and alignment program for mRNA and EST sequences. Bioinformatics 21, 1859-1875.

Yang Y Y, Yin G L, Darnell R B. 1998. The neuronal RNA-binding protein Nova-2 is implicated as the autoantigen targeted in POMA patients with dementia. *Proc Natl Acad Sci USA* 95: 13254-13259.

Yano M, Hayakawa-Yano Y, Mele A, Darnell R B. 2010. Nova2 regulates neuronal migration through an RNA switch in disabled-1 signaling. *Neuron* 66: 848-858.

Zhang, Y., Chen, K., Sloan, S. A., Bennett, M. L., Scholze, A. R., O'Keeffe, S., Phatnani, H. P., Guarnieri, P., Caneda, C., Ruderisch, N., et al. (2014). An RNA-Sequencing Transcriptome and Splicing Database of Glia, Neurons, and Vascular Cells of the Cerebral Cortex. J Neurosci 34, 11929-11947.

Zheng S, Black D L. 2013. Alternative pre-mRNA splicing in neurons: growing up and extending its reach. *Trends Genet* 29: 442-448.

The invention claimed is:

1. A method of increasing neurite outgrowth or increasing neuron survival in a population of cortical neurons comprising administering MG132 to a subject in need thereof.

2. The method of claim 1, wherein the method is for increasing neurite outgrowth.

3. The method of claim 1, wherein the method is for increasing neuron survival.

4. The method of claim 1, wherein the subject is a human.

5. The method of claim 1, wherein the subject is a mouse.

* * * * *